United States Patent
Ban et al.

(10) Patent No.: US 10,898,469 B2
(45) Date of Patent: Jan. 26, 2021

(54) IMIDAZOLYLAMIDE DERIVATIVE

(71) Applicant: Sumitomo Dainippon Pharma Co., Ltd., Osaka (JP)

(72) Inventors: Hitoshi Ban, Osaka (JP); Manabu Kusagi, Osaka (JP); Shingo Tojo, Osaka (JP); Tsuguteru Otsubo, Osaka (JP); Eiji Sugaru, Osaka (JP); Hiroki Yamaguchi, Osaka (JP); Nobuyuki Sawada, Fujisawa (JP); Chiang Jia Li, Cambridge, MA (US)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/079,952

(22) PCT Filed: Feb. 23, 2017

(86) PCT No.: PCT/JP2017/006746
§ 371 (c)(1),
(2) Date: Aug. 24, 2018

(87) PCT Pub. No.: WO2017/146128
PCT Pub. Date: Aug. 31, 2017

(65) Prior Publication Data
US 2019/0060282 A1    Feb. 28, 2019

Related U.S. Application Data

(60) Provisional application No. 62/300,317, filed on Feb. 26, 2016.

(51) Int. Cl.
*A61K 31/4178* (2006.01)
*C07D 417/14* (2006.01)
(Continued)

(52) U.S. Cl.
CPC ...... *A61K 31/4178* (2013.01); *A61K 31/4174* (2013.01); *A61K 31/437* (2013.01); *A61K 31/4365* (2013.01); *A61K 31/4375* (2013.01); *A61K 31/454* (2013.01); *A61K 31/4709* (2013.01); *A61K 31/497* (2013.01); *A61K 31/501* (2013.01); *A61K 31/506* (2013.01); *A61P 35/00* (2018.01); *A61P 35/02* (2018.01); *C07D 233/88* (2013.01); *C07D 233/90* (2013.01); *C07D 401/06* (2013.01); *C07D 401/12* (2013.01); *C07D 401/14* (2013.01); *C07D 403/10* (2013.01); *C07D 403/12* (2013.01); *C07D 405/06* (2013.01); *C07D 405/12* (2013.01); *C07D 409/06* (2013.01); *C07D 409/12* (2013.01);
(Continued)

(58) Field of Classification Search
CPC .................................................. A61K 31/4178
See application file for complete search history.

(56) References Cited

U.S. PATENT DOCUMENTS

| 4,140,788 A | 2/1979 | Atsumi et al. |
| 5,817,677 A | 10/1998 | Linz et al. |

(Continued)

FOREIGN PATENT DOCUMENTS

| JP | S 5359664 | 5/1978 |
| WO | WO 2005/092864 | 10/2005 |

(Continued)

OTHER PUBLICATIONS

Yamaguchi "Anti-Obesity and SCD1 Inhibitors" Fine Chemical 2009, 38(8), 12-24 (English Translation).*
Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: Sand Diego, 2015, p. xxi.*
Carlo C. Maley and Mel Greaves Frontiers in Cancer Research Springer: 2016, pp. 18-19.*
Ponti "Isolation and in vitro Propagation of Tumorigenic Breast Cancer Cells with Stem/Progenitor Cell Properties" Cancer Res 2005; 65: (13). Jul. 1, 2005, 5506.*
Damia "Contemporary pre-clinical development of anticancer agents—What are the optimal preclinical models?" European Journal of Cancer 2009, 45, 2768-2781.*

(Continued)

*Primary Examiner* — David K O'Dell
(74) *Attorney, Agent, or Firm* — Fish & Richardson P.C.

(57) ABSTRACT

The present invention pertains to an imidazolylamide derivative represented by formula (1) that exhibits an exceptional suppressive effect on cancer cell sphere formation ability and that is useful as an antitumor agent that can be administered orally, or a pharmacologically acceptable salt thereof. [In the formula, ring $Q^1$ represents a $C_{6-10}$ aryl group or the like; m represents 0, 1, 2, 3, 4, or 5; $R^3$, independently when multiple, represent(s) a halogen atom or the like; $R^1$ and $R^2$ independently represent a hydrogen atom or the like; $W^1$ represents a $C_{1-4}$ alkylene group (said group may be substituted by 1-3 fluorine atoms or $C_{3-7}$ cycloalkyls); $W^2$ represents —$NR^{4a}C(O)$— or the like (where $R^{4a}$ represents a hydrogen atom or $C_{1-6}$ alkyl group); and ring $Q^2$ represents a $C_{6-10}$ arylgroup or the like]

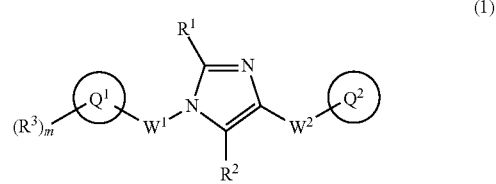

(1)

18 Claims, 8 Drawing Sheets

(51) Int. Cl.

| | |
|---|---|
| C07D 403/12 | (2006.01) |
| C07D 401/06 | (2006.01) |
| C07D 233/90 | (2006.01) |
| C07D 403/10 | (2006.01) |
| C07D 405/06 | (2006.01) |
| C07D 487/04 | (2006.01) |
| C07D 413/12 | (2006.01) |
| C07D 409/12 | (2006.01) |
| C07D 233/88 | (2006.01) |
| C07D 401/14 | (2006.01) |
| C07D 471/04 | (2006.01) |
| C07D 417/12 | (2006.01) |
| C07D 495/04 | (2006.01) |
| C07D 409/06 | (2006.01) |
| A61P 35/00 | (2006.01) |
| C07D 401/12 | (2006.01) |
| C07D 405/12 | (2006.01) |
| A61K 31/4174 | (2006.01) |
| A61K 31/4709 | (2006.01) |
| A61K 31/497 | (2006.01) |
| A61K 31/501 | (2006.01) |
| A61K 31/506 | (2006.01) |
| A61P 35/02 | (2006.01) |
| A61K 31/4365 | (2006.01) |
| A61K 31/437 | (2006.01) |
| A61K 31/4375 | (2006.01) |
| A61K 31/454 | (2006.01) |

(52) U.S. Cl.
CPC ......... *C07D 413/12* (2013.01); *C07D 417/12* (2013.01); *C07D 417/14* (2013.01); *C07D 471/04* (2013.01); *C07D 487/04* (2013.01); *C07D 495/04* (2013.01)

(56) References Cited

U.S. PATENT DOCUMENTS

| | | | |
|---|---|---|---|
| 6,310,070 | B1 | 10/2001 | Yokoyama et al. |
| 9,101,141 | B2 | 8/2015 | Kohn et al. |
| 9,828,362 | B2 | 11/2017 | Ban et al. |
| 2016/0376263 | A1 | 12/2016 | Patron et al. |
| 2017/0015677 | A1 | 1/2017 | Ban et al. |
| 2017/0166552 | A1* | 6/2017 | Ban ................. C07D 403/12 |

FOREIGN PATENT DOCUMENTS

| | | | |
|---|---|---|---|
| WO | WO 2006/001750 | 1/2006 | |
| WO | WO 2006/087355 | 8/2006 | |
| WO | WO 2006/114313 | 11/2006 | |
| WO | WO 2007/034326 | 3/2007 | |
| WO | WO 2007/073299 | 6/2007 | |
| WO | WO 2007/138072 | 12/2007 | |
| WO | WO 2008/073461 | 6/2008 | |
| WO | WO 2008/138842 | 11/2008 | |
| WO | WO 2008/138843 | 11/2008 | |
| WO | WO 2009/060054 | 5/2009 | |
| WO | WO 2011/106114 | 9/2011 | |
| WO | WO-2012017020 A1 * | 2/2012 | ........... C07D 403/12 |
| WO | WO 2014/125444 | 8/2014 | |
| WO | WO 2015/151490 | 10/2015 | |
| WO | WO 2016/208591 | 12/2016 | |
| WO | WO 2016/208592 | 12/2016 | |

OTHER PUBLICATIONS

Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer". Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Baell "New Substructure Filters for Removal of Pan Assay Interference Compounds (PAINS) from Screening Libraries and for Their Exclusion in Bioassays" J. Med. Chem. 2010, 53, 2719-2740.*
Hodson "Stearoyl-CoA desaturase: rogue or innocent bystander?" Progress in Lipid Research 52 (2013) 15-42.*
Boman et al., "Cancer Stem Cells: A Step Toward the Cure", Journal of Clinical Oncology 26 (17): 2795-2799. 2008.
Al-Hajj et al., "Self-renewal and solid tumor stem cells", Oncogene 23 (43): 7274-82. 2004.
Atkinson et al., "N-Benzylimidazole carboxamides as potent, orally active stearoyl CoA desaturase-1 inhibitors", Bioorganic & Medicinal Chemistry Letters, 21(6), pp. 1621-1625, 2011.
Delest et al., "Synthesis of 1-benzyl-8, 9-dihydroimidazo [4, 5-c] pyrrolo [3, 2-g]-quinolin-4 (5H)-one via palladium-catalyzed intramolecular arylation", Tetrahedron Letters, 2004, vol. 60, p. 6079-6083, Scheme 4 Compounds 9-10, ISSN: 0040-4020.
Deng et al.,"Discovery of liver-targeted inhibitors of stearoyl-CoA desaturase(SCD1)," Bioorganic & Medicinal Chemistry Letters, 23: 791-796, 2013.
English translation of the International Preliminary Report on Patentability (Chapter I) with PCT/IB/338 in International Application No. PCT/JP2017/006746, dated Sep. 7, 2018.
Haberhauer et al., "Synthesis and Structural Investigation of C4- and C2-Symmetric Molecular Scaffolds Based on Imidazole Peptides"European Journal of Chemistry, 11, 1779-1792, 2007.
Helal et al.,"Potent and cellularly active 4-aminoimidazole inhibitors of cyclindependent kinase 5/p25 for the treatment of Alzheimer's disease,"Bioorganic & Medicinal Chemistry Letters, 5703-5707, 2009.
Hiroki Yamaguchi (presenter), Nobuyuki Sawada, Miki Hashizume, Toshiyuki Kamei, Futoshi Hasegawa, and Tsutomu Mimoto, "Research and Synthesis of stearoyl-CoA desaturase 1 inhibitors" The 27th medicinal chemistry symposium, Nov. 26-28, 2008, Mielparque Osaka, Partial English Translation.
Hiroki Yamaguchi, "Inhibitors of Stearoyl-CoA Desaturase 1 as Anti-obesity Drug", Monthly Fine Chemicals, Aug. 2009 (issued date: Jul. 15, 2009), vol. 38, No. 8, p. 12-24, published by CMC Publishing Co., Ltd. and English abstract thereof.
Hiroki Yamaguchi, Nobuyuki Sawada, Miki Hashizume, Toshiyuki Kamei, Futoshi Hasegawa, and Tsutomu Mimoto , "Research and Synthesis of stearoyl-CoA desaturase 1 inhibitors", The 27th medicinal chemistry symposium abstracts (edited by executive committee of the 27th medicinal chemistry symposium), p. 166-167, Nov. 10, 2008, published by the Pharmaceutical Society of Japan, Division of Medicinal Chemistry (with English abstract).
International Search Report and Written Opinion in International Application No. PCT/JP2017/006746, dated Aug. 31, 2017, 5 pages, English translation.
Lobo et al., "The biology of cancer stem cells.", Annu Rev Cell Dev Biol 23: 675-99. 2007.
Monthly Fine Chemicals, CMC Publishing Co., Ltd, pp. 12-24, Aug. 2009, Partial English Abstract.
Ponti et al., "Isolation and in vitro propagation of tumorigenic breast cancer cells with stem/progenitor cell properties.", 65(13) :5506-11. 2005.
STN Registry [online] RN: 1351788-43-6 (ED: Dec. 23, 2011), RN: 1351771-27-1 (ED: Dec. 23, 2011) RN: 1251699-10-1 (ED: Nov. 3, 2010), RN: 1251594-36-1 (ED: Nov. 3, 2010).
"Su and Buchwald,"A Bulky Biaryl Phosphine Ligand Allows for Palladium-Catalyzed Amidation of Five-Membered Heterocycles as Electrophiles,"Angew Chem Int Ed, 51: 4710-4713, 2012".
Zhang et al., "Synergistic Effect of the δ☐Secretase Inhibitor PF☐03084014 and Docetaxel in Breast Cancer Models", Stem Cells Translational Medicine 2:233-242, 2013.
Uto et al., "Novel and potent inhibitors of stearoyl-CoA desaturase-1. Part I: Discovery of 3-(2-hydroxyethoxy)-4-methoxy-N-[5-(3

(56) References Cited

OTHER PUBLICATIONS trifluoromethylbenzyl)thiazol-2-yl]benzamide," Bioorganic & Medicinal Chemistry Letters, 2009, 19:4151-4158.

* cited by examiner

[Fig. 1]
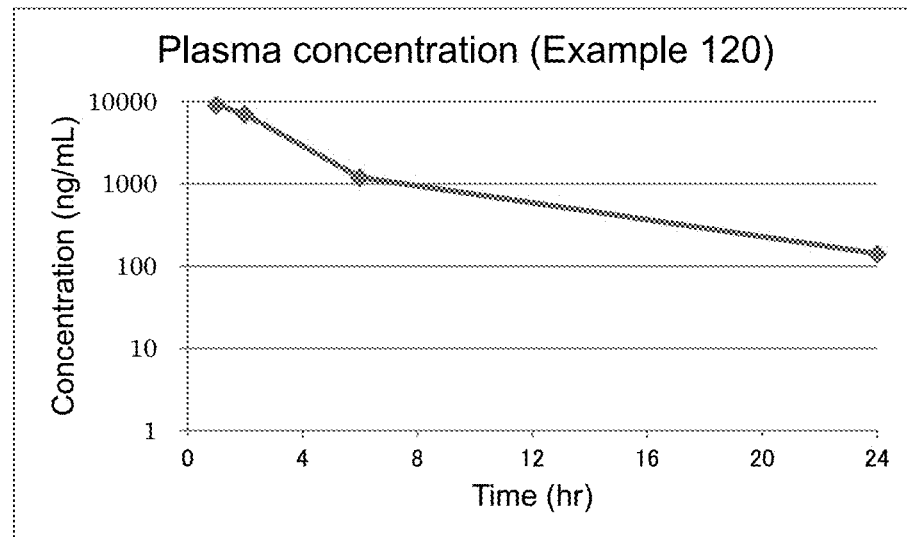
[Fig. 2]
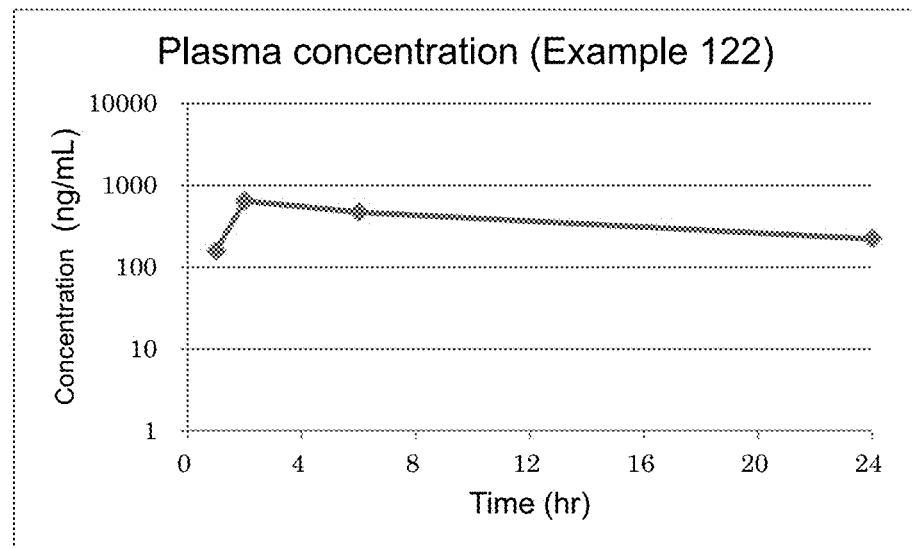

[Fig. 3]
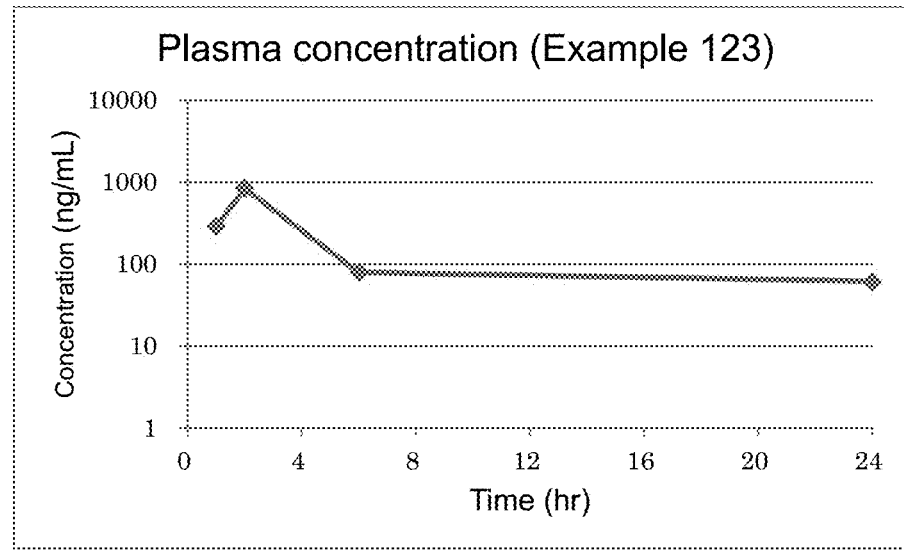
[Fig. 4]
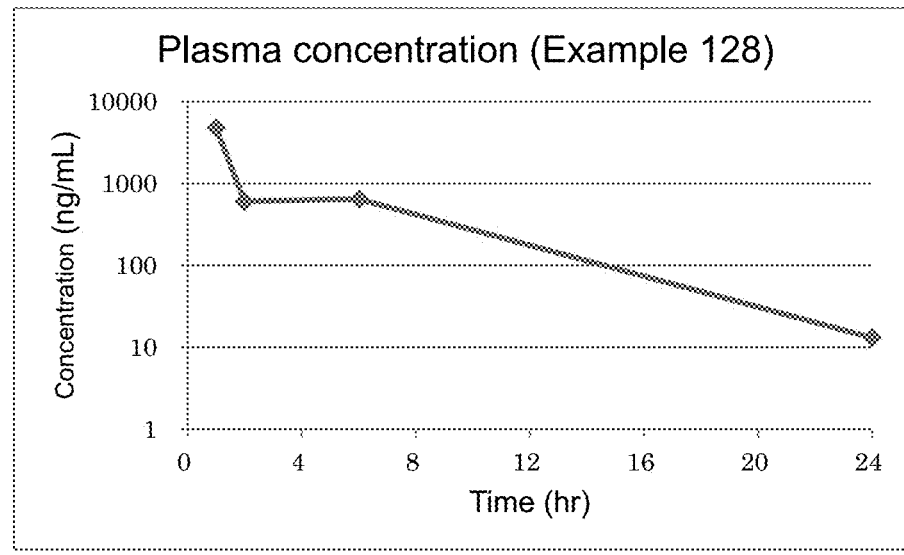

[Fig. 5]
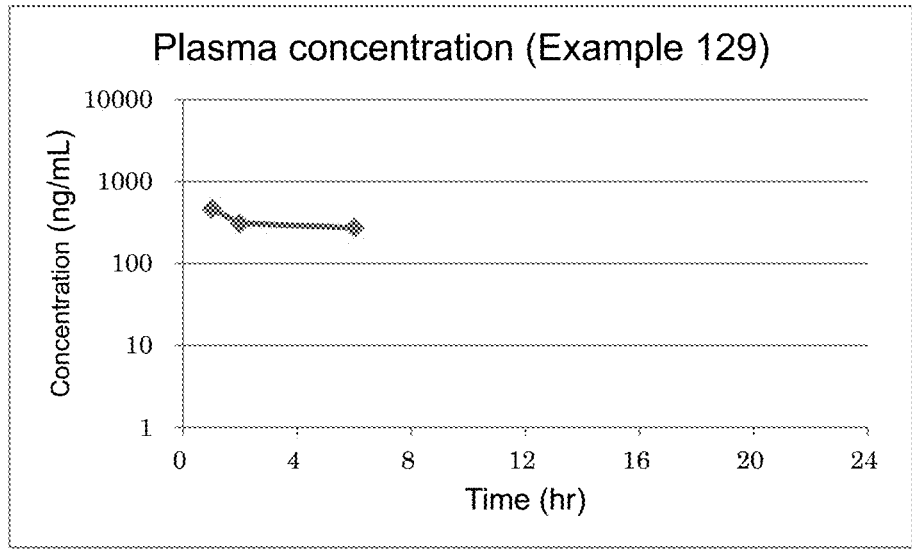
[Fig. 6]
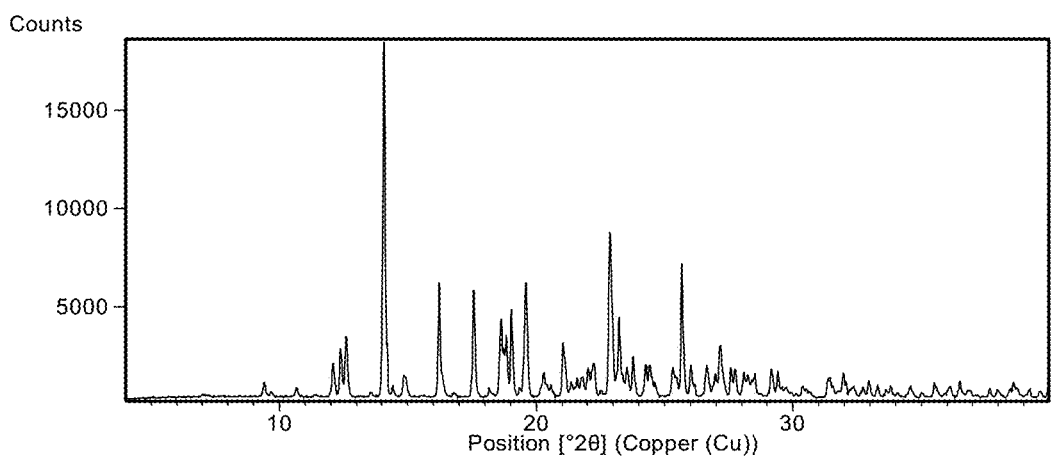

[Fig. 7]
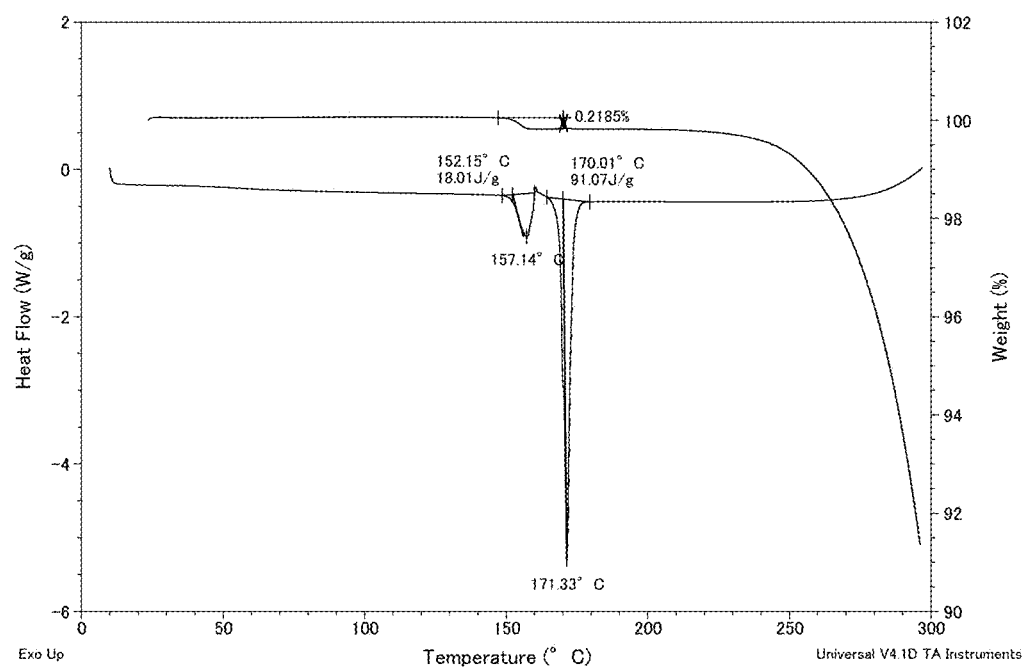

[Fig. 8]
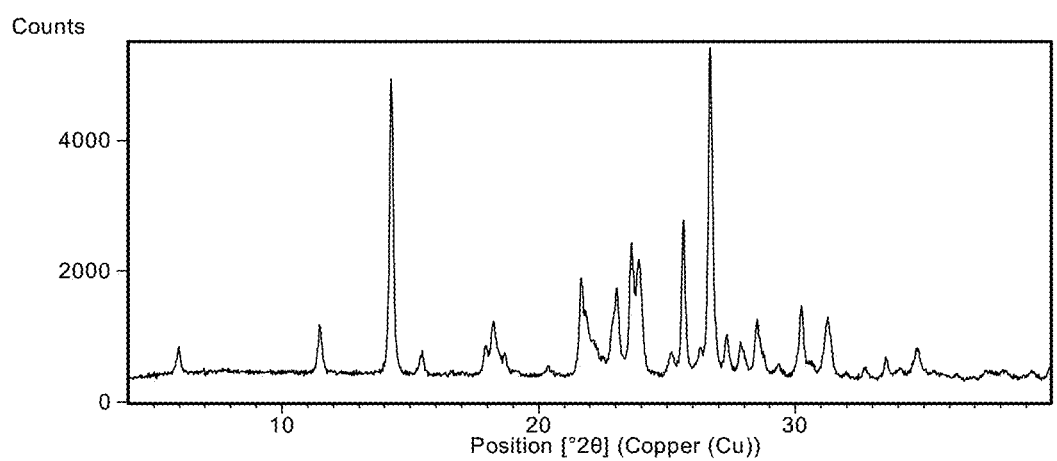

[Fig. 9]
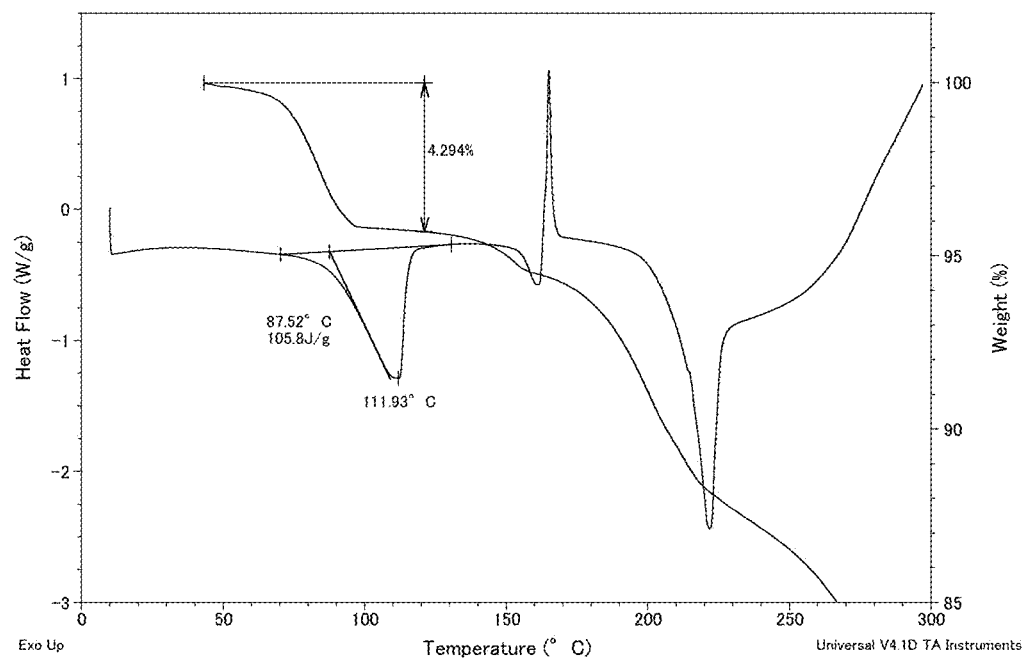

[Fig. 10]
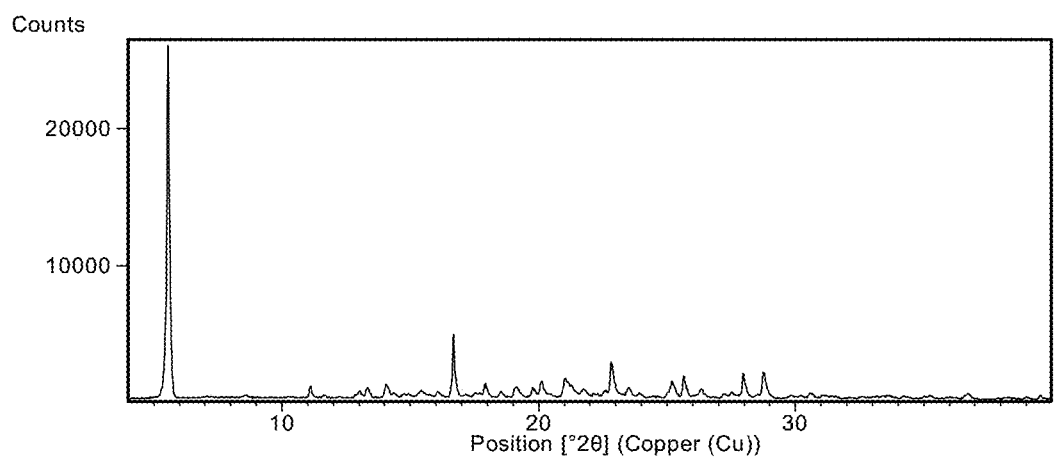

[Fig. 11]
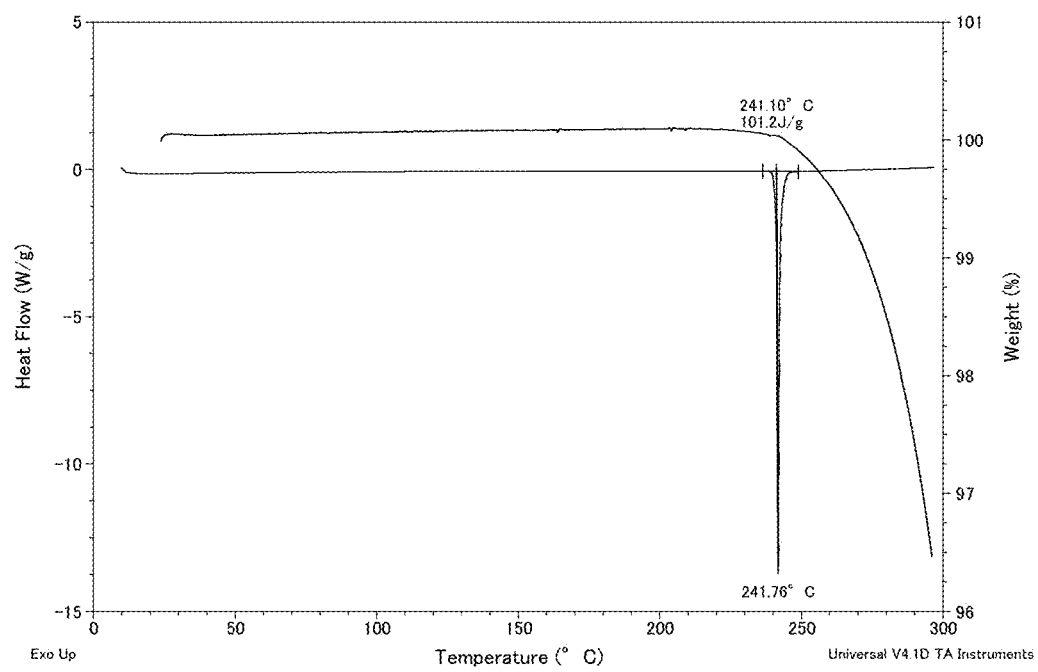

IMIDAZOLYLAMIDE DERIVATIVE

TECHNICAL FIELD

The present invention relates to pharmaceutically-useful imidazolylamide derivatives and pharmaceutically acceptable salts thereof, and anti-tumor agents comprising the same as an active ingredient.

BACKGROUND ART

Conventional cancer treatments are sometimes not expected to bring in meaningful survival effects even if they can induce the regression of tumors, partly because nowadays, it has been suggested that cancer stem cells (hereinafter referred to as "CSCs" as necessary) are closely involved in the persistent proliferation of malignant tumors, metastasis or recurrence of cancer, and resistance to anti-tumor agents. CSCs have been identified in almost all types of major cancers in human such as breast cancer, colon cancer, lung cancer, and hematological malignancy (Non Patent Literature 1). Also, CSCs can be greatly different in the biological features from normal cancer cells that differentiate from CSCs, and thus the development of an anti-tumor agent that targets CSCs is expected to lead to a new strategy for cancer treatments (Non Patent Literature 2).

One of the features in CSCs is the self-renewal ability (Non Patent Literature 3). Reliable methods established for measuring the self-renewal ability of cells include, for example, a method for measuring the sphere-forming ability of cancer cells in non-adherent condition in the absence of serum (Non Patent Literature 4).

Non Patent Literature 5 discloses that PF-03084014 having an N-imidazolylamide scaffold can inhibit CSCs to exhibit an anti-cancer effect.

Non Patent Literatures 6 and 7 disclose the following 4-aminoimidazole derivates useful for an anti-obesity drug. They, however, do not disclose that these compounds have an anti-cancer effect.

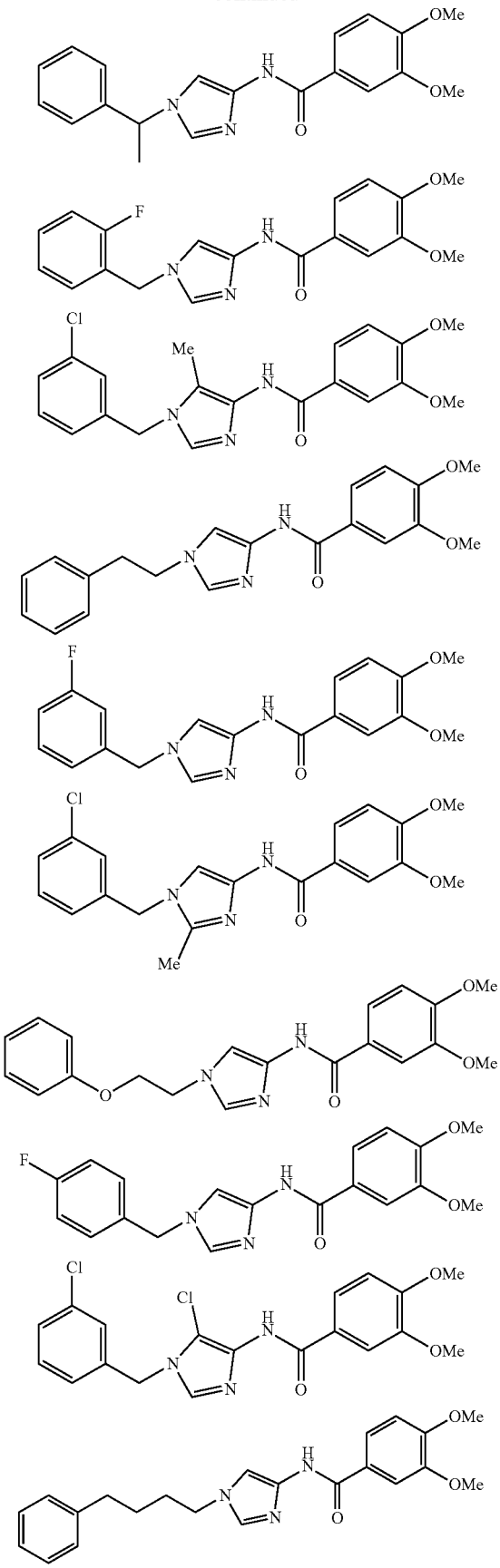

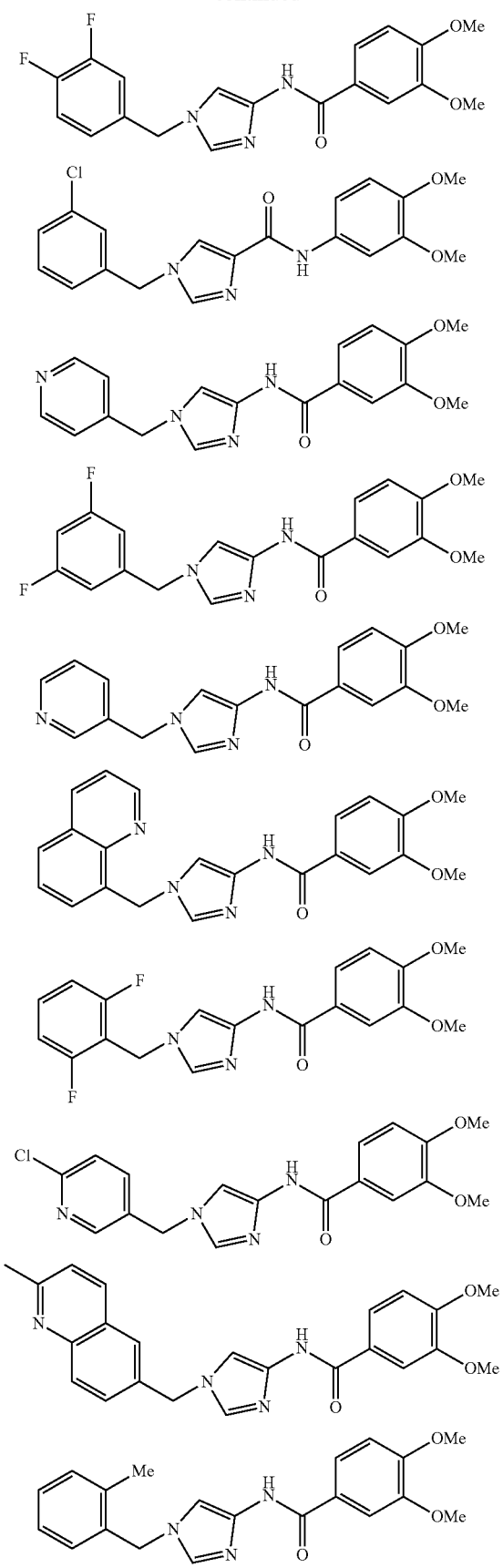
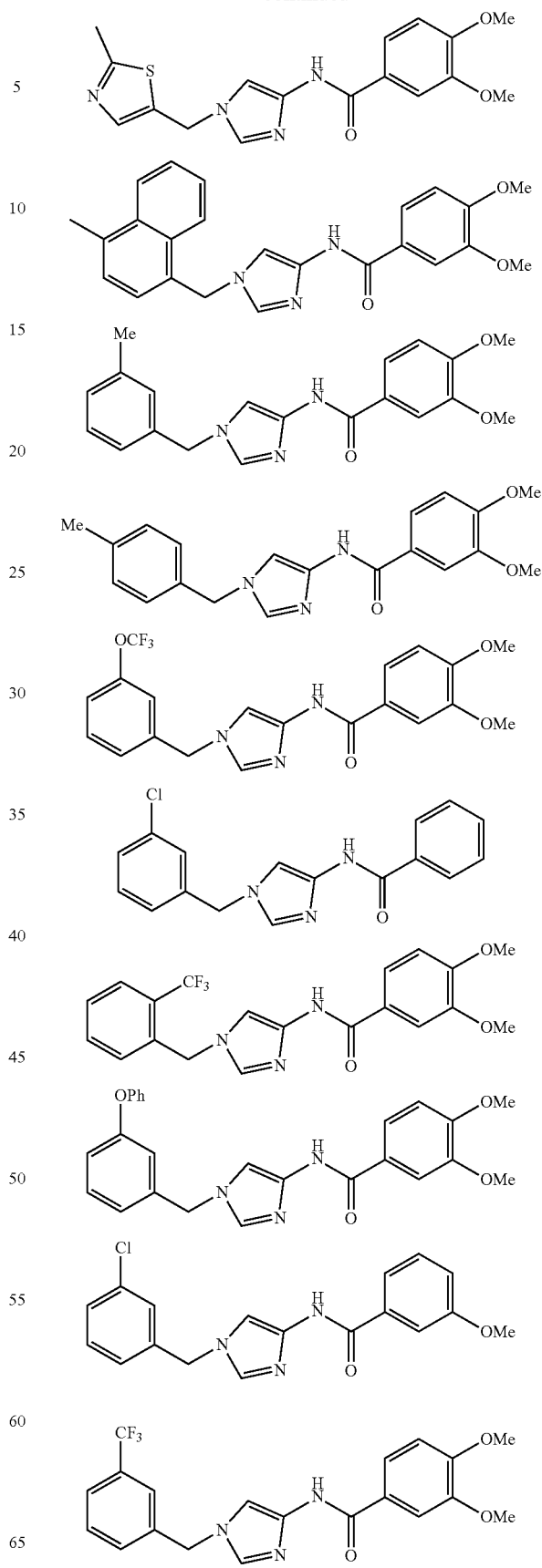

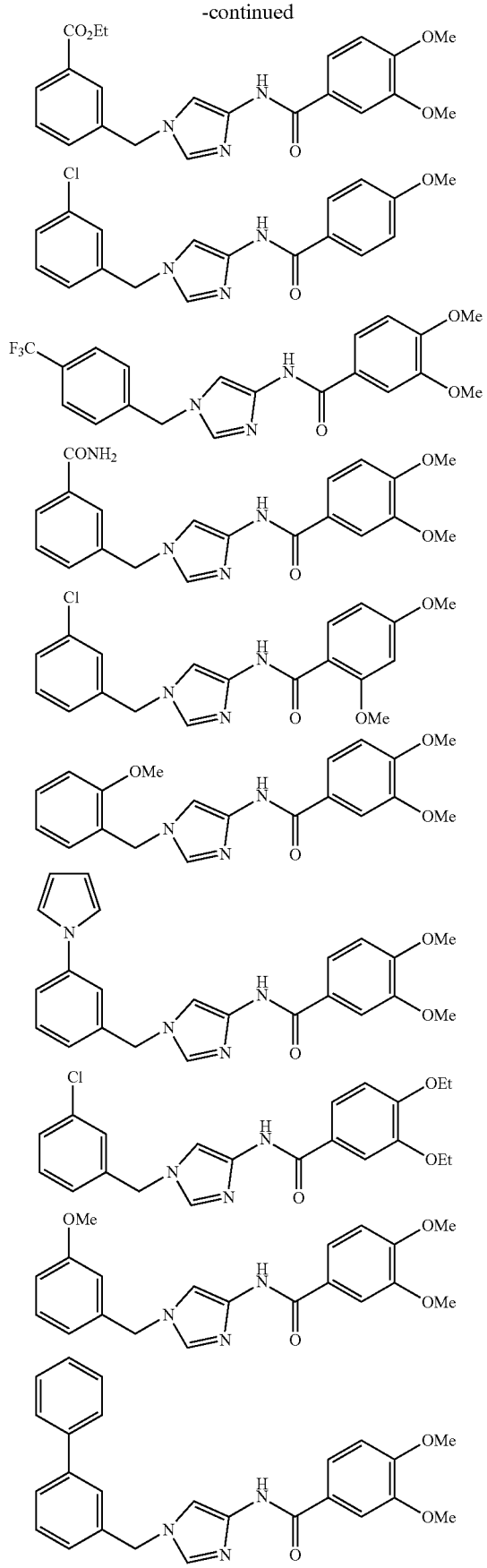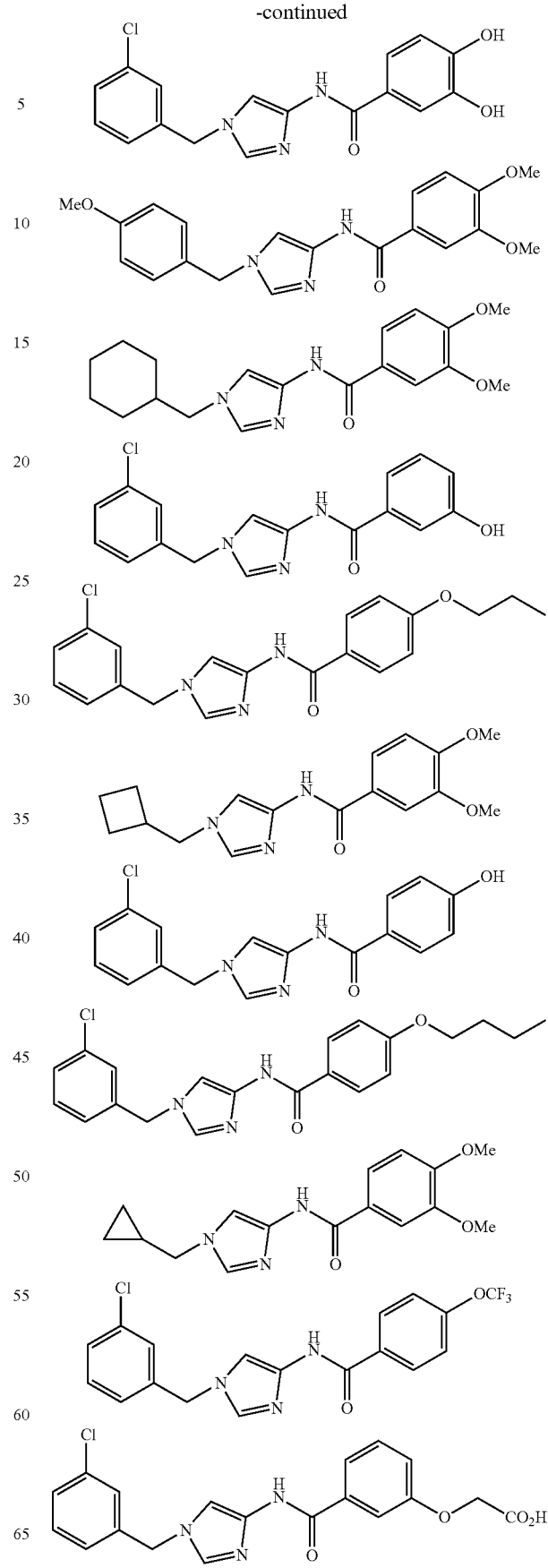

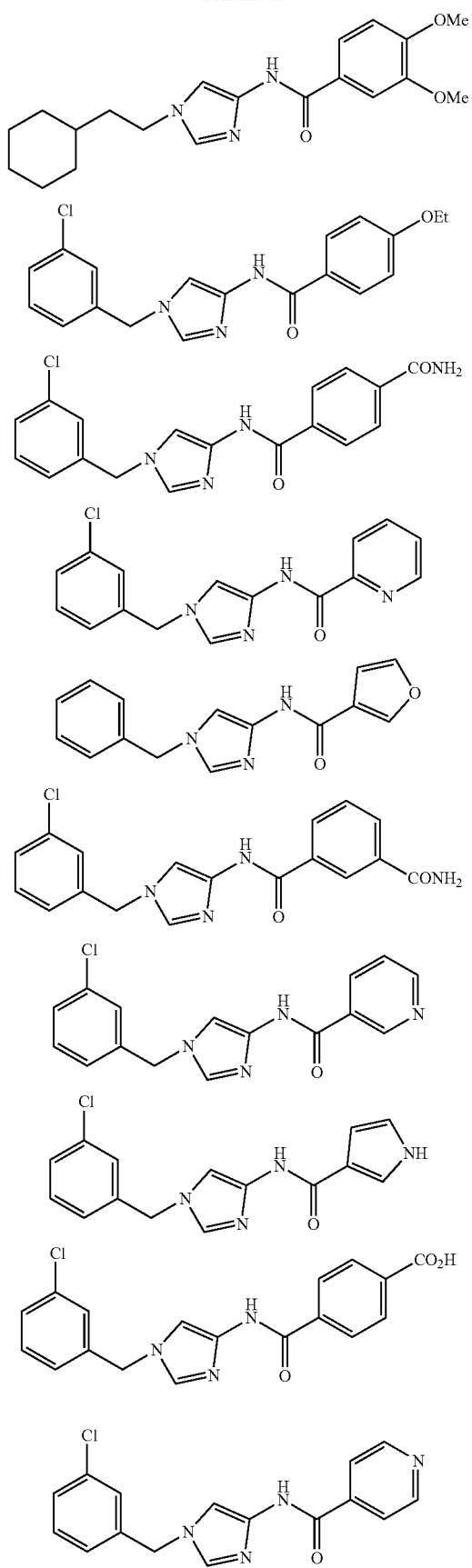
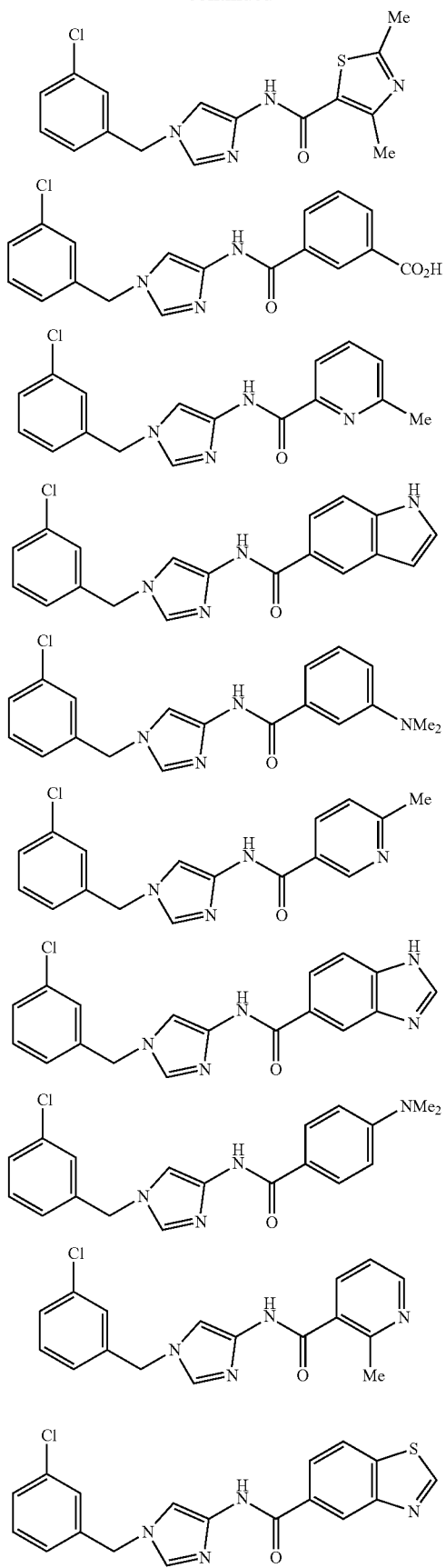

-continued
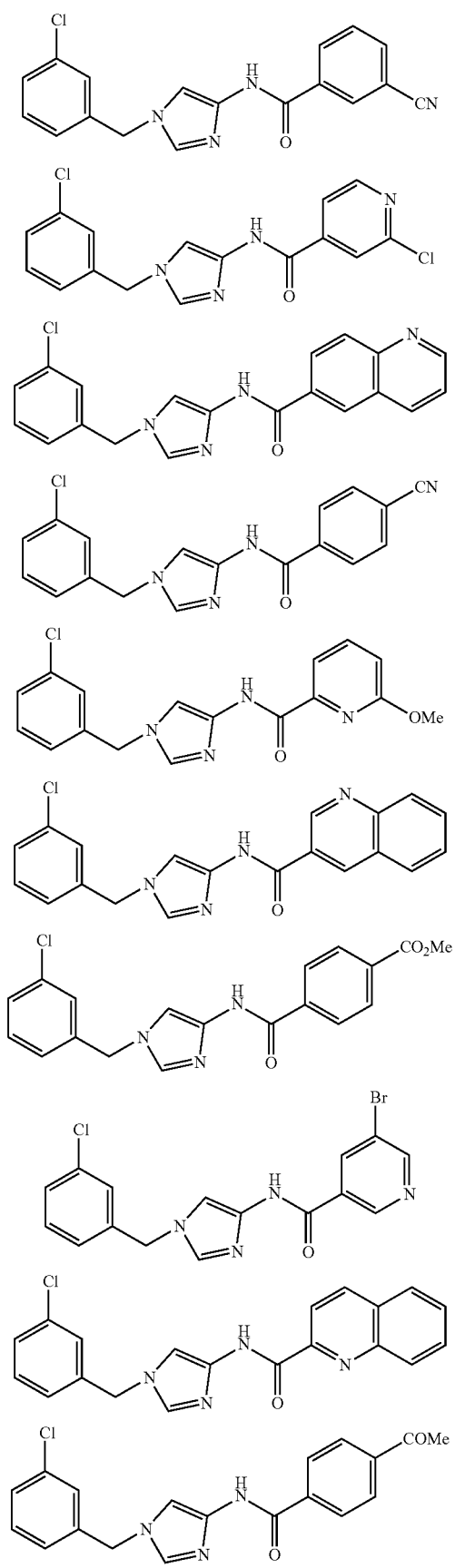
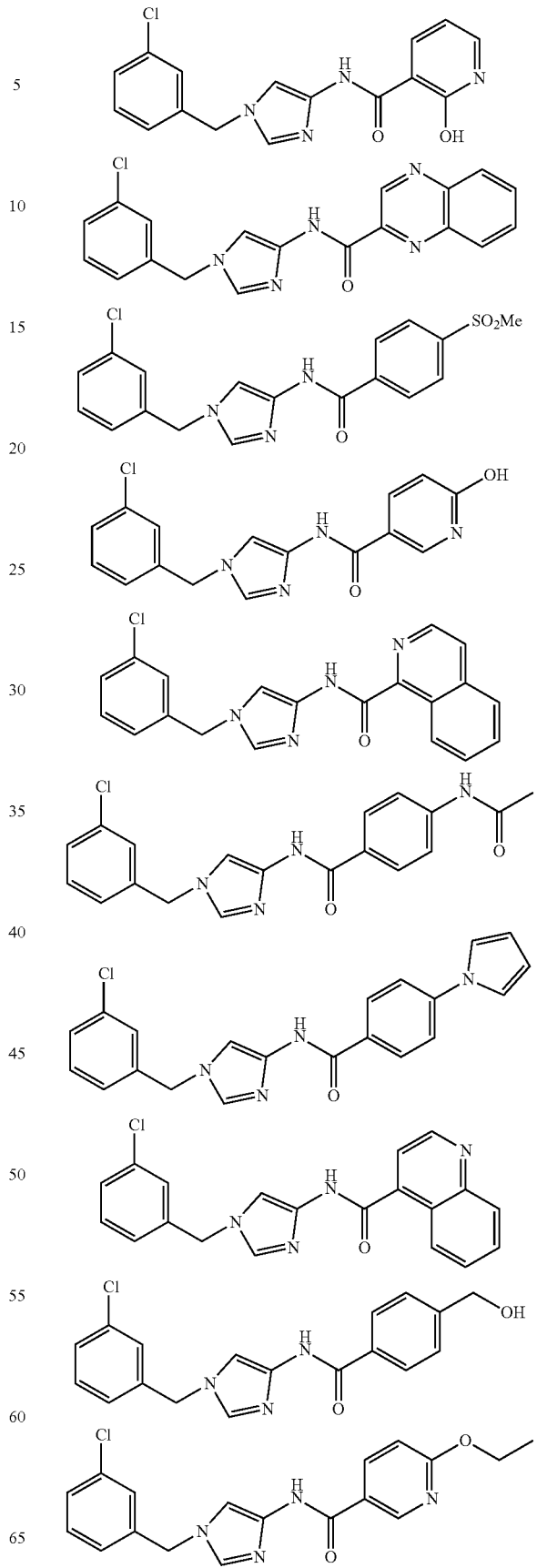

-continued

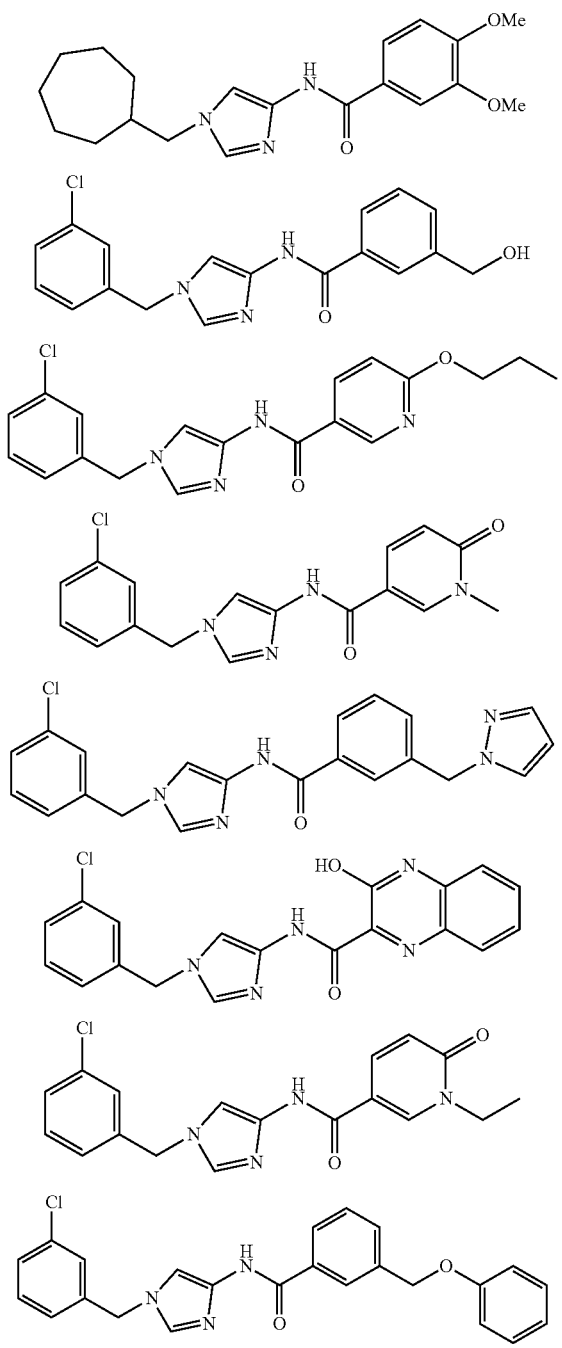

Other known imidazolylamide compounds include, for example, the following compounds. It, however, has not been known that these compounds have an anti-cancer effect.

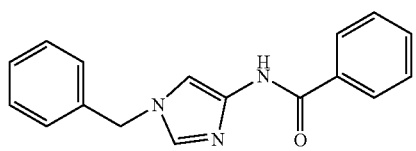

-continued

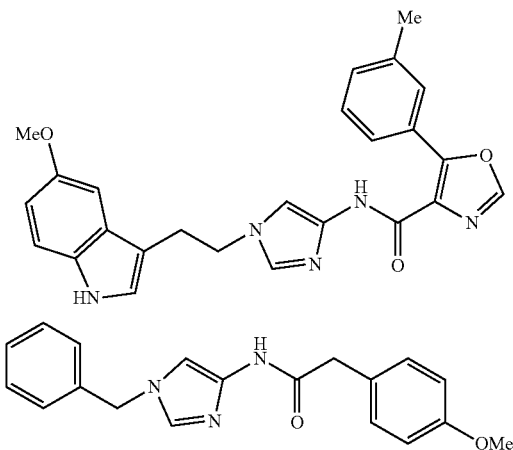

CITATION LIST

Non Patent Literatures

[Non Patent Literature 1] Boman et al., Journal of Clinical Oncology 26(17): 2795-2799. 2008
[Non Patent Literature 2] Lobo et al., Annu Rev Cell Dev Biol 23:675-99. 2007
[Non Patent Literature 3] Al-Hajj et al., Oncogene 23(43): 7274-82. 2004
[Non Patent Literature 4] Ponti et al., Cancer Res 65(13): 5506-11. 2005
[Non Patent Literature 5] Zhang et al., Stem Cells Translational Medicine 2:233-242. 2013
[Non Patent Literature 6] Presentation abstracts of The 27th Medicinal Chemistry Symposium, pages 166-167
[Non Patent Literature 7] Monthly Fine Chemicals, August 2009, CMC Publishing Co., Ltd, pages 12-24

SUMMARY OF THE INVENTION

Problem to be Solved by the Invention

An object of the present invention is to provide useful compounds as a novel anti-tumor agent that targets CSCs which are thought to be closely involved in the persistent proliferation of malignant tumor, metastasis or recurrence of cancer, and resistance to anti-tumor agents.

Means for Solving the Problems

The present inventors have extensively studied to reach the above object, and then have found that a compound of the following Formula (1) or a pharmaceutically acceptable salt thereof (hereinafter referred to as "the present compound", as necessary) has a potent inhibitory effect on the sphere-forming ability of cancer cells and is highly useful as a novel anti-tumor agent. Based upon the findings, the present invention has been achieved.

The present invention is as described below.
[1] A compound of Formula (1):

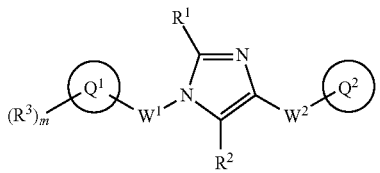

wherein $Q^1$ is $C_{6-10}$ aryl, $C_{6-10}$ aryloxy, $C_{6-10}$ arylthio, $C_{3-10}$ cycloalkyl, or 5- to 10-membered heteroaryl;
m is 0, 1, 2, 3, 4, or 5;
$R^3$ is a substituent on Ring Q and each independently
(1) halogen atom,
(2) optionally-substituted $C_{1-6}$ alkyl,
(3) optionally-substituted $C_{1-6}$ alkoxy,
(4) optionally-substituted amino,
(5) optionally-substituted $C_{6-10}$ aryl,
(6) optionally-substituted $C_{6-10}$ aryloxy,
(7) optionally-substituted 5- to 10-membered heteroaryl,
(8) optionally-substituted $C_{1-6}$ alkoxy-carbonyl,
(9) optionally-substituted aminocarbonyl,
(10) optionally-substituted $C_{1-6}$ alkyl-carbonyl,
(11) optionally-substituted $C_{1-6}$ alkylsulfonyl,
(12) optionally-substituted $C_{1-6}$ alkyl-carbonylamino,
(13) optionally-substituted $C_{1-6}$ alkylsulfonylamino,
(14) optionally-substituted $C_{1-6}$ alkoxy-carbonylamino,
(15) optionally-substituted $C_{1-6}$ alkyl-carbonyloxy,
(16) hydroxy,
(17) cyano,
(18) optionally-substituted aminosulfonyl, or
(19) optionally-substituted $C_{3-10}$ cycloalkyl;
provided that when two $R^3$s bind to any of the adjacent carbon atoms on Ring $Q^1$, the $R^3$s may combine together with the carbon atoms to which they bind to form a 5- to 8-membered saturated carbocyclic ring or non-aromatic heterocyclic ring, the ring being optionally substituted with 1 to 2 groups independently selected from the group consisting of halogen atom, $C_{1-6}$ alkyl, and $C_{1-6}$ alkoxy,
$R^1$ and $R^2$ are each independently hydrogen atom, halogen atom, or $C_{1-6}$ alkyl which may be optionally substituted with the same or different 1 to 3 halogen atoms;
$W^1$ is $C_{1-4}$ alkylene which may be optionally substituted with 1 to 3 fluorine atoms or $C_{3-7}$ cycloalkyl;
$W^2$-$Q^2$ is —$NR^{4a}C(O)$-$Q^2$, —$NR^{4a}C(O)O$-$Q^2$, —$NR^{4a}C(O)OCH_2$-$Q^2$, —$NR^{4a}C(O)NR^{3b}$-$Q^2$, —$NR^{4a}C(O)NR^{4b}CH_2$-$Q^2$, —$NR^{4a}C(O)CH_2O$-$Q^2$, —$NR^{4a}C(O)CH_2$-$Q^2$, —$NR^{4a}C(O)CH_2CH_2$-$Q^2$, —$C(O)NR^{4a}$-$Q^2$, —$C(O)NR^{4a}CH_2$-$Q^2$, —$C(O)NR^{4a}CH_2CH_2$-$Q^2$, or —$NR^{4a}C(O)$—$(CR^{4c}$=$CR^{4d})_n$-$Q^2$ (wherein n is 1, 2, 3, or 4; $R^{4a}$ and $R^{4b}$ are independently hydrogen atom or $C_{1-6}$ alkyl; $R^{4c}$ and $R^{4d}$ are independently hydrogen atom, fluorine atom, or $C_{1-6}$ alkyl);
Ring $Q^2$ is
(1) $C_{6-10}$ aryl which may be optionally substituted with the same or different 1 to 4 groups selected from the group consisting of:
(a) halogen atom,
(b) hydroxy,
(c) optionally-substituted $C_{1-6}$ alkyl,
(d) optionally-substituted $C_{1-6}$ alkoxy,
(e) optionally-substituted $C_{3-10}$ cycloalkyl,
(f) optionally-substituted $C_{3-10}$ cycloalkoxy,
(g) optionally-substituted $C_{2-6}$ alkenyl,
(h) optionally-substituted $C_{2-6}$ alkynyl,
(i) cyano,
(j) formyl,
(k) optionally-substituted $C_{6-10}$ aryl,
(l) optionally-substituted $C_{6-10}$ aryloxy,
(m) optionally-substituted 5- to 10-membered heteroaryl,
(n) optionally-substituted $C_{1-6}$ alkyl-carbonyl,
(o) optionally-substituted $C_{1-6}$ alkylsulfonyl,
(p) optionally-substituted $C_{1-6}$ alkoxy-carbonyl,
(q) optionally-substituted $C_{1-6}$ alkyl-carbonylamino,
(r) optionally-substituted $C_{1-6}$ alkylsulfonylamino,
(s) optionally-substituted $C_{1-6}$ alkoxy-carbonylamino,
(t) optionally-substituted $C_{1-6}$ alkyl-carbonyloxy,
(u) optionally-substituted amino,
(v) optionally-substituted aminocarbonyl,
(w) optionally-substituted aminosulfonyl,
(x) optionally-substituted 5- or 6-membered cyclic amino,
(y) optionally-substituted 5- or 6-membered cyclic aminocarbonyl,
(z) nitro, and
(aa) carboxyl,
(2) 5- to 10-membered heteroaryl which may be optionally substituted with the same or different 1 to 4 groups selected from the group consisting of:
(a) halogen atom,
(b) hydroxy,
(c) $C_{1-6}$ alkyl which may be optionally substituted with the same or different 1 to 3 groups selected from the group consisting of halogen atom, phenyl, phenoxy, aminocarbonyl (wherein the amino moiety may be optionally substituted with the same or different 1 to 2 $C_{1-6}$ alkyl), $C_{1-6}$ alkoxy-carbonyl, carboxyl, and 5- or 6-membered heteroaryl,
(d) optionally-substituted $C_{1-6}$ alkoxy,
(e) optionally-substituted $C_{3-10}$ cycloalkyl,
(f) optionally-substituted $C_{3-10}$ cycloalkoxy,
(g) optionally-substituted $C_{2-6}$ alkenyl,
(h) optionally-substituted $C_{2-6}$ alkynyl,
(i) cyano,
(j) formyl,
(k) optionally-substituted $C_{6-10}$ aryl,
(l) optionally-substituted $C_{6-10}$ aryloxy,
(m) optionally-substituted 5- to 10-membered heteroaryl,
(n) optionally-substituted $C_{1-6}$ alkyl-carbonyl,
(o) optionally-substituted $C_{1-6}$ alkylsulfonyl,
(p) optionally-substituted $C_{1-6}$ alkoxy-carbonyl,
(q) optionally-substituted $C_{1-6}$ alkyl-carbonylamino,
(r) optionally-substituted $C_{1-6}$ alkylsulfonylamino,
(s) optionally-substituted $C_{1-6}$ alkoxy-carbonylamino,
(t) optionally-substituted $C_{1-6}$ alkyl-carbonyloxy,
(u) optionally-substituted amino,
(v) optionally-substituted aminocarbonyl,
(w) optionally-substituted aminosulfonyl,
(x) optionally-substituted 5- or 6-membered cyclic amino,
(y) optionally-substituted 5- or 6-membered cyclic aminocarbonyl,
(z) nitro, and
(aa) carboxyl, or
(3) a group of the following Formula (2):

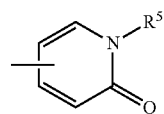

wherein $R^5$ is hydrogen atom or $C_{1-6}$ alkyl;
provided that when $W^2$-$Q^2$ is —$C(O)NR^{4a}$-$Q^2$, Ring $Q^2$ is phenyl; m is 1, 2, 3, 4, or 5; $R^3$ is each independently halogen atom, or $C_{1-6}$ alkyl which may be optionally substituted with the same or different 1 to 3 halogen atoms;

Ring $Q^2$ is (1) phenyl which may be optionally substituted with the same or different 1 to 4 groups selected from the group consisting of:

(a) halogen atom, (b) hydroxy, (c) $C_{1-6}$ alkyl which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (d) $C_{1-6}$ alkoxy which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (e) $C_{3-10}$ cycloalkyl which may be optionally substituted with the same or different 1 to 4 groups selected from the group consisting of halogen atom, hydroxy, and $C_{1-6}$ alkoxy, (f) $C_{3-10}$ cycloalkoxy which may be optionally substituted with the same or different 1 to 4 groups selected from the group consisting of halogen atom, hydroxy, and $C_{1-6}$ alkoxy, (g) $C_{2-6}$ alkenyl which may be optionally substituted with the same or different 1 to 2 halogen atoms, (h) $C_{2-6}$ alkynyl which may be optionally substituted with the same or different 1 to 2 halogen atoms, (i) cyano, (j) formyl, (k) $C_{6-10}$ aryl which may be optionally substituted with the same or different 1 to 4 groups selected from the group consisting of halogen atom, hydroxy, hydroxymethyl, $C_{1-6}$ alkyl, and $C_{1-6}$ alkoxy, (l) $C_{6-10}$ aryloxy which may be optionally substituted with the same or different 1 to 4 groups selected from the group consisting of halogen atom, hydroxy, hydroxymethyl, $C_{1-6}$ alkyl, and $C_{1-6}$ alkoxy, (m) 5- to 10-membered heteroaryl which may be optionally substituted with the same or different 1 to 4 groups selected from the group consisting of halogen atom, hydroxy, hydroxymethyl, $C_{1-6}$ alkyl, and $C_{1-6}$ alkoxy, (n) $C_{1-6}$ alkyl-carbonyl which may be optionally substituted with the same or different 1 to 4 groups selected from the group consisting of halogen atom, hydroxy, and $C_{1-6}$ alkoxy, (o) $C_{1-6}$ alkylsulfonyl (wherein the alkyl moiety may be optionally substituted with the same or different 1 to 3 halogen atoms), (p) $C_{1-6}$ alkoxy-carbonyl (wherein the alkoxy moiety may be optionally substituted with the same or different 1 to 3 halogen atoms), (q) $C_{1-6}$ alkyl-carbonylamino (wherein the alkyl moiety may be optionally substituted with the same or different 1 to 3 halogen atoms), (r) $C_{1-6}$ alkylsulfonylamino (wherein the alkyl moiety may be optionally substituted with the same or different 1 to 3 halogen atoms), (s) $C_{1-6}$ alkoxy-carbonylamino (wherein the alkyl moiety may be optionally substituted with the same or different 1 to 3 halogen atoms), (t) $C_{1-6}$ alkyl-carbonyloxy (wherein the alkyl moiety may be optionally substituted with the same or different 1 to 3 halogen atoms), (u) amino which may be optionally substituted with the same or different 1 to 2 $C_{1-6}$ alkyl, the alkyl group being optionally substituted with the same or different 1 to 4 groups selected from the group consisting of halogen atom, hydroxy, and $C_{1-6}$ alkoxy, (v) aminocarbonyl (wherein the amino moiety may be optionally substituted with the same or different 1 to 2 $C_{1-6}$ alkyl, the alkyl group being optionally substituted with the same or different 1 to 3 halogen atoms), (w) aminosulfonyl (wherein the amino moiety may be optionally substituted with the same or different 1 to 2 $C_{1-6}$ alkyl, the alkyl group being optionally substituted with the same or different 1 to 3 halogen atoms), (x) 5- or 6-membered cyclic amino which may be optionally substituted with the same or different 1 to 4 groups selected from the group consisting of halogen atom, hydroxy, $C_{1-6}$ alkyl, and $C_{1-6}$ alkoxy, (y) 5- or 6-membered cyclic aminocarbonyl which may be optionally substituted with the same or different 1 to 4 groups selected from the group consisting of halogen atom, hydroxy, $C_{1-6}$ alkyl, and $C_{1-6}$ alkoxy, (z) nitro, and (aa) carboxyl, (2) pyridyl which may be optionally substituted with the same or different 1 to 4 groups selected from the group consisting of:

(a) halogen atom, (b) hydroxy, (c) $C_{1-6}$ alkyl which may be optionally substituted with the same or different 1 to 3 groups selected from the group consisting of halogen atom, phenyl, phenoxy, aminocarbonyl, $C_{1-6}$ alkoxy-carbonyl, carboxyl, and 5- or 6-membered heteroaryl, the amino moiety being optionally substituted with the same or different 1 to 2 $C_{1-6}$ alkyl, (d) $C_{1-6}$ alkoxy which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (e) $C_{3-10}$ cycloalkyl which may be optionally substituted with the same or different 1 to 4 groups selected from the group consisting of halogen atom, hydroxy, and $C_{1-6}$ alkoxy, (f) $C_{3-10}$ cycloalkoxy which may be optionally substituted with the same or different 1 to 4 groups selected from the group consisting of halogen atom, hydroxy, and $C_{1-6}$ alkoxy, (g) $C_{2-6}$ alkenyl which may be optionally substituted with the same or different 1 to 2 halogen atoms, (h) $C_{2-6}$ alkynyl which may be optionally substituted with the same or different 1 to 2 halogen atoms, (i) cyano, (j) formyl, (k) $C_{6-10}$ aryl which may be optionally substituted with the same or different 1 to 4 groups selected from the group consisting of halogen atom, hydroxy, hydroxymethyl, $C_{1-6}$ alkyl, and $C_{1-6}$ alkoxy, (l) $C_{6-10}$ aryloxy which may be optionally substituted with the same or different 1 to 4 groups selected from the group consisting of halogen atom, hydroxy, hydroxymethyl, $C_{1-6}$ alkyl, and $C_{1-6}$ alkoxy, (m) 5- to 10-membered heteroaryl which may be optionally substituted with the same or different 1 to 4 groups selected from the group consisting of halogen atom, hydroxy, hydroxymethyl, $C_{1-6}$ alkyl, and $C_{1-6}$ alkoxy, (n) $C_{1-6}$ alkyl-carbonyl which may be optionally substituted with the same or different 1 to 4 groups selected from the group consisting of halogen atom, hydroxy, and $C_{1-6}$ alkoxy, (o) $C_{1-6}$ alkylsulfonyl (wherein the alkyl moiety may be optionally substituted with the same or different 1 to 3 halogen atoms), (p) $C_{1-6}$ alkoxy-carbonyl (wherein the alkoxy moiety may be optionally substituted with the same or different 1 to 3 halogen atoms), (q) $C_{1-6}$ alkyl-carbonylamino (wherein the alkyl moiety may be optionally substituted with the same or different 1 to 3 halogen atoms), (r) $C_{1-6}$ alkylsulfonylamino (wherein the alkyl moiety may be optionally substituted with the same or different 1 to 3 halogen atoms), (s) $C_{1-6}$ alkoxy-carbonylamino (wherein the alkyl moiety may be optionally substituted with the same or different 1 to 3 halogen atoms), (t) $C_{1-6}$ alkyl-carbonyloxy (wherein the alkyl moiety may be optionally substituted with the same or different 1 to 3 halogen atoms), (u) amino which may be optionally substituted with the same or different 1 to 2 $C_{1-6}$ alkyl, the alkyl group being optionally substituted with the same or different 1 to 4 groups selected from the group consisting of halogen atom, hydroxy, and $C_{1-6}$ alkoxy, (v) aminocarbonyl (wherein the amino moiety may be optionally substituted with the same or different 1 to 2 $C_{1-6}$ alkyl, the alkyl group being optionally substituted with the same or different 1 to 3 halogen atoms), (w) aminosulfonyl (wherein the amino moiety may be optionally substituted with the same or different 1 to 2 $C_{1-6}$ alkyl, the alkyl group being optionally substituted with the same or different 1 to 3 halogen atoms), (x) 5- or 6-membered cyclic amino which may be optionally substituted with the same or different 1 to 4 groups selected from the group consisting of halogen atom, hydroxy, $C_{1-6}$ alkyl, and $C_{1-6}$ alkoxy, (y) 5- or 6-membered cyclic aminocarbonyl which may be optionally substituted with the same or different 1 to 4 groups selected from the group consisting of halogen atom, hydroxy, $C_{1-6}$ alkyl, and $C_{1-6}$ alkoxy, (z) nitro, and
(aa) carboxyl, or
(3) a group of the following Formula (2):

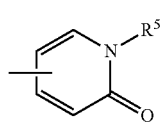

(2)

wherein $R^5$ is hydrogen atom or $C_{1-6}$ alkyl, or a pharmaceutically acceptable salt thereof.

[2] The compound of Formula (1) according to [1], or a pharmaceutically acceptable salt thereof,
provided that the compounds that are disclosed in Non Patent Literatures 6 and 7 and were publicly known prior to the filing of the present application are disclaimed.

[3] The compound according to [1] or [2], wherein $Q^1$ is phenyl, or a pharmaceutically acceptable salt thereof.

[4] The compound according to any one of [1] to [3], wherein m is 3 or 4, or a pharmaceutically acceptable salt thereof.

[5] The compound according to any one of [1] to [4], wherein $R^3$ is each independently
(1) halogen atom,
(2) $C_{1-6}$ alkyl which may be optionally substituted with the same or different 1 to 3 groups selected from the group consisting of halogen atom, hydroxy, and $C_{1-6}$ alkoxy,
(3) $C_{1-6}$ alkoxy which may be optionally substituted with the same or different 1 to 3 groups selected from the group consisting of halogen atom, hydroxy, $C_{1-6}$ alkoxy, and phenyl,
(4) amino which may be optionally substituted with the same or different 1 to 2 $C_{1-6}$ alkyl,
(5) $C_{6-10}$ aryl which may be optionally substituted with the same or different 1 to 4 groups selected from the group consisting of halogen atom, $C_{1-6}$ alkyl, and $C_{1-6}$ alkoxy,
(6) $C_{6-10}$ aryloxy which may be optionally substituted with the same or different 1 to 4 groups selected from the group consisting of halogen atom, $C_{1-6}$ alkyl, and $C_{1-6}$ alkoxy,
(7) 5- to 10-membered heteroaryl which may be optionally substituted with the same or different 1 to 4 groups selected from the group consisting of halogen atom, $C_{1-6}$ alkyl, and $C_{1-6}$ alkoxy, or
(8) $C_{1-6}$ alkoxy-carbonyl, or a pharmaceutically acceptable salt thereof.

[6] The compound according to any one of [1] to [4], wherein $R^3$ is each independently halogen atom or $C_{1-6}$ alkyl which may be optionally substituted with the same or different 1 to 3 halogen atoms, or a pharmaceutically acceptable salt thereof.

[7] The compound according to any one of [1] to [6], wherein $Q^1$ is phenyl;
m is 3 or 4;
$R^3$ is each independently halogen atom or $C_{1-6}$ alkyl which may be optionally substituted with the same or different 1 to 3 halogen atoms; and
$W^2$-$Q^2$ is —$NR^{4a}C(O)$-$Q^2$ or —$C(O)NR^{4a}$-$Q^2$ (wherein $R^{4a}$ is hydrogen atom or $C_{1-6}$ alkyl), or a pharmaceutically acceptable salt thereof.

[8] The compound according to any one of [1] to [7], wherein any or all of $R^3$ is fluorine atom, or a pharmaceutically acceptable salt thereof.

[9] The compound according to any one of [1] to [8], wherein $W^2$-$Q^2$ is —NHC(O)-$Q^2$, or a pharmaceutically acceptable salt thereof.

[10] The compound according to any one of [1] to [7], wherein $W^2$-$Q^2$ is —NHC(O)—CH═CH-$Q^2$, or a pharmaceutically acceptable salt thereof.

[11] The compound according to any one of [1] to [10], wherein $W^1$ is methylene, or a pharmaceutically acceptable salt thereof.

[12] The compound according to any one of [1] to [11], wherein Ring $Q^2$ is
(1) $C_{6-10}$ aryl which may be optionally substituted with the same or different 1 to 4 groups selected from the group consisting of:
(a) halogen atom,
(b) hydroxy,
(c) $C_{1-6}$ alkyl which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (d) $C_{1-6}$ alkoxy which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (e) $C_{3-10}$ cycloalkyl which may be optionally substituted with the same or different 1 to 4 groups selected from the group consisting of halogen atom, hydroxy, and $C_{1-6}$ alkoxy, (f) $C_{3-10}$ cycloalkoxy which may be optionally substituted with the same or different 1 to 4 groups selected from the group consisting of halogen atom, hydroxy, and $C_{1-6}$ alkoxy, (g) $C_{2-6}$ alkenyl which may be optionally substituted with the same or different 1 to 2 halogen atoms, (h) $C_{2-6}$ alkynyl which may be optionally substituted with the same or different 1 to 2 halogen atoms, (i) cyano, (j) formyl, (k) $C_{6-10}$ aryl which may be optionally substituted with the same or different 1 to 4 groups selected from the group consisting of halogen atom, hydroxy, hydroxymethyl, $C_{1-6}$ alkyl, and $C_{1-6}$ alkoxy, (l) $C_{6-10}$ aryloxy which may be optionally substituted with the same or different 1 to 4 groups selected from the group consisting of halogen atom, hydroxy, hydroxymethyl, $C_{1-6}$ alkyl, and $C_{1-6}$ alkoxy, (m) 5- to 10-membered heteroaryl which may be optionally substituted with the same or different 1 to 4 groups selected from the group consisting of halogen atom, hydroxy, hydroxymethyl, $C_{1-6}$ alkyl, and $C_{1-6}$ alkoxy, (n) $C_{1-6}$ alkyl-carbonyl which may be optionally substituted with the same or different 1 to 4 groups selected from the group consisting of halogen atom, hydroxy, and $C_{1-6}$ alkoxy, (o) $C_{1-6}$ alkylsulfonyl (wherein the alkyl moiety may be optionally substituted with the same or different 1 to 3 halogen atoms), (p) $C_{1-6}$ alkoxy-carbonyl (wherein the alkoxy moiety may be optionally substituted with the same or different 1 to 3 halogen atoms), (q) $C_{1-6}$ alkyl-carbonylamino (wherein the alkyl moiety may be optionally substituted with the same or different 1 to 3 halogen atoms), (r) $C_{1-6}$ alkylsulfonylamino (wherein the alkyl moiety may be optionally substituted with the same or different 1 to 3 halogen atoms), (s) $C_{1-6}$ alkoxy-carbonylamino (wherein the alkyl moiety may be optionally substituted with the same or different 1 to 3 halogen atoms), (t) $C_{1-6}$ alkyl-carbonyloxy (wherein the alkyl moiety may be optionally substituted with the same or different 1 to 3 halogen atoms), (u) amino which may be optionally substituted with the same or different 1 to 2 $C_{1-6}$ alkyl, the alkyl group being optionally substituted with the same or different 1 to 4 groups selected from the group consisting of halogen atom, hydroxy, and $C_{1-6}$ alkoxy, (v) aminocarbonyl (wherein the amino moiety may be optionally substituted with the same or different 1 to 2 $C_{1-6}$ alkyl, the alkyl group being optionally substituted with the same or different 1 to 3 halogen atoms), (w) aminosulfonyl (wherein the amino moiety may be optionally substituted with the same or different 1 to 2 $C_{1-6}$ alkyl, the alkyl group being optionally substituted with the same or different 1 to 3 halogen atoms), (x) 5- or 6-membered cyclic amino which may be optionally substituted with the same or different 1 to 4 groups selected from the group consisting of halogen atom, hydroxy, $C_{1-6}$ alkyl, and $C_{1-6}$ alkoxy, (y) 5- or 6-membered cyclic aminocarbonyl which may be optionally substituted with the same or different 1 to 4 groups selected from the group consisting of halogen atom, hydroxy, $C_{1-6}$ alkyl, and $C_{1-6}$ alkoxy, (z) nitro, and (aa) carboxyl, (2) 5- to 10-membered heteroaryl which may be optionally substituted with the same or different 1 to 4 groups selected from the group consisting of:

(a) halogen atom, (b) hydroxy, (c) $C_{1-6}$ alkyl which may be optionally substituted with the same or different 1 to 3 groups selected from the group consisting of halogen atom, phenyl, phenoxy, aminocarbonyl (wherein the amino moiety may be optionally substituted with the same or different 1 to 2 $C_{1-6}$ alkyl), $C_{1-6}$ alkoxy-carbonyl, carboxyl, and 5- or 6-membered heteroaryl, (d) $C_{1-6}$ alkoxy which may be optionally substituted with the same or different 1 to 3 groups selected from the group consisting of halogen atom, hydroxy, phenyl, phenoxy, 5- or 6-membered heteroaryl, amino (which may be optionally substituted with the same or different 1 to 2 $C_{1-6}$ alkyl), aminocarbonyl (wherein the amino moiety may be optionally substituted with the same or different 1 to 2 $C_{1-6}$ alkyl), $C_{1-6}$ alkoxy, $C_{1-6}$ alkoxy-carbonyl, and carboxyl, (e) $C_{3-10}$ cycloalkyl which may be optionally substituted with the same or different 1 to 4 groups selected from the group consisting of halogen atom, hydroxy, and $C_{1-6}$ alkoxy, (f) $C_{3-10}$ cycloalkoxy which may be optionally substituted with the same or different 1 to 4 groups selected from the group consisting of halogen atom, hydroxy, and $C_{1-6}$ alkoxy, (g) $C_{2-6}$ alkenyl which may be optionally substituted with the same or different 1 to 2 halogen atoms, (h) $C_{2-6}$ alkynyl which may be optionally substituted with the same or different 1 to 2 halogen atoms, (i) cyano, (j) formyl, (k) $C_{6-10}$ aryl which may be optionally substituted with the same or different 1 to 4 groups selected from the group consisting of halogen atom, hydroxy, hydroxymethyl, $C_{1-6}$ alkyl, and $C_{1-6}$ alkoxy, (l) $C_{6-10}$ aryloxy which may be optionally substituted with the same or different 1 to 4 groups selected from the group consisting of halogen atom, hydroxy, hydroxymethyl, $C_{1-6}$ alkyl, and $C_{1-6}$ alkoxy, (m) 5- to 10-membered heteroaryl which may be optionally substituted with the same or different 1 to 4 groups selected from the group consisting of halogen atom, hydroxy, hydroxymethyl, $C_{1-6}$ alkyl, and $C_{1-6}$ alkoxy, (n) $C_{1-6}$ alkyl-carbonyl which may be optionally substituted with the same or different 1 to 4 groups selected from the group consisting of halogen atom, hydroxy, and $C_{1-6}$ alkoxy, (o) $C_{1-6}$ alkylsulfonyl (wherein the alkyl moiety may be optionally substituted with the same or different 1 to 3 halogen atoms), (p) $C_{1-6}$ alkoxy-carbonyl (wherein the alkoxy moiety may be optionally substituted with the same or different 1 to 3 halogen atoms), (q) $C_{1-6}$ alkyl-carbonylamino (wherein the alkyl moiety may be optionally substituted with the same or different 1 to 3 halogen atoms), (r) $C_{1-6}$ alkylsulfonylamino (wherein the alkyl moiety may be optionally substituted with the same or different 1 to 3 halogen atoms), (s) $C_{1-6}$ alkoxy-carbonylamino (wherein the alkyl moiety may be optionally substituted with the same or different 1 to 3 halogen atoms), (t) $C_{1-6}$ alkyl-carbonyloxy (wherein the alkyl moiety may be optionally substituted with the same or different 1 to 3 halogen atoms), (u) amino which may be optionally substituted with the same or different 1 to 2 $C_{1-6}$ alkyl, the alkyl being optionally substituted with the same or different 1 to 4 groups selected from the group consisting of halogen atom, hydroxy, and $C_{1-6}$ alkoxy, (v) aminocarbonyl (wherein the amino moiety may be optionally substituted with the same or different 1 to 2 $C_{1-6}$ alkyl, the alkyl being optionally substituted with the same or different 1 to 3 halogen atoms), (w) aminosulfonyl (wherein the amino moiety may be optionally substituted with the same or different 1 to 2 $C_{1-6}$ alkyl, the alkyl being optionally substituted with the same or different 1 to 3 halogen atoms), (x) 5- or 6-membered cyclic amino which may be optionally substituted with the same or different 1 to 4 groups selected from the group consisting of halogen atom, hydroxy, $C_{1-6}$ alkyl, and $C_{1-6}$ alkoxy, (y) 5- or 6-membered cyclic aminocarbonyl which may be optionally substituted with the same or different 1 to 4 groups selected from the group consisting of halogen atom, hydroxy, $C_{1-6}$ alkyl, and $C_{1-6}$ alkoxy, (z) nitro, and (aa) carboxyl, or (3) a group of the following Formula (2):

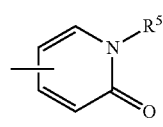

(2)

wherein $R^5$ is hydrogen atom or $C_{1-6}$ alkyl, or a pharmaceutically acceptable salt thereof.

[13] The compound according to any one of [1] to [11], wherein Ring $Q^2$ is (1) phenyl which may be optionally substituted with the same or different 1 to 4 groups selected from the group consisting of:

(a) cyano, (b) $C_{1-6}$ alkyl which may be optionally substituted with the same or different 1 to 3 halogen atoms or hydroxy, (c) amino which may be optionally substituted with the same or different 1 to 2 $C_{1-6}$ alkyl, the alkyl group being optionally substituted with the same or different 1 to 3 halogen atoms, (d) $C_{1-6}$ alkyl-carbonylamino (wherein the alkyl moiety may be optionally substituted with the same or different 1 to 3 halogen atoms, hydroxy, or $C_{1-6}$ alkoxy), (e) $C_{1-6}$ alkoxy which may be optionally substituted with the same or different 1 to 3 halogen atoms, hydroxy, or $C_{1-6}$ alkoxy, (f) phenoxy which may be optionally substituted with the same or different 1 to 4 groups selected from the group consisting of halogen atom, $C_{1-6}$ alkyl, and $C_{1-6}$ alkoxy, and (g) halogen atom, or (2) pyridyl which may be optionally substituted with the same or different 1 to 4 groups selected from the group consisting of:

(a) cyano, (b) $C_{1-6}$ alkyl which may be optionally substituted with the same or different 1 to 3 halogen atoms, (c) amino which may be optionally substituted with the same or different 1 to 2 $C_{1-6}$ alkyl, the alkyl group being optionally substituted with the same or different 1 to 3 halogen atoms, and (d) $C_{1-6}$ alkyl-carbonylamino (wherein the alkyl moiety may be optionally substituted with the same or different 1 to 3 halogen atoms, hydroxy, or $C_{1-6}$ alkoxy), or a pharmaceutically acceptable salt thereof.

[14] The compound according to any one of [1] to [11], wherein Ring $Q^2$ is phenyl substituted with the same or different 1 to 3 groups selected from the group consisting of hydroxy, $C_{1-6}$ alkoxy (which may be optionally substituted with the same or different 1 to 3 halogen atoms, hydroxy, or $C_{1-6}$ alkoxy), and $C_{1-6}$ alkyl-carbonylamino (wherein the alkyl moiety may be optionally substituted with the same or different 1 to 3 halogen atoms, hydroxy, or $C_{1-6}$ alkoxy), or a pharmaceutically acceptable salt thereof.

[15] The compound according to any one of [1] to [11], wherein Ring $Q^2$ is phenyl substituted with the same or different 1 to 3 $C_{1-6}$ alkoxy which may be optionally substituted with the same or different 1 to 3 halogen atoms, hydroxy, or $C_{1-6}$ alkoxy, or a pharmaceutically acceptable salt thereof.

[16] The compound according to any one of [1] to [15], wherein both $R^1$ and $R^2$ are hydrogen atom, or a pharmaceutically acceptable salt thereof.

[17] The compound according to [1], which has the structure of the following Formula (1a):

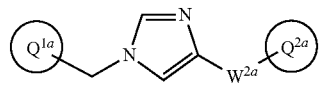

(1a)

wherein Ring $Q^{1a}$ is trifluorophenyl or trifluoromethylphenyl;

Ring $Q^{2a}$ is phenyl substituted with the same or different 1 to 3 groups selected from the group consisting of hydroxy, $C_{1-6}$ alkoxy (which may be optionally substituted with the same or different 1 to 3 halogen atoms, hydroxy, or $C_{1-6}$ alkoxy), and $C_{1-6}$ alkyl-carbonylamino (wherein the alkyl moiety may be optionally substituted with the same or different 1 to 3 halogen atoms, hydroxy, or $C_{1-6}$ alkoxy); and $W^{2a}$-$Q^2$a is —NHC(O)-$Q^2$a, —NHC(O)—CH=CH-$Q^2$a, or —C(O)NH-$Q^2$a;

provided that N-[1-(2-trifluoromethylbenzyl)-1H-imidazol-4-yl]-3,4-dimethoxybenzamide, N-[1-(3-trifluoromethylbenzyl)-1H-imidazol-4-yl]-3,4-dimethoxybenzamide, and N-[1-(4-trifluoromethylbenzyl)-1H-imidazol-4-yl]-3,4-dimethoxybenzamide are disclaimed, or a pharmaceutically acceptable salt thereof.

[18] The compound according to [17], wherein $W^{2a}$-$Q^{2a}$ is —NHC(O)-$Q^2$a, or a pharmaceutically acceptable salt thereof.

[19] The compound according to [17], wherein $W^{2a}$-$Q^{2a}$ is —NHC(O)—CH=CH-$Q^2$a, or a pharmaceutically acceptable salt thereof.

[20] The compound according to any one of [17] to [19], wherein Ring $Q^{1a}$ is trifluorophenyl, or a pharmaceutically acceptable salt thereof.

[21] The compound according to [1], which is selected from the following compounds:
3,4-dimethoxy-N-[1-(3,4,5-trifluorobenzyl)-1H-imidazol-4-yl]benzamide (Example 236),
(2E)-3-[4-(acetylamino)phenyl]-N-[1-(3-chlorobenzyl)-1H-imidazol-4-yl]prop-2-enamide (Example 9),
(2E)-N-[1-(3-chlorobenzyl)-1H-imidazol-4-yl]-3-(pyridin-3-yl)prop-2-enamide (Example 41),
(2E)-N-[1-(3-chlorobenzyl)-1H-imidazol-4-yl]-3-[4-cyano-3-(2-hydroxyethoxy)phenyl]prop-2-enamide (Example 35),
(2E)-3-[4-(acetylamino)phenyl]-N-{1-[3-(trifluoromethyl)benzyl]-1H-imidazol-4-yl}prop-2-enamide (Example 8),
(2E)-3-[3-(2-hydroxyethoxy)-4-methoxyphenyl]-N-{1[3-(trifluoromethyl)benzyl]-1H-imidazol-4-yl}prop-2-enamide (Example 34),
(2E)-N-[1-(3-chlorobenzyl)-1H-imidazol-4-yl]-3-[3-(2-hydroxyethoxy)-4-methoxyphenyl]prop-2-enamide (Example 33),
(2E)-3-[4-(acetylamino)phenyl]-N-[1-(3,4,5-trifluorobenzyl)-1H-imidazol-4-yl]prop-2-enamide (Example 11), and
(2E)-3-[4-(acetylamino)phenyl]-N-{1-[3-(trifluoromethoxy)benzyl]-1H-imidazol-4-yl}prop-2-enamide (Example 10), or a pharmaceutically acceptable salt thereof.

[22] 3,4-Dimethoxy-N-[1-(3,4,5-trifluorobenzyl)-1H-imidazol-4-yl]benzamide (Example 236), or a pharmaceutically acceptable salt thereof.

[23] 3,4-Dimethoxy-N-[1-(3,4,5-trifluorobenzyl)-1H-imidazol-4-yl]benzamide besilate (Example 239).

[24] 3,4-Dimethoxy-N-[1-(3,4,5-trifluorobenzyl)-1H-imidazol-4-yl]benzamide tosilate (Example 238).

[25] A medicine comprising a compound according to any one of [1] to [24] or a pharmaceutically acceptable salt thereof as an active ingredient.

[26] An anti-tumor agent comprising a compound according to any one of [1] to [24] or a pharmaceutically acceptable salt thereof as an active ingredient.

[27] The anti-tumor agent according to [26], wherein the tumor is acute leukemia, chronic lymphocytic leukemia, chronic myeloid leukemia, polycythemia vera, malignant lymphoma, myeloma, brain tumor, head and neck cancer, esophageal cancer, pharyngeal cancer, thyroid cancer, small cell lung cancer, non-small-cell lung cancer, breast cancer, gastric cancer, gallbladder/bile duct cancer, liver cancer, pancreatic cancer, colon cancer, rectal cancer, ovarian cancer, chorioepithelioma, uterine body cancer, cervical cancer, urothelial carcinoma, renal cell cancer, prostate cancer, testicular neoplasm, Wilms tumor, malignant melanoma, neuroblastoma, osteosarcoma, Ewing's tumor, or soft tissue sarcoma.

[28] The anti-tumor agent according to [26], wherein the tumor is acute leukemia, pharyngeal cancer, non-small-cell lung cancer, breast cancer, liver cancer, colon cancer, rectal cancer, or prostate cancer.

[29] The anti-tumor agent according to [26], wherein the tumor is colon cancer, rectal cancer, or pharyngeal cancer.

[30] The anti-tumor agent according to any one of [26] to [29], wherein the active ingredient is any of the following compounds:
(E)-N-(1-(3-chlorobenzyl)-1H-imidazol-4-yl)-3-(pyridin-3-yl)acrylamide (Example 120),
(E)-N-(1-(3-trifluoromethyl-benzyl)-1H-imidazol-4-yl)-3-(4-(acetylamino)phenyl)acrylamide (Example 122),
N-[1-(3-chlorobenzyl)-1H-imidazol-4-yl]-3,4-dimethoxybenzamide (Example 141),
3,4-dimethoxy-N-[1-(3,4-difluorobenzyl)-1H-imidazol-4-yl]benzamide (Example 151),
3,4-dimethoxy-N-[1-(3,5-difluorobenzyl)-1H-imidazol-4-yl]benzamide (Example 152), or
3,4-dimethoxy-N-[1-(3,4,5-trifluorobenzyl)-1H-imidazol-4-yl]benzamide (Example 237), or a pharmaceutically acceptable salt thereof.

[31] A method for treating cancer, comprising administering a compound of any one of [1] to [24] or a pharmaceutically acceptable salt thereof to a patient in need thereof.

[32] A method for inhibiting the sphere-forming ability of cancer cells, comprising administering a compound of any one of [1] to [24] or a pharmaceutically acceptable salt thereof to a patient in need thereof.

[33] Use of a compound of any one of [1] to [24] or a pharmaceutically acceptable salt thereof in the manufacture of a medicinal agent for treating cancer.

[34] A pharmaceutical composition for use in treating cancer, comprising a compound of any one of [1] to [24] or a pharmaceutically acceptable salt thereof.

Effects of the Invention

The present compound has a potent inhibitory effect on the sphere-forming ability of cancer cells. In addition, a preferred embodiment of the present compound has high bioavailability after oral administration. Thus, the present compound is useful for an orally-available anti-cancer agent.

BRIEF DESCRIPTION OF DRAWINGS

FIG. 1 This is a chart showing plasma concentrations of Example 120 compound.
FIG. 2 This is a chart showing plasma concentrations of Example 122 compound.
FIG. 3 This is a chart showing plasma concentrations of Example 123 compound.
FIG. 4 This is a chart showing plasma concentrations of Example 128 compound.
FIG. 5 This is a chart showing plasma concentrations of Example 129 compound.
FIG. 6 This is a X-ray powder diffraction (XRD) chart for Example 236 compound.
FIG. 7 This is a chart showing the results of differential scanning calorimeter measurement (DSC) and thermal gravimetric analysis (TGA) for Example 236 compound.
FIG. 8 This is a X-ray powder diffraction (XRD) chart for Example 237 compound.
FIG. 9 This is a chart showing the results of differential scanning calorimeter measurement (DSC) and thermal gravimetric analysis (TGA) for Example 237 compound.
FIG. 10 This is a X-ray powder diffraction (XRD) chart for Example 238 compound.
FIG. 11 This is a chart showing the results of differential scanning calorimeter measurement (DSC) and thermal gravimetric analysis (TGA) for Example 238 compound.

DESCRIPTION OF EMBODIMENTS

Hereinafter, the present invention is explained in detail. The number of carbon atoms in the definition of "substituent" used herein may be expressed as, for example, "$C_{1-6}$". Specifically, the term "$C_{1-6}$ alkyl" is used for the same meaning as alkyl group having 1 to 6 carbon atoms.

Specific examples of the term "halogen atom" used herein include fluorine atom, chlorine atom, bromine atom, and iodine atom. Preferred examples thereof include fluorine atom and chlorine atom.

The term "$C_{1-6}$ alkyl group" used herein means a straight or branched saturated hydrocarbon group having 1 to 6 carbon atoms. Preferred examples thereof include "$C_{1-4}$ alkyl group". Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethyl-propyl, hexyl, isohexyl, 1,1-dimethylbutyl, 2,2-dimethyl-butyl, 3,3-dimethylbutyl, and 2-ethylbutyl.

The term "$C_{2-6}$ alkenyl group" used herein means a straight or branched unsaturated hydrocarbon group having 2 to 6 carbon atoms and 1 to 3 carbon-carbon double bonds. Preferred examples thereof include "$C_{2-4}$ alkenyl group". Specific examples of the "$C_{2-6}$ alkenyl group" include ethenyl, propenyl, butenyl, pentenyl, and hexenyl.

The term "$C_{2-6}$ alkynyl group" used herein means a straight or branched unsaturated hydrocarbon group having 2 to 6 carbon atoms and 1 to 3 carbon-carbon triple bonds. Preferred examples thereof include "$C_{2-4}$ alkynyl group". Specific examples of the "$C_{2-6}$ alkynyl group" include ethynyl, propynyl, butynyl, pentynyl, and hexynyl.

The term "$C_{1-4}$ alkylene group" used herein means a straight or branched divalent saturated hydrocarbon group having 1 to 4 carbon atoms.

Specific examples of the "$C_{1-4}$ alkylene group" include methylene, ethylene, propylene, butylene, 1-methylmethylene, 1-ethylmethylene, 1-propylmethylene, 1-methylethylene, 2-methylethylene, and 1-ethylethylene. Preferred examples thereof include methylene and ethylene.

The "$C_{1-6}$ alkyl" moiety of the term "$C_{1-6}$ alkoxy group" used herein is as defined in the above "$C_{1-6}$ alkyl". Preferred examples thereof include "$C_{1-4}$ alkoxy group". Specific examples of the "$C_{1-6}$ alkoxy group" include methoxy, ethoxy, propoxy, isopropoxy, butoxy, isobutoxy, sec-butoxy, and tert-butoxy.

The term "$C_{3-10}$ cycloalkyl group" used herein means a 3- to 10-membered monocyclic or polycyclic, saturated or partially-unsaturated hydrocarbon group. Preferred examples thereof include "$C_{3-7}$ cycloalkyl group". Specific examples of the "$C_{3-10}$ cycloalkyl group" include cyclopropyl, cyclobutyl, cyclopentyl, cyclohexyl, cycloheptyl, cyclopentenyl, cyclohexenyl, decalinyl, adamantyl, and norbornyl.

The term "$C_{6-10}$ aryl group" used herein means an aromatic hydrocarbon group having 6 to 10 carbon atoms. Preferred examples thereof include "$C_6$ aryl group" (phenyl) Specific examples of the "$C_{6-10}$ aryl group" include phenyl, 1-naphthyl, and 2-naphthyl. When $Q^1$ is "$C_{6-10}$ aryloxy" or "$C_{6-10}$ arylthio", it binds to $W^1$ via the "oxy" or "thio" moiety, respectively.

Examples of the term "5- to 10-membered heteroaryl group" used herein include a 5- to 10-membered mono- or poly-cyclic aromatic group that contains the same or different one or more (e.g., 1 to 4) heteroatoms selected from the group consisting of nitrogen atom, sulfur atom, and oxygen atom. Preferred examples of the "polycyclic heteroaryl group" include bi- or tri-cyclic groups, and more preferred examples include bicyclic groups. Specific examples of the "heteroaryl group" include the groups of the following formulae:

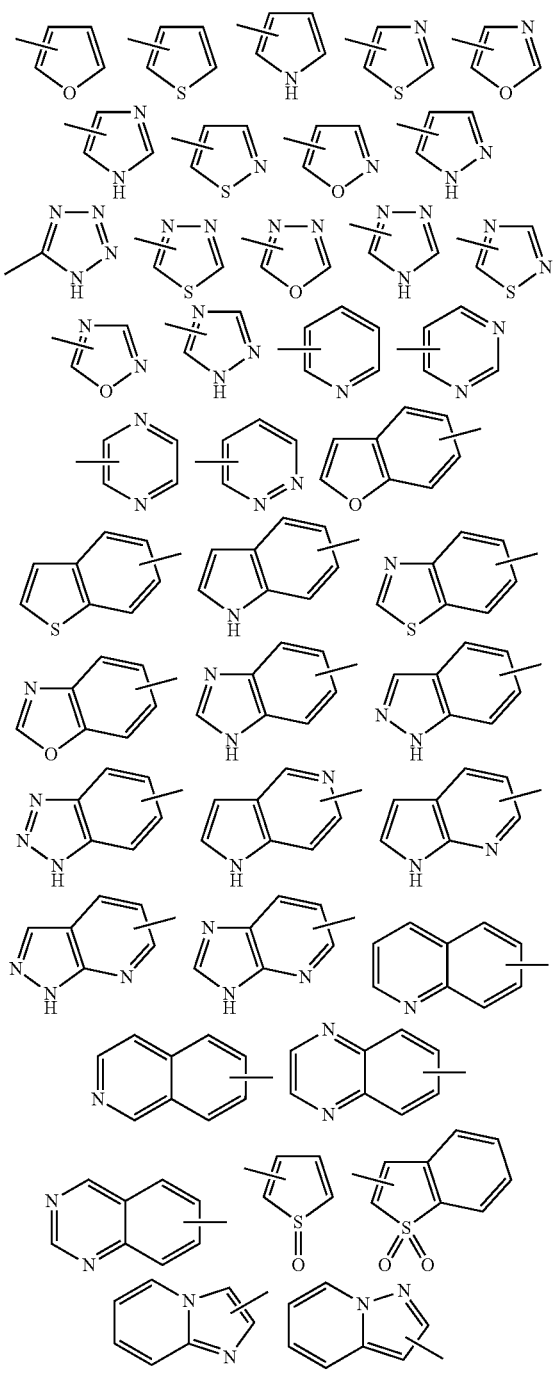

The bond across a ring in the above formulae means that a "group" is linked at any substitutable position in the ring. For example, a heteroaryl group of the following formula:

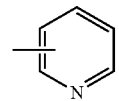

means 2-pyridyl group, 3-pyridyl group, or 4-pyridyl group.

Furthermore, when a "heteroaryl group" is a polycyclic group, for example, a group of the following formula:

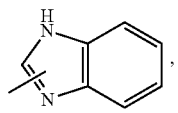

the group may be 1-benzimidazolyl, 2-benzimidazolyl, or 4-, 5-, 6-, or 7-benzimidazolyl.

The term "5- or 6-membered cyclic amino group" means a monocyclic amino group consisting of a 5- or 6-membered ring. It also means a group where the nitrogen atom of ring is a direct binding site with a "group". Specific examples thereof include pyrrolidino, piperidino, morpholino, thiomorpholino, thiomorpholinooxide, thiomorpholinodioxide, and piperazino. The group also includes cyclic amino groups which are a partially-unsaturated ring.

The "$C_{1-6}$ alkyl" moiety of the term "$C_{1-6}$ alkyl-carbonylamino group" used herein is as defined in the above "$C_{1-6}$ alkyl". Preferred examples thereof include "$C_{1-4}$ alkyl-carbonylamino group", and more preferably methylcarbonylamino group (acetamido group).

Examples of the substituents in the terms "optionally-substituted $C_{1-6}$ alkyl group", "optionally-substituted $C_{2-6}$ alkenyl group", "optionally-substituted $C_{2-6}$ alkynyl group", "optionally-substituted $C_{1-4}$ alkylene group", and "optionally-substituted $C_{1-6}$ alkoxy" include hydroxy group, halogen atom, $C_{3-7}$ cycloalkyl group, and $C_{1-6}$ alkoxy group, and preferably fluorine atom.

Examples of the substituents in the terms "optionally-substituted $C_{6-10}$ aryl group", "optionally-substituted $C_{3-10}$ cycloalkyl group", "optionally-substituted 5- to 10-membered heteroaryl group", and "optionally-substituted 5- or 6-membered cyclic amino" include:

(a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) cyano,
(e) phenyl which may be optionally substituted with the same or different 1 to 4 groups selected from the group consisting of halogen atom, $C_{1-6}$ alkyl, and $C_{1-6}$ alkoxy, and
(f) 5- or 6-membered heteroaryl which may be optionally substituted with the same or different 1 to 4 groups selected from the group consisting of halogen atom, $C_{1-6}$ alkyl, and $C_{1-6}$ alkoxy,
(g) phenoxy which may be optionally substituted with the same or different 1 to 4 groups selected from the group consisting of halogen atom, $C_{1-6}$ alkyl, and $C_{1-6}$ alkoxy,
(h) hydroxy,
(i) amino which may be optionally substituted with the same or different 1 to 2 $C_{1-6}$ alkyl, and
(j) aminocarbonyl (wherein the amino moiety may be optionally substituted with the same or different 1 to 2 $C_{1-6}$ alkyl)

Examples of the substituents in the term "optionally-substituted amino" include $C_{1-6}$ alkyl (which may be optionally substituted with the same or different 1 to 4 groups selected from the group consisting of halogen atom, hydroxy, and $C_{1-6}$ alkoxy) and $C_{3-7}$ cycloalkyl, and preferably $C_{1-3}$ alkyl.

In a compound of Formula (1), when n is 2 to 4, each of $R^{4c}$ and $R^{4d}$ is independent. For example, when n is 2, each $R^{4c}$ substituted on $C^1$ and $C^3$ as shown in the following formula:

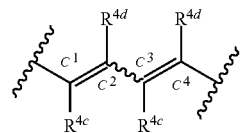

is independent. Accordingly, $R^{4c}$ on $C^1$ and $R^{4c}$ on $C^3$ are independent with each other, and the compounds of the following Formulae:

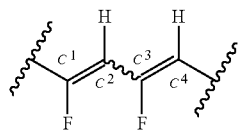 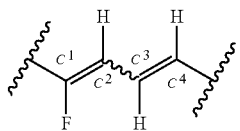

are encompassed.

In the case where two $R^3$s bind to any of the adjacent carbon atoms on Ring $Q^1$, a 5- to 8-membered saturated carbocyclic ring or non-aromatic heterocyclic ring that is formed with the two $R^3$s and the carbon atoms to which they bind means a 5- to 8-membered saturated carbocyclic ring or non-aromatic heterocyclic ring where the respective $R^3$s substituted on the respective adjacent carbon atoms of a carbon-carbon bond on Ring $Q^1$ are linked to form. Specific examples of the ring that is formed with two $R^3$ and Ring $Q^1$ include the groups of the following formulae:

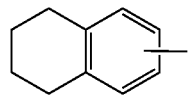 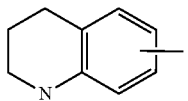
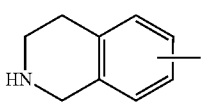 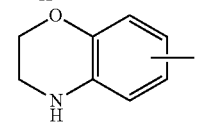

The present compound may be in the forms of a hydrate and/or solvate. Thus, the present compound also encompasses hydrates and/or solvates such as ethanol solvates. Furthermore, the present compound encompasses all types of crystal forms of the present compound.

Specific examples of pharmaceutically acceptable salts of a compound of Formula (1) include inorganic acid salts such as hydrochloride, hydrobromide, sulfate, phosphate, and nitrate; and organic acid salts such as acetate, propionate, oxalate, succinate, lactate, malate, tartrate, citrate, maleate, fumarate, methanesulfonate, p-toluenesulfonate, benzenesulfonate, and ascorbate.

A compound of Formula (1) may be in the form of a tautomer. Thus, the present compound also encompasses tautomers of a compound of Formula (1).

A compound of Formula (1) may contain at least one asymmetric carbon atom. Thus, the present compound encompasses not only racemic forms of a compound of Formula (1) but also optically-active forms thereof. When a compound of Formula (1) contains two or more asymmetric carbon atoms, such a compound may result in various stereoisomerisms. Thus, the present compound also encompasses stereoisomers of the compound and a mixture or isolate thereof.

Also, a compound of Formula (1) encompasses the compound wherein one or more of 1H are replaced with $^2$H(D) (i.e., deuterated form).

General preparations of a compound of Formula (1) in the present invention are illustrated with examples, but the present invention is not limited thereto.

A compound of Formula (1) can be prepared according to the processes shown below and according to any processes in combination with known compounds and known synthesis processes.

As appropriate, each compound used as a starting compound may be used in its salt form. The processes illustrated are mere examples, and may be optionally modified with other methods to prepare the present compound by those skilled in the organic synthesis field.

Preparation 1

One of the compounds of Formula (1), a compound of Formula (1-7), is prepared by linking each fragment at positions a and b:

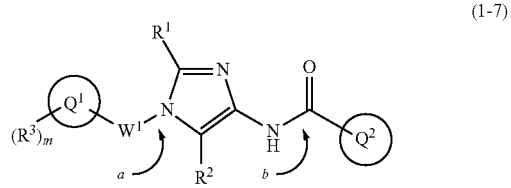

wherein $W^1$, $R^1$, $R^2$, $R^3$, m, Ring $Q^1$, and Ring $Q^2$ are as defined in the above [1].

Processes for forming the respective bonds in positions a and b can be illustrated as follows, but the order of procedures for forming the bonds may be optionally changed:

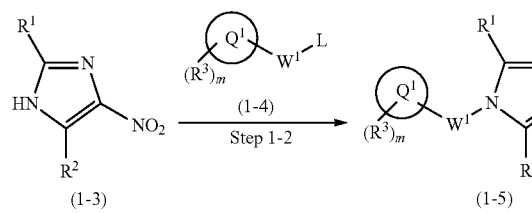

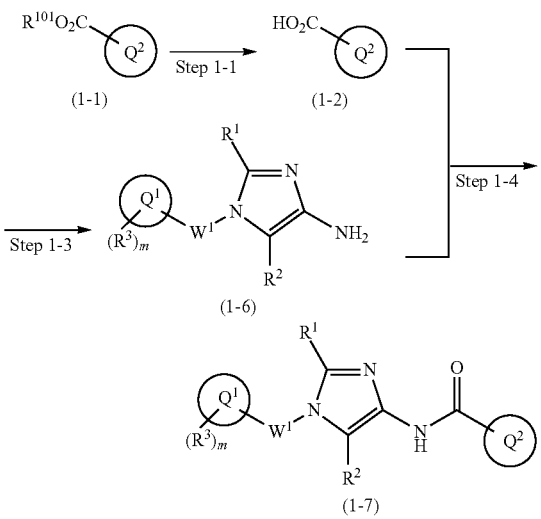

In each process illustrated below, any functional groups that need to be protected may be optionally protected and then deprotected after a reaction or a series of reactions are completed to give a desired compound, even though the use of protective groups is not specifically described.

The protective group used herein includes any conventional groups described in various literatures, for example, T. W. Greene and P. G. M. Wuts, "Protective Groups in Organic Synthesis", 3rd Ed., John Wiley and Sons, inc., New York (1999). In more detail, specific examples of protective groups for amino group include benzyloxycarbonyl, tert-butoxycarbonyl, acetyl, and benzyl, and specific examples of protective groups for hydroxy group include trialkylsilyl, acetyl, and benzyl.

The protective groups can be introduced and cleaved according to commonly-used methods in synthetic organic chemistry (e.g., the method described in T. W. Greene and P. G. M. Wuts, "Protective Groups in Organic Synthesis", 3rd Ed., John Wiley and Sons, inc., New York (1999)) and similar methods thereto.

In the scheme, $W^1$, $R^1$, $R^2$, $R^3$, m, Ring $Q^1$, and Ring $Q^2$ are as defined in the above [1]; $R^{101}$ is $C_{1-6}$ alkyl group; and L is a leaving group such as iodine atom, bromine atom, chlorine atom, and substituted sulfonyloxy group (e.g., methanesulfonyloxy group and p-toluenesulfonyloxy group).

Compound (1-1) may be a commercially available product or be prepared according to known synthesis processes (e.g., New Version of Heterocyclic Compound (advanced level) edited by Kodansha Scientific Ltd.).

Step 1-1: Preparation Process of Compound (1-2)

Compound (1-2) is prepared by hydrolyzing Compound (1-1) according to a similar process to a known process (e.g., Protective Groups in Organic Synthesis $3^{rd}$ Edition (John Wiley & Sons, Inc.), Comprehensive Organic Transformation, by R. C. Larock, VCH publisher Inc., 1989).

Step 1-2: Preparation Process of Compound (1-5)

Compound (1-5) is prepared by the alkylation reaction of Compound (1-3) and Compound (1-4) in an inert solvent in the presence of a base.

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific examples of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, N,N-dimethylformamide, N-methyl-2-pyrrolidinone, and dimethylsulfoxide; a basic solvent such as pyridine; and a mixture thereof.

The reaction temperature is typically 0° C. to 150° C., preferably 20° C. to 100° C., but is not limited thereto. The reaction time is typically 30 minutes to 48 hours, preferably 30 minutes to 10 hours.

Step 1-3: Preparation Process of Compound (1-6)

Compound (1-6) is prepared by reducing the nitro group in Compound (1-5). For example, reduction under an acidic condition with a metal such as zinc, iron, and tin or a metal salt such as tin (II) chloride; reduction with a sulfide such as sodium hypodisulfite ($Na_2S_2O_4$); and catalytic reduction with a metal catalyst such as palladium/carbon, Raney nickel, platinum oxide/carbon, and rhodium/carbon under hydrogen atmosphere may be used.

In the reduction with a metal or a metal salt, the amount of the metal or metal salt to be used is typically about 1 mole to 100 moles, preferably about 10 moles to 30 moles per mole of Compound (1-5). Also, the amount of the acid to be used is typically about 1 mole to 100 moles, preferably about 10 moles to 30 moles per mole of Compound (1-5). The reduction is typically carried out in a solvent which has no negative effect on the reaction (e.g., ethanol). The reaction temperature is typically 0° C. to 100° C., but is not limited thereto. The reaction time is typically 30 minutes to 8 hours.

In the catalytic reduction reaction, the amount of the metal catalyst to be used for Compound (1-5) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically 1 atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

Also, the reaction may be carried out in the presence of an acid catalyst, as appropriate. For example, an organic acid such as formic acid, acetic acid, and trifluoroacetic acid, and an inorganic acid such as sulfuric acid, hydrochloric acid, and hydrobromic acid are used as the acid catalyst. The amount of the acid to be used is 0.1 mole or more per mole of Compound (1-5).

Step 1-4: Preparation Process of Compound (1-7)

Compound (1-7) is prepared by reacting Compound (1-2) with Compound (1-6) in an inert solvent in the presence of a condensation agent.

The reaction may be carried out in the presence of a base, as appropriate. The reaction temperature is typically about −20° C. to the boiling point of a solvent used, but is not limited thereto. The reaction time is typically 10 minutes to 48 hours, which may vary according to various conditions such as a reaction temperature, a condensation agent, starting materials, and a solvent to be used.

Specific examples of the condensation agent include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonyl diamide (DPPA), N,N-carbonyldiimidazole (CDI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and diphenyl chlorophosphate. As appropriate, the reaction may be carried out with the addition of an additive such as N-hydroxysuccinimide (HOSu), 1-hydroxybenzotriazole (HOBt), and 3-hydroxy-4-oxo-3,4-dihydro-1,2,3-benzotriazine (HOOBt).

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific examples of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, dimethylformamide, N-methyl-2-pyrrolidinone, and dimethylsulfoxide; a basic solvent such as pyridine; and a mixture thereof.

Compound (1-7) is also prepared by reacting an acid halide or an acid anhydride derived from Compound (1-2) with Compound (1-6) in an inert solvent in the presence of a base.

Preparation 2

One of the compounds of Formula (1), a compound of Formula (2-4), is prepared by, for example, the following processes.

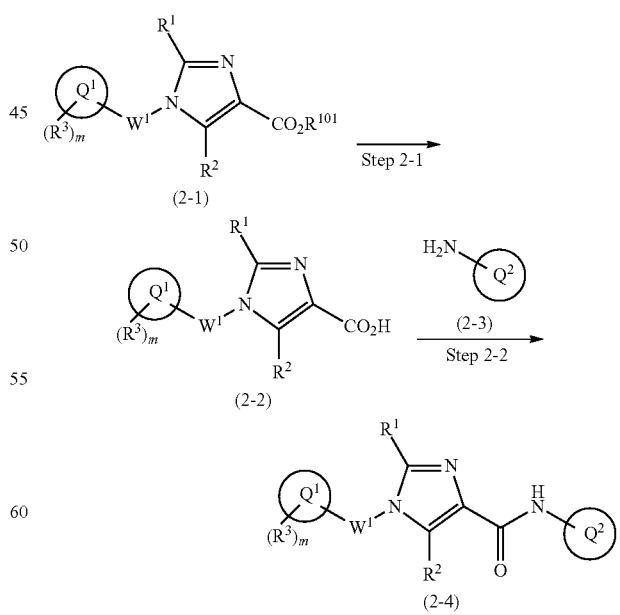

In the scheme, $W^1$, $R^1$, $R^2$, $R^3$, m, Ring $Q^1$, and Ring $Q^2$ are as defined in the above [1]; $R^{101}$ is $C_{1-6}$ alkyl group.

Compound (2-1) may be a commercially available product or prepared according to known synthesis processes (e.g., WO 2014/125444).

Step 2-1: Preparation Process of Compound (2-2)

Compound (2-2) is prepared by hydrolyzing Compound (2-1) according to a similar process to a known process (e.g., Protective Groups in Organic Synthesis 3$^{rd}$ Edition (John Wiley & Sons, Inc.), Comprehensive Organic Transformation, by R. C. Larock, VCH publisher Inc., 1989).

Step 2-2: Preparation Process of Compound (2-4)

Compound (2-4) is prepared from Compound (2-2) and Compound (2-3) according to the process described in Step 1-4.

Preparation 3

One of the compounds of Formula (1), a compound of Formula (1-7), is prepared by, for example, the following processes.

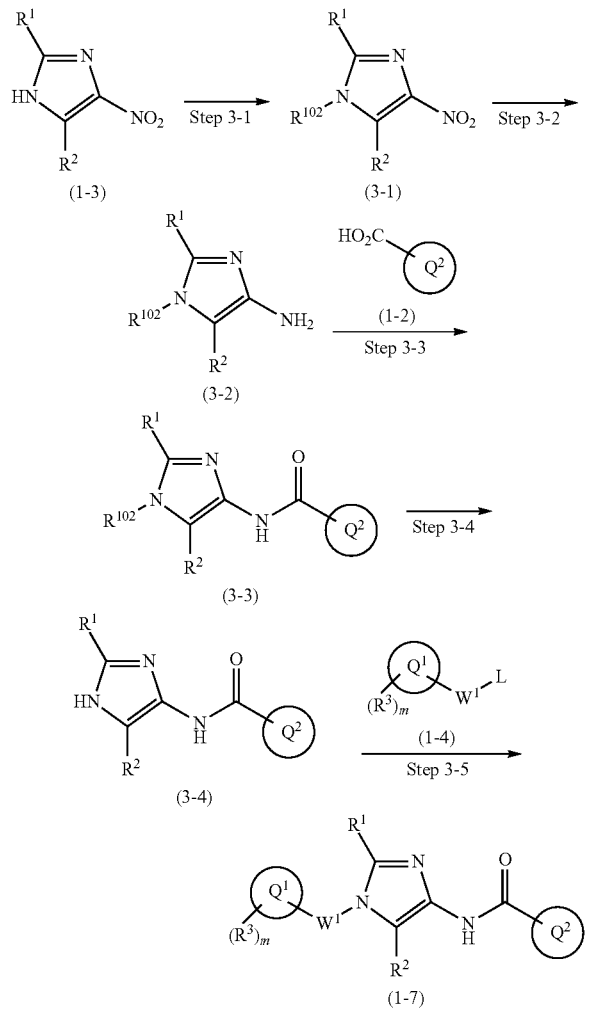

In the scheme, $W^1$, $R^1$, $R^2$, $R^3$, m, Ring $Q^1$, and Ring $Q^2$ are as defined in the above [1]; $R^{102}$ is a protective group; L is a leaving group (e.g., iodine atom, bromine atom, chlorine atom, and a substituted sulfonyloxy group (e.g., methanesulfonyloxy group and p-toluenesulfonyloxy group)

Step 3-1: Preparation Process of Compound (3-1)

Compound (3-1) is prepared by introducing a protective group into the nitrogen atom on the imidazole moiety of Compound (1-3) in an inert solvent. Examples of the protective group include 2-(trimethylsilyl)ethoxymethyl, benzyloxycarbonyl, tert-butoxycarbonyl, acetyl, and benzyl.

For example, the reaction where 2-(trimethylsilyl) ethoxymethyl group is introduced is performed by reacting 2-(trimethylsilyl)ethoxymethyl chloride in an inert solvent in the presence of a base.

Specific examples of the base include potassium carbonate, sodium carbonate, cesium carbonate, potassium-tert-botoxide, sodium hydride, sodium bis(trimethylsilyl)amide, lithium bis(trimethylsilyl)amide, potassium bis(trimethylsilyl)amide, and lithium diisopropylamide.

Specific examples of the inert solvent include DMF, THF, acetonitrile, and a mixture thereof.

The reaction temperature is typically 0° C. to 150° C., preferably 0° C. to 100° C., but is not limited thereto. The reaction time is typically 10 minutes to 24 hours, preferably 20 minutes to 6 hours.

Step 3-2: Preparation Process of Compound (3-2)

Compound (3-2) is prepared from Compound (3-1) according to the process described in Step 1-3.

Step 3-3: Preparation Process of Compound (3-3)

Compound (3-3) is prepared from Compound (3-2) and Compound (1-2) according to the process described in Step 1-4.

Step 3-4: Preparation Process of Compound (3-4)

Compound (3-4) is prepared by deprotecting the protective group on the nitrogen atom of the imidazole moiety in Compound (3-3) in an inert solvent.

For example, the deprotection of 2-(trimethylsilyl) ethoxymethyl group is performed with an acid or fluorine reagent in an inert solvent.

Specific examples of the acid include TFA, formic acid, hydrochloric acid, sulfuric acid, p-toluenesulfonic acid, methanesulfonic acid, and (±) 10-camphorsulfonic acid.

Specific examples of the fluorine reagent include tetrabutylammonium fluoride.

Specific examples of the solvent used include dichloromethane, 1,2-dichloroethane, 1,4-dioxane, THF, toluene, ethyl acetate, methanol, ethanol, 2-propanol, and a mixture thereof.

The reaction temperature is typically 0° C. to 150° C., preferably 0° C. to 50° C., but is not limited thereto. The reaction time is typically 5 minutes to 24 hours, preferably 1 hour to 9 hours.

Step 3-5: Preparation Process of Compound (1-7)

Compound (1-7) is prepared from Compound (3-4) and Compound (1-4) according to the process described in Step 1-2.

Preparation 4

One of the compounds of Formula (1), a compound of formula (4-4), is prepared according to, for example, the following processes.

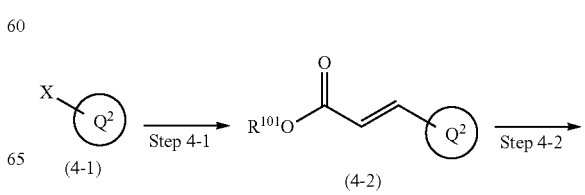

-continued (4-3) + (1-6) → (4-4)  [Step 4-3]

In the scheme, $W^1$, $R^1$, $R^2$, $R^3$, m, Ring $Q^1$, and Ring $Q^2$ are as defined in the above [1]; $R^{101}$ is $C_{1-6}$ alkyl group; and X is halogen atom.

Step 4-1: Preparation Process of Compound (4-2)

Compound (4-2) is prepared by reacting Compound (4-1) with acrylic acid ester in the presence of a palladium catalyst and a base in an inert solvent.

Specific examples of the palladium catalyst include tetrakis(triphenylphosphine)palladium (O), dichloro di(tri(o-tolylphosphine))palladium, bis(dibenzylideneacetone)palladium (O), tris(dibenzylideneacetone)dipalladium (O), bis(tri-tert-butylphosphine)palladium (O), and [1,1'-bis(diphenylphosphino)ferrocene]palladium (II) dichloride.

Specific examples of the base include an inorganic base such as potassium carbonate, sodium carbonate, cesium carbonate, potassium phosphate, potassium hydroxide, and sodium hydroxide; triethylamine; and diisopropylethylamine.

Specific examples of the inert solvent include toluene, 1,2-dimethoxyethane, 1,4-dioxane, DMF, water, and a mixture thereof.

The reaction temperature is typically 50° C. to 150° C., preferably 80° C. to 120° C., but is not limited thereto. Also, the reaction may be carried out under microwave irradiation. The reaction time is typically 1 hour to 24 hours, preferably 2 hours to 12 hours.

Step 4-2: Preparation Process of Compound (4-3)

Compound (4-3) is prepared by hydrolyzing Compound (4-2) according to a similar process to a known process (e.g., Protective Groups in Organic Synthesis 3$^{rd}$ Edition (John Wiley & Sons, Inc.), Comprehensive Organic Transformation, by R. C. Larock, VCH publisher Inc., 1989).

Step 4-3: Preparation Process of Compound (4-4)

Compound (4-4) is prepared from Compound (4-3) and Compound (1-6) according to the process of Step 1-4.

The intermediates and desired compounds in the above preparations may be isolated and purified by a conventional purification method in organic synthetic chemistry such as neutralization, filtration, extraction, washing, drying, concentration, recrystallization, and various types of chromatography. Intermediates may also be used in a next reaction without any specific purification.

An optically-active product of the present compound can be prepared from an optically-active starting material or intermediate, or by the optical resolution of racemates of a final product. The optical resolution method includes a physical separation method with an optically-active column, and a chemical separation method such as fractional crystallization. A diastereomer of the present compound can be prepared by, for example, fractional crystallization.

A pharmaceutically acceptable salt of a compound of Formula (1) can be prepared by, for example, mixing a compound of Formula (1) with a pharmaceutically acceptable acid in a solvent such as water, methanol, ethanol, and acetone.

The present compound is used as, for example, an anti-tumor agent (anti-cancer agent). The cancer type indicated includes hematopoietic tumor and solid cancer, but is not limited thereto. Specific examples of the hematopoietic tumor include acute leukemia, chronic lymphocytic leukemia, chronic myeloid leukemia, polycythemia vera, malignant lymphoma, and myeloma, and specific examples of the solid cancer include brain tumor, head and neck cancer, esophageal cancer, pharyngeal cancer, thyroid cancer, small cell lung cancer, non-small-cell lung cancer, breast cancer, gastric cancer, gallbladder/bile duct cancer, liver cancer, pancreatic cancer, colon cancer, rectal cancer, ovarian cancer, chorioepithelioma, uterine body cancer, cervical cancer, urothelial carcinoma, renal cell cancer, prostate cancer, testicular neoplasm, Wilms tumor, malignant melanoma, neuroblastoma, osteosarcoma, Ewing's tumor, and soft tissue sarcoma.

The anti-tumor agent is used for the prophylaxis and/or treatment of a cancer, and is expected to produce the reduction or disappearance of carcinoma or inhibit the growth of carcinoma down to a certain level. The "prophylaxis" used herein means the administration of the active ingredient of the present invention to a healthy subject who does not develop a disease. For example, the prophylaxis is intended to prevent the development of a disease. The "treatment" used herein means the administration of the active ingredient of the present invention to a person diagnosed with the development of a disease by a doctor (i.e., a patient). For example, the treatment is intended to alleviate a disease or symptom thereof, inhibit the growth of carcinoma, or improve the condition of a patient to the previous condition before a disease is developed. Also, even if an anti-tumor agent is administered for the purpose of preventing the worsening of a disease or symptom thereof or the growth of carcinoma, the administration is referred to as "treatment" when the subject to be administered is a patient.

The present compound has any remarkable effects for inhibiting self-renewal ability of CSCs, and thus is expected to be useful as a novel anti-tumor agent for inhibiting the persistent proliferation, metastasis, and recurrence of malignant tumors derived from CSCs.

The present compound may be formulated into a suitable dosage form and administered orally or parenterally. Examples of the dosage form include a tablet, a capsule, a powder, a granule, a solution, a suspension, an injection, a patch, and a poultice, but are not limited thereto. Preparations are formulated with pharmaceutically acceptable additive(s) according to a known method.

As appropriate, an additive such as an excipient, a disintegrant, a binder, a fluidizer, a lubricant, a coating agent, a solubilizer, a solubilizing agent, a thickening agent, a dispersant, a stabilizing agent, a sweetening agent, and a flavor may be used. Specific examples thereof include lactose, mannitol, crystalline cellulose, low substituted hydroxypropylcellulose, corn starch, partly pregelatinized starch, carmellose calcium, croscarmellose sodium, hydroxypropylcellulose, hydroxypropylmethylcellulose, polyvinylalcohol, magnesium stearate, sodium stearyl fumarate, polyethylene glycol, propylene glycol, titanium oxide, and talc.

Dosage can vary depending on various conditions such as patient's disease, age, body weight, sex, symptom, and administration route. Typically, the present compound is administered to an adult (body weight: 50 kg) at a dose of 0.1 to 1000 mg/day, preferably at a dose of 0.1 to 300 mg/day, which may be administered once a day or 2 or 3 times a day. In addition, the present compound may be administered once in several days to several weeks.

EXAMPLES

Hereinafter, the invention is illustrated in more detail with Reference Examples, Examples, and Test Examples, but should not be limited thereto. The compound names as shown in the following Reference Examples and Examples do not necessarily follow the IUPAC nomenclature system.

The following abbreviations may be used herein.
THF: tetrahydrofuran
TFA: trifluoroacetic acid
$(Boc)_2O$: di-tert-butyl dicarbonate
DMF: N,N-dimethylformamide
DIEA: N-ethyldiisopropylamine
WSC: 1-(3-dimethylaminopropyl)-3-ethylcarbodiimide
WSCI: 1-(3-dimethylaminopropyl)-3-ethylcarbodiimide
WSCI.HCl: 1-(3-dimethylaminopropyl)-3-ethylcarbodiimide hydrochloride
HOBt: 1-hydroxybenzotriazole
HOBt.$H_2O$: 1-hydroxybenzotriazole monohydrate
HBTU: O-(benzotriazol-1-yl)-N,N,N',N'-tetramethyluronium hexafluorophosphate
HATU: O-(7-azabenzotriazol-1-yl)-N,N,N,N',N'-tetramethyluronium hexafluorophosphate
Me: methyl
Et: ethyl
Ac: acetyl
Ms: mesyl
Bs: besyl
Ts: tosyl
Boc: tert-butoxycarbonyl
THP: tetrahydropyranyl
MOM: methoxymethyl
SEM: trimethylsilylethoxymethyl
Besyl (Bs): benzenesulfonyl
Tosyl (Ts): p-toluenesulfonyl
Mesyl (Ms): methanesulfonyl LC/MS analysis conditions in the compound identification are as follows.

The compounds in Reference Examples and Examples were analyzed under the following LC-MS Analysis condition A, Analysis condition B, Analysis condition C, Analysis condition D, Analysis condition E, Analysis condition F, Analysis condition G, or Analysis condition H. Unless otherwise specified, measurement was performed under Condition D.

| Analysis condition A: LC/MS | |
|---|---|
| MS | detector Perkin-Elmer Sciex API 150EX Mass spectrometer (40 eV), |
| HPLC | Shimadzu LC 10ATVP |
| Column | Shiseido CAPCELL PAK C18 ACR (S-5 µm, 4.6 mm × 50 mm) |
| solvent | A: 0.035% TFA/MeCN, B: 0.05% TFA/$H_2O$, |
| flow rate | 3.5 mL/min |
| Gradient condition; | 0.0-0.5 min A 10%, 0.5-4.8 min Linear gradient from A 10% to 99%, 4.8-5.0 min A 99% |

| Analysis condition B: UPLCMS | |
|---|---|
| UPLCMS | ACQUITY UltraPerfomanc LC-PDA-ELSD-SQD (Waters) |
| Column | ACQUITY UPLC BEH C18 1.7 µm, 2.1 × 30 mm (Part. No. 186002349) |
| solvent | A: MeCN, B: 0.05% formic acid/$H_2O$, |
| flow rate | 0.8 mL/min |
| Gradient condition; | 0.0 min A 10%, 0.0-4.3 min Linear gradient from A 10% to 95% |

| Analysis condition C: LC/MS | |
|---|---|
| MS | detector Perkin-Elmer Sciex API 150EX Mass spectrometer (40 eV), |
| HPLC | Shimadzu LC 8A |
| Column | Shiseido CAPCELL PAK C18 Type-MG (5 µm, 4.6 mm × 50 mm), Cat. No.-90105 or Shiseido CAPCELL PAK C18 Type-ACR (5 µm, 4.6 mm × 50 mm), Cat. No.-91105 |
| detector | UV: 220 nm |
| solvent | A: 0.035% TFA/$CH_3CN$, B: 0.05% TFA/$H_2O$, |
| flow rate | 3.5 mL/min |
| Gradient condition; | 0.0-0.5 min A 10%, 0.5-4.2 min Linear gradient from A 10% to 99%, 4.2-6.3 min A 99% |

Analysis Condition D
LC/MS measurement:
Detection device: ACQUITY® SQ detector (Waters)
HPLC: ACQUITY UPLC® system
Column: Waters ACQUITY UPLC® BEH C18 (1.7 µm, 2.1 mm×30 mm)
Solvent: A solution: 0.06% formic acid/$H_2O$, B solution: 0.06% formic acid/MeCN
Gradient condition: 0.0-1.3 min Linear gradient from B 2% to 96%
Flow rate: 0.8 mL/min
UV: 220 nm and 254 nm

| Analysis condition E: LC/MS | |
|---|---|
| MS | detector Perkin-Elmer Sciex API 150EX Mass spectrometer (40 eV), |
| HPLC | Agilent 1100 Series |
| Column | YMC CombiScreen ODS-A (S-5 µm, 12 nm) 50 × 4.6 mm |
| detector | UV: 220 nm |
| solvent | A: 0.035% TFA/$CH_3CN$, B: 0.05% TFA/$H_2O$, |
| flow rate | 3.5 mL/min |
| Gradient condition; | 0.0-1 min A 10%, 1-4.7 min Linear gradient from A 10% to 99%, 4.7-4.9 min A 99% |

| Analysis condition F: LC/MS | |
|---|---|
| MS | detector Perkin-Elmer Sciex API 150EX Mass spectrometer (40 eV), |
| HPLC | Shimadzu LC 8A |
| Column | Shiseido CAPCELL PAK C18 Type-MG (5 µm, 4.6 mm × 50 mm), Cat. No.-90105 or Shiseido CAPCELL PAK C18 Type-ACR (5 µm, 4.6 mm × 50 mm), Cat. No.-91105 |

| Analysis condition F: LC/MS | |
|---|---|
| detector | UV: 220 nm |
| solvent | A: 0.035% TFA/CH$_3$CN, B: 0.05% TFA/H$_2$O, |
| flow rate | 3.5 mL/min |
| Gradient condition; | 0.0-0.5 min A 25%, 0.5-4.2 min Linear gradient from A 25% to 99%, 4.2-6.3 min A 99% |

| Analysis condition G: LC/MS | |
|---|---|
| MS | detector Perkin-Elmer Sciex API 150EX Mass spectrometer (40 eV), |
| HPLC | Shimadzu LC 8A |
| Column | Shiseido CAPCELL PAK C18 Type-MG (5 μm, 4.6 mm × 50 mm), Cat. No.-90105 or Shiseido CAPCELL PAK C18 Type-ACR (5 μm, 4.6 mm × 50 mm), Cat. No.-91105 |
| detector | UV: 220 nm |
| solvent | A: 0.035% TFA/CH$_3$CN, B: 0.05% TFA/H$_2$O, |
| flow rate | 3.5 mL/min |
| Gradient condition; | 0.0-0.5 min A 1%, 0.5-4.2 min Linear gradient from A 1% to 99%, 4.2-6.3 min A 99% |

| Analysis condition H: LC/MS | |
|---|---|
| MS | detector Perkin-Elmer Sciex API 150EX Mass spectrometer (40 eV), |
| HPLC | Shimadzu LC 8A |
| Column | Shiseido CAPCELL PAK C18 Type-MG (5 μm, 4.6 mm × 50 mm), Cat. No.-90105 or Shiseido CAPCELL PAK C18 Type-ACR (5 μm, 4.6 mm × 50 mm), Cat. No.-91105 |
| detector | UV: 220 nm |
| solvent | A: 0.035% TFA/CH$_3$CN, B: 0.05% TFA/H$_2$O, |
| flow rate | 3.5 mL/min |
| Gradient condition; | 0.0-0.5 min A 40%, 0.5-4.2 min Linear gradient from A 40% to 99%, 4.2-6.3 min A 99% |

The measurement condition for powder X-ray diffractometry is as follows.

Device: X-ray Diffraction system X'pert MPD (PANAlytical, Spectris)

X ray: Cu Kα$_1$/45 kV/40 mA

Q1000 (rate of temperature increase: 10° C./min) manufactured by TA Instruments was used for differential scanning calorimetry (DSC). Q500 (rate of temperature increase: 10° C./min) manufactured by TA Instruments was used for thermal gravimetric analysis (TGA).

±5° C. is accepted for the extrapolated onset temperature (Tim) in differential scanning calorimetry (DSC).

Reference Example 1

1-(3-(Trifluoromethyl)benzyl)-1H-imidazol-4-amine Hydrochloride

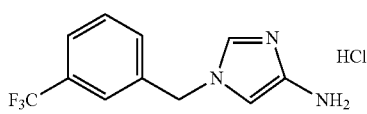

To a solution of 4-nitroimidazole (20 g) in acetonitrile (150 mL) were added potassium carbonate (26.9 g) and potassium iodide (0.074 g), and then thereto was added dropwise a solution of 3-trifluoromethylbenzyl bromide (42.3 g) in acetonitrile (50 mL) at room temperature. The mixture was stirred at 80° C. for 4 hours, and then cooled to room temperature. Water was added thereto, and the mixture was extracted with ethyl acetate. The organic layer was dried over anhydrous sodium sulfate, and then filtered and concentrated under reduced pressure. To a solution of the resulting crude product (46.1 g) in ethyl acetate (500 mL) was added rhodium-carbon (23.1 g), and the mixture was stirred at room temperature under hydrogen. After 20 hours, the mixture was filtered through Celite. To the resulting filtrate was added 4 mol/L hydrochloric acid-dioxane (55.3 mL), and the mixture was stirred at room temperature. The resulting precipitate was filtered and washed with ethyl acetate to give the title compound (22.8 g).

LC/MS, Condition D, Retention time 0.529 min, obs MS[M+1]242.1

Reference Examples 2 to 5

The compounds of Reference examples 2 to 5 were obtained by reaction/treatment using corresponding starting compounds in a similar manner to the process of Reference example 1.

| Reference example | Chemical structure | LC/MS, retention time (min) | LC/MS, MS obs [M + 1] |
|---|---|---|---|
| 2 | ![Cl-benzyl-imidazole-NH2·HCl] | 0.461 | 208.1 |
| 3 | ![F3CO-benzyl-imidazole-NH2·HCl] | 0.564 | 258.1 |
| 4 | ![trifluoro-benzyl-imidazole-NH2·HCl] | 0.473 | 228.1 |
| 5 | ![Me,F-benzyl-imidazole-NH2·HCl] | 0.461 | 224.1 |

Reference Example 6

1-Methyl-6-oxo-1,6-dihydropyridine-3-carbaldehyde

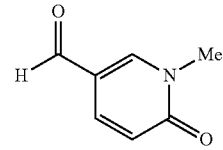

To a solution of 6-oxo-1,6-dihydropyridine-3-carbaldehyde (1.0 g) in dimethylformamide (20 mL) were added potassium carbonate (2.81 g) and methyl iodide (0.66 mL), and the mixture was stirred at room temperature for 4 hours. To the reaction mixture was added aqueous saturated sodium bicarbonate solution, and the mixture was extracted with ethyl acetate. The organic layer was dried over anhydrous sodium sulfate and filtered, and then the solvent was removed under reduced pressure. The residue was purified by silica gel column chromatography (chloroform/methanol) to give the title compound (0.387 g) (yield 35%).

$^1$H-NMR (300 MHz, DMSO-d$_6$) δ 9.60 (s, 1H), 7.91 (d, J=2.4 Hz, 1H), 7.80 (dd, J=2.4, 9.2 Hz, 1H), 6.59 (d, J=9.2 Hz, 1H), 3.62 (s, 3H).

Reference Example 7

(E)-3-(1-Methyl-6-oxo-1,6-dihydropyridin-3-yl)acrylic Acid

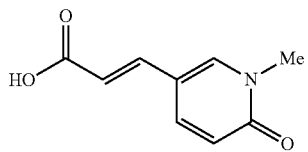 [SMILES: Cn1cc(/C=C/C(=O)O)ccc1=O]

To a solution of sodium hydride (0.126 g) in tetrahydrofuran (15 ml) was added a solution of diethylphosphonoethyl acetate (0.586 mL) in tetrahydrofuran (5 mL) at 0° C. The mixture was stirred at 0° C. for 30 minutes, and then thereto was added the compound of Reference example 6 (0.329 g). The mixture was stirred at room temperature for 5 hours, and then thereto was added aqueous saturated sodium bicarbonate solution. The mixture was extracted with ethyl acetate. The organic layer was dried over anhydrous sodium sulfate and filtered, and then the solvent was removed under reduced pressure. The residue was purified by silica gel column chromatography (chloroform/methanol).

To a mixed solution of the resulting crude product (0.511 g) in methanol (8 mL)-tetrahydrofuran (5 mL) was added 1 mol/L aqueous sodium hydroxide solution (5 ml). The mixture was stirred at room temperature for 4 hours, and then the organic solvent was removed under reduced pressure. Then, 1 mol/L hydrochloric acid was added thereto, and the resulting precipitate was filtered, washed with water and hexane, and then dried under reduced pressure to give the title compound (0.356 g) (yield 83%).

LC/MS, Condition D, Retention time 0.42 min, obs MS[M+1]180.1

Reference Example 8

Tert-Butyl (5-bromopyridin-2-yl)(2,2-difluoroethyl)carbamate

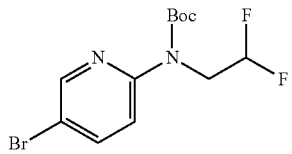 [SMILES: CC(C)(C)OC(=O)N(CC(F)F)c1ccc(Br)cn1]

To a solution of tert-butyl (5-bromopyridin-2-yl)carbamate (0.502 g) in dimethylformamide (25 mL) was added sodium hydride (0.085 g) at 0° C. The mixture was stirred at 0° C. for 30 minutes, and then thereto was added 2,2-difluoroethyl trifluoromethanesulfonate (0.473 mL). The mixture was stirred at room temperature overnight, and then thereto was added aqueous saturated sodium bicarbonate solution. The mixture was extracted with ethyl acetate. The organic layer was dried over anhydrous sodium sulfate and filtered, and then the solvent was removed under reduced pressure. The residue was purified by silica gel column chromatography (hexane/ethyl acetate) to give the title compound (0.533 g) (yield 86%).

LC/MS, Condition D, Retention time 1.23 min, obs MS[M+1]339.1

Reference Example 9

Ethyl (E)-3-(6-((tert-butoxycarbonyl)(2,2-difluoroethyl)amino)pyridin-3-yl)acrylate

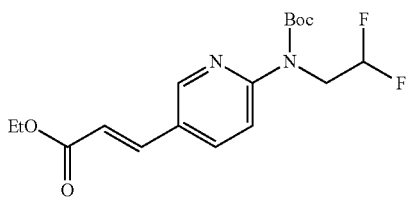 [SMILES: CC(C)(C)OC(=O)N(CC(F)F)c1ccc(/C=C/C(=O)O)cn1]

To a solution of the compound of Reference example 8 (0.529 g) in dimethylformamide (10 mL) were added ethyl acrylate (0.188 mL), triethylamine (0.283 mL), and dichloro di(tri(o-tolylphosphine))palladium (0.127 g). The mixture was stirred at 100° C. for 6 hours, and then thereto was added aqueous saturated sodium bicarbonate solution. The mixture was extracted with ethyl acetate. The organic layer was dried over anhydrous sodium sulfate and filtered, and then the solvent was removed under reduced pressure. The residue was purified by silica gel column chromatography (hexane/ethyl acetate) to give the title compound (0.322 g) (yield 58%).

LC/MS, Condition D, Retention time 1.22 min, obs MS[M+1]357.2

Reference Example 10

(E)-3-(6-((tert-Butoxycarbonyl)(2,2-difluoroethyl)amino)pyridin-3-yl)acrylic Acid

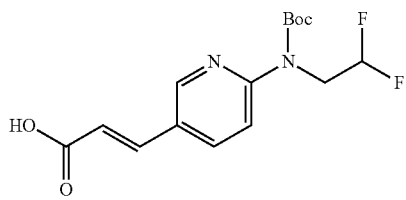

To a mixed solution of the compound of Reference example 9 (0.320 g) in methanol (3 mL)-tetrahydrofuran (3 mL) was added 1 mol/L aqueous sodium hydroxide solution (3 ml). The mixture was stirred at room temperature for 3 hours, and then the organic solvent was removed under reduced pressure. 1 mol/L hydrochloric acid was added thereto, and the resulting precipitate was filtered, washed with water and hexane, and then dried under reduced pressure to give the title compound (0.260 g) (yield 88%).

LC/MS, Condition D, Retention time 0.97 min, obs MS[M+1]329.4

Reference Example 11

The compound of Reference example 11 was obtained by reaction/treatment using a corresponding starting compound in a similar manner to the processes of Reference examples 8 to 10.

| Reference example | Chemical structure | LC/MS, retention time (min) | LC-MS, obs MS [M + 1] |
|---|---|---|---|
| 11 | 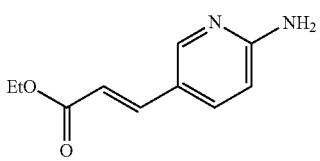 [SMILES: CCOC(=O)/C=C/c1ccc(N)nc1] | 1.03 | 347.2 |

Reference Example 12

Ethyl (E)-3-(6-aminopyridin-3-yl)acrylate

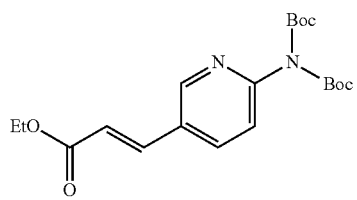 [SMILES: CCOC(=O)/C=C/c1ccc(N(C(=O)OC(C)(C)C)C(=O)OC(C)(C)C)nc1]

To a solution of 5-bromopyridin-2-amine (0.568 g) in dimethylformamide (6 mL) were added ethyl acrylate (0.429 mL), triethylamine (0.682 mL), and dichloro di(tri(o-tolylphosphine))palladium (0.262 g). The mixture was stirred at 100° C. for 6 hours, and then thereto was added aqueous saturated sodium bicarbonate solution. The mixture was extracted with ethyl acetate. The organic layer was dried over anhydrous sodium sulfate and filtered, and then the solvent was removed under reduced pressure. The residue was purified by silica gel column chromatography (hexane/ethyl acetate) to give the title compound (0.520 g) (yield 82%).

LC/MS, Condition D, Retention time 0.59 min, obs MS[M+1]193.1

Reference Example 13

Ethyl (E)-3-(6-(di(tert-butoxycarbonyl)amino)pyridin-3-yl)acrylate

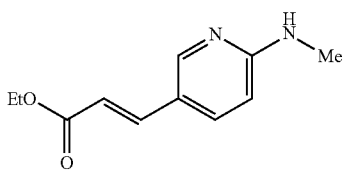 [SMILES: CCOC(=O)/C=C/c1ccc(NC)nc1]

To a solution of the compound of Reference example 12 (0.517 g) in tetrahydrofuran (15 mL) were added triethylamine (0.935 mL), di-tert-butyldicarbonate (1.26 g), and dimethylaminopyridine (0.035 g), and the mixture was stirred at room temperature overnight. The solvent was removed under reduced pressure, and then the residue was purified by silica gel column chromatography (hexane/ethyl acetate) to give the title compound (0.811 g) (yield 77%).

LC/MS, Condition D, Retention time 1.19 min, obs MS[M+1]394.3

Reference Example 14

Ethyl (E)-3-(6-(methylamino)pyridin-3-yl)acrylate

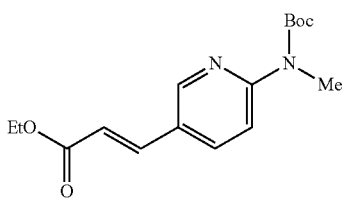 [SMILES: CN(C(=O)OC(C)(C)C)c1ccc(/C=C/C(=O)O)cn1]

To a solution of 5-bromo-N-methylpyridin-2-amine (0.522 g) in dimethylformamide (15 mL) were added ethyl acrylate (0.335 mL), triethylamine (0.503 mL), and dichloro di(tri(o-tolylphosphine))palladium (0.227 g). The mixture was stirred at 100° C. for 7 hours, and then thereto was added aqueous saturated sodium bicarbonate solution. The mixture was extracted with ethyl acetate. The organic layer was dried over anhydrous sodium sulfate and filtered, and then the solvent was removed under reduced pressure. The residue was purified by silica gel column chromatography (hexane/ethyl acetate) to give the title compound (0.415 g) (yield 72%).

LC/MS, Condition D, Retention time 0.50 min, obs MS[M+1]207.4

Reference Example 15

Ethyl (E)-3-(6-((tert-butoxycarbonyl)(methyl)amino)pyridin-3-yl)acrylate

To a solution of the compound of Reference example 14 (0.413 g) in tetrahydrofuran (10 mL) were added triethylamine (0.416 mL), di-tert-butyldicarbonate (525 g), and dimethylaminopyridine (0.013 g). The mixture was stirred at room temperature overnight. The solvent was removed under reduced pressure, and then the residue was purified by silica gel column chromatography (hexane/ethyl acetate) to give the title compound (0.613 g) (yield 100%).

LC/MS, Condition D, Retention time 1.19 min, obs MS[M+1]307.2

Reference Example 16

(E)-3-(6-((tert-Butoxycarbonyl)(methyl)amino)pyridin-3-yl)acrylic Acid

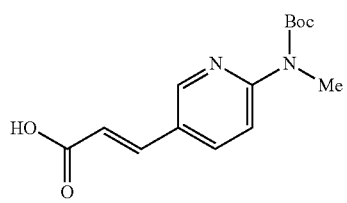

To a mixed solution of the compound of Reference example 15 (0.602 g) in methanol (6 mL)-tetrahydrofuran (6 mL) was added 1 mol/L aqueous sodium hydroxide solution (6 ml). The mixture was stirred at room temperature for 4 hours, and then the organic solvent was removed under reduced pressure. 1 mol/L hydrochloric acid was added thereto, and the resulting precipitate was filtered, washed with water and hexane, and then dried under reduced pressure to give the title compound (0.500 g) (yield 91%).

LC/MS, Condition D, Retention time 0.92 min, obs MS[M+1]279.2

Reference Example 17

The compound of Reference example 17 was obtained by reaction/treatment using a corresponding starting compound in a similar manner to the processes of Reference examples 14 to 16.

| Reference example | Chemical structure | LC/MS, retention time (min) | LC-MS obs MS [M + 1] |
|---|---|---|---|
| 17 | HO₂C―=―〈pyridine〉―N(Et)(Boc) | 1.01 | 293.4 |

Reference Example 18

(E)-3-(6-(Methoxycarbonyl)pyridin-3-yl)acrylic Acid Hydrochloride

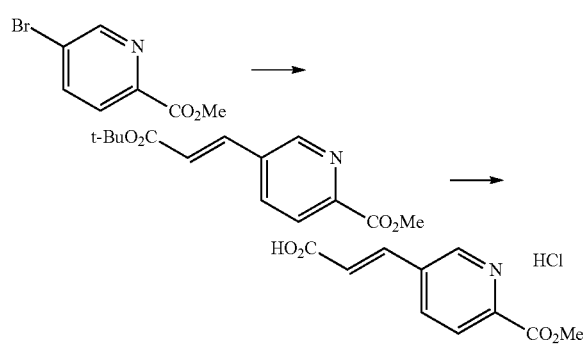

(A) Methyl (E)-5-(3-(tert-butoxy)-3-oxoprop-1-en-1-yl)picolinate

To a solution of methyl 5-bromo-picolinate (2.0 g) in propionitrile (50 mL) were added t-butyl acrylate (2.2 mL), N,N-diisopropylethylamine (3.2 mL), palladium acetate (0.21 g), and tris(o-tolyl)phosphine (0.56 g), and the mixture was stirred at 80° C. for 5.5 hours. Water was added to the reaction mixture, and the mixture was extracted with ethyl acetate. The organic layer was washed with brine and dried over magnesium sulfate, and filtered. Then, the filtrate was concentrated under reduced pressure. The residue was purified by silica gel column chromatography (hexane/ethyl acetate) to give the title compound (2.2 g) (yield 90%).

LC/MS, Condition D, Retention time 0.896 min, obs MS[M+1]264.1

(B) (E)-3-(6-(Methoxycarbonyl)pyridin-3-yl)acrylic Acid Hydrochloride

To the compound obtained in the above (A) (2.10 g) was added a solution of 4 mol/L hydrochloric acid-dioxane (30 mL), and the mixture was stirred at room temperature overnight. Water was added thereto, and the resulting precipitate was filtered and washed with diisopropyl ether to give the title compound (1.32 g) (yield 68%).

LC/MS, Condition D, Retention time 0.512 min, obs MS[M+1]208.1

Reference Example 19

(E)-2-Methoxy-5-(3-oxo-3-((1-(3-(trifluoromethyl)benzyl)-1H-imidazol-4-yl)amino)prop-1-en-1-yl)phenol Acetate

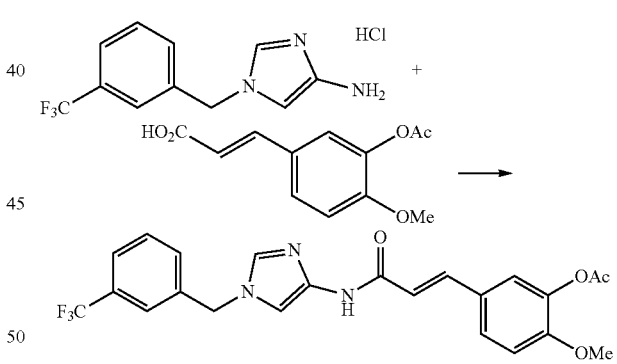

To a solution of (E)-3-(3-acetoxy-4-methoxyphenyl)acrylic acid (71.0 mg) in dichloroethane (2 mL) were added oxalyl chloride (39 µL) and DMF (2 µL), and the mixture was stirred at room temperature for 1 hour. The reaction mixture was concentrated under reduced pressure and dried to give an acid chloride. To a solution of the compound of Reference example 1 (70.0 mg) in dichloromethane (5 mL) was added dropwise the acid chloride to which triethylamine was added (105 µL). The mixture was stirred overnight, and thereto was added water. The mixture was extracted with chloroform. The organic layer was washed with brine, dried over magnesium sulfate, filtered, and then concentrated under reduced pressure. The residue was purified by silica gel column chromatography (chloroform/methanol) to give the title compound (30 mg) (yield 33%).

LC/MS, Condition D, Retention time 1.01 min, obs MS[M+1]460.2

Reference Example 20

(E)-3-(4-Methoxy-3-(2-((tetrahydro-2H-pyran-2-yl)oxy)ethoxy)phenyl)acrylic Acid

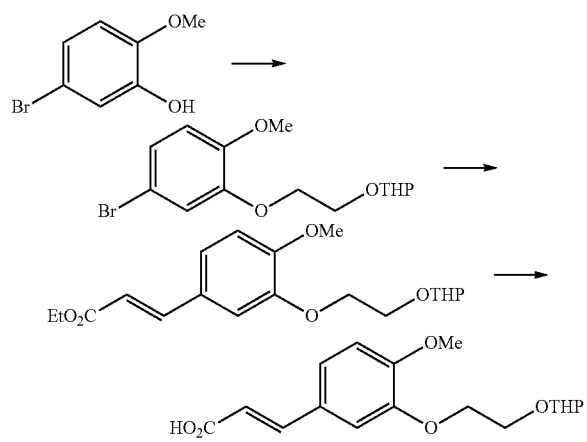

(A) 2-(2-(5-Bromo-2-methoxyphenoxy)ethoxy)tetrahydro-2H-pyran

To a solution of 5-bromo-2-methoxyphenol (10.0 g) in DMF (50 mL) were added 2-(2-bromoethoxy)tetrahydro-2H-pyran (10.8 g) and potassium carbonate (8.86 g), and the mixture was stirred at 80° C. for 2.5 hours. To the reaction mixture was added water, and the mixture was extracted with ethyl acetate. The organic layer was washed with brine, dried over magnesium sulfate, filtered, and then concentrated under reduced pressure to give the title compound (15.1 g) (yield 92%).

$^1$H-NMR (400 MHz, CDCl$_3$) δ 7.12 (d, J=2.0 Hz, 1H), 7.05 (dd, J=8.4, 2.0 Hz, 1H), 6.75 (d, J=8.4 Hz, 1H), 4.72 (t, J=3.6 Hz, 1H), 4.26-4.19 (m, 2H), 4.14-4.03 (m, 1H), 3.92-3.82 (m, 2H), 3.85 (s, 3H), 3.57-3.50 (m, 1H), 1.90-1.78 (m, 1H), 1.78-1.70 (m, 1H), 1.68-1.53 (m, 4H).

(B) Ethyl (E)-3-(4-methoxy-3-(2-((tetrahydro-2H-pyran-2-yl)oxy)ethoxy)phenyl)acrylate To a solution of the compound in the above (A) (14.0 g) in propionitrile (120 mL) were added ethyl acrylate (6.9 mL), N,N-diisopropylethylamine (14.7 mL), palladium acetate (0.48 g), and tris(o-tolyl)phosphine (1.29 g), and the mixture was stirred at 100° C. for 13 hours. To the reaction mixture was added water, and the mixture was extracted with ethyl acetate. The organic layer was washed with brine, dried over magnesium sulfate, filtered, and then concentrated under reduced pressure. The residue was purified by silica gel column chromatography (hexane/ethyl acetate) to give the title compound (8.0 g) (yield 54%).

$^1$H-NMR (400 MHz, CDCl$_3$) δ 7.62 (d, J=16.0 Hz, 1H), 7.19 (d, J=2.0 Hz, 1H), 7.12 (dd, J=8.4, 2.0 Hz, 1H), 6.87 (d, J=8.4 Hz, 1H), 6.31 (d, J=16.0 Hz, 1H), 4.73 (t, J=3.6 Hz, 1H), 4.31-4.22 (m, 4H), 4.15-4.08 (m, 1H), 3.93-3.86 (m, 5H), 3.57-3.51 (m, 1H), 1.88-1.81 (m, 1H), 1.78-1.71 (m, 1H), 1.68-1.53 (m, 4H), 1.35 (t, J=6.8 Hz, 3H).

(C) (E)-3-(4-Methoxy-3-(2-((tetrahydro-2H-pyran-2-yl)oxy)ethoxy)phenyl)acrylic Acid To a solution of the compound in the above (B) (3.6 g) in THF/methanol (20 mL/20 mL) was added 2 mol/L aqueous sodium hydroxide solution (15 mL), and the mixture was stirred at 60° C. for 7 hours. The reaction mixture was adjusted to pH 5.0 by the addition of aqueous hydrochloric acid solution and extracted with ethyl acetate. The organic layer was washed with brine, dried over magnesium sulfate, filtered, and then concentrated under reduced pressure to give the title compound (3.1 g) (yield 93%).

$^1$H-NMR (400 MHz, CDCl$_3$) δ 7.72 (d, J=15.6 Hz, 1H), 7.23 (d, J=1.6 Hz, 1H), 7.15 (dd, J=8.4, 2.0 Hz, 1H), 6.89 (d, J=8.4 Hz, 1H), 6.33 (d, J=15.6 Hz, 1H), 4.74 (t, J=3.6 Hz, 1H), 4.33-4.25 (m, 2H), 4.15-4.07 (m, 1H), 3.95-3.86 (m, 5H), 3.58-3.53 (m, 1H), 1.88-1.81 (m, 1H), 1.79-1.71 (m, 1H), 1.69-1.51 (m, 4H).

Reference Example 21

The compound of Reference example 21 was obtained by reaction/treatment using a corresponding starting compound in a similar manner to the process of Reference example 20.

| Reference example | Chemical structure | $^1$H-NMR (400 MHz, CDCl$_3$) |
|---|---|---|
| 21 | 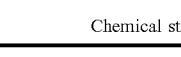 | δ 7.74 (d, J = 15.6 Hz, 1H), 7.61 (d, J = 8.0 Hz, 1H), 7.24-7.19 (m, 2H), 6.53 (d, J = 15.6 Hz, 1H), 4.78-4.76 (m, 1H), 4.40-4.33 (m, 2H), 4.18-4.13 (m, 1H), 3.97-3.89 (m, 2H), 3.60-3.56 (m, 1H), 1.87-1.73 (m, 2H), 1.67-1.51 (m, 4H). |

Reference Example 22

(E)-N-(1-(3-Chlorobenzyl)-1H-imidazol-4-yl)-3-(4-methoxy-3-(2-((tetrahydro-2H-pyran-2-yl)oxy)ethoxy)phenyl)acrylamide

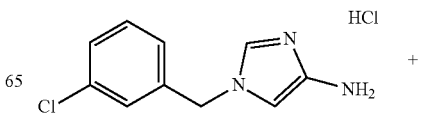

-continued

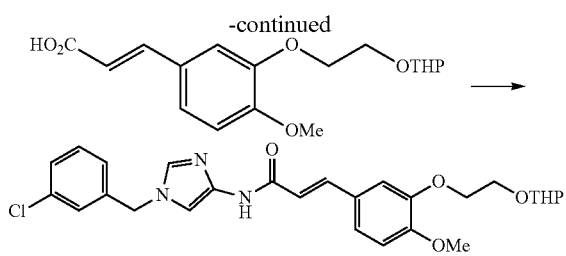

To a solution of the compound of Reference example 2 (1.20 g) in DMF (30 mL) were added the compound of Reference example 20 (1.90 g), WSCI.HCl (1.13 g), HOBt (0.80 g), and triethylamine (2.2 mL), and the mixture was stirred at room temperature for 2 hours. To the reaction mixture was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (1.25 g) (yield 52%).

$^1$H-NMR (400 MHz, CDCl$_3$) δ 8.84 (s, 1H), 7.64 (d, J=16.0 Hz, 1H), 7.48-7.43 (m, 2H), 7.35-7.29 (m, 2H), 7.23-7.17 (m, 2H), 7.14-7.10 (m, 2H), 6.87 (d, J=8.0 Hz, 1H), 6.43 (d, J=16.0 Hz, 1H), 5.10 (s, 2H), 4.73 (t, J=4.0 Hz, 2H), 4.29-4.24 (m, 2H), 4.16-4.07 (m, 1H), 3.94-3.85 (m, 5H), 3.56-3.51 (m, 1H), 1.88-1.80 (m, 1H), 1.78-1.71 (m, 1H), 1.64-1.52 (m, 4H).

Reference Examples 23 to 26

The compound of Reference examples 23 to 26 were obtained by reaction/treatment using corresponding starting compounds in a similar manner to the processes of Reference example 22.

| Reference example | Chemical structure | LC/MS retention time (min) | LC-MS obs MS [M + 1] |
|---|---|---|---|
| 23 | 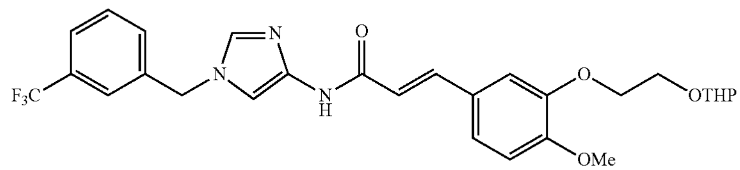 | 0.968 | 546.8 |
| 24 | 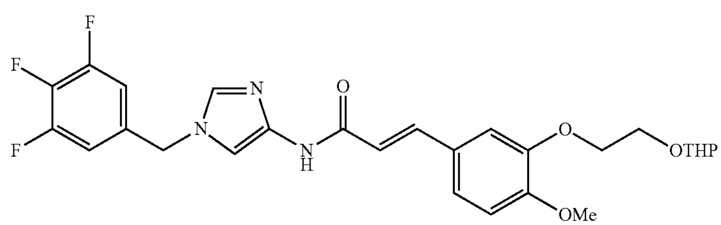 | 0.964 | 532.3 |
| 25 | 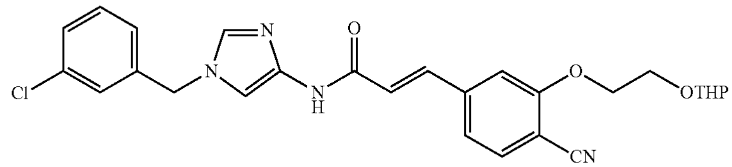 | 1.010 | 507.2 |
| 26 | 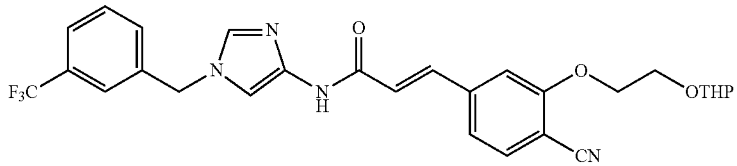 | 1.048 | 541.6 |

Reference Example 27

(E)-3-(4-Fluoro-3-(methoxymethoxy)phenyl)acrylic Acid

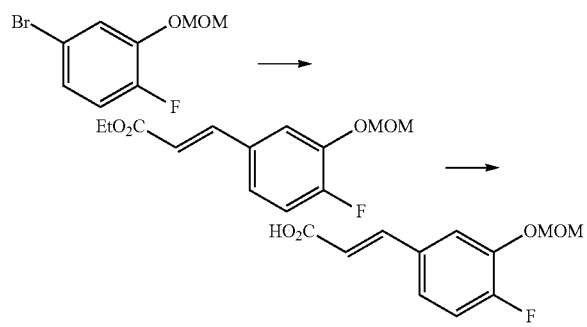

(A) Ethyl (E)-3-(4-fluoro-3-(methoxymethoxy)phenyl)acrylate

To a solution of 4-bromo-1-fluoro-2-(methoxymethoxy) benzene (5.2 g) in DMF (80 mL) were added ethyl acrylate (2.65 mL), triethylamine (4.0 mL), palladium acetate (0.48 g), and dichlorobis(tri-o-tolylphosphine)palladium (II) (1.74 g), and the mixture was stirred at 90° C. for 4 hours. Water was added to the reaction mixture, and the mixture was extracted with ethyl acetate. The organic layer was washed with brine, dried over magnesium sulfate, filtered, and then concentrated under reduced pressure. The residue was purified by silica gel column chromatography (hexane/ethyl acetate) to give the title compound (2.7 g) (yield 48%).

$^1$H-NMR (400 MHz, CDCl$_3$) δ 7.62 (d, J=16.0 Hz, 1H), 7.40 (dd, J=8.0, 2.0 Hz, 1H), 7.18-7.08 (m, 2H), 6.37 (d, J=16.0 Hz, 1H), 5.26 (s, 2H), 4.28 (q, J=7.6 Hz, 2H), 3.55 (s, 3H), 1.36 (t, J=7.6 Hz, 3H).

(B) (E)-3-(4-Fluoro-3-(methoxymethoxy)phenyl) acrylic Acid

To a solution of the compound in the above (A) (2.7 g) in THF/methanol (10 mL/10 mL) was added 2 mol/L aqueous sodium hydroxide solution (10.6 mL), and the mixture was stirred at 60° C. for 3 hours. The reaction mixture was adjusted to pH 4.0 by the addition of aqueous hydrochloric acid solution and extracted with chloroform. The organic layer was washed with brine, dried over magnesium sulfate, filtered, and then concentrated under reduced pressure to give the title compound (2.2 g) (yield 92%).

$^1$H-NMR (400 MHz, CDCl$_3$) δ 7.73 (d, J=16.0 Hz, 1H), 7.43 (dd, J=7.6, 2.8 Hz, 1H), 7.22-7.11 (m, 2H), 6.38 (d, J=16.0 Hz, 1H), 5.27 (s, 2H), 3.56 (s, 3H).

Reference Example 28

(E)-3-(4-Fluoro-3-(methoxymethoxy)phenyl)-N-(1-(3-(trifluoromethyl)benzyl)-1H-imidazol-4-yl)acrylamide

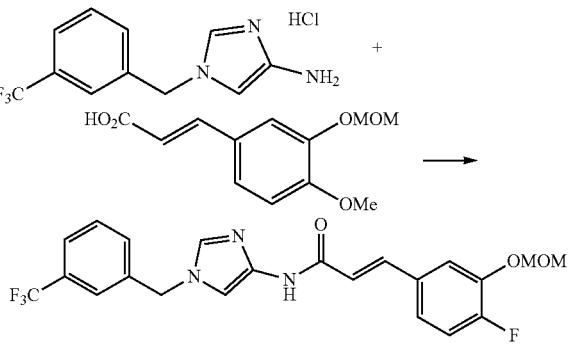

To a solution of the compound of Reference example 1 (736 mg) in DMF (10 mL) were added the compound of Reference example 27 (600 mg), WSCI.HCl (559 mg), HOBt (395 g), and N,N-diisopropylethylamine (1.0 mL), and the mixture was stirred at room temperature overnight. Water was added to the reaction mixture, and the mixture was extracted with ethyl acetate. The organic layer was washed with brine, dried over magnesium sulfate, filtered, and then concentrated under reduced pressure. The resulting solid was washed with chloroform and filtered. The filtrate was concentrated under reduced pressure, and the residue was purified by silica gel column chromatography (chloroform/methanol) to give the title compound in combination with the above solid (473 mg) (yield 40%).

$^1$H-NMR (400 MHz, DMSO-d$_6$) δ 10.55 (s, 1H), 7.71-7.57 (m, 3H), 7.47-7.29 (m, 2H), 7.46-7.31 (m, 3H), 7.31-7.20 (m, 2H), 6.80 (d, J=16.0 Hz, 1H), 5.28 (s, 4H), 3.45 (s, 3H).

LC/MS, Condition D, Retention time 0.991 min, obs MS[M+1]450.2

Reference Example 29

The compound of Reference example 29 was obtained by reaction/treatment using a corresponding starting compound in a similar manner to the process of Reference example 28.

| Reference example | Chemical structure | LC-MS retention time (min) | LC-MS obs MS [M + 1] |
|---|---|---|---|
| 29 | 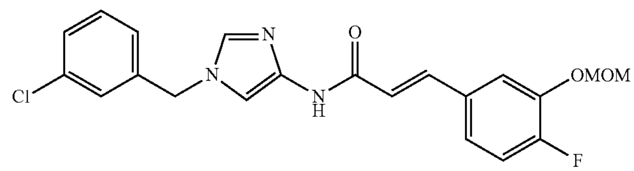 | 1.005 | 416.2 |

Reference Example 30

(E)-3-(1-Tosyl-1H-indol-5-yl)acrylic Acid

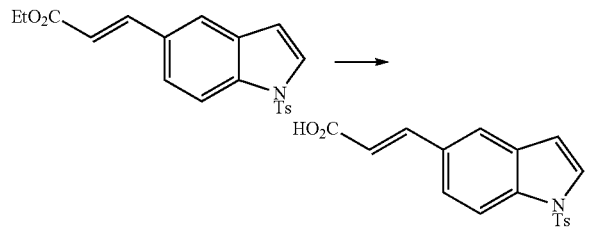

To a solution of ethyl (E)-3-(1-tosyl-1H-indol-5-yl)acrylate (60 mg) in THF/methanol (2 mL/2 mL) was added 2 mol/L aqueous sodium hydroxide solution (0.12 mL), and the mixture was stirred at room temperature overnight. The reaction mixture was neutralized with aqueous hydrochloric acid solution and extracted with chloroform. The organic layer was washed with brine, dried over magnesium sulfate, filtered, and then concentrated under reduced pressure. The residue was purified by silica gel column chromatography (ethyl acetate/hexane) to give the title compound (31 mg) (yield 56%).

LC/MS, Condition D, Retention time 0.975 min, obs MS[M+1]342.1

Reference Example 31

(E)-3-(4-Morpholinophenyl)acrylic Acid

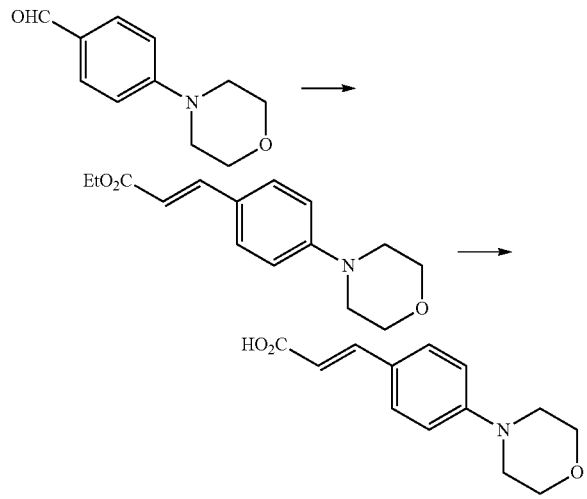

(A) Ethyl (E)-3-(4-morpholinophenyl)acrylate

To a solution of 4-morpholinobenzaldehyde (1.0 g) in THF (30 mL) was added (carbethoxymethylene)triphenyl phosphorane (2.2 g), and the mixture was stirred at 40° C. for 3 hours. The reaction mixture was concentrated under reduced pressure, and the residue was purified by silica gel column chromatography (ethyl acetate/hexane) to give the title compound (290 mg) (yield 21%).

$^1$H-NMR (300 MHz, DMSO-$d_6$) δ 7.64 (d, J=16.0 Hz, 1H), 7.46 (d, J=7.2 Hz, 2H), 6.89 (d, J=7.2 Hz, 2H), 6.29 (d, J=16.0 Hz, 1H), 4.26 (q, J=7.2 Hz, 2H), 3.89-3.84 (m, 4H), 3.29-3.22 (m, 4H), 1.34 (t, J=7.2 Hz, 3H).

(B) (E)-3-(4-Morpholinophenyl)acrylic Acid

To a solution of the compound in the above (A) (290 mg) in methanol (3 mL) was added 2 mol/L sodium hydroxide solution (1.1 mL). Then, thereto were added tetrahydrofuran (1 mL) and water (1 mL), and the mixture was stirred at room temperature for 5 hours. The reaction mixture was neutralized with 5 mol/L aqueous hydrochloric acid solution and extracted with chloroform. The organic layer was washed with brine, dried over magnesium sulfate, filtered, and then concentrated under reduced pressure. The resulting solid was washed with diisopropyl ether and filtered to give the title compound (140 mg).

LC/MS, Condition D, Retention time 0.670 min, obs MS[M+1]234.2

Reference Example 32

(E)-5-(3-((1-(3-Chlorobenzyl)-1H-imidazol-4-yl)amino)-3-oxoprop-1-en-1-yl)picolinic Acid

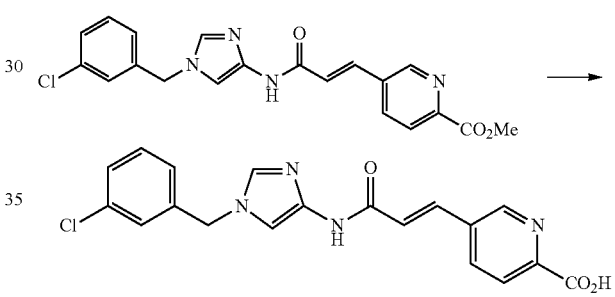

To a solution of the compound of Example 25 (0.65 g) in methanol/THF (2 mL/2 mL) was added 2 mol/L aqueous sodium hydroxide solution (1.22 mL), and the mixture was stirred at room temperature for 4 hours. The reaction mixture was concentrated under reduced pressure, and then adjusted to pH 5.0 by the addition of water and 5 mol/L aqueous hydrochloric acid solution. The resulting solid was washed with water, and then azeotroped with toluene to give the title compound (0.46 g) (yield 73%).

LC/MS, Condition D, Retention time 0.664 min, obs MS[M+1]383.1

Reference Example 33

(E)-3-(4-Fluoro-3-(2-((tetrahydro-2H-pyran-2-yl)oxyethoxy)phenyl)-N-(1-(3-(trifluoromethyl)benzyl)-1H-imidazol-4-yl)acrylamide

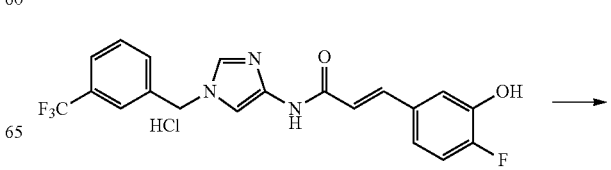

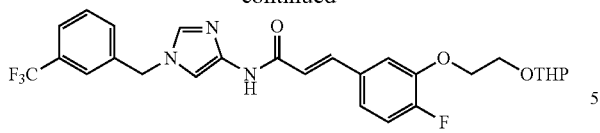

To a solution of the compound of Example 37 (200 mg) in DMF (5 mL) were added 2-(2-bromoethoxy)tetrahydro-2H-pyran (114 mg) and potassium carbonate (155 mg), and the mixture was stirred at 90° C. for 1.5 hours. To the reaction mixture was added water, and the mixture was extracted with ethyl acetate. The organic layer was washed with brine, dried over magnesium sulfate, filtered, and then concentrated under reduced pressure. The residue was purified by silica gel column chromatography (chloroform/methanol) to give the title compound (215 mg) (yield 90%).

LC/MS, Condition D, Retention time 1.078 min, obs MS[M+1]533.9

Reference Example 34

The compound of Reference example 34 was obtained by reaction/treatment using a corresponding starting compound in a similar manner to the process of Reference example 33.

Reference Example 35-2

1-(3,4,5-Trifluorobenzyl)-1H-imidazole-4-carboxylic Acid

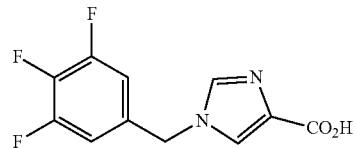

To a solution of the compound of Reference example 35-1 (4.75 g) in methanol/THF (50 mL/50 mL) was added 2 mol/L aqueous sodium hydroxide solution (13.2 mL), and the mixture was stirred at 50° C. for 5 hours. The reaction mixture was concentrated under reduced pressure, and the residue was dissolved in water, and then the solution was adjusted to pH 5 with aqueous hydrochloric acid solution. The resulting precipitate was filtered, washed with water and hexane, and then dried at 50° C. under reduced pressure to give the title compound (4.52 g).

LC/MS ([M+H]$^+$/Rt (min)): 257.1/0.513

| Reference example | Chemical structure | LC-MS retention time (min) | LC-MS obs MS [M + 1] |
|---|---|---|---|
| 34 | 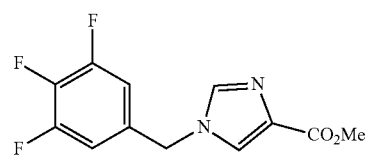 [SMILES: COC(=O)c1cn(Cc2cc(F)c(F)c(F)c2)cn1] | 1.114 | 500.2 |

Reference Example 35-1

Methyl 1-(3,4,5-trifluorobenzyl-1H-imidazole-4-carboxylate

F, F, F-C6H2-CH2-N(imidazole)-CO2Me

To a solution of methyl 1H-imidazole-4-carboxylate (14.0 g) in acetonitrile (200 mL) were added potassium carbonate (19.9 g) and potassium iodide (0.092 g), and then thereto was added dropwise 3,4,5-trifluorobenzyl bromide (14.6 mL) at room temperature. The mixture was stirred at 70° C. for 6 hours and cooled to room temperature. Then, water was added to the reaction mixture, and the mixture was extracted with ethyl acetate. The organic layer was dried over anhydrous magnesium sulfate, filtered, and then concentrated under reduced pressure. The resulting crude product was washed with hexane/ethyl acetate (1/2, 60 mL) to give the title compound (14.0 g).

LC/MS ([M+H]$^+$/Rt (min)): 271.4/0.725

Reference Example 36

N-(1H-Imidazol-4-yl)-3,4-dimethoxybenzamide

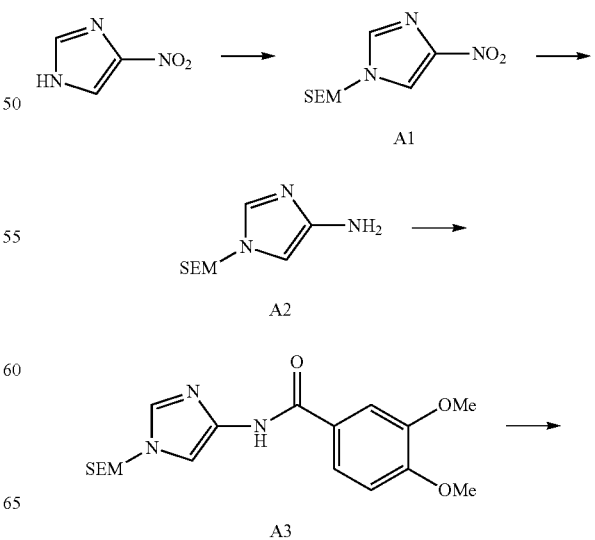

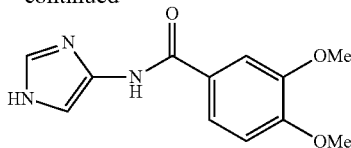

Sodium hydride (60%) (6.0 g) was added to dried dimethylformamide (30 mL) under nitrogen atmosphere, and cooled to 0° C. with an ice bath. Then, thereto was added dropwise 4-nitroimidazole (11.32 g)/DMF (64 mL), and the mixture was stirred at 0° C. for 1.5 hours. Then, thereto was added trimethylsilylethoxymethyl chloride (18.34 g), and the mixture was stirred at 0° C. for 1 hour. To the mixture was added a small amount of methanol, and then the reaction solution was poured into an ice bath and extracted with ethyl acetate 3 times. The organic layer was washed with brine twice, and concentrated under reduced pressure to give a crude product. The crude product was purified by silica gel column chromatography (hexane-ethyl acetate) to give Compound A1 (18.88 g) (yield 78%).

Compound A1 (18.7 g) was dissolved in ethyl acetate (100 mL), and thereto was added 10% Pd/C (4.3 g). The mixture was hydrogenated at room temperature (5100 ml absorbed). After replacement with nitrogen, the reaction solution was filtered through Celite, and to the filtrate were added 3,4-dimethoxybenzoic acid (14 g), WSCI.HCl (14.7 g), and HOBt (10.4 g). The mixture was stirred at room temperature overnight. Thereto was added ethyl acetate, and the mixture was washed with 5% aqueous sodium carbonate solution (twice) and brine (once). The mixture was dried over anhydrous magnesium sulfate and concentrated under reduced pressure to give a crude product (29.6 g). The crude product was purified by silica gel column chromatography (chloroform-methanol) to give Compound A3 (19.43 g) (yield 68%).

To Compound A3 (19.0 g) were added ethanol (30 mL) and 6 mol/L aqueous hydrochloric acid solution (200 mL), and the mixture was stirred with heating at 50° C. for 6 hours. The reaction solution was poured into ice water and washed with hexane once. The aqueous layer was basified with 5% aqueous sodium carbonate solution and extracted with ethyl acetate 3 times. The organic layer was washed with brine once, dried over magnesium sulfate, and concentrated under reduced pressure to give Reference example 36 (5.35 g) (yield 43%).

LC/MS, Condition D, Retention time 0.421 min, obs MS[M+1]248.1

Reference Example 37

The compound of Reference example 37 was obtained by reaction/treatment using a corresponding starting compound in a similar manner to the process of Reference example 22. The corresponding carboxylic acid may be synthesized by, for example, the process of Chemical Communications 2014, 50(41), 5510-5513.

| Reference example | Chemical structure | LC-MS retention time (min) | LC-MS obs MS [M + 1] |
| --- | --- | --- | --- |
| 37 | 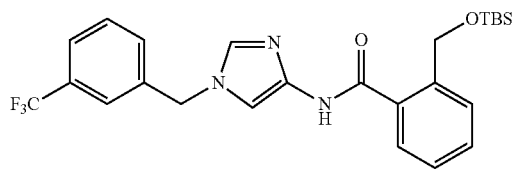 [SMILES: CC(C)(C)[Si](C)(C)OCc1ccccc1C(=O)Nc1cn(Cc2cccc(C(F)(F)F)c2)cn1] | 1.307 | 490.3 |

Reference Example 38

N-{1-[3-(Trifluoromethyl)benzyl]-1H-imidazol-4-yl}prop-2-enamide

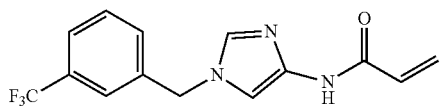

To a solution of the compound of Reference example 1 (1 g) and DIEA (1.4 mL) in THF (25 mL) was slowly added acryloyl chloride (0.32 mL). The reaction mixture was stirred at room temperature for 1.5 hours, and then thereto was added water. The mixture was extracted with chloroform. The organic layer was washed with brine, dried over anhydrous sodium sulfate, filtered, and then concentrated under reduced pressure. The resulting residue was purified by silica gel column chromatography (chloroform/methanol) to give the title compound (0.13 g) (yield 12%).

LC/MS, Condition D, Retention time 0.718 min, obs MS[M+1]296.2

$^1$H-NMR (DMSO-d$_6$) δ 10.56 (s, 1H), 7.69-7.66 (m, 3H), 7.62-7.57 (m, 2H), 7.33 (s, 1H), 6.44 (dd, J=17.1, 10.4 Hz, 1H), 6.15 (dd, J=17.1, 2.4 Hz, 1H), 5.63 (dd, J=10.4, 2.4 Hz, 1H), 5.27 (s, 2H).

Reference Example 39

Ethyl (2E)-3-[6-(hydroxymethyl)pyridin-3-yl]prop-2-enoate

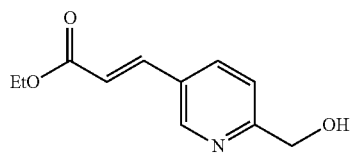 [SMILES: CCOC(=O)/C=C/c1ccc(CO)nc1]

To a solution of 2-ethoxycarbonylvinylboronic acid pinacol ester (361 mg) in 1,4-dioxane (15 mL)/water (1.5 mL) were added 5-bromo-2-hydroxymethylpyridine (300 mg), bis(tri-t-butylphosphine)palladium (O) (122 mg), and potassium carbonate (662 mg), and the mixture was stirred at 130° C. for 1.5 hours under microwave irradiation. The reaction mixture was cooled to room temperature, and then thereto was added water. The mixture was extracted with ethyl acetate. The organic layer was washed with brine, dried over anhydrous sodium sulfate, filtered, and then concentrated under reduced pressure. The resulting residue was purified by silica gel column chromatography (hexane/ethyl acetate) to give the title compound (204 mg) (yield 62%).

LC/MS, Condition D, Retention time 0.476 min, obs MS[M+1]208.1

Reference Example 40

The compound of Reference example 40 was obtained by reaction/treatment using a corresponding starting compound in a similar manner to the process of Reference example 39.

| Reference example | Chemical structure | LC-MS condition | LC-MS retention time (min) | LC-MS obs MS [M + 1] |
|---|---|---|---|---|
| 40 | 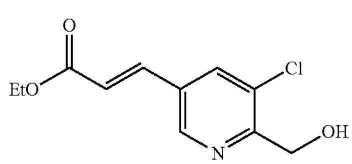 [SMILES: CCOC(=O)/C=C/c1cnc(CO)c(Cl)c1] | D | 0.719 | 242.1 |

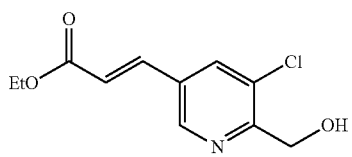

Reference Example 41

2-Bromo-5-(dimethoxymethyl)pyridine

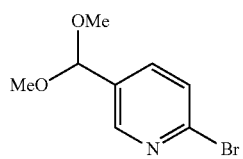

To a solution of 6-bromo-pyridine-3-carboaldehyde (2 g) in methanol (30 mL) were added methyl orthoformate (2.35 mL) and p-toluenesulfonic acid monohydrate (205 mg), and the mixture was stirred at room temperature for 15.5 hours. The reaction solution was concentrated under reduced pressure, and then the residue was neutralized with saturated aqueous sodium bicarbonate solution and extracted with ethyl acetate. The organic layer was washed with brine, dried over anhydrous sodium sulfate, filtered, and then concentrated under reduced pressure to give the title compound (2.41 g) (yield 97%).

LC/MS, Condition D, Retention time 0.738 min, obs MS[M+1]232.0

Reference Example 42

1-[5-(Dimethoxymethyl)pyridin-2-yl]-2,2-difluoroethanone

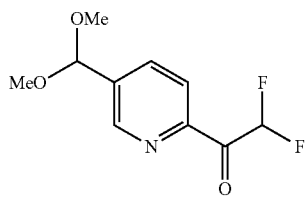 [SMILES: COC(OC)c1ccc(C(=O)C(F)F)nc1]

A solution of the compound of Reference example 41 (3.03 g) in THF (50 mL) was cooled to −78° C., and thereto was added n-butyllithium (1.63M in hexane, 16 mL). The mixture was stirred at the same temperature for 35 minutes. Then, thereto was added methyl difluoroacetate (2.83 mL), and the mixture was stirred at the same temperature for 1 hour and 10 minutes. Thereto was added saturated aqueous ammonium chloride solution, and the reaction mixture was stirred at room temperature for 2 hours and 45 minutes. The mixture was extracted with ethyl acetate. The organic layer was washed with brine, dried over anhydrous sodium sulfate, filtered, and then concentrated under reduced pressure. The resulting residue was purified by silica gel column chromatography (hexane/ethyl acetate) to give the title compound (2.01 g) (yield 66%).

LC/MS, Condition D, Retention time 0.662 min, obs MS[M+MeOH+1] 264.1

Reference Example 43

1-[5-(Dimethoxymethyl)pyridin-2-yl]-2,2-difluoro-ethanol

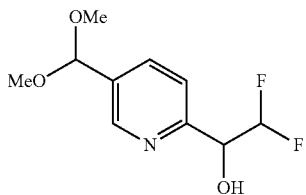 [SMILES: COC(OC)c1ccc(C(O)C(F)F)nc1]

To a solution of the compound of Reference example 42 (2.00 g) in methanol (20 mL) was added sodium borohydride (327 mg), and the mixture was stirred at room temperature for 20 minutes. Water was added to the mixture, and the mixture was extracted with ethyl acetate. The organic layer was washed with brine, dried over anhydrous sodium sulfate, filtered, and then concentrated under reduced pressure to give the title compound (1.89 g) (yield 93%).

LC/MS, Condition D, Retention time 0.537 min, obs MS[M+1]234.1

Reference Example 44

1-[5-(Dimethoxymethyl)pyridin-2-yl]-2,2-difluoro-ethyl Methanesulfonate

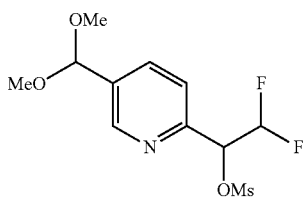 [SMILES: COC(OC)c1ccc(C(OS(C)(=O)=O)C(F)F)nc1]

To a solution of the compound of Reference example 43 (1.87 g) in THF (40 mL) was added sodium hydride (55%, 1.05 g), and the mixture was stirred at room temperature for 15 minutes. Thereto was added methanesulfonyl chloride (1.9 mL), and the mixture was stirred at room temperature for 1 hour. Thereto was added saturated aqueous ammonium chloride solution, and the mixture was extracted with ethyl acetate. The organic layer was washed with brine, dried over anhydrous sodium sulfate, filtered, and then concentrated under reduced pressure. The resulting residue was purified by silica gel column chromatography (hexane/ethyl acetate) to give the title compound (1.99 g) (yield 80%).

LC/MS, Condition D, Retention time 0.735 min, obs MS[M+1]312.1

Reference Example 45

2,2-Difluoro-1-(5-formylpyridin-2-yl)ethyl Methanesulfonate

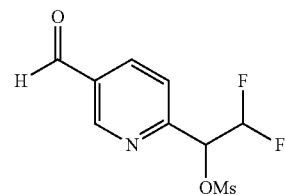 [SMILES: CS(=O)(=O)OC(c1ccc(C=O)cn1)C(F)F]

To a mixed solution of the compound of Reference example 44 (100 mg) in THF (0.5 mL)/acetone (1 mL)/water (1 mL) was added p-toluenesulfonic acid monohydrate (12 mg), and the mixture was stirred at room temperature for 1 hour 10 minutes. Then, thereto was added p-toluenesulfonic acid monohydrate (48 mg), and the mixture was stirred at room temperature for 5.5 hours. Thereto was added saturated aqueous sodium bicarbonate solution, and the mixture was extracted with ethyl acetate. The organic layer was washed with brine, dried over anhydrous sodium sulfate, filtered, and then concentrated under reduced pressure. The resulting residue was purified by silica gel column chromatography (hexane/ethyl acetate) to give the title compound (83 mg) (yield 97%).

LC/MS, Condition D, Retention time 0.611 min, obs MS[M+1]266.1

Reference Example 46

6-{2,2-Difluoro-1-[(methylsulfonyl)oxy]ethyl}nicotinic Acid

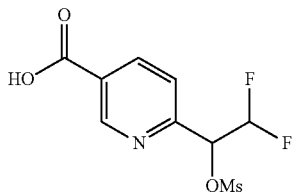 [SMILES: CS(=O)(=O)OC(c1ccc(C(=O)O)cn1)C(F)F]

To a mixed solution of the compound of Reference example 45 (82 mg) in acetone (4 mL)/water (2 mL) were added sodium phosphate monohydrate (128 mg), 2-methyl 2-butene (0.328 mL), and sodium chlorite (84 mg), and the mixture was stirred at room temperature for 1 hour and 10 minutes. Water was added thereto, and the mixture was extracted with ethyl acetate. The organic layer was washed with brine, dried over anhydrous sodium sulfate, filtered, and then concentrated under reduced pressure to give the title compound (54 mg) (yield 62%).

LC/MS, Condition D, Retention time 0.553 min, obs MS[M+1]282.0

Reference Example 47

6-(2,2-Difluoroethyl)nicotinic Acid

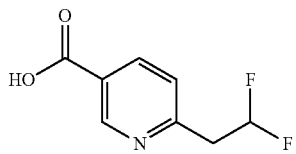 [SMILES: O=C(O)c1ccc(CC(F)F)nc1]

To a solution of the compound of Reference example 46 (5 mg) in ethyl acetate (2 mL) were added DIEA (0.0045 mL) and 10% palladium/carbon (25 mg), and the mixture was stirred for 1 hour at room temperature under hydrogen. Similarly, to a solution of the compound of Reference example 46 (44 mg) in ethyl acetate (4 mL) were added DIEA (0.040 mL) and 10% palladium/carbon (88 mg), and the mixture was stirred for 2 hours and 15 minutes at room temperature under hydrogen. The above two reaction mixtures were combined and filtered through Celite, and a substance on the filter was washed with ethyl acetate, and then the filtrate was concentrated under reduced pressure to give the title compound (32 mg) (crude yield 100%).

LC/MS, Condition D, Retention time 0.445 min, obs MS[M+1]188.0

Example 1

(E)-N-(1-(3-Chlorobenzyl)-1H-imidazol-4-yl)-3-(6-ethoxypyridin-3-yl)acrylamide

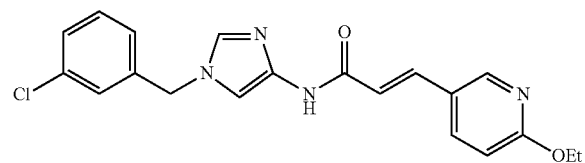 [SMILES: CCOc1ccc(/C=C/C(=O)Nc2cn(Cc3cccc(Cl)c3)cn2)cn1]

To a solution of the compound of Reference example 2 (29.0 mg) in DMF (3 mL) were added (E)-3-(6-ethoxypyridin-3-yl)acrylic acid (27.5 mg), WSCI.HCl (29.7 mg), HOBt (20.9 mg), and triethylamine (41 μL), and the mixture was stirred at room temperature overnight. To the reaction mixture was added water, and the mixture was extracted with ethyl acetate. The organic layer was washed with brine, dried over magnesium sulfate, filtered, and then concentrated under reduced pressure. The residue was purified by silica gel column chromatography (chloroform/methanol) to give the title compound (15 mg) (yield 33%).

¹H-NMR (400 MHz, DMSO-d₆) δ 10.63 (s, 1H), 8.42 (d, J=1.6 Hz, 1H), 7.96 (dd, J=9.2, 2.4 Hz, 1H), 7.74 (d, J=1.2 Hz, 1H), 7.54 (d, J=16.0 Hz, 1H), 7.51-7.43 (m, 4H), 7.36-7.33 (m, 1H), 6.95 (d, J=8.4 Hz, 1H), 6.86 (d, J=16.0 Hz, 1H), 5.27 (s, 2H), 4.41 (q, J=6.8 Hz, 2H), 1.40 (t, J=6.8 Hz, 3H).

Example 2

The compound of Example 2 was obtained by reaction/treatment using a corresponding starting compound in a similar manner to the process of Example 1.

| Example | Chemical structure | LC/MS, retention time (min) | LC-MS obs MS [M + 1] |
|---|---|---|---|
| 2 | 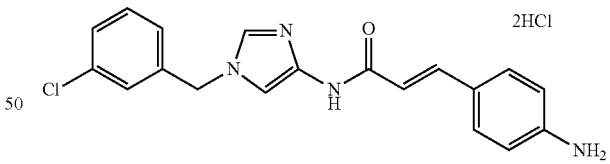 | 0.995 | 453.2 |

Example 3

(E)-3-(4-Aminophenyl)-N-(1-(3-chlorobenzyl)-1H-imidazol-4-yl)acrylamide Dihydrochloride To a solution of the compound of Example 2 (50 mg) in methanol (2 mL) was added 2 mol/L hydrochloric acid-methanol (1.5 mL), and the mixture was stirred at 40° C. for 3 hours. The resulting precipitate was filtered to give the title compound (35 mg) (yield 75%).

¹H-NMR (400 MHz, DMSO-d₆) δ 10.99-10.83 (m, 1H), 8.64-8.48 (m, 1H), 7.54-7.32 (m, 8H), 6.82-6.69 (m, 2H), 6.57-6.52 (m, 1H), 5.31 (s, 2H), 4.60 (brs, 2H).

LC/MS, Condition D, Retention time 0.761 min, obs MS[M+1]353.1

Example 4

(E)-N-(1-(3-Chlorobenzyl)-1H-imidazol-4-yl)-3-(4-(methylsulfonamide)phenyl)acrylamide

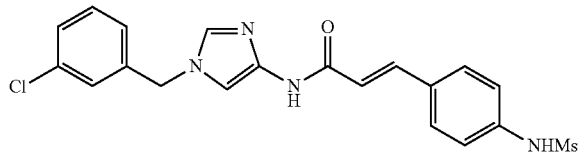

To a solution the compound of Example 3 (35 mg) in dichloromethane (5 mL) were added mesyl chloride (40 µL) and triethylamine (178 µL), and the mixture was stirred at room temperature overnight. Water was added to the reaction mixture, and the mixture was extracted with chloroform. The organic layer was washed with brine, dried over magnesium sulfate, filtered, and then concentrated under reduced pressure. The residue was dissolved in methanol (5 mL), and thereto was added 2 mol/L aqueous sodium hydroxide solution (0.8 mL). The mixture was stirred for 1 hour. Then, the mixture was extracted with chloroform, washed with brine, and then dried over magnesium sulfate. The mixture was filtered, and then concentrated under reduced pressure. The resulting solid was washed with methanol to give the title compound (3.9 mg) (yield 11%).

$^1$H-NMR (400 MHz, DMSO-$d_6$) δ 10.52 (s, 1H), 9.99 (brs, 1H), 7.64 (s, 1H), 7.51 (d, J=8.0 Hz, 2H), 7.44-7.34 (m, 5H), 7.26-7.20 (m, 3H), 6.76 (d, J=15.2 Hz, 1H), 5.18 (s, 2H), 3.02 (s, 3H).

LC/MS, Condition D, Retention time 0.805 min, obs MS[M+1]431.2

Example 5

(E)-3-(4-Aminophenyl)-N-(1-(3-chlorobenzyl)-1H-imidazol-4-yl)acrylamide

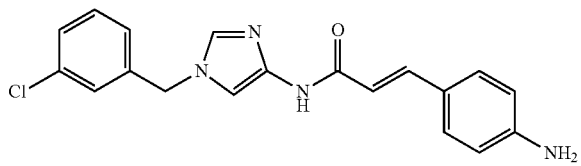 [SMILES: Nc1ccc(/C=C/C(=O)Nc2cn(Cc3cccc(Cl)c3)cn2)cc1]

To a solution of the compound of Example 2 (650 mg) in methanol (10 mL) was added 4 mol/L hydrochloric acid-dioxane (1.4 mL), and the mixture was stirred at 80° C. for 1.5 hours. The reaction mixture was concentrated under reduced pressure, and then adjusted to pH=10 by the addition of aqueous sodium hydroxide solution. The mixture was extracted with chloroform, washed with brine, and then dried over magnesium sulfate. The mixture was filtered, and then concentrated under reduced pressure. The residue was purified by silica gel column chromatography (chloroform/methanol) to give the title compound (0.22 g) (yield 43%).

$^1$H-NMR (400 MHz, DMSO-$d_6$) δ 10.29 (s, 1H), 7.61 (d, J=1.2 Hz, 1H), 7.44-7.34 (m, 3H), 7.31-7.19 (m, 5H), 6.55 (d, J=8.4 Hz, 2H), 6.51 (d, J=16.0 Hz, 1H), 5.59 (s, 2H), 5.17 (s, 2H).

LC/MS, Condition D, Retention time 0.709 min, obs MS[M+1]353.1

Example 6

(E)-N-(4-(3-((1-(3-Chlorobenzyl)-1H-imidazol-4-yl)amino)-3-oxoprop-1-en-1-yl)phenyl)butylamide

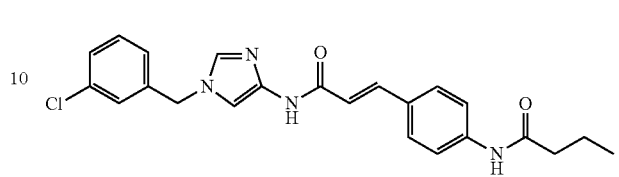

To a solution of the compound of Example 5 (40 mg) in THF (5 mL) were added butyryl chloride (18 µL) and diisopropylethylamine (57 µL), and the mixture was stirred at room temperature for 20 minutes. Then, thereto were added methanol (3 mL) and 2 mol/L aqueous sodium hydroxide solution (2 mL), and the mixture was stirred at 50° C. for 30 minutes. To the reaction mixture was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (6.5 mg) (yield 14%).

$^1$H-NMR (400 MHz, DMSO-$d_6$) δ 10.50 (s, 1H), 10.03 (s, 1H), 7.66-7.61 (m, 3H), 7.50-7.46 (m, 2H), 7.44-7.33 (m, 5H), 7.27-7.23 (m, 1H), 6.75 (d, J=16.0 Hz, 1H), 5.18 (s, 2H), 2.29 (t, J=7.2 Hz, 2H), 1.65-1.55 (m, 2H), 0.91 (t, J=7.2 Hz, 3H).

LC/MS, Condition D, Retention time 0.834 min, obs MS[M+1]423.3

Example 7

(E)-N-(1-(3-Chlorobenzyl)-1H-imidazol-4-yl)-3-(4-(2-hydroxyacetylamino)phenyl)acrylamide

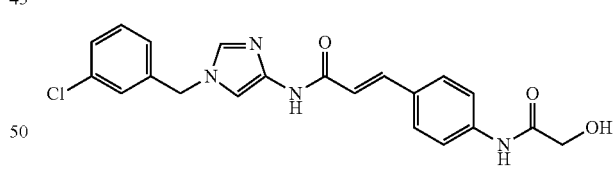

To a solution of the compound of Example 5 (83 mg) in THF (5 mL) were added 2-chloro-2-oxoethyl acetate (28 µL) and diisopropylethylamine (82 µL), and the mixture was stirred at room temperature overnight. Then, thereto were added methanol (2 mL) and 2 mol/L aqueous sodium hydroxide solution (1 mL), and the mixture was stirred at 50° C. for 30 minutes. Thereto were added chloroform and water, and the resulting precipitate was washed with water and ethyl acetate to give the title compound (51 mg) (yield 53%).

$^1$H-NMR (400 MHz, DMSO-$d_6$) δ 10.51 (s, 1H), 9.84 (s, 1H), 7.76 (d, J=8.8 Hz, 2H), 7.64 (d, J=2.0 Hz, 1H), 7.49 (d, J=8.4 Hz, 2H), 7.45-7.33 (m, 5H), 7.27-7.23 (m, 1H), 6.76 (d, J=16.0 Hz, 1H), 5.70 (brs, 1H), 5.18 (s, 2H), 4.00 (s, 2H).

LC/MS, Condition D, Retention time 0.690 min, obs MS[M+1]411.2

Example 8

(2E)-3-[4-(Acetylamino)phenyl]-N-(1-[3-(trifluoromethyl)benzyl]-1H-imidazol-4-yl)prop-2-enamide

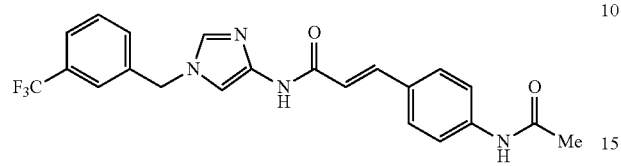

To a solution of the compound of Reference example 1 (2.0 g) in dimethylformamide (20 mL) were added (E)-3-(4-acetylaminophenyl)acrylic acid (1.41 g), HATU (2.88 g), and diisopropylethylamine (2.97 mL), and the mixture was stirred at room temperature overnight. To the reaction mixture were added aqueous saturated sodium bicarbonate solution and water, and the resulting precipitate was filtered and washed with water and acetonitrile. The resulting solid was purified by silica gel column chromatography (chloroform/methanol) to give the title compound (0.706 g) (yield 24%).

$^1$H-NMR (400 MHz, DMSO-$d_6$) δ 10.51 (s, 1H), 10.09 (s, 1H), 7.71-7.66 (m, 3H), 7.63-7.59 (m, 4H), 7.47 (d, J=8.5 Hz, 2H), 7.40 (d, J=15.9 Hz, 1H), 7.36 (d, J=1.8 Hz, 1H), 6.74 (d, J=15.9 Hz, 1H), 5.28 (s, 2H), 2.05 (s, 3H).

LC/MS, Condition D, Retention time 0.88 min, obs MS[M+1]429.5

Examples 9 to 13

The compounds of Examples 9 to 13 were obtained by reaction/treatment using corresponding starting compounds in a similar manner to the process of Example 8.

| Example | Chemical structure | $^1$H-NMR (400 MHz, DMSO-$d_6$) | LC/MS retention time (min) | LC-MS obs MS [M + 1] |
|---|---|---|---|---|
| 9 | (3-Cl-benzyl imidazole acrylamide acetamide) | δ 10.51 (s, 1H), 10.10 (s, 1H), 7.64 (d, J = 1.2 Hz, 1H), 7.62 (d, J = 8.5 Hz, 2H), 7.47 (d, J = 8.5 Hz, 2H), 7.42-7.36 (m, 4H), 7.33 (d, J = 1.2 Hz, 1H), 7.27-7.24 (m, 1H), 6.74 (d, J = 15.8 Hz, 1H), 5.18 (s, 2H), 2.05 (s, 3H). | 0.80 | 395.2 |
| 10 | (3-F3CO-benzyl imidazole acrylamide acetamide) | δ 10.50 (s, 1H), 10.09 (s, 1H), 7.64 (brs, 1H), 7.61 (d, J = 8.5 Hz, 2H), 7.53-7.50 (m, 1H), 7.47 (d, J = 8.5 Hz, 2H), 7.40 (d, J = 15.9 Hz, 1H), 7.35-7.29 (m, 4H), 6.74 (d, J = 15.9 Hz, 1H), 5.23 (s, 2H), 2.05 (s, 3H). | 0.89 | 445.2 |
| 11 | (3,4,5-trifluorobenzyl imidazole acrylamide acetamide) | δ 10.51 (s, 1H), 10.10 (s, 1H), 7.64-7.61 (m, 3H), 7.47 (d, J = 8.5 Hz, 2H), 7.41 (d, J = 15.9 Hz, 1H), 7.37 (d, J = 1.2 Hz, 1H), 7.34-7.29 (m, 2H), 6.74 (d, J = 15.9 Hz, 1H), 5.15 (s, 2H), 2.05 (s, 3H). | 0.78 | 415.3 |

-continued

| Example | Chemical structure | ¹H-NMR (400 MHz, DMSO-d₆) | LC/MS retention time (min) | LC-MS obs MS [M + 1] |
|---|---|---|---|---|
| 12 | 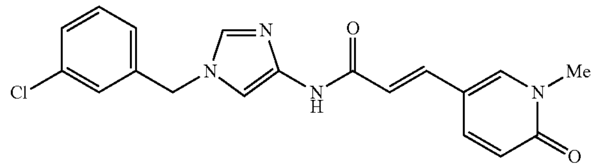 [SMILES: Cn1cc(/C=C/C(=O)Nc2cn(Cc3cccc(Cl)c3)cn2)ccc1=O] | δ 10.44 (s, 1H), 8.05 (d, J = 2.4 Hz, 1H), 7.64-7.63 (m, 1H), 7.59 (dd, J = 2.4, 6.7 Hz, 1H), 7.42-7.36 (m, 3H), 7.31 (d, J = 1.8 Hz, 1H), 7.28-7.24 (m, 2H), 6.53 (d, J = 15.9 Hz, 1H), 6.48 (d, J = 7.9 Hz), 5.17 (s, 2H), 3.42 (s, 3H). | 0.83 | 369.1 |
| 13 | 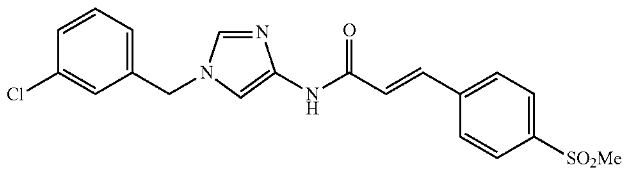 [SMILES: CS(=O)(=O)c1ccc(/C=C/C(=O)Nc2cn(Cc3cccc(Cl)c3)cn2)cc1] | δ 10.73 (s, 1H), 7.95 (d, J = 8.5 Hz, 2H), 7.80 (d, J = 8.5 Hz, 2H), 7.66 (d, J = 1.2 Hz, 2H), 7.56 (d, J = 15.9 Hz, 1H), 7.42-7.36 (m, 4H), 7.27-7.24 (m, 1H), 7.01 (d, J = 15.9 Hz, 1H), 5.19 (s, 2H), 3.23 (s, 3H). | 0.75 | 416.2 |

Example 14

(E)-N-(1-(3-Chlorobenzyl)-1H-imidazol-4-yl)-3-(6-((2,2-difluoroethyl)amino)pyridin-3-yl)acrylamide

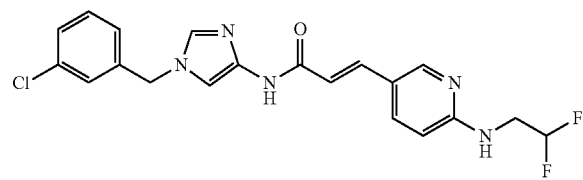 [SMILES: O=C(/C=C/c1ccc(NCC(F)F)nc1)Nc1cn(Cc2cccc(Cl)c2)cn1]

To a solution of the compound of Reference example 2 (0.16 g) in dimethylformamide (5 mL) were added the compound of Reference example 10 (0.204 g), HATU (0.356 g), and diisopropylethylamine (0.268 mL), and the mixture was stirred at room temperature for 5 hours. To the reaction mixture were added aqueous saturated sodium bicarbonate solution and water, and the resulting precipitate was filtered and washed with water. The resulting solid was roughly purified by silica gel column chromatography (chloroform/methanol), and then to the residue was added trifluoroacetic acid (8 mL). The mixture was stirred at room temperature for 3 hours, and then concentrated under reduced pressure to remove trifluoroacetic acid. Then, thereto were added water (5 mL) and acetonitrile (5 mL), followed by 28% ammonia water (1 mL). The resulting precipitate was filtered, washed with water and acetonitrile, and then dried under reduced pressure to give the title compound (0.139 g) (yield 53%).

¹H-NMR (400 MHz, DMSO-d₆) δ 10.44 (s, 1H), 8.17 (d, J=2.4 Hz, 1H), 7.70 (brs, 1H), 7.63 (dd, J=1.8, 8.5 Hz, 2H), 7.46 (brs, 1H), 7.42-7.33 (m, 5H), 7.27-7.24 (m, 1H), 6.65 (d, J=9.2 Hz, 1H), 6.61 (d, J=15.9 Hz, 1H), 6.10 (tt, J=4.3, 48.2 Hz, 1H), 5.19 (s, 2H), 3.79-3.68 (m, 2H).

LC/MS, Condition D, Retention time 1.09 min, obs MS[M+1]418.2

Examples 15 to 18

The compounds of Examples 15 to 18 were obtained by reaction/treatment using corresponding starting compounds in a similar manner to the process of Example 14.

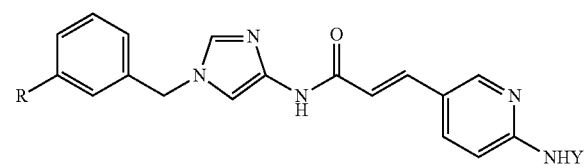

| Example | R | Y | ¹H-NMR (400 MHz, DMSO-d₆) | LC-MS retention time (min) | LC-MS obs MS [M + 1] |
|---|---|---|---|---|---|
| 15 | Cl | CH₂CF₃ | δ 10.43 (s, 1H), 8.19 (d, J = 2.4 Hz, 1H), 7.67-7.63 (m, 2H), 7.60-7.57 (m, 1H), 7.42-7.32 (m, 5H), 7.26-7.23 (m, 1H), | 0.86 | 436.2 |

| Example | R | Y | ¹H-NMR (400 MHz, DMSO-d₆) | LC-MS retention time (min) | LC-MS obs MS [M + 1] |
|---|---|---|---|---|---|
| | | | 6.68 (d, J = 8.5 Hz, 1H), 6.64 (d, J = 15.9 Hz, 1H), 5.18 (s, 2H), 4.20 (dq, J = 3.1, 6.7 Hz, 2H). | | |
| 16 | Cl | Me | δ 10.35 (s, 1H), 8.13 (d, J = 2.4 Hz, 1H), 7.62 (brs, 1H), 7.55 (dd, J = 1.8, 8.5 Hz, 1H), 7.42-7.31 (m, 5H), 7.27-7.22 (m, 1H), 7.01-6.96 (m, 1H), 6.57 (d, J = 15.9 Hz, 1H), 6.48 (d, J = 9.1 Hz, 1H), 5.17 (s, 2H), 2.79 (d, J = 4.3 Hz, 3H). | 0.65 | 368.2 |
| 17 | CF₃ | Me | δ 10.36 (s, 1H), 8.13 (d, J = 2.4 Hz, 1H), 7.71-7.53 (m, 6H), 7.33 (dd, J = 1.8, 8.5 Hz, 1H), 7.01-6.96 (m, 1H), 6.57 (d, J = 15.9 Hz, 1H), 6.49 (d, J = 8.5 Hz, 1H), 5.27 (s, 2H), 2.79 (d, J = 4.9 Hz, 3H). | 0.69 | 402.2 |
| 18 | Cl | Et | δ 10.36 (s, 1H), 8.11 (brs, 1H), 7.56-7.52 (m, 1H), 7.42-7.31 (m, 5H), 7.25 (dd, J = 1.2, 6.7 Hz, 1H), 7.03-7.00 (m, 1H), 6.56 (dd, J = 1.2, 15.3 Hz, 1H), 6.48 (d, J = 8.5 Hz, 2H), 5.17 (s, 1H), 3.36-3.26 (m, 2H), 1.12 (dt, J = 1.2, 7.3 Hz, 3H). | 0.72 | 382.2 |

Example 19

(E)-3-(6-Aminopyridin-3-yl)-N-(1-(3-chlorobenzyl)-1H-imidazol-4-yl)acrylamide

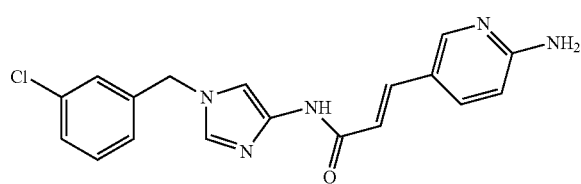 [SMILES: Nc1ccc(/C=C/C(=O)Nc2cn(Cc3cccc(Cl)c3)cn2)cn1]

To a mixed solution of the compound of Reference example 13 (0.809 g) in methanol (9 mL)-tetrahydrofuran (9 mL) was added 1 mol/L aqueous sodium hydroxide solution (9 ml). The mixture was stirred at room temperature for 2 hours, and then the organic solvent was removed under reduced pressure. Then, thereto was added 1 mol/L hydrochloric acid, and the resulting precipitate was filtered, washed with water and hexane, and then dried under reduced pressure. To a solution of the resulting solid in dimethylformamide (5 mL) were added the compound of Reference example 2 (0.132 g), HATU (0.247 g), and diisopropylethylamine (0.280 mL), and the mixture was stirred at room temperature overnight. To the reaction mixture were added aqueous saturated sodium bicarbonate solution and water, and the resulting precipitate was filtered. The resulting solid was washed with water and acetonitrile, and then thereto was added trifluoroacetic acid (5 mL). The mixture was stirred at room temperature for 3 hours, and then concentrated under reduced pressure to remove trifluoroacetic acid. Thereto were added water (5 mL) and acetonitrile (5 mL), followed by 28% ammonia water (1 mL). The resulting precipitate was filtered, washed with water and acetonitrile, and then dried under reduced pressure to give the title compound (0.042 g) (yield 23%).

¹H-NMR (400 MHz, DMSO-d₆) δ 10.35 (s, 1H), 8.06 (d, J=2.4 Hz, 1H), 7.62 (d, J=1.8 Hz, 1H), 7.55 (dd, J=1.8, 8.5 Hz, 2H), 7.42-7.30 (m, 5H), 7.26-7.23 (m, 1H), 6.57 (d, J=15.3 Hz, 1H), 6.47 (d, J=8.5 Hz, 1H), 6.42 (s, 2H), 5.17 (s 2H).

LC/MS, Condition D, Retention time 0.61 min, obs MS[M+1]354.2

Example 20

(E)-3-(6-Acetylaminopyridin-3-yl)-N-(1-(3-chlorobenzyl)-1H-imidazol-4-yl)acrylamide

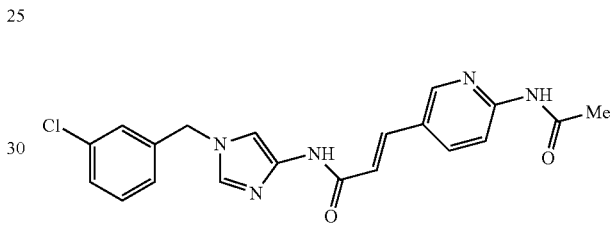

To a solution of the compound of Example 19 (0.042 g) in pyridine (3 mL) was added anhydrous acetic acid (1 ml). The mixture was stirred at 70° C. for 4 hours, and then the organic solvent was removed under reduced pressure. Thereto were added aqueous saturated sodium bicarbonate solution and water, and the resulting precipitate was filtered, washed with water and acetonitrile, and then dried under reduced pressure to give the title compound (0.026 g) (yield 55%).

¹H-NMR (400 MHz, DMSO-d₆) δ 10.66 (s, 1H), 10.57 (s, 1H), 8.47 (d, J=1.8 Hz, 1H), 8.12 (d, J=8.5 Hz, 1H), 7.94 (dd, J=1.8, 8.5 Hz, 2H), 7.65 (brs, 1H), 7.45 (d, J=15.9 Hz, 1H), 7.42-7.35 (m, 4H), 7.25 (d, J=6.7 Hz, 1H), 6.84 (d, J=15.9 Hz, 1H), 5.18 (s, 2H), 2.10 (s 3H).

LC/MS, Condition D, Retention time 0.74 min, obs MS[M+1]396.2

Example 21

(E)-N-(1-(3-Chlorobenzyl)-1H-imidazol-4-yl)-3-(3,4-dihydroxyphenyl)acrylamide

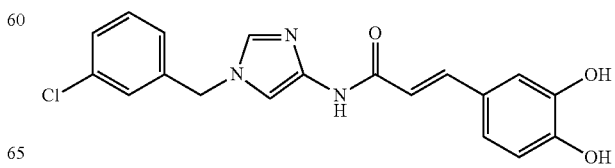

To a solution of the compound of Reference example 2 (73.0 mg) in DMF (3 mL) were added (E)-3-(3,4-dihydroxyphenyl)acrylic acid (64.9 mg), HBTU (136.5 mg), and triethylamine (92 µL), and the mixture was stirred at room temperature for 4 hours. To the reaction mixture was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (8 mg) (yield 33%).

$^1$H-NMR (400 MHz, DMSO-d$_6$) δ 10.43 (s, 1H), 9.24 (brs, 2H), 7.63 (d, J=1.6 Hz, 1H), 7.42-7.35 (m, 3H), 7.32-7.23 (m, 3H), 6.95 (d, J=2.0 Hz, 1H), 7.83 (dd, J=8.0, 2.0 Hz, 1H), 6.73 (d, J=8.0 Hz, 1H), 6.56 (d, J=16.0 Hz, 1H), 5.17 (s, 2H).

Example 22

The compound of Example 22 was obtained by reaction/treatment using a corresponding starting compound in a similar manner to the process of Example 21.

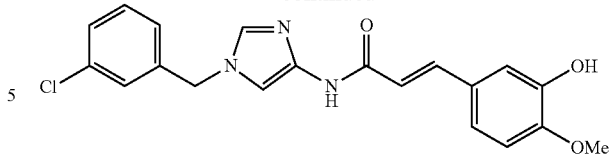

To a solution of the compound of Reference example 2 (1.70 g) in DMF (30 mL) were added (E)-3-(3-acetoxy-4-methoxyphenyl)acrylic acid (1.97 g), HBTU (3.17 g), and triethylamine (2.1 mL), and the mixture was stirred at room temperature overnight. To the reaction mixture was added water, and the mixture was extracted with chloroform. The organic layer was washed with brine and dried over magnesium sulfate. Poorly soluble substances were removed by filtration, and then the filtrate was concentrated under reduced pressure. The resulting solid was washed with methanol to give a crude product. The washings were concentrated under reduced pressure, and the residue was

| Example | Chemical structure | LC/MS, retention time (min) | LC-MS obs MS [M + 1] |
|---|---|---|---|
| 22 | 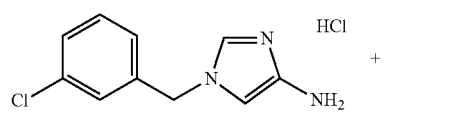 | 0.867 | 363.1 |

Example 23

(E)-N-(1-(3-Chlorobenzyl)-1H-imidazol-4-yl)-3-(3-hydroxy-4-methoxyphenyl)acrylamide

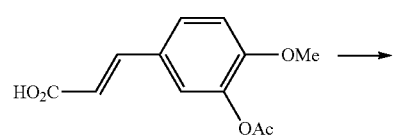

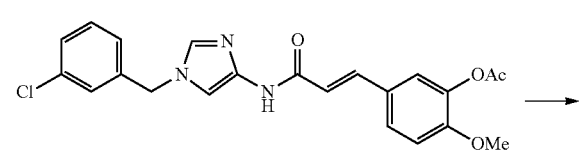

purified by silica gel column chromatography (chloroform/methanol). The resulting product was suspended with the crude product in methanol (20 mL), and then thereto was added potassium carbonate (0.79 g). The mixture was stirred at room temperature for 40 minutes. The mixture was concentrated under reduced pressure to remove methanol, and then thereto was added chloroform/water. The resulting solid was filtered, washed with water, followed by methanol and ethyl acetate to give the title compound (0.86 g).

$^1$H-NMR (400 MHz, DMSO-d$_6$) δ 10.43 (s, 1H), 7.63-7.61 (m, 1H), 7.42-7.36 (m, 3H), 7.32-7.23 (m, 3H), 6.68-6.63 (m, 3H), 6.56 (d, J=16.0 Hz, 1H), 5.17 (s, 2H), 3.73 (s, 3H).

LC/MS, Condition D, Retention time 0.771 min, obs MS[M+1]384.2

Example 24

The compound of Example 24 was obtained by reaction/treatment using a corresponding starting compound in a similar manner to the process of Example 23 with the exception that WSCI.HCl and 1-hydroxybenztriazole anhydride were used instead of HBTU.

| Example | Chemical structure | ¹H-NMR (400 MHz, DMSO-d₆) |
|---|---|---|
| 24 | 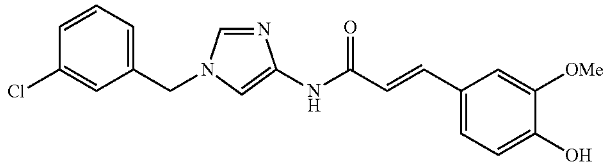 [SMILES: COc1cc(/C=C/C(=O)Nc2cn(Cc3cccc(Cl)c3)cn2)ccc1O] | δ 10.38 (s, 1H), 9.45 (s, 1H), 7.63 (d, J = 1.2 Hz, 1H), 7.42-7.32 (m, 5H), 7.27-7.24 (m, 1H), 7.10 (d, J = 2.0 Hz, 1H), 6.79 (d, J = 8.8 Hz, 1H), 6.68 (d, J = 16.0 Hz, 1H), 5.17 (s, 2H), 3.80 (s, 3H). |

Example 25

Methyl (E)-5-(3-((1-(3-chlorobenzyl)-1H-imidazol-4-yl)amino)-3-oxoprop-1-en-1-yl)picolinate

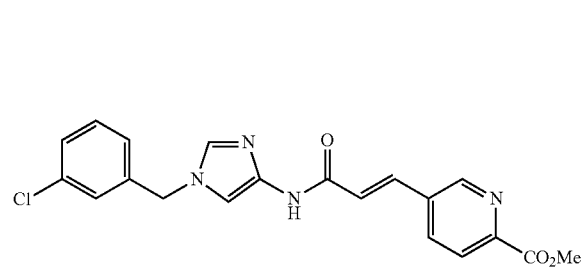 [SMILES: COC(=O)c1ccc(/C=C/C(=O)Nc2cn(Cc3cccc(Cl)c3)cn2)cn1]

To a solution of the compound of Reference example 2 (700 mg) in DMF (3 mL) were added the compound of Reference example 18 (835 mg), WSCI.HCl (659 mg), HOBt (465 mg), and triethylamine (1.39 mL), and the mixture was stirred at room temperature for 2 hours. To the reaction mixture was added water, and the mixture was extracted with chloroform. The organic layer was washed with brine, dried over magnesium sulfate, filtered, and then concentrated under reduced pressure. The resulting solid was washed with methanol and diisopropyl ether to give the title compound (0.79 g) (yield 69%).

LC/MS, Condition D, Retention time 0.753 min, obs MS[M+1]397.2

Example 26

(E)-5-(3-((1-(3-Chlorobenzyl)-1H-imidazol-4-yl)amino)-3-oxoprop-1-en-1-yl)-N-ethylpicolinamide

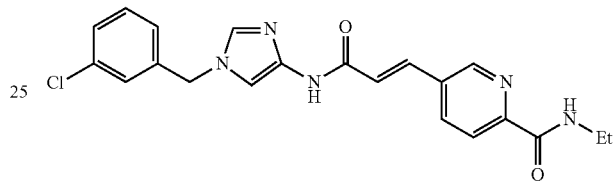

To a solution of the compound of Reference example 32 (35 mg) in DMF (3 mL) were added 70% aqueous ethylamine solution (36 μL), HBTU (52 mg), and triethylamine (64 μL), and the mixture was stirred at room temperature for 5 hours. Then, thereto were added 70% aqueous ethylamine solution (36 μL), HBTU (104 mg), and triethylamine (64 μL), and the mixture was stirred at room temperature for 2 hours. To the reaction mixture was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (9 mg) (yield 24%).

LC/MS, Condition D, Retention time 0.817 min, obs MS[M+1] 410.2

Examples 27 to 28

The compounds of Examples 27 to 28 were obtained by reaction/treatment using corresponding starting compounds in a similar manner to the process of Example 26.

| Example | Chemical structure | LC-MS retention time (min) | LC-MS obs MS [M + 1] |
|---|---|---|---|
| 27 | 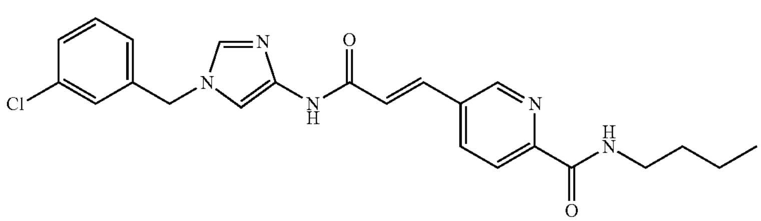 [SMILES: CCCCNC(=O)c1ccc(/C=C/C(=O)Nc2cn(Cc3cccc(Cl)c3)cn2)cn1] | 0.945 | 438.3 |

| Example | Chemical structure | LC-MS retention time (min) | LC-MS obs MS [M + 1] |
|---|---|---|---|
| 28 | 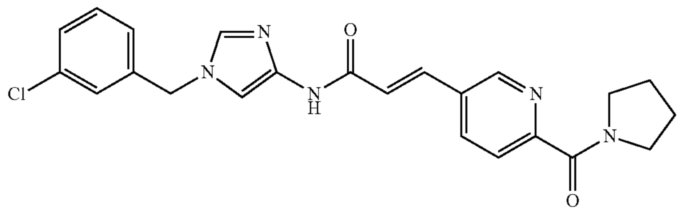 [SMILES: O=C(/C=C/c1ccc(C(=O)N2CCCC2)nc1)Nc1cn(Cc2cccc(Cl)c2)cn1] | 0.793 | 436.2 |

Example 29

(E)-N-(1-(3-Chlorobenzyl)-1H-imidazol-4-yl)-3-(4-methoxy-3-(2-methoxyethoxy)phenyl)acrylamide

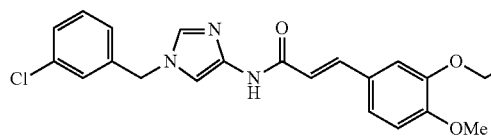

To a solution of the compound of Example 23 (20.0 mg) in DMF (3 mL) were added potassium carbonate (11.0 mg) and 1-chloro-2-methoxyethane (12 μL), and the mixture was stirred at 80° C. for 3 hours. To the reaction mixture was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (9 mg) (yield 39%).

LC/MS, Condition D, Retention time 0.836 min, obs MS[M+1]442.2

Example 30

The compound of Example 30 was obtained by reaction/treatment using a corresponding starting compound in a similar manner to the process of Example 29.

Example 31

(E)-3-(3-Hydroxy-4-methoxyphenyl)-N-(1-(3-(trifluoromethyl)benzyl)-1H-imidazol-4-yl)acrylamide

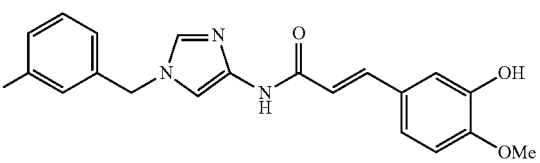

To a solution of the compound of Reference example 19 (30.0 mg) in methanol (4 mL) was added potassium carbonate (27.0 mg), and the mixture was stirred at room temperature for 2 hours. The reaction mixture was concentrated under reduced pressure, and then neutralized with aqueous hydrochloric acid solution and extracted with chloroform. The organic layer was washed with brine, dried over magnesium sulfate, filtered, and then concentrated under reduced pressure. The residue was purified by silica gel column chromatography (chloroform/methanol) to give the title compound (10 mg) (yield 37%).

$^1$H-NMR (400 MHz, CDCl$_3$) δ 8.67 (s, 1H), 7.64-7.45 (m, 6H), 7.41-7.36 (m, 2H), 7.16 (s, 1H), 7.04 (d, J=8.4 Hz, 1H), 6.85 (d, J=8.8 Hz, 1H), 6.41 (d, J=15.2 Hz, 1H), 5.17 (s, 2H), 3.94 (s, 3H).

LC/MS, Condition D, Retention time 0.954 min, obs MS[M+1]418.2

| Example | Chemical structure | LC-MS retention time (min) | LC-MS obs MS [M + 1] |
|---|---|---|---|
| 30 | 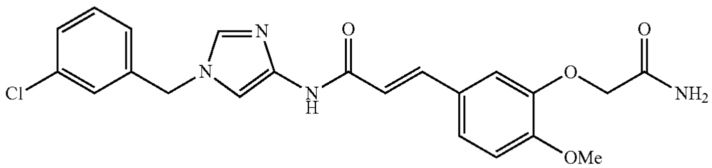 [SMILES: COc1ccc(/C=C/C(=O)Nc2cn(Cc3cccc(Cl)c3)cn2)cc1OCC(N)=O] | 0.720 | 441.2 |

Example 32

(E)-3-(3-(2-Hydroxyethoxy)-4-methoxyphenyl)-N-(1-(3,4,5-trifluorobenzyl)-1H-imidazol-4-yl)acrylamide

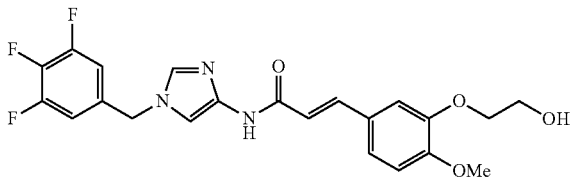 [SMILES: COc1ccc(/C=C/C(=O)Nc2cn(Cc3cc(F)c(F)c(F)c3)cn2)cc1OCCO]

To a solution of the compound of Reference example 24 (125 mg) in methanol (10 mL) was added 4 mol/L hydrochloric acid-dioxane (88 µL), and the mixture was stirred at 80° C. for 40 minutes. The reaction mixture was concentrated under reduced pressure, and then thereto was added 2 mol/L aqueous sodium hydroxide solution. The mixture was extracted with chloroform. The organic layer was washed with brine, dried over magnesium sulfate, filtered, and then concentrated under reduced pressure. The residue was purified by silica gel column chromatography (chloroform/methanol) to give the title compound (72 mg) (yield 68%).

$^1$H-NMR (400 MHz, DMSO-$d_6$) δ 10.39 (s, 1H), 7.63 (d, J=1.2 Hz, 1H), 7.42-7.30 (m, 4H), 7.15-7.11 (m, 2H), 6.99 (d, J=8.8 Hz, 1H), 6.74 (d, J=16.0 Hz, 1H), 5.15 (s, 2H), 4.85 (t, J=5.6 Hz, 1H), 4.02-3.98 (m, 2H), 3.78 (s, 3H), 3.74-3.70 (m, 2H).

LC/MS, Condition D, Retention time 0.758 min, obs MS[M+1]448.3

Example 33

(2E)-N-[1-(3-Chlorobenzyl)-1H-imidazol-4-yl]-3-[3-(2-hydroxyethoxy)-4-methoxyphenyl]prop-2-enamide

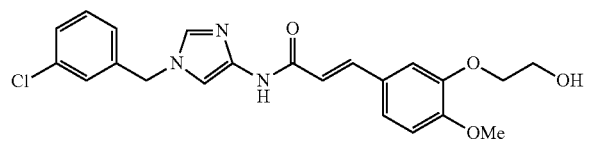 [SMILES: COc1ccc(/C=C/C(=O)Nc2cn(Cc3cccc(Cl)c3)cn2)cc1OCCO]

To a solution of the compound of Reference example 22 (1.25 g) in methanol (10 mL) was added tosic acid monohydrate (0.46 g), and the mixture was stirred at 40° C. for 2.5 hours. To the reaction mixture were added aqueous saturated sodium bicarbonate solution and chloroform, and the resulting precipitate was washed with water and dried. The filtrate was extracted with chloroform, washed with brine, and then dried over magnesium sulfate and filtered. Then, the reaction mixture was concentrated under reduced pressure, and the resulting solid was washed with methanol and ethyl acetate. The resultant was combined with the solid obtained above to give the title compound (0.84 g) (yield 81%).

$^1$H-NMR (400 MHz, DMSO-$d_6$) δ 10.40 (s, 1H), 7.64 (d, J=1.2 Hz, 1H), 7.43-7.36 (m, 4H), 7.33 (d, J=1.2 Hz, 1H), 7.27-7.24 (m, 1H), 7.16-7.10 (m, 2H), 7.00 (d, J=8.8 Hz, 1H), 6.75 (d, J=16.0 Hz, 1H), 5.18 (s, 2H), 4.87 (t, J=5.6 Hz, 1H), 4.02-3.98 (m, 2H), 3.78 (s, 3H), 3.75-3.70 (m, 2H)

LC/MS, Condition D, Retention time 0.772 min, obs MS[M+1]428.2

Example 34

The compound of Example 34 was obtained by reaction/treatment using a corresponding starting compound in a similar manner to the process of Example 33.

| Example | Chemical structure | LC-MS retention time (min) | LC obs MS [M + 1] |
|---|---|---|---|
| 34 | 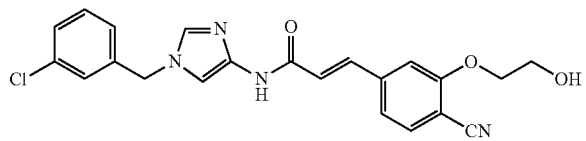 [SMILES: N#Cc1ccc(/C=C/C(=O)Nc2cn(Cc3cccc(Cl)c3)cn2)cc1OCCO] | 0.86 | 462.2 |

Example 35

(2E)-N-(1-(3-Chlorobenzyl)-1H-imidazol-4-yl)-3-[4-cyano-3-(2-hydroxyethoxy)phenyl]prop-2-enamide To a solution of the compound of Reference example 25 (125 mg) in methanol (5 mL) was added tosic acid monohydrate (47.0 mg), and the mixture was stirred at 40° C. for 5 hours. To the reaction mixture was added aqueous saturated sodium bicarbonate solution, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (73 mg) (yield 69%).

$^1$H-NMR (400 MHz, DMSO-$d_6$) δ 10.65 (s, 1H), 7.78-7.66 (m, 1H), 7.68-7.65 (m, 1H), 7.54-7.36 (m, 6H), 7.30-7.24 (m, 2H), 7.00 (d, J=15.2 Hz, 1H), 5.18 (s, 2H), 4.97-4.94 (m, 1H), 4.26-4.20 (m, 2H), 3.81-3.73 (m, 2H).

LC/MS, Condition D, Retention time 0.815 min, obs MS[M+1]423.2

Example 36

(E)-3-(4-Cyano-3-(2-hydroxyethoxy)phenyl)-N-(1-(3-(trifluoromethyl)benzyl)-1H-imidazol-4-yl)acrylamide

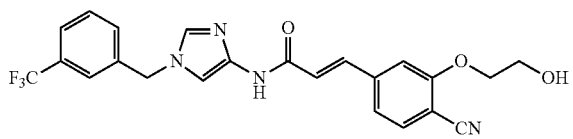 [SMILES: N#Cc1ccc(/C=C/C(=O)Nc2cn(Cc3cccc(C(F)(F)F)c3)cn2)cc1OCCO]

To a solution of the compound of Reference example 26 (180 mg) in methanol (5 mL) was added tosic acid monohydrate (63.0 mg), and the mixture was stirred at 40° C. for 5 hours. To the reaction mixture was added aqueous saturated sodium bicarbonate solution, and the mixture was extracted with chloroform. The organic layer was washed with brine, dried over magnesium sulfate, filtered, and then the reaction mixture was concentrated under reduced pressure. The resulting solid was washed with diisopropyl ether and ethyl acetate to give the title compound (103 mg) (yield 68%).

$^1$H-NMR (400 MHz, DMSO-$d_6$) δ 10.66 (s, 1H), 7.75 (d, J=8.0 Hz, 1H), 7.72-7.67 (m, 3H), 7.63-7.57 (m, 2H), 7.51 (d, J=16.0 Hz, 1H), 7.43-7.39 (m, 2H), 7.26 (d, J=8.0 Hz, 1H), 7.00 (d, J=16.0 Hz, 1H), 5.29 (s, 2H), 4.95 (t, J=5.6 Hz, 1H), 4.22-4.19 (m, 2H), 3.78-3.73 (m, 2H).

LC/MS, Condition D, Retention time 0.854 min, obs MS[M+1]457.2

Example 37

(E)-3-(4-Fluoro-3-hydroxyphenyl)-N-(1-(3-(trifluoromethyl)benzyl)-1H-imidazol-4-yl)acrylamide Hydrochloride

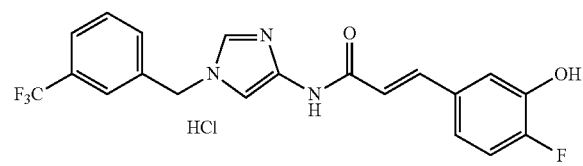 [SMILES: O=C(/C=C/c1ccc(F)c(O)c1)Nc1cn(Cc2cccc(C(F)(F)F)c2)cn1 ; Cl]

To a solution of the compound of Reference example 28 (425 mg) in methanol (5 mL) was added 2 mol/L hydrochloric acid-methanol (1.4 mL), and the mixture was stirred at 70° C. for 4 hours. The resulting precipitate was filtered and washed with ethyl acetate to give the title compound (399 mg) (yield 95%).

$^1$H-NMR (400 MHz, DMSO-$d_6$) δ 11.01 (s, 1H), 10.15 (brs, 1H), 8.40 (brs, 1H), 7.82 (brs, 1H), 7.73-7.62 (m, 3H), 7.53-7.52 (m, 1H), 7.45 (d, J=15.6 Hz, 1H), 7.21-7.15 (m, 2H), 7.04-7.01 (m, 1H), 6.69 (d, J=15.6 Hz, 1H), 5.39 (s, 2H).

LC/MS, Condition D, Retention time 0.897 min, obs MS[M+1]406.2

Example 38

The compound of Example 38 was obtained by reaction/treatment using a corresponding starting compound in a similar manner to the process of Example 37.

| Example | Chemical structure | LC-MS retention time (min) | LC-MS obs MS [M + 1] |
|---|---|---|---|
| 38 | (structure shown with Cl-benzyl imidazole acrylamide phenyl-OH, F, HCl) | 0.875 | 372.1 |

Example 39

(E)-3-(4-Fluoro-3-(2-hydroxyethoxy)phenyl)-N-(1-(3-(trifluoromethyl)benzyl)-1H-imidazol-4-yl)acrylamide Hydrochloride To a solution of the compound of Reference example 33 (215 mg) in methanol (5 mL) was added 4 mol/L hydrochloric acid-dioxane (0.15 mL), and the mixture was stirred at 80° C. for 1.5 hours. The reaction mixture was concentrated under reduced pressure, and the resulting solid was washed with ethyl acetate and filtered to give the title compound (168 mg) (yield 86%).

$^1$H-NMR (400 MHz, DMSO-$d_6$) δ 11.03 (brs, 1H), 8.49 (brs, 1H), 7.86-7.80 (m, 1H), 7.75-7.62 (m, 3H), 7.57-7.51 (m, 2H), 7.44-7.39 (m, 1H), 7.30-7.24 (m, 1H), 7.22-7.17 (m, 1H), 6.83 (d, J=16.0 Hz, 1H), 5.41 (s, 2H), 4.14-4.08 (m, 2H), 3.76-3.72 (m, 2H).

LC/MS, Condition D, Retention time 0.895 min, obs MS[M+1]450.2

Example 40

The compound of Example 40 was obtained by reaction/treatment using a corresponding starting compound in a similar manner to the process of Example 39.

| Example | Chemical structure | LC-MS retention time (min) | LC-MS obs MS [M + 1] |
|---|---|---|---|
| 40 | 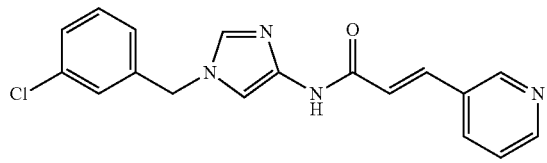 [SMILES: O=C(/C=C/c1cccnc1)Nc1cn(Cc2cccc(Cl)c2)cn1]<br>HCl | 0.858 | 416.2 |

Example 41

(2E)-N-(1-(3-Chlorobenzyl)-1H-imidazol-4-yl)-3-(pyridin-3-yl)prop-2-enamide

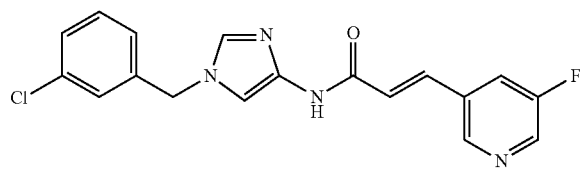 [SMILES: O=C(/C=C/c1cncc(F)c1)Nc1cn(Cc2cccc(Cl)c2)cn1]

To a solution of the compound of Reference example 2 (2.00 g) in DMF (100 mL) were added (E)-3-pyridin-3-yl) acrylic acid (1.47 g), WSCI.HCl (2.03 g), HOBt (1.43 g), and triethylamine (3.76 mL), and the mixture was stirred at room temperature overnight. To the reaction mixture was added water, and the mixture was extracted with ethyl acetate. The organic layer was washed with brine, dried over magnesium sulfate, filtered, and then concentrated under reduced pressure. The resulting solid was washed with chloroform. The filtrate was concentrated under reduced pressure, and the residue was purified by silica gel column chromatography (chloroform/methanol). The resultant was combined with the solid obtained above to give the title compound (1.46 g) (yield 53%).

$^1$H-NMR (300 MHz, DMSO-$d_6$) δ 10.7 (s, 1H), 8.75 (s, 1H), 8.56-8.55 (m, 1H), 7.95 (d, 1H, J=9.0 Hz), 7.67 (s, 1H), 7.55-7.38 (m, 6H), 7.27-7.25 (m, 1H), 6.96 (d, 1H, J=15.0 Hz), 5.19 (s, 2H).

Example 42

(E)-N-(1-(3-Chlorobenzyl)-1H-imidazol-4-yl)-3-(5-fluoropyridin-3-yl)acrylamide

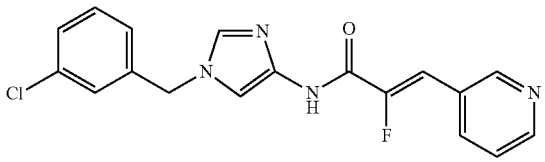 [SMILES: O=C(Nc1cn(Cc2cccc(Cl)c2)cn1)/C(F)=C/c1cccnc1]

To a solution of the compound of Reference example 2 (70.0 mg) in DMF (5 mL) were added (E)-3-(5-fluoropyridin-3-yl)acrylic acid (57.5 mg), WSCI.HCl (65.9 mg), HOBt (50.4 mg), and triethylamine (0.132 mL), and the mixture was stirred at room temperature overnight. To the reaction mixture was added water, and then the mixture was extracted with ethyl acetate. The organic layer was washed with brine, dried over magnesium sulfate, filtered, and then concentrated under reduced pressure. The residue was purified by silica gel column chromatography (chloroform/methanol). The resulting solid was washed with chloroform to give the title compound (58.8 mg) (yield 57%).

$^1$H-NMR (300 MHz, DMSO-$d_6$) δ 10.7 (s, 1H), 8.65 (s, 1H), 8.57 (s, 1H), 7.90-7.87 (m, 1H), 7.67 (s, 1H), 7.54 (d, 1H, J=18.0 Hz), 7.40-7.38 (m, 4H), 7.28-7.25 (m, 1H), 7.00 (d, 1H, J=15.0 Hz), 5.19 (s, 2H).

Example 43

(Z)—N-(1-(3-Chlorobenzyl)-1H-imidazol-4-yl)-2-fluoro-3-(pyridin-3-yl)acrylamide

To a solution of the compound of Reference example 2 (70.0 mg) in DMF (5 mL) were added (Z)-2-fluoro-3-(pyridin-3-yl)acrylic acid (57.5 mg), WSCI.HCl (65.9 mg), HOBt (50.4 mg), and triethylamine (0.132 mL), and the mixture was stirred at room temperature overnight. To the reaction mixture was added water, and then the mixture was extracted with ethyl acetate. The organic layer was washed with brine, dried over magnesium sulfate, filtered, and then concentrated under reduced pressure. The resulting solid was washed with diethyl ether and chloroform to give the title compound (11.1 mg) (yield 69%).

$^1$H-NMR (300 MHz, DMSO-$d_6$) δ 11.0 (s, 1H), 8.80 (s, 1H), 8.56-8.54 (s, 1H), 7.71 (s, 1H), 7.50-7.36 (m, 5H), 7.28-7.25 (m, 1H), 7.04 (d, 1H, J=39.0 Hz), 5.21 (s, 2H).

Examples 44 to 45

The compounds of Examples 44 to 45 were obtained by reaction/treatment using corresponding starting compounds in a similar manner to the process of Example 43.

| Example | Chemical structure | 1H-NMR |
|---|---|---|
| 44 | 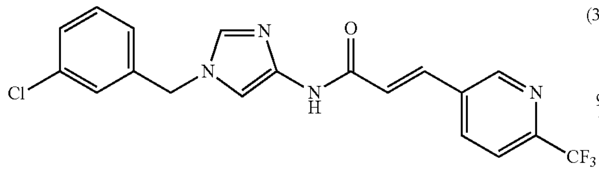 | (300 MHz, DMSO-d6) δ 10.8 (s, 1H), 8.94 (s, 1H), 8.24-8.21 (m, 1H), 7.97 (d, 1H, J = 9.0 Hz), 7.67 (s, 1H), 7.61 (d, 1H, J = 15.0 Hz), 7.40-7.37 (m, 4H), 7.28-7.25 (m, 1H), 7.09 (d, 1H, J = 15.0 Hz), 5.19 (s, 2H). |
| 45 | 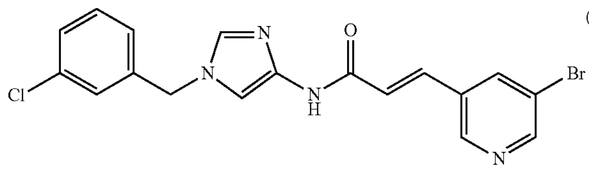 [SMILES: O=C(/C=C/c1cncc(Br)c1)Nc1cn(Cc2cccc(Cl)c2)cn1] | (400 MHz, DMSO-d6) δ 10.7 (s, 1H), 8.75 (s, 1H), 8.68 (s, 1H), 8.22-8.21 (m, 1H), 7.67 (s, 1H), 7.49 (d, 1H, J = 15.0 Hz), 7.40-7.37 (m, 4H), 7.27-7.25 (m, 1H), 7.00 (d, 1H, J = 15.0 Hz), 5.19 (s, 2H). |

Example 46

(2E,4E)-N-(1-(3-Chlorobenzyl)-1H-imidazol-4-yl)-5-phenylpenta-2,4-dienamide

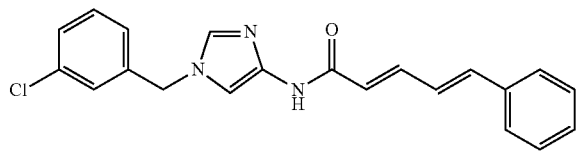 [SMILES: O=C(/C=C/C=C/c1ccccc1)Nc1cn(Cc2cccc(Cl)c2)cn1]

To a solution of the compound of Reference example 2 (100.0 mg) in DMF (10 mL) were added (2E,4E)-5-phenyl-penta-2,4-dienoic acid (85.6 mg), WSCI.HCl (93.9 mg), HOBt (72.0 mg), and triethylamine (0.188 mL), and the mixture was stirred at room temperature overnight. To the reaction mixture was added water, and then the mixture was extracted with ethyl acetate. The organic layer was washed with brine, dried over magnesium sulfate, filtered, and then concentrated under reduced pressure. The resulting solid was washed with diethyl ether to give the title compound (78.8 mg) (yield 53%).

LC/MS, Condition D, Retention time 0.980 min, obs MS[M+1]364.4

Example 47

(E)-N-(1-(3-Chlorobenzyl)-1H-imidazol-4-yl)-3-(1H-indol-5-yl)acrylamide

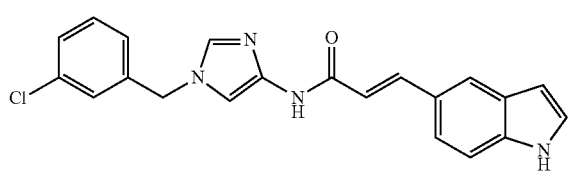 [SMILES: O=C(/C=C/c1ccc2[nH]ccc2c1)Nc1cn(Cc2cccc(Cl)c2)cn1]

To a solution of the compound of Reference example 2 (24.0 mg) in DMF (3 mL) were added the compound of Reference example 30 (28.0 mg), HBTU (40.0 g), and triethylamine (29 μL), and the mixture was stirred at room temperature overnight. To the reaction mixture was added water, and then the mixture was extracted with chloroform. The organic layer was washed with brine, dried over magnesium sulfate, filtered, and then concentrated under reduced pressure. The resulting crude product was dissolved in methanol (5 mL), and thereto was added 2 mol/L aqueous sodium hydroxide solution (0.5 mL). The mixture was stirred at 50° C. for 5 hours. The solvent was removed under reduced pressure, and then thereto was added water, and the mixture was extracted with chloroform. The organic layer was washed with brine, dried over magnesium sulfate, filtered, and then concentrated under reduced pressure. The residue was purified by silica gel column chromatography (chloroform/methanol) to give the title compound (16 mg) (yield 48%).

1H-NMR (400 MHz, DMSO-d6) δ 11.28 (s, 1H), 10.45 (s, 1H), 7.72 (s, 1H), 7.64 (s, 1H), 7.55 (d, J=16.0 Hz, 1H), 7.43-7.24 (m, 8H), 6.76 (d, J=16.0 Hz, 1H), 6.47 (s, 1H), 5.18 (s, 2H).

Example 48

(E)-N-(1-(3-Chlorobenzyl)-1H-imidazol-4-yl)-3-(4-(trifluoromethyl)phenyl)acrylamide

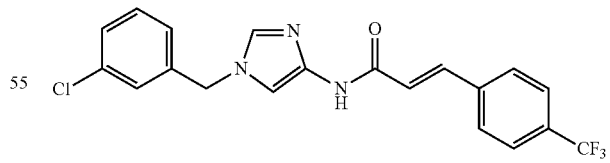

To a solution of the compound of Reference example 2 (25.0 mg) in DMF (1.0 mL) were added (E)-3-(4-(trifluoromethyl)phenyl)acrylic acid (26.5 mg), WSC.HCl (25.5 mg), HOBt (18.0 mg), and triethylamine (43 μL) under nitrogen atmosphere, and the mixture was stirred at room temperature overnight. To the reaction mixture was added 5% aqueous sodium carbonate solution, and the mixture was extracted with chloroform. The solvent was removed under reduced pressure. Then, the residue was dissolved in methanol (1 mL), purified by reverse phase HPLC, and desalted to give the title compound (yield 90%).

LC/MS, Condition A, Retention time 3.63 min, obs MS[M+1]406.3

Examples 49 to 86

The compounds of Examples 49 to 86 were synthesized in a similar manner to the process of Example 48.

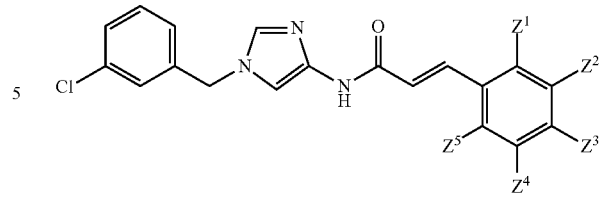

| Example | $Z^1$ | $Z^2$ | $Z^3$ | $Z^4$ | $Z^5$ | LC-MS Condition | LC-MS retention time (min) | LC-MS obs MS [M + 1] |
|---|---|---|---|---|---|---|---|---|
| 49 | H | H | Me | H | H | A | 3.40 | 352.1 |
| 50 | F | H | H | H | H | A | 3.30 | 356.2 |
| 51 | Cl | H | H | H | H | A | 3.47 | 372.1 |
| 52 | OMe | OMe | H | H | H | A | 3.23 | 398.1 |
| 53 | OMe | H | H | OMe | H | A | 3.29 | 398.4 |
| 54 | OH | H | H | H | H | A | 2.98 | 354.1 |
| 55 | $CF_3$ | H | H | H | H | A | 3.57 | 406.3 |
| 56 | H | Br | H | H | H | A | 3.53 | 417.9 |
| 57 | H | F | H | H | H | A | 3.32 | 356.2 |
| 58 | H | Cl | H | H | H | A | 3.50 | 372.0 |
| 59 | H | Cl | Cl | H | H | A | 3.69 | 408.2 |
| 60 | H | $CF_3$ | H | H | H | A | 3.56 | 406.3 |
| 61 | H | H | Br | H | H | A | 3.52 | 418.0 |
| 62 | H | H | F | H | H | A | 3.30 | 356.0 |
| 63 | H | H | $NMe_2$ | H | H | A | 3.07 | 381.4 |
| 64 | H | OEt | H | H | H | A | 3.44 | 382.0 |
| 65 | H | OH | H | H | H | A | 2.96 | 354.1 |
| 66 | H | OMe | OMe | H | H | A | 3.12 | 398.1 |
| 67 | H | OMe | OH | OMe | H | A | 2.90 | 414.1 |
| 68 | H | H | $NO_2$ | H | H | A | 3.36 | 383.2 |
| 69 | F | H | F | H | H | A | 3.40 | 374.2 |
| 70 | H | H | Ph | H | H | A | 3.78 | 414.3 |
| 71 | OMe | H | OMe | H | H | A | 3.31 | 398.2 |
| 72 | Me | H | H | H | H | A | 3.40 | 352.2 |
| 73 | H | Me | H | H | H | A | 3.43 | 352.2 |
| 74 | H | H | OEt | H | H | A | 3.42 | 382.3 |
| 75 | $NO_2$ | H | OMe | OMe | H | A | 3.30 | 443.2 |
| 76 | OMe | H | H | H | OMe | A | 3.33 | 398.0 |
| 77 | OMe | H | H | H | H | A | 3.32 | 368.1 |
| 78 | Br | H | F | H | H | A | 3.57 | 436.1 |
| 79 | H | OPh | H | H | H | A | 3.78 | 430.3 |
| 80 | H | Cl | OMe | H | H | A | 3.44 | 402.2 |
| 81 | H | F | OH | H | H | A | 3.00 | 372.1 |
| 82 | H | OMe | OMe | OMe | H | A | 3.16 | 428.2 |
| 83 | Cl | H | H | Cl | H | A | 3.67 | 408.1 |
| 84 | H | H | OH | H | H | A | 2.92 | 354.3 |
| 85 | H | OMe | H | OMe | H | A | 3.33 | 398.3 |
| 86 | OMe | H | OMe | OMe | H | A | 3.16 | 428.3 |

Examples 87 to 102

The compounds of Examples 87 to 102 were synthesized in a similar manner to the process of Example 48.

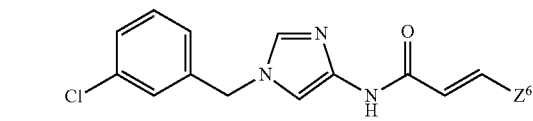

| Example | Z⁶ | LC-MS Condition | LC-MS retention time (min) | LC-MS obs MS [M+1] |
|---|---|---|---|---|
| 87 | 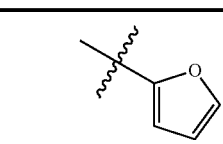 | A | 3.02 | 328.0 |
| 88 | | A | 2.99 | 327.9 |
| 89 | 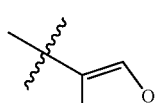 | A | 3.10 | 377.1 |
| 90 | 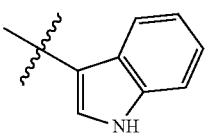 [SMILES: *c1c[nH]c2ccccc12] | A | 2.37 | 328.0 |
| 91 | | B | 0.98 | 353.3 |
| 92 | | B | 1.58 | 389.1 |
| 93 | | A | 3.35 | 356.2 |
| 94 | 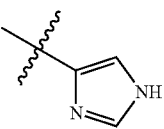 [SMILES: *c1c[nH]cn1] | B | 1.68 | 344.0 |
| 95 | | A | 3.61 | 388.2 |
| 96 | | B | 1.67 | 423.2 |
| 97 | | A | 2.45 | 339.1 |
| 98 | | A | 2.59 | 339.1 |

Example 99

6-Ethenyl-5-fluoro-N-{1-[3-(trifluoromethyl)benzyl]-1H-imidazol-4-yl}nicotinamide To a mixed solution of the compound of Reference example 38 (300 mg) in 1,4-dioxane (5 mL)/water (0.5 mL) were added vinylboronic acid pinacol ester (0.232 mL), tetrakis(triphenylphosphine)palladium (78 mg), and potassium carbonate (281 mg), and the mixture was stirred under microwave irradiation at 120° C. for 1 hour. The reaction mixture was cooled to room temperature, and then thereto was added water, and the mixture was extracted with ethyl acetate. The organic layer was washed with brine, dried over sodium sulfate, filtered, and then concentrated under reduced pressure. The residue was purified by silica gel column chromatography (hexane/ethyl acetate, ethyl acetate/methanol) to give the title compound (122 mg).

LC/MS, Condition D, Retention time 0.936 min, obs MS[M+1]391.2

Examples 100 to 101

The compounds of Examples 100 to 101 were synthesized in a similar manner to the process of Example 99.

| Example | Chemical structure | LC-MS Condition | LC-MS retention time (min) | LC-MS obs MS [M + 1] |
|---|---|---|---|---|
| 100 | (3-F₃C-benzyl)-imidazole-N-H-C(O)-pyridine with OMe and vinyl | D | 0.895 | 403.3 |
| 101 | (3-F₃C-benzyl)-imidazole-N-H-C(O)-pyridine with Br and vinyl | D | 1.017 | 451.2 |

Example 102

The compound of Example 102 was synthesized in a similar manner to the process of Example 141 using 1-(3-(chloro)benzyl)-1H-imidazole-2-methyl-4-amine hydrochloride.

| Example | Chemical structure | LC-MS Condition | LC-MS retention time (min) | LC-MS obs MS [M + 1] |
|---|---|---|---|---|
| 102 | (3-Cl-benzyl)-2-Me-imidazole-N-H-C(O)-benzene-3,4-di-OMe | C | 3.49 | 386.6 |

Examples 103 to 117

The compounds of Examples 103 to 117 were synthesized in a similar manner to the process of Example 48.

| Example | Chemical structure | LC-MS Condition | LC-MS retention time (min) | LC-MS obs MS [M + 1] |
|---|---|---|---|---|
| 103 | (3-F₃C-benzyl)-imidazole-N-H-C(O)-CH=CH-pyridine | B | 1.17 | 373.3 |
| 104 | (3-F₃C-benzyl)-imidazole-N-H-C(O)-CH=CH-phenyl-OPh | B | 2.54 | 464.3 |

-continued

| Example | Chemical structure | LC-MS Condition | LC-MS retention time (min) | LC-MS obs MS [M + 1] |
|---|---|---|---|---|
| 105 | 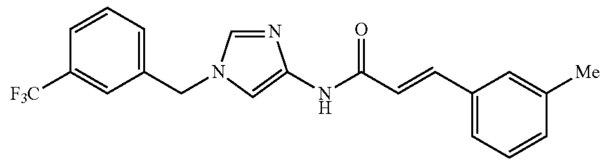 [SMILES: Cc1cccc(/C=C/C(=O)Nc2cn(Cc3cccc(C(F)(F)F)c3)cn2)c1] | B | 2.13 | 386.3 |
| 106 | 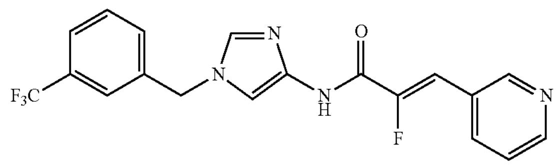 [SMILES: O=C(Nc1cn(Cc2cccc(C(F)(F)F)c2)cn1)/C(F)=C/c1cccnc1] | B | 1.38 | 391.2 |
| 107 | 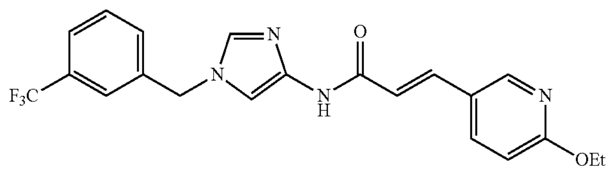 [SMILES: CCOc1ccc(/C=C/C(=O)Nc2cn(Cc3cccc(C(F)(F)F)c3)cn2)cn1] | B | 1.91 | 417.3 |
| 108 | 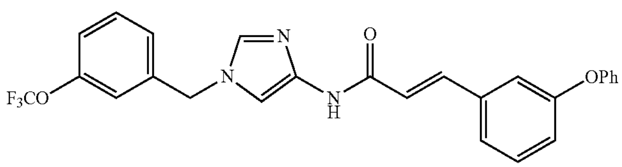 [SMILES: O=C(/C=C/c1cccc(Oc2ccccc2)c1)Nc1cn(Cc2cccc(OC(F)(F)F)c2)cn1] | B | 2.61 | 480.3 |
| 109 | 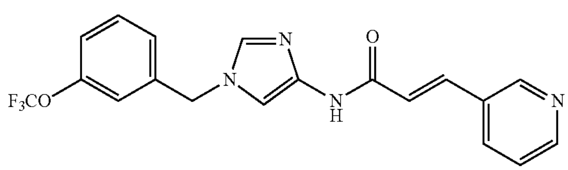 [SMILES: O=C(/C=C/c1cccnc1)Nc1cn(Cc2cccc(OC(F)(F)F)c2)cn1] | B | 1.27 | 389.3 |
| 110 | 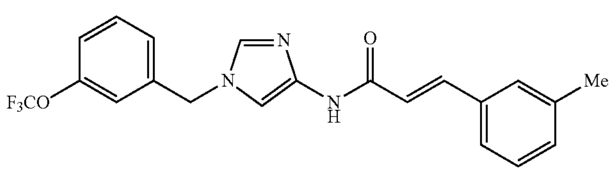 [SMILES: Cc1cccc(/C=C/C(=O)Nc2cn(Cc3cccc(OC(F)(F)F)c3)cn2)c1] | B | 2.21 | 402.3 |
| 111 | 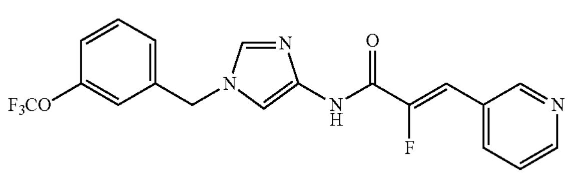 [SMILES: O=C(Nc1cn(Cc2cccc(OC(F)(F)F)c2)cn1)/C(F)=C/c1cccnc1] | B | 1.49 | 407.3 |
| 112 | 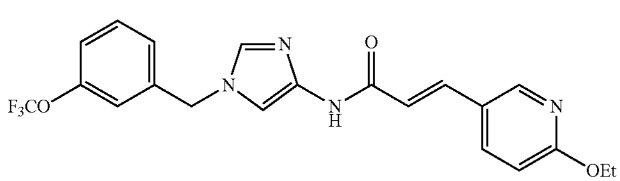 [SMILES: CCOc1ccc(/C=C/C(=O)Nc2cn(Cc3cccc(OC(F)(F)F)c3)cn2)cn1] | B | 2.00 | 433.3 |

| Example | Chemical structure | LC-MS Condition | LC-MS retention time (min) | LC-MS obs MS [M + 1] |
|---|---|---|---|---|
| 113 | 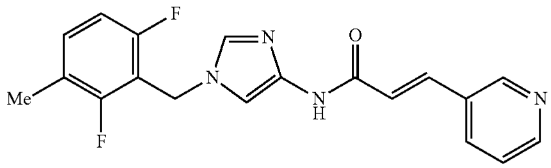 [SMILES: Cc1ccc(F)c(Cn2cnc(NC(=O)/C=C/c3cccnc3)c2)c1F] | B | 1.03 | 355.3 |
| 114 | 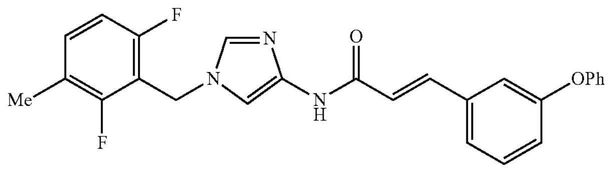 [SMILES: Cc1ccc(F)c(Cn2cnc(NC(=O)/C=C/c3cccc(Oc4ccccc4)c3)c2)c1F] | B | 2.48 | 446.4 |
| 115 | 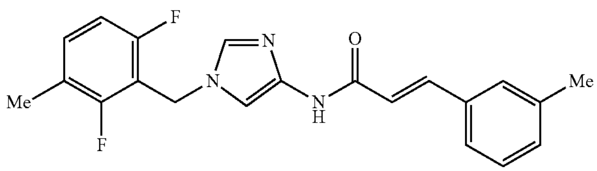 [SMILES: Cc1cccc(/C=C/C(=O)Nc2cn(Cc3c(F)ccc(C)c3F)cn2)c1] | B | 2.03 | 368.3 |
| 116 | 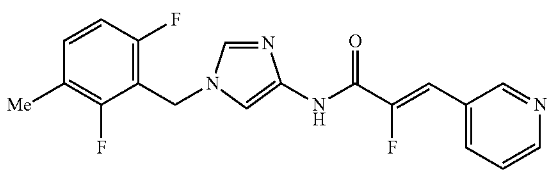 [SMILES: Cc1ccc(F)c(Cn2cnc(NC(=O)/C(F)=C/c3cccnc3)c2)c1F] | B | 1.27 | 373.2 |
| 117 | 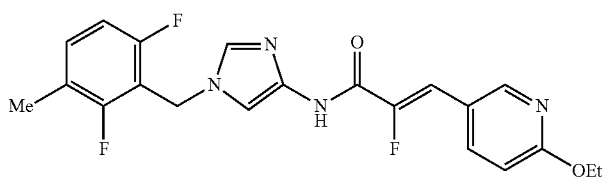 [SMILES: CCOc1ccc(/C=C(\F)C(=O)Nc2cn(Cc3c(F)ccc(C)c3F)cn2)cn1] | B | 1.80 | 399.2 |

Example 118

(E)-N-(1-(3-Chlorobenzyl)-1H-imidazol-4-yl)-3-(4-methoxyphenyl)acrylamide

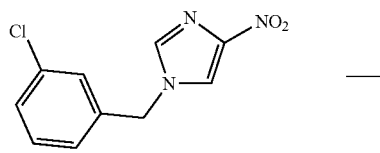

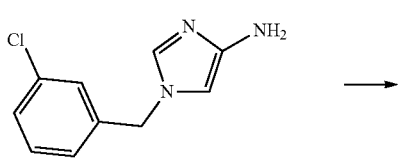

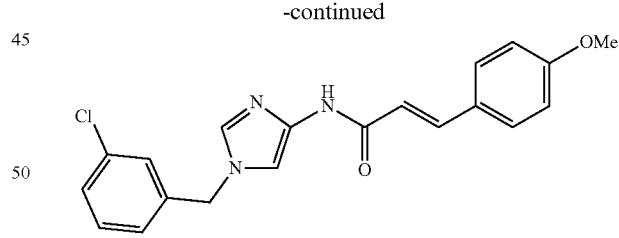

Under nitrogen atmosphere, 1-(3-chlorobenzyl)-4-nitro-1H-imidazole (950.6 mg) was dissolved in ethyl acetate (12 ml), and thereto was added 5% Rh/C (480 mg). Nitrogen was replaced with hydrogen gas through burette, and the mixture was stirred vigorously at room temperature for 3 hours. After hydrogen gas was absorbed, hydrogen was replaced with nitrogen, and the mixture was filtered quickly through Celite. The mixture was washed with ethyl acetate (6 ml), and then the filtrate was combined with the washings. The combined solution was divided equally into 13 portions. To one of the divided portions were added (E)-3-(4-methoxyphenyl)acrylic acid (0.25 mmol), 1-ethyl-3-(3-dimethylaminopropyl)-carbodiimide hydrochloride (WSCl.HCl) (47.9 mg), and 1-hydroxybenzotriazole anhydride (33.8 mg), and the mixture was stirred at room temperature overnight. Thereto were added ethyl acetate and 5% aqueous sodium carbonate solution, and the mixture was extracted with ethyl acetate 3 times. The organic layer was washed with water, and then concentrated under reduced pressure to give the title compound (crude). Then, the crude compound was dissolved in methanol (1 ml) and purified by reverse phase HPLC. CombiPrep ODS-A (20 mm I.D.×50 mmL) manufactured by YMC Co., Ltd. was used for the column and water (0.05% trifluoroacetic acid (TFA) included)/acetonitrile (0.035% TFA included) was used for the mobile phase. After purification, the crude compound was concentrated, dissolved in methanol, and then desalted with piperidine resin to remove TFA, which resulted in the title compound.

LC/MS, Condition C, Retention time 3.84 min, obs MS[M+1]368.4

Example 119

The compound of Example 119 was synthesized in a similar manner to the process of Example 118.

| Example | Chemical structure | LC-MS Condition | LC-MS retention time (min) | LC-MS obs MS [M + 1] |
|---|---|---|---|---|
| 119 | 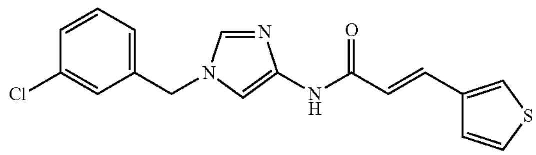 [SMILES: O=C(/C=C/c1ccsc1)Nc1cn(Cc2cccc(Cl)c2)cn1] | C | 3.71 | 344.1 |

Example 120

(E)-N-(1-(3-Chlorobenzyl)-1H-imidazol-4-yl)-3-(pyridin-3-yl)acrylamide Dihydrochloride

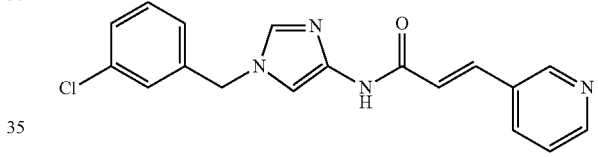

2HCl

To a solution of the compound of Example 41 (2.00 g) in 1,4-dioxane (30 mL) was added 4 mol/L hydrochloric acid-dioxane (2.27 mL), and the mixture was stirred at room temperature for 2 hours. The reaction mixture was concentrated under reduced pressure, and the resulting solid was washed with ethyl acetate to give the title compound (1.70 g) (yield 100%).

$^1$H-NMR (300 MHz, DMSO-$d_6$) δ 11.6 (s, 1H), 9.02 (s, 1H), 8.78 (d, 1H, J=3.0 Hz), 8.65 (s, 1H), 8.46 (d, 1H, J=6.0 Hz), 7.88-7.83 (m, 1H), 7.71 (d, 1H, J=15.0 Hz), 7.58 (d, 1H, J=21.0 Hz), 7.44-7.38 (m, 3H), 7.16 (d, 1H, J=15.0 Hz), 5.34 (s, 2H).

Examples 121 to 129

The compounds of Examples 121 to 129 were obtained by reaction/treatment using corresponding starting compounds in a similar manner to the process of Example 120.

| Example | Chemical structure | $^1$H-NMR (400 MHz, DMSO-$d_6$) |
|---|---|---|
| 121 | 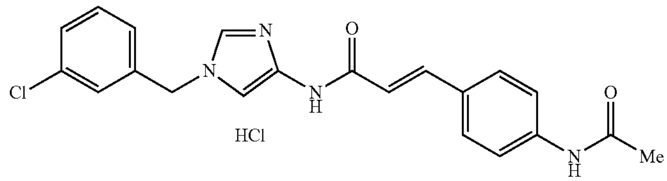 [SMILES: CC(=O)Nc1ccc(/C=C/C(=O)Nc2cn(Cc3cccc(Cl)c3)cn2)cc1 ; Cl] | δ 11.11 (brs, 1H), 10.20 (brs, 1H), 8.58 (brs, 1H), 7.65 (d, J = 7.9 Hz, 1H), 7.55-7.46 (m, 5H), 7.44-7.41 (m, 2H) 7.39-7.33 (m, 1H), 6.73 (d, J = 15.9 Hz, 1H), 5.32 (brs, 2H), 2.05 (s, 3H). |

-continued
| Example | Chemical structure | ¹H-NMR (400 MHz, DMSO-d₆) |
|---|---|---|
| 122 | 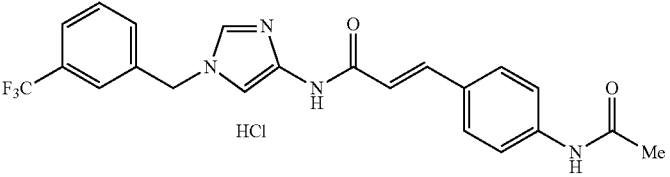 [SMILES: CC(=O)Nc1ccc(/C=C/C(=O)Nc2cn(Cc3cccc(C(F)(F)F)c3)cn2)cc1 ; Cl] | δ 11.08 (s, 1H), 10.19 (s, 1H), 8.57 (brs, 1H), 7.85 (brs, 1H), 7.75-7.68 (m, 2H), 7.67-7.62 (m, 3H), 7.56 (d, J = 1.8 Hz, 1H), 7.53 (d, J = 2.4 Hz, 1H), 7.52 (d, J = 15.9 Hz, 1H), 6.73 (d, J = 15.9 Hz, 1H), 5.41 (s, 2H), 2.06 (s, 3H). |
| 123 | 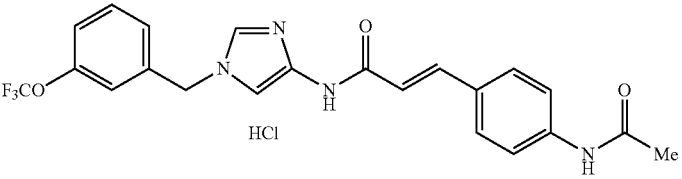 [SMILES: CC(=O)Nc1ccc(/C=C/C(=O)Nc2cn(Cc3cccc(OC(F)(F)F)c3)cn2)cc1 ; Cl] | δ 10.85 (s, 1H), 10.15 (s, 1H), 8.28 (brs, 1H), 7.63 (d, J = 8.5 Hz, 2H), 7.55-7.53 (m, 2H), 7.51-7.33 (m, 7H), 6.72 (d, J = 15.9 Hz, 1H), 5.33 (s, 2H), 2.05 (s, 3H). |
| 124 | 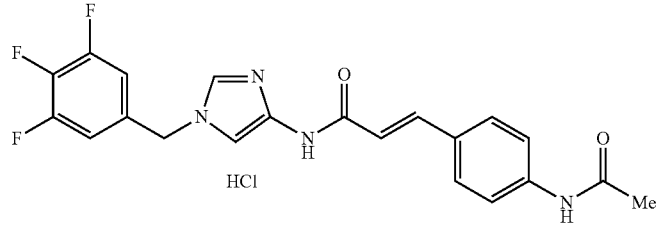 [SMILES: CC(=O)Nc1ccc(/C=C/C(=O)Nc2cn(Cc3cc(F)c(F)c(F)c3)cn2)cc1 ; Cl] | δ 10.85 (brs, 1H), 10.14 (brs, 1H), 8.29 (brs, 1H), 7.68-7.60 (m, 2H), 7.55-7.37 (m, 6H), 6.73 (d, J = 15.6 Hz, 1H), 5.24 (s, 2H), 2.06 (s, 3H). |
| 125 | 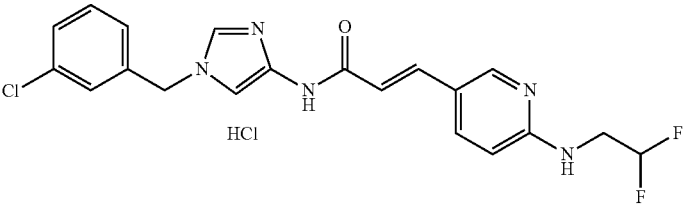 [SMILES: O=C(/C=C/c1ccc(NCC(F)F)nc1)Nc1cn(Cc2cccc(Cl)c2)cn1 ; Cl] | δ 11.36 (s, 1H), 8.86-8.72 (m, 2H), 8.28 (s, 1H), 8.00 (brs, 1H), 7.60-7.53 (m, 3H), 7.47-7.38 (m, 3H), 7.06 (brs, 1H), 6.81-6.73 (m, 1H), 6.36-6.08 (m, 2H), 5.36 (s, 2H), 4.00-3.87 (m, 2H). |
| 126 | 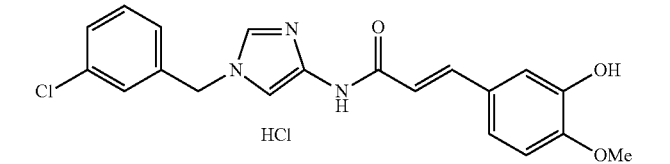 [SMILES: COc1ccc(/C=C/C(=O)Nc2cn(Cc3cccc(Cl)c3)cn2)cc1O ; Cl] | δ 11.03 (s, 1H), 9.25 (brs, 1H), 8.53 (brs, 1H), 7.53-7.28 (m, 6H), 7.04-6.92 (m, 3H), 6.61 (d, J = 15.6 Hz, 1H), 5.31 (s, 2H), 3.79 (s, 3H). |
| 127 | 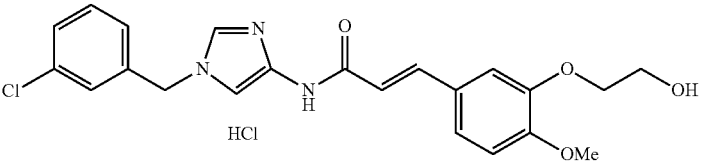 [SMILES: COc1ccc(/C=C/C(=O)Nc2cn(Cc3cccc(Cl)c3)cn2)cc1OCCO ; Cl] | δ 11.01 (s, 1H), 8.59 (brs, 1H), 7.55-7.35 (m, 6H), 7.22-7.16 (m, 2H), 7.01 (d, J = 8.0 Hz, 1H), 6.73 (d, J = 15.6 Hz, 1H), 5.32 (s, 2H), 4.03-3.99 (m, 2H), 3.79 (s, 3H), 3.74-3.71 (m, 2H). |
| 128 | 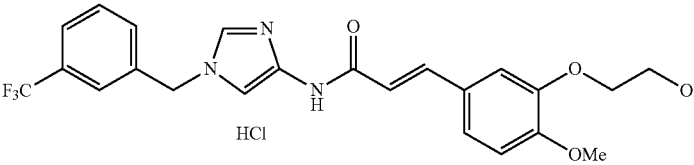 | δ 10.81 (s, 1H), 8.39 (brs, 1H), 7.82 (brs, 1H), 7.73-7.61 (m, 3H), 7.52-7.45 (m, 2H), 7.19-7.14 (m, 2H), 7.01 (d, J = 8.4 Hz, 1H), 6.71 (d, J = 16.0 Hz, 1H), 5.38 (s, 2H), 4.03-3.98 (m, 2H), 3.80 (s, 3H), 3.74-3.70 (m, 2H). |

| Example | Chemical structure | $^1$H-NMR (400 MHz, DMSO-$d_6$) |
|---|---|---|
| 129 | 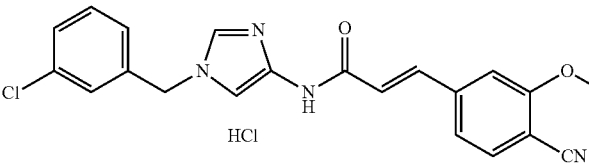 | δ 10.95-10.85 (m, 1H), 8.20-8.05 (m, 1H), 7.78-7.74 (m, 1H), 7.60-7.52 (m, 1H), 7.49-7.39 (m, 5H), 7.03-6.97 (m, 2H), 7.00 (d, J = 16.0 Hz, 1H), 5.29-5.23 (m, 2H), 4.23-4.19 (m, 2H), 3.79-3.75 (m, 2H). |

Example 130

(E)-N-(1-(3-Chlorobenzyl)-1H-imidazol-4-yl)-3-(4-hydroxyphenyl)acrylamide Hydrochloride

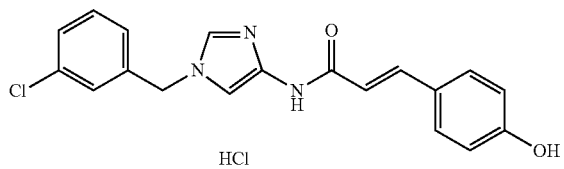 [SMILES: O=C(/C=C/c1ccc(O)cc1)Nc1cn(Cc2cccc(Cl)c2)cn1 ; Cl]

To the compound of Example 84 (2.81 g) was added 2 mol/L hydrochloric acid-methanol (50 mL), and the mixture was stirred at room temperature overnight. The reaction mixture was concentrated under reduced pressure, and the resulting solid was washed with ethyl acetate to give the title compound (2.50 g) (yield 90%).

$^1$H-NMR (400 MHz, DMSO-$d_6$): δ 11.3 (s, 1H), 8.79 (s, 1H), 7.66-7.39 (m, 8H), 6.84 (d, 2H, J=8.0 Hz), 6.67 (d, 1H, J=16 Hz), 5.37 (s, 2H).

Example 131

Methyl 5-[(1E)-3-oxo-3-({1-[3-(trifluoromethyl)benzyl]-1H-imidazol-4-yl}amino) prop-1-en-1-yl]picolinate

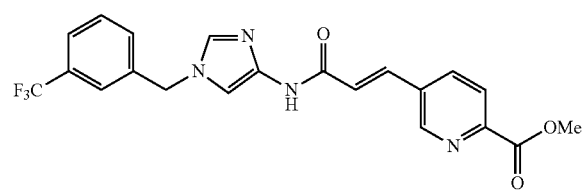 [SMILES: COC(=O)c1ccc(/C=C/C(=O)Nc2cn(Cc3cccc(C(F)(F)F)c3)cn2)cn1]

To a solution of the compound of Reference example 38 (60 mg) in DMF (2 mL) were added methyl 5-bromopyridine-2-carboxylate (53 mg), dichlorobis(tri-O-tolylphosphine)palladium (II) (16 mg), and triethylamine (0.042 mL), and the mixture was stirred at 90° C. for 3.5 hours and at 130° C. for 2 hours. The mixture was cooled to room temperature, and then thereto were added water and a small amount of methanol. The mixture was extracted with ethyl acetate. The organic layer was washed with brine, dried over anhydrous sodium sulfate, filtered, and then concentrated under reduced pressure. The resulting residue was purified by amino silica gel column chromatography (ethyl acetate/methanol) to give the title compound (42 mg) (yield 48%).

LC/MS, Condition D, Retention time 0.790 min, obs MS[M+1]431.2

$^1$H-NMR (DMSO-$d_6$) δ 10.73 (s, 1H), 8.87 (s, 1H), 8.14-8.08 (m, 2H), 7.71-7.56 (m, 6H), 7.41 (s, 1H), 7.07 (d, J=15.8 Hz, 1H), 5.29 (s, 2H), 3.88 (s, 3H).

Example 132-1

Methyl 5-(2-tert-butoxy-2-oxoethoxy)picolinate

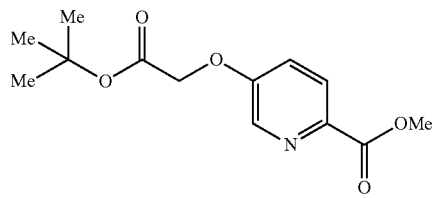 [SMILES: COC(=O)c1ccc(OCC(=O)OC(C)(C)C)cn1]

To a solution of methyl 5-hydroxypyridine-2-carboxylate (200 mg) in DMF (5 mL) were added potassium carbonate (361 mg) and tert-butyl bromoacetate, and the mixture was stirred at 70° C. for 20 minutes. The mixture was cooled to room temperature, and then to the reaction mixture was added water. The mixture was extracted with ethyl acetate. The organic layer was washed with brine twice, dried over anhydrous sodium sulfate, filtered, and then concentrated under reduced pressure to give the title compound (320 mg).

LC/MS, Condition D, Retention time 0.777 min, obs MS[M+1]268.2

Example 132-2

{[6-(Methoxycarbonyl)pyridin-3-yl]oxy}acetic Acid

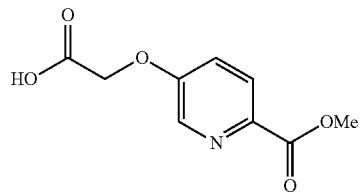 [SMILES: COC(=O)c1ccc(OCC(=O)O)cn1]

To a solution of the compound of Example 132-1 (320 mg) in dichloromethane (4 mL) was added TFA (2 mL), and the mixture was stirred at room temperature for 2 hours. The solvent was removed to give the title compound (253 mg). LC-MS ([M+H]⁺/Rt (min)): 212.1/0.394 LC/MS, Condition D, Retention time 0.394 min, obs MS[M+1]212.1

Example 132-3

Methyl 5-(2-oxo-2-{[1-(3,4,5-trifluorobenzyl)-1H-imidazol-4-yl]amino}ethoxy)picolinate

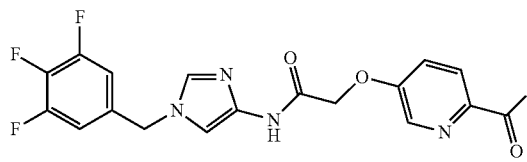

The compound of Reference example 132-2 was treated according to the process of Example 1 to give the title compound.

LC/MS, Condition D, Retention time 0.731 min, obs MS[M+1]421.2

Example 133

4-[1-(3-Chlorobenzyl)-1H-imidazole-4-carboxamide]benzoic acid

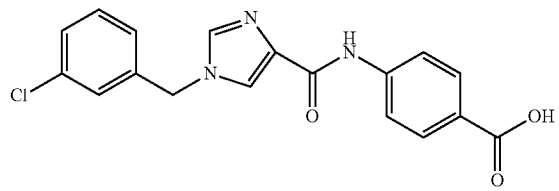 [SMILES: O=C(O)c1ccc(NC(=O)c2cn(Cc3cccc(Cl)c3)cn2)cc1]

To a solution of the compound of Example 320 (48 mg) in methanol (1 mL) and tetrahydrofuran (1 mL) was added 2M aqueous lithium hydroxide solution (0.5 mL), and the mixture was stirred at room temperature overnight. The reaction solution was neutralized with hydrochloric acid, and the resulting precipitate was filtered, washed with water, and then dried under reduced pressure to give the compound of Example 133 (42 mg) (yield 90%).

LC/MS, Condition E, Retention time 2.96 min, obs MS[M+1] 356.3

Example 134

N-[1-(3-Chlorobenzyl)-1H-imidazol-4-yl]isophthalamide

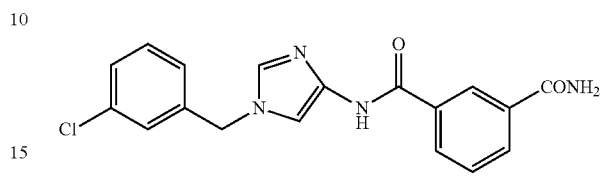

To a solution of the compound of Example 270 (70 mg) in dimethylsulfoxide (1 mL) and water (0.1 mL) were added potassium carbonate (7 mg) and 34.5% hydrogen peroxide water (18.5 µL) under ice cooling, and the mixture was stirred at room temperature overnight. The reaction solution was diluted with water, and thereto was added 30% aqueous sodium bisulfite solution under ice cooling. The mixture was adjusted to pH 8 to 9 with aqueous sodium bicarbonate solution and extracted with ethyl acetate. The resulting precipitate was filtered, and the resulting solid was dried under reduced pressure. The filtrate was washed with water and brine, dried over anhydrous sodium sulfate, filtered, and then the solvent was removed under reduced pressure. The resulting residue was purified by silica gel column (chloroform/methanol), and the resultant was combined with the solid obtained above to give the compound of Example 134 (60 mg) (yield 89%).

LC/MS, Condition E, Retention time 2.48 min, obs MS[M+1] 355.2

Examples 135 to 139

The compounds of Examples 135 to 139 were synthesized in a similar manner to Example 118.

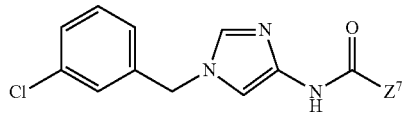

| Example | Z⁷ | LC-MS Condition | LC-MS retention time (min) | LC-MS obs MS [M + 1] |
|---|---|---|---|---|
| 135 | 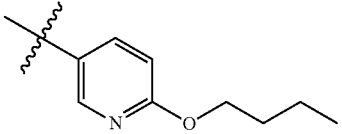 [SMILES: *c1ccc(OCCCC)nc1] | E | 3.30 | 384.3 |
| 136 | 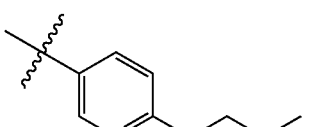 | E | 3.17 | 370.3 |

-continued

| Example | Z⁷ | LC-MS Condition | LC-MS retention time (min) | LC-MS obs MS [M + 1] |
|---|---|---|---|---|
| 137 | 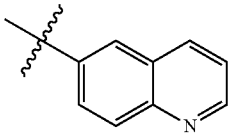 [SMILES: *c1ccc2ncccc2c1] | C | 3.10 | 363.2 |
| 138 | 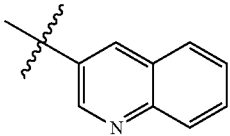 [SMILES: *c1cnc2ccccc2c1] | C | 3.44 | 363.3 |
| 139 | 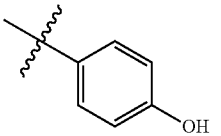 [SMILES: *c1ccc(O)cc1] | E | 2.57 | 328.3 |

Example 140

The compound of Example 140 was obtained by reaction/treatment using a corresponding starting compound in a similar manner to the process of Example 118.

$^1$H-NMR (400 MHz, DMSO-$d_6$) δ 10.64 (s, 1H), 7.63 (d, J=1.2 Hz, 1H), 7.60-7.56 (m, 2H), 7.39-7.31 (m, 4H), 7.25-7.21 (m, 1H), 6.97 (d, J=8.4 Hz, 1H), 5.16 (s, 2H), 3.78 (s, 3H), 3.76 (s, 3H).

| Example | Chemical structure | $^1$H-NMR |
|---|---|---|
| 140 | 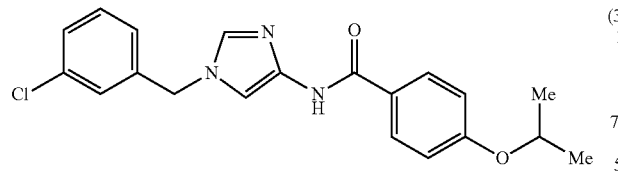 | (300 MHz, DMSO-$d_6$) δ 10.59 (s, 1H), 7.95 (d, 2H, J = 9.0 Hz), 7.67 (d, 1H, J = 1.7 Hz), 7.45-7.35 (m, 4H), 7.31-7.25 (m, 1H), 6.95 (d, 1H, J = 9.0 Hz), 5.19 (s, 2H), 4.75-4.66 (m, 1H), 1.28 (d, 6H, J = 6.1 Hz). |

Example 141

N-[1-(3-Chlorobenzyl)-1H-imidazol-4-yl]-3,4-dimethoxybenzamide

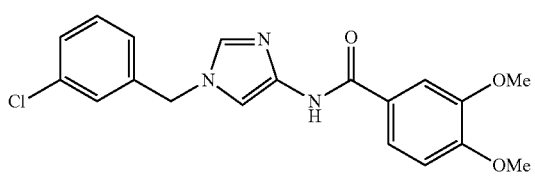 [SMILES: COc1ccc(C(=O)Nc2cn(Cc3cccc(Cl)c3)cn2)cc1OC]

To a solution of the compound of Reference example 2 (11.0 g) in methylene chloride (240 mL) were added triethylamine (15.8 mL) and 3,4-dimethoxybenzoyl chloride (9.04 g), and the mixture was stirred at room temperature overnight. The reaction solution was concentrated under reduced pressure, and the resulting solid was washed with ethyl acetate and filtered to give the title compound (9.7 g).

LC/MS, Condition E, Retention time 2.69 min, obs MS[M+1]372.0

Example 141-2

N-[1-(3-Chlorobenzyl)-1H-imidazol-4-yl]-3,4-dimethoxybenzamide Hydrochloride

To a solution of the compound of Example 141 (70.0 g) in 1,4-dioxane (1.5 L) were added 4 mol/L hydrochloric acid-dioxane (94 mL) and a seed crystal, and the mixture was put inside an ultrasonic bath. The solvent was removed, and to the residue was added ethanol (500 mL). The mixture was again put inside an ultrasonic bath, and the resulting precipitate was filtered and dried under reduced pressure to give a hydrochloride salt of Example 141, the title compound (72.4 g).

$^1$H-NMR (400 MHz, DMSO-$d_6$) δ 11.53 (1H, s), 8.87 (1H, s), 7.68-7.64 (3H, m), 7.58 (1H, s), 7.46-7.40 (3H, m), 7.09 (1H, d, J=8.8 Hz), 5.40 (2H, s), 3.83 (3H, s), 3.82 (3H, s).

Example 142

The compound of Example 142 was synthesized in a similar manner to Example 141.

| Example | Chemical structure | LC-MS Condition | LC-MS retention time (min) | LC-MS obs MS [M + 1] |
|---|---|---|---|---|
| 142 | 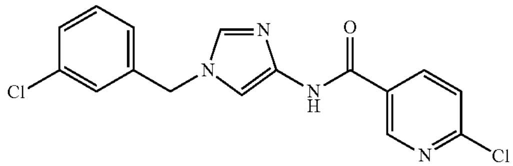 [SMILES: O=C(Nc1cn(Cc2cccc(Cl)c2)cn1)c1ccc(Cl)nc1] | D | 0.888 | 347.2 |

Example 143

3,4-Dimethoxy-N-[1-(2,4,5-trifluorobenzyl)-1H-imidazol-4-yl]benzamide

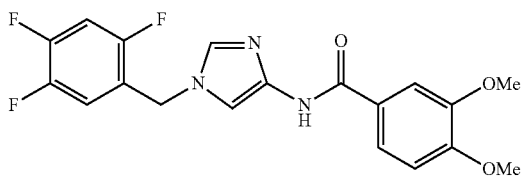 [SMILES: COc1ccc(C(=O)Nc2cn(Cc3cc(F)c(F)cc3F)cn2)cc1OC]

To a solution of N-(1H-imidazol-4-yl)-3,4-dimethoxybenzamide (52 mg) in DMF (1 mL) were added potassium carbonate (57 mg) and 2,4,5-trifluorobenzyl bromide (55 µL), and the mixture was stirred at 60° C. for 2 hours. The residue was purified by silica gel column chromatography (Mobile phase: hexane and ethyl acetate). The resulting solid was washed with a mixed solvent of hexane and ethyl acetate to give the title compound (50 mg).

LC/MS, Condition D, Retention time 0.747 min, obs MS[M+1]392.2

Examples 144 to 169

The compounds of Examples 144 to 169 were synthesized in a similar manner to Example 143.

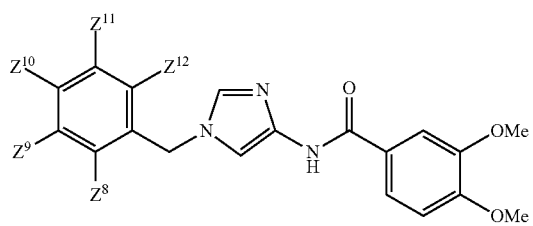

| Example | $Z^8$ | $Z^9$ | $Z^{10}$ | $Z^{11}$ | $Z^{12}$ | LC-MS Condition | LC-MS retention time (min) | LC-MS obs MS [M + 1] |
|---|---|---|---|---|---|---|---|---|
| 144 | F | H | H | H | H | C | 3.30 | 356.3 |
| 145 | H | F | H | H | H | C | 3.36 | 356.3 |
| 146 | H | H | F | H | H | C | 3.28 | 356.3 |
| 147 | F | F | H | H | H | C | 3.78 | 374.5 |
| 148 | F | H | F | H | H | C | 3.40 | 374.5 |
| 149 | F | H | H | F | H | C | 3.38 | 374.5 |
| 150 | F | H | H | H | F | D | 0.71 | 374.2 |
| 151 | H | F | F | H | H | C | 3.47 | 374.5 |
| 152 | H | F | H | F | H | C | 3.49 | 374.5 |
| 153 | F | F | F | H | H | D | 0.76 | 392.3 |
| 154 | F | F | H | F | H | D | 0.77 | 392.3 |
| 155 | F | F | H | H | F | D | 0.74 | 392.3 |
| 156 | F | F | F | F | H | D | 0.81 | 410.2 |
| 157 | F | F | F | F | F | D | 0.83 | 428.2 |
| 158 | H | H | Cl | H | H | D | 0.805 | 372.21 |
| 159 | H | F | H | Cl | H | C | 3.58 | 390.4 |
| 160 | H | Cl | F | H | H | C | 3.52 | 390.4 |
| 161 | H | $CF_3$ | F | H | H | C | 3.71 | 424.3 |
| 162 | H | $CF_3$ | H | F | H | C | 3.73 | 424.3 |
| 163 | $CF_3$ | H | F | H | H | D | 0.85 | 424.2 |
| 164 | H | H | OMe | H | H | E | 2.45 | 368.1 |
| 165 | H | $CF_3$ | H | H | H | C | 3.69 | 406.5 |
| 166 | H | $OCF_3$ | H | H | H | C | 3.78 | 422.2 |
| 167 | F | Me | H | H | F | D | 0.841 | 388.22 |
| 168 | H | H | iPr | H | H | D | 0.943 | 380.31 |
| 169 | H | OBn | H | H | H | D | 0.951 | 444.34 |

Examples 151-2 to 152-2

Corresponding starting compounds (Examples 151 and 152) were reacted/treated in a similar manner to the process of Example 141-2 to give hydrochloride salts of the respective starting compounds, Examples 151-2 and 152-2.

| Example | Chemical structure | $^1$H-NMR (400 MHz, DMSO-$d_6$) |
|---|---|---|
| 151-2 | 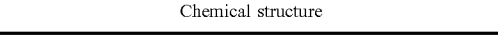 | δ 11.3 (s, 1H), 8.68 (s, 1H), 7.62-7.52 (m, 4H), 7.49-7.41 (m, 1H), 7.28 (s, 1H), 7.05 (1H, d, J = 8.4 Hz), 5.31 (s, 2H), 3.79 (s, 3H), 3.78 (s, 3H). |

| Example | Chemical structure | ¹H-NMR (400 MHz, DMSO-d₆) |
|---|---|---|
| 152-2 | 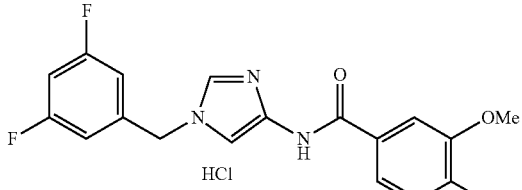 | δ 11.1 (s, 1H), 8.53 (s, 1H), 7.62-7.52 (m, 3H), 7.25-7.13 (m, 3H), 7.04 (1H, d, J = 8.4 Hz), 5.32 (s, 2H), 3.79 (s, 6H). |

Examples 170 to 173

The compounds of Examples 170 to 173 were synthesized in a similar manner to Example 143.

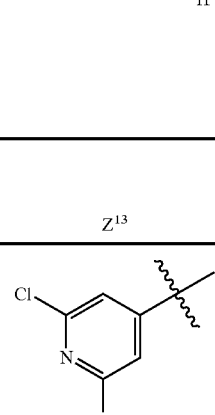

| Example | Z¹³ | LC-MS Condition | LC-MS retention time (min) | LC-MS obs MS [M + 1] |
|---|---|---|---|---|
| 170 | 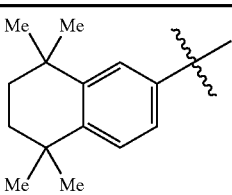 | D | 0.808 | 407.18 |
| 171 | 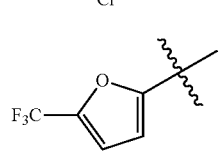 | D | 0.838 | 396.22 |
| 172 | 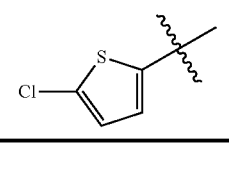 | D | 1.147 | 448.39 |
| 173 | 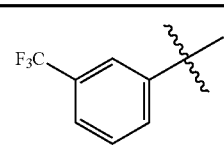 | D | 0.828 | 378.16 |

Examples 174 to 228

The compounds of Examples 174 to 228 were synthesized in a similar manner to Example 1.

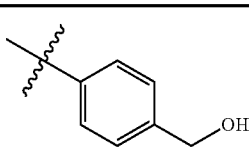

| Example | Z¹⁴ | Z¹⁵ | LC-MS Condition | LC-MS retention time (min) | LC-MS obs MS [M + 1] |
|---|---|---|---|---|---|
| 174 | 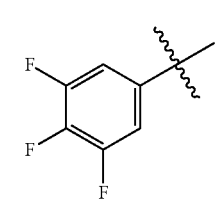 [SMILES: *c1cc(F)c(F)c(F)c1] | 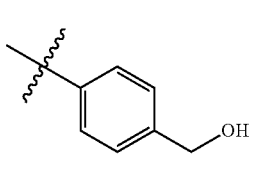 [SMILES: *c1ccc(CO)cc1] | D | 0.769 | 377.21 |
| 175 | | | D | 0.737 | 362.21 |

-continued

| Example | Z¹⁴ | Z¹⁵ | LC-MS Condition | LC-MS retention time (min) | LC-MS obs MS [M + 1] |
|---|---|---|---|---|---|
| 176 | 3-Cl-phenyl | imidazo[1,2-a]pyridin-6-yl | B | 0.84 | 352.0 |
| 177 | 3-Cl-phenyl | 1H-pyrrolo[2,3-b]pyridin-5-yl | D | 0.711 | 352.18 |
| 178 | 3-CF₃-phenyl | isoquinolin-3-yl | D | 0.961 | 397.25 |
| 179 | 3-CF₃-phenyl | pyrimidin-4-yl | D | 0.775 | 348.18 |
| 180 | 3-CF₃-phenyl | pyrimidin-5-yl | D | 0.726 | 348.18 |
| 181 | 3-CF₃-phenyl | quinolin-3-yl | D | 0.846 | 397.25 |
| 182 | 3-CF₃-phenyl | pyridazin-3-yl | D | 0.747 | 348.18 |
| 183 | 3-CF₃-phenyl | quinolin-6-yl | D | 0.768 | 397.30 |
| 184 | 3-CF₃-phenyl | 1,5-naphthyridin-6-yl | D | 0.859 | 398.25 |
| 185 | 3-CF₃-phenyl | pyrazin-2-yl | D | 0.762 | 349.18 |

-continued
| Example | Z¹⁴ | Z¹⁵ | LC-MS Condition | LC-MS retention time (min) | LC-MS obs MS [M + 1] |
|---|---|---|---|---|---|
| 186 | 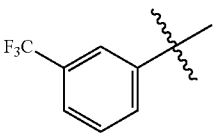 [SMILES: *c1cccc(C(F)(F)F)c1] | 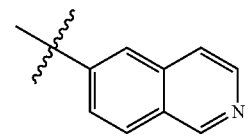 [SMILES: *c1ccc2cnccc2c1] | D | 0.738 | 397.20 |
| 187 | 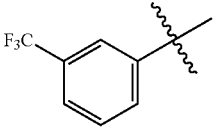 [SMILES: *c1cccc(C(F)(F)F)c1] | 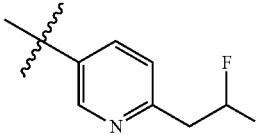 | D | 0.850 | 411.2 |
| 188 | 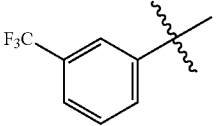 [SMILES: *c1cccc(C(F)(F)F)c1] | 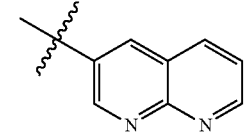 [SMILES: *c1cnc2ncccc2c1] | D | 0.724 | 398.20 |
| 189 | 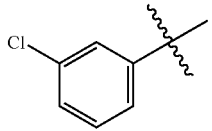 [SMILES: *c1cccc(Cl)c1] | 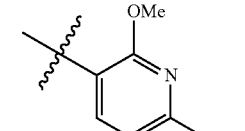 | C | 3.85 | 373.41 |
| 190 | 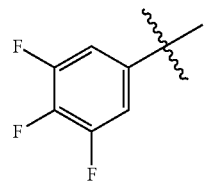 [SMILES: *c1cc(F)c(F)c(F)c1] | 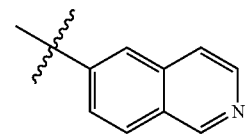 [SMILES: *c1ccc2cnccc2c1] | D | 0.693 | 383.20 |
| 191 | 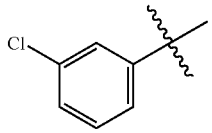 [SMILES: *c1cccc(Cl)c1] | 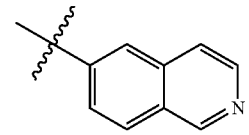 [SMILES: *c1ccc2cnccc2c1] | D | 0.657 | 363.20 |
| 192 | 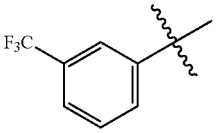 [SMILES: *c1cccc(C(F)(F)F)c1] | 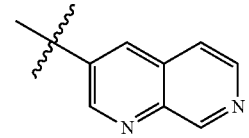 [SMILES: *c1cnc2cnccc2c1] | D | 0.752 | 397.90 |
| 193 | 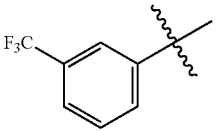 [SMILES: *c1cccc(C(F)(F)F)c1] | 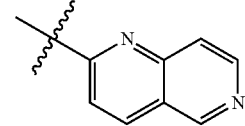 [SMILES: *c1ccc2cnccc2n1] | D | 0.81 | 397.90 |
| 194 | 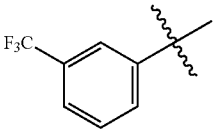 [SMILES: *c1cccc(C(F)(F)F)c1] | 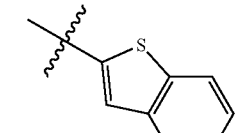 | D | 0.71 | 402.90 |

| Example | Z14 | Z15 | LC-MS Condition | LC-MS retention time (min) | LC-MS obs MS [M + 1] |
|---|---|---|---|---|---|
| 195 | 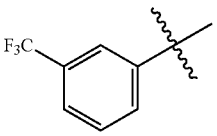 [SMILES: *c1cccc(C(F)(F)F)c1] | 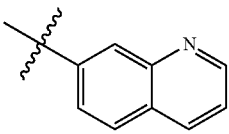 [SMILES: *c1ccc2cccnc2c1] | D | 0.800 | 397.20 |
| 196 | 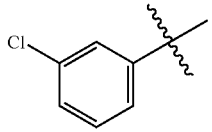 [SMILES: *c1cccc(Cl)c1] | 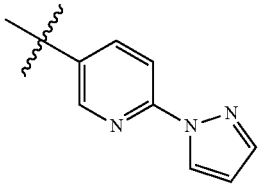 [SMILES: *c1ccc(-n2cccn2)nc1] | D | 0.85 | 379.25 |
| 197 | 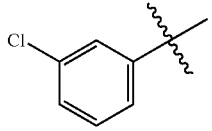 [SMILES: *c1cccc(Cl)c1] | 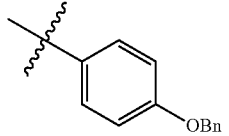 [SMILES: *c1ccc(OCc2ccccc2)cc1] | D | 1.070 | 418.23 |
| 198 | 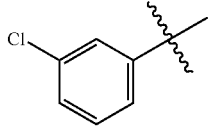 [SMILES: *c1cccc(Cl)c1] | 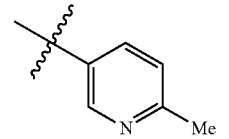 [SMILES: *c1ccc(C)nc1] | D | 0.695 | 327.1 |
| 199 | 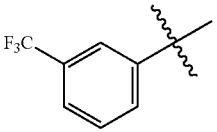 [SMILES: *c1cccc(C(F)(F)F)c1] | 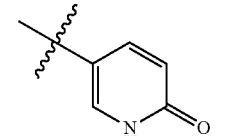 | D | 0.694 | 363.21 |
| 200 | 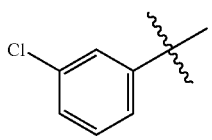 [SMILES: *c1cccc(Cl)c1] | 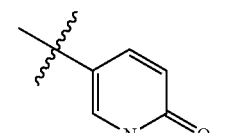 | E | 2.32 | 329.2 |
| 201 | 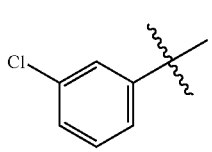 [SMILES: *c1cccc(Cl)c1] | 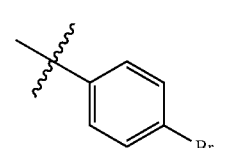 | D | 1.00 | 424.20 |
| 202 | 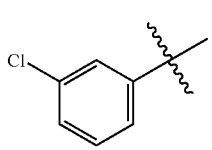 [SMILES: *c1cccc(Cl)c1] | 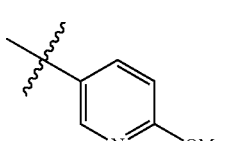 | A | 2.92 | 342.90 |
| 203 | 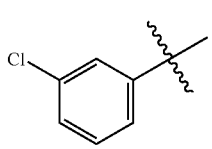 [SMILES: *c1cccc(Cl)c1] | 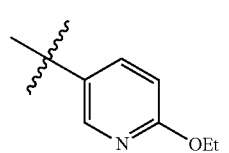 [SMILES: *c1ccc(OCC)nc1] | B | 1.65 | 357.2 |

-continued

| Example | Z¹⁴ | Z¹⁵ | LC-MS Condition | LC-MS retention time (min) | LC-MS obs MS [M + 1] |
|---|---|---|---|---|---|
| 204 | 3-Cl-phenyl | 5-(2-(3-methoxypropoxy))pyridyl | B | 1.64 | 401.3 |
| 205 | 3-Cl-phenyl | 5-(2-(2-(dimethylamino)ethoxy))pyridyl | B | 0.86 | 400.4 |
| 206 | 3-Cl-phenyl | 5-(2-OBn)pyridyl | B | 2.20 | 419.3 |
| 207 | 3-Cl-phenyl | 5-(2-OiPr)pyridyl | B | 1.88 | 371.2 |
| 208 | 3-Cl-phenyl | 5-(2-O-cyclopentyl)pyridyl | B | 2.15 | 397.3 |
| 209 | 3-CF₃-phenyl | 5-(2-OMe)pyridyl | B | 1.60 | 377.2 |
| 210 | 3-CF₃-phenyl | 5-(2-OEt)pyridyl | B | 1.81 | 391.3 |
| 211 | 3-CF₃-phenyl | 5-(2-OiPr)pyridyl | B | 2.02 | 495.2 |
| 212 | 3-CF₃O-phenyl | 5-(2-OMe)pyridyl | B | 1.69 | 393.2 |
| 213 | 3-CF₃O-phenyl | 5-(2-OEt)pyridyl | B | 1.89 | 407.2 |

-continued
| Example | Z¹⁴ | Z¹⁵ | LC-MS Condition | LC-MS retention time (min) | LC-MS obs MS [M + 1] |
|---|---|---|---|---|---|
| 214 | 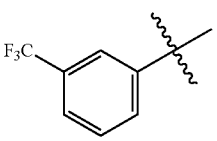 [SMILES: *c1cccc(C(F)(F)F)c1] | 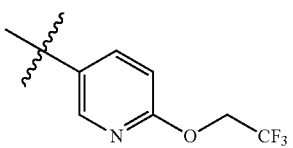 | B | 2.15 | 445.3 |
| 215 | 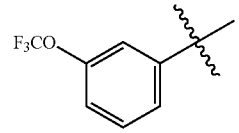 [SMILES: *c1cccc(OC(F)(F)F)c1] | 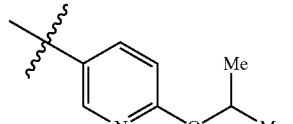 | B | 2.11 | 421.3 |
| 216 | 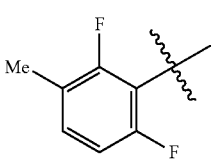 | 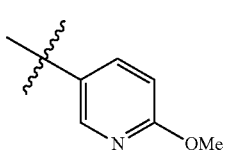 [SMILES: *c1ccc(OC)nc1] | B | 1.46 | 359.3 |
| 217 | 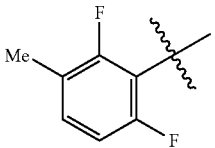 | 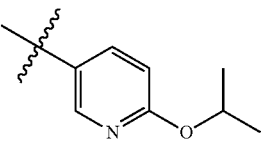 [SMILES: *c1ccc(OC(C)C)nc1] | B | 1.92 | 387.3 |
| 218 | 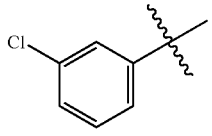 [SMILES: *c1cccc(Cl)c1] | 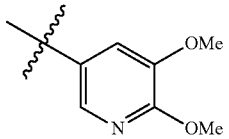 [SMILES: *c1cnc(OC)c(OC)c1] | A | 2.96 | 373.2 |
| 219 | 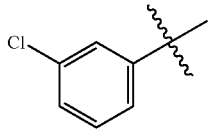 [SMILES: *c1cccc(Cl)c1] | 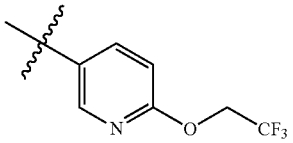 [SMILES: *c1ccc(OCC(F)(F)F)nc1] | A | 3.44 | 411.1 |
| 220 | 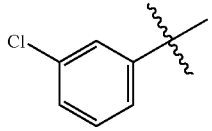 [SMILES: *c1cccc(Cl)c1] | 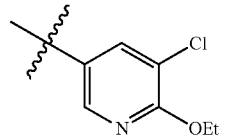 [SMILES: *c1cnc(OCC)c(Cl)c1] | B | 2.20 | 391.2 |
| 221 | 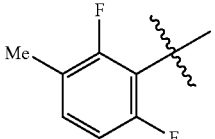 | 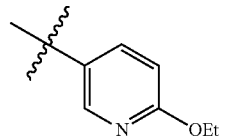 [SMILES: *c1ccc(OCC)nc1] | B | 1.71 | 373.5 |
| 222 | 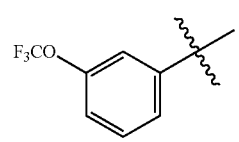 [SMILES: *c1cccc(OC(F)(F)F)c1] | 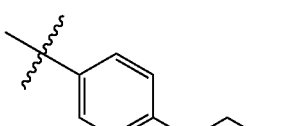 | B | 2.23 | 461.3 |

-continued
| Example | $Z^{14}$ | $Z^{15}$ | LC-MS Condition | LC-MS retention time (min) | LC-MS obs MS [M + 1] |
|---|---|---|---|---|---|
| 223 | | | B | 2.07 | 427.3 |
| 224 | | | D | 0.678 | 328.1 |
| 225 | | | D | 0.542 | 342.1 |
| 226 | | | D | 0.82 | 365.2 |
| 227 | | | D | 0.960 | 443.1 |
| 228 | | | D | 0.897 | 411.2 |
Example 229
The compound of Example 229 was obtained by reaction/treatment using a corresponding starting compound in a similar manner to the process of Example 118.
| Example | Chemical structure | $^1$H-NMR |
|---|---|---|
| 229 | 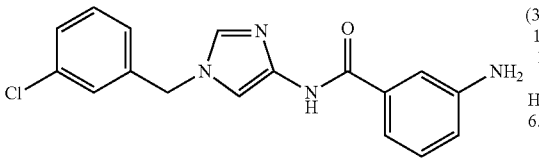 | (300 MHz, DMSO-d$_6$) δ 10.45 (s, 1H), 7.66 (d, 1H, J = 1.5 Hz), 7.28 (dt, 1H, J = 6.7, 1.8 Hz), 7.13-7.05 (m, 3H), 6.70-6.68 (m, 1H), 5.22 (s, 2H), 5.20 (s, 2H). |

Examples 230 to 234

The compounds of Examples 230 to 234 were synthesized in a similar manner to Example 1.

| Example | Chemical structure | LC-MS Condition | LC-MS retention time (min) | LC-MS obs MS [M + 1] |
|---|---|---|---|---|
| 230 | 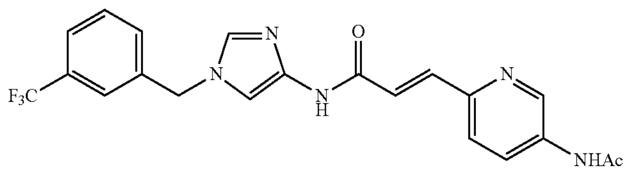 [SMILES: CC(=O)Nc1ccc(/C=C/C(=O)Nc2cn(Cc3cccc(C(F)(F)F)c3)cn2)nc1] | D | 0.727 | 430.26 |
| 231 | 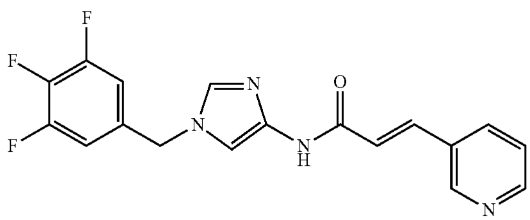 [SMILES: O=C(/C=C/c1cccnc1)Nc1cn(Cc2cc(F)c(F)c(F)c2)cn1] | D | 0.666 | 359.19 |
| 232 | 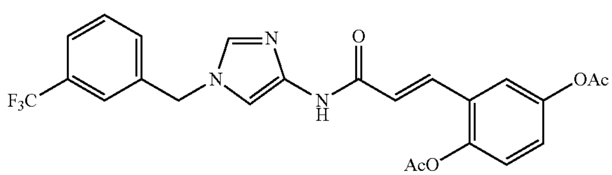 [SMILES: CC(=O)Oc1ccc(OC(C)=O)c(/C=C/C(=O)Nc2cn(Cc3cccc(C(F)(F)F)c3)cn2)c1] | D | 0.916 | 487.9 |
| 233 | 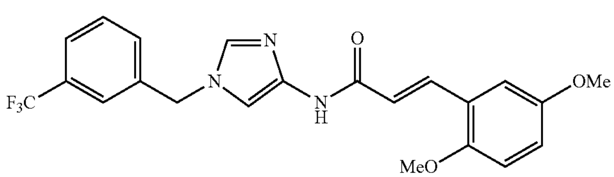 [SMILES: COc1ccc(OC)c(/C=C/C(=O)Nc2cn(Cc3cccc(C(F)(F)F)c3)cn2)c1] | D | 0.937 | 431.9 |
| 234 | 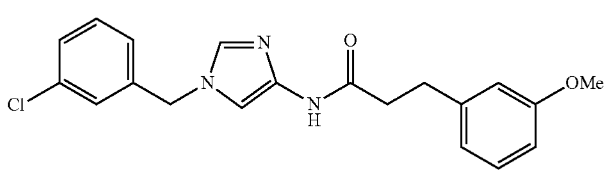 [SMILES: COc1cccc(CCC(=O)Nc2cn(Cc3cccc(Cl)c3)cn2)c1] | D | 0.645 | 365.26 |

Example 235

(2E)-3-(2,5-Dihydroxyphenyl)-N-{1-[3-(trifluoromethyl)benzyl]-1H-imidazol-4-yl}prop-2-enamide Hydrochloride

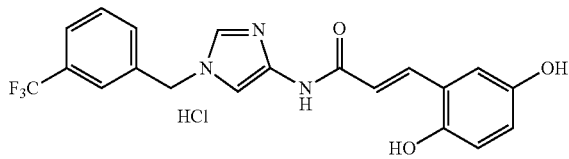 [SMILES: O=C(/C=C/c1cc(O)ccc1O)Nc1cn(Cc2cccc(C(F)(F)F)c2)cn1 ; Cl]

To the compound of Example 232 (15 mg) was added hydrochloric acid/methanol (2 mol/L), and the mixture was stirred at room temperature overnight. The reaction mixture was concentrated under reduced pressure, and the resulting residue was washed with ethyl acetate to give the title compound (8.4 mg).

LC/MS, Condition D, Retention time 0.716 min, obs MS[M+1]403.9

Example 236

3,4-Dimethoxy-N-[1-(3,4,5-trifluorobenzyl)-1H-imidazol-4-yl]benzamide

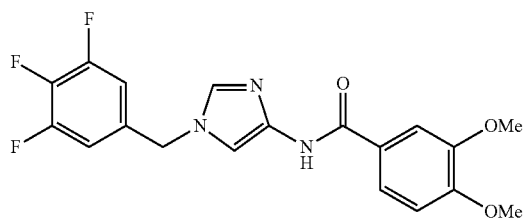 [SMILES: COc1ccc(C(=O)Nc2cn(Cc3cc(F)c(F)c(F)c3)cn2)cc1OC]

To a solution of Reference example 4 (5.21 g) and 3,4-dimethoxybenzoic acid (3.0 g) in DMF (30 mL) were added WSC (3.47 g), HOBt (2.67 g), and diisopropylethylamine (5.75 mL), and the mixture was stirred at room temperature overnight. Thereto was added 2 mol/L aqueous sodium hydroxide solution, and the mixture was extracted with chloroform. The organic layer was washed with brine, dried over anhydrous magnesium sulfate, filtered, and then concentrated under reduced pressure. The resulting residue was purified by silica gel column chromatography (chloroform/methanol) to give the title compound (3.62 g) (yield 56%).

LC/MS, Condition D, Retention time 0.794 min, obs MS[M+1]392.3

$^1$H-NMR (400 MHz, DMSO-d$_6$) δ 10.63 (s, 1H), 7.64-7.57 (m, 3H), 7.40-7.39 (m, 1H), 7.32-7.26 (m, 2H), 6.97 (d, J=8.8 Hz, 1H), 5.13 (s, 2H), 3.78 (s, 3H), 3.76 (s, 3H).

Example 237

3,4-Dimethoxy-N-[1-(3,4,5-trifluorobenzyl)-1H-imidazol-4-yl]benzamide Hydrochloride Monohydrate

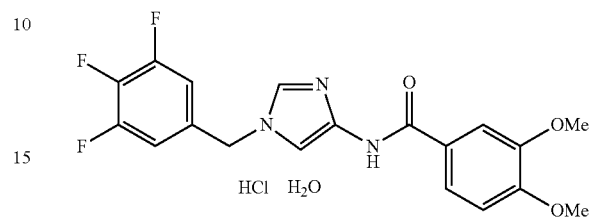

To a suspension of the compound of Example 236 (1.66 g) in ethyl acetate (15 mL) was added 1 mol/L hydrochloric acid-ethyl acetate (5.51 mL), and the mixture was stirred at room temperature for 2 hours. The resulting precipitate was filtered and washed with ethyl acetate/hexane (1/1) to give the title compound (1.82 g) (yield 96%).

$^1$H-NMR (400 MHz, DMSO-d$_6$) δ 11.2 (s, 1H), 8.50 (s, 1H), 7.62-7.55 (m, 3H), 7.48-7.39 (m, 2H), 7.04 (d, 1H, J=8.4 Hz), 5.28 (s, 2H), 3.79 (s, 3H), 3.78 (s, 3H).

Example 238

3,4-Dimethoxy-N-[1-(3,4,5-trifluorobenzyl)-1H-imidazol-4-yl]benzamide Tosilate

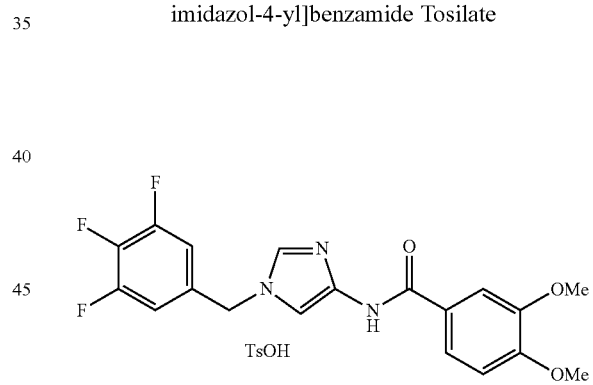

To a suspension of the compound of Example 236 (153 mg) in acetone (20 mL) was added tosic acid monohydrate (82.0 mg), and the mixture was stirred at 50° C. for 1.5 hours. The resulting precipitate was filtered and washed with acetone to give the title compound (175 mg) (yield 79%).

$^1$H-NMR (400 MHz, DMSO-d$_6$) δ 10.9 (s, 1H), 8.51 (s, 1H), 7.58-7.50 (m, 3H), 7.46-7.39 (m, 4H), 7.08-7.02 (m, 3H), 5.27 (s, 2H), 3.79 (s, 3H), 3.78 (s, 3H), 2.24 (s, 3H).

FIG. 11 shows a differential scanning calorimetry (DSC) chart of the compound of Example 238. The compound of Example 238 showed an endothermic peak for melting with the extrapolated onset temperature (Tim) at 241° C. (+5° C.) in DSC.

Example 239

3,4-Dimethoxy-N-[1-(3,4,5-trifluorobenzyl)-1H-imidazol-4-yl]benzamide Besilate

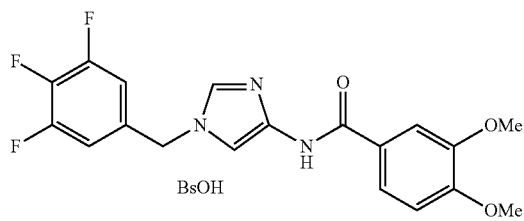

To a suspension of the compound of Example 236 (150.5 mg) in acetone (20 mL) was added benzenesulfonic acid (66.9 mg), and the mixture was stirred at 50° C. for 2 hours. The resulting precipitate was filtered and washed with acetone to give the title compound (172 mg) (yield 81%).

$^1$H-NMR (400 MHz, DMSO-$d_6$) δ 11.0 (s, 1H), 8.70 (s, 1H), 7.59-7.54 (m, 4H), 7.50-7.42 (m, 3H), 7.31-7.24 (m, 3H), 7.06 (d, 1H, J=8.8 Hz), 5.30 (s, 2H), 3.79 (s, 3H), 3.78 (s, 3H).

Example 240

3,4-Dimethoxy-N-[1-(3,4,5-trifluorobenzyl)-1H-imidazol-4-yl]benzamide Mesilate

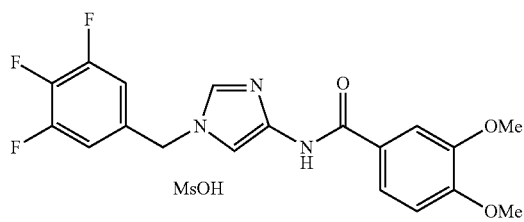

To a solution of the compound of Example 236 (100 mg) in acetone (7 mL) was added mesylic acid (20 μL), and the mixture was stirred at 50° C. for 2 hours. The resulting precipitate was filtered and washed with acetone and diisopropyl ether to give the title compound (99.0 mg) (yield 79%).

$^1$H-NMR (400 MHz, DMSO-$d_6$) δ 10.9 (s, 1H), 8.43 (s, 1H), 7.59-7.55 (m, 1H), 7.54-7.51 (m, 2H), 7.46-7.37 (m, 2H), 7.04 (d, 1H, J=8.0 Hz), 5.27 (s, 2H), 3.78 (s, 6H), 2.28 (s, 3H).

Example 241

3,4-Dimethoxy-N-[1-(3,4,5-trifluorobenzyl)-1H-imidazol-4-yl]benzamide Hydrobromide

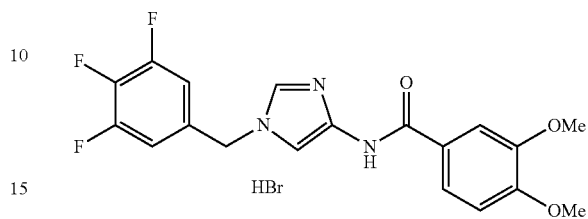

To a solution of the compound of Example 236 (80 mg) in ethanol (2 mL) was added hydrobromic acid (33% acetic acid solution, 53 μL), and the mixture was stirred at 40° C. for 2 hours. The resulting precipitate was filtered and washed with diisopropyl ether to give the title compound (82.0 mg) (yield 85%).

$^1$H-NMR (400 MHz, DMSO-$d_6$) δ 10.9 (s, 1H), 8.58 (s, 1H), 7.59-7.49 (m, 3H), 7.48-7.38 (m, 2H), 7.08-7.03 (m, 1H), 5.27 (s, 2H), 3.79 (s, 6H).

Example 242

1-Methyl-6-oxo-N-{1-[3-(trifluoromethyl)benzyl]-1H-imidazol-4-yl}-1,6-dihydropyridine-3-carboxamide

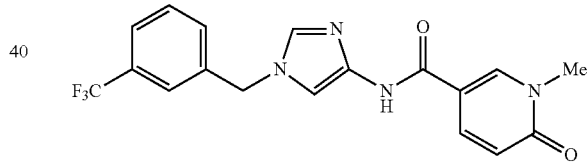

Under nitrogen atmosphere, the compound of Example 199 (100 mg) was dissolved in N,N-dimethylformamide (1.5 mL), and thereto was added t-butoxypotassium (35 mg). The mixture was stirred at room temperature for 10 minutes. Then, thereto was added methyl iodide (26 μL), and the mixture was stirred at room temperature overnight. To the reaction solution was added water, and the mixture was extracted with ethyl acetate twice. The organic layer was washed with water and brine, and then dried over sodium sulfate. The organic layer was concentrated under reduced pressure, and the residue was purified by column chromatography (chloroform-methanol) to give the title compound (37.7 mg) (yield 36%).

LC/MS, Condition D, Retention time 0.733 min, obs MS[M+1]377.21

Example 243

The compound of Example 243 was synthesized in a similar manner to Example 242.

| Example | Chemical structure | LC-MS Condition | LC-MS retention time (min) | LC-MS obs MS [M + 1] |
|---|---|---|---|---|
| 243 | 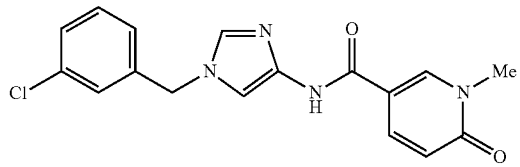 [SMILES: Cn1cc(C(=O)Nc2cn(Cc3cccc(Cl)c3)cn2)ccc1=O] | D | 0.670 | 343.2 |

Example 244

N-[1-(3-Chlorobenzyl)-1H-imidazol-4-yl]-6-(2-methoxyethoxy)nicotinamide

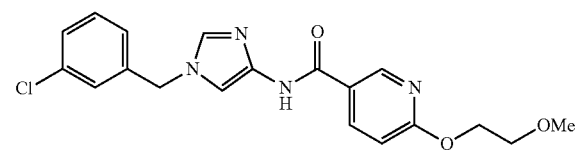 [SMILES: COCCOc1ccc(C(=O)Nc2cn(Cc3cccc(Cl)c3)cn2)cn1]

To sodium hydride (60 mg) was added 2-methoxyethanol (1 mL) under ice cooling, and the mixture was stirred at room temperature for 10 minutes. Then, thereto was added the compound of Example 142 (70 mg), and the mixture was stirred in the range of 90° C. and 100° C. overnight. The reaction solution was cooled to room temperature, and thereto was added water. The mixture was extracted with ethyl acetate twice. The organic layer was washed with water and brine, and then dried over sodium sulfate. The organic layer was concentrated under reduced pressure, and the residue was purified by column chromatography (chloroform-methanol) to give the title compound (54.2 mg) (yield 69%).

LC/MS, Condition D, Retention time 0.827 min, obs MS[M+1]387.27

Example 245

The compound of Example 245 was synthesized in a similar manner to Example 1.

Example 246

4-[6-(Hydroxymethyl)pyridin-3-yl]-N-{-[3-(trifluoromethyl)benzyl]-1H-imidazol-4-yl}benzamide

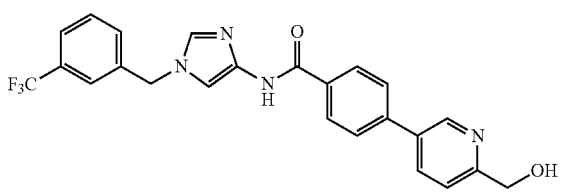

The compound of Example 245 (70 mg), 6-hydroxymethylpyridine-3-boronic acid (30 mg), potassium carbonate (91 mg), and tetrakis(triphenylphosphine)palladium (O) (19 mg) were put into a reaction vessel, and the air inside was replaced with nitrogen. Then, thereto were added 1,4-dioxane (2 mL) and water (0.4 mL), and the mixture was heated at 100° C. for 3 hours. The reaction solution was cooled to room temperature, and thereto was added water. The mixture was extracted with ethyl acetate twice, and the organic layer was washed with water and brine, and then dried over sodium sulfate. The organic layer was concentrated under reduced pressure, and the residue was purified by column chromatography (chloroform-methanol) to give the title compound (46 mg) (yield 62%).

LC/MS, Condition D, Retention time 0.731 min, obs MS[M+1]453.3

| Example | Chemical structure | LC-MS Condition | LC-MS retention time (min) | LC-MS obs MS [M + 1] |
|---|---|---|---|---|
| 245 | 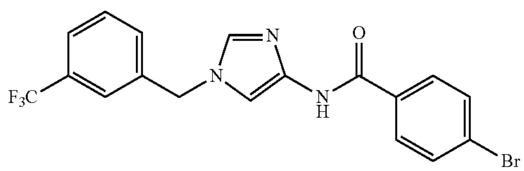 [SMILES: O=C(Nc1cn(Cc2cccc(C(F)(F)F)c2)cn1)c1ccc(Br)cc1] | D | 1.001 | 424.3 |

Example 247

6-(Acetylamino)-N-[1-(3-chlorobenzyl)-1H-imidazol-4-yl]nicotinamide

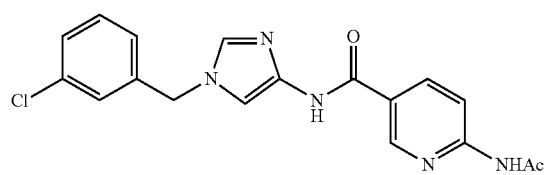 [SMILES: CC(=O)Nc1ccc(C(=O)Nc2cn(Cc3cccc(Cl)c3)cn2)cn1]

To the compound of Example 224 (45 mg) were added anhydrous acetic acid (1.37 mL) and pyridine (3 mL), and the mixture was stirred at room temperature overnight. The reaction solution was poured into ice water, and the resulting precipitate was washed with ethyl acetate to give the title compound (25.6 mg) (yield 50%).

LC/MS, Condition D, Retention time 0.678 min, obs MS[M+1]370.5

Example 248

6-[(2-Hydroxyethyl)amino]-N-{1-[3-(trifluoromethyl)benzyl]-1H-imidazol-4-yl}nicotinamide

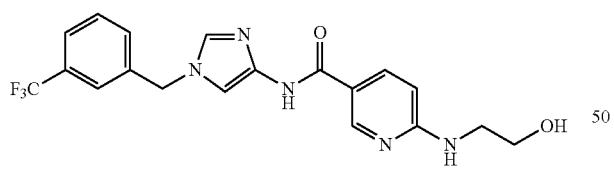

To a solution of Reference example 226 in DMF (1 mL) were added 2-aminoethanol (0.025 mL) and potassium carbonate (57 mg), and the mixture was stirred at 150° C. under microwave irradiation for 1 hour. The reaction mixture was cooled to room temperature, and then thereto was added water, and the mixture was extracted with ethyl acetate. The organic layer was washed with brine, dried over anhydrous sodium sulfate, filtered, and then concentrated under reduced pressure. To the resulting residue was added ethyl acetate (1 mL), and the mixture was put inside an ultrasonic bath. Then, thereto was added hexane (1 mL). The mixture was again put inside an ultrasonic bath, and the resulting precipitate was filtered, and then washed with hexane/ethyl acetate (1/1, 1 mL) twice and dried under reduced pressure at 50° C. for 2 hours to give the title compound (38 mg) (yield 68%).

LC/MS, Condition D, Retention time 0.630 min, obs MS[M+1]406.3

$^1$H-NMR (DMSO-d$_6$) δ 10.42 (s, 1H), 8.61 (d, J=1.2 Hz, 1H), 7.91 (dd, J=9.1, 2.4 Hz, 1H), 7.70-7.58 (m, 5H), 7.37 (d, J=1.2 Hz, 1H), 7.08 (t, J=5.5 Hz, 1H), 6.48 (d, J=9.1 Hz, 1H), 5.28 (s, 2H), 4.71 (t, J=5.5 Hz, 1H), 3.51 (td, J=11.0, 5.5 Hz, 2H), 3.36 (td, J=11.0, 5.5 Hz, 2H)

Example 249

The compound of Example 249 was synthesized in a similar manner to Example 248.

| Example | Chemical structure | LC-MS Condition | LC-MS retention time (min) | LC-MS obs MS [M + 1] |
|---|---|---|---|---|
| 249 | 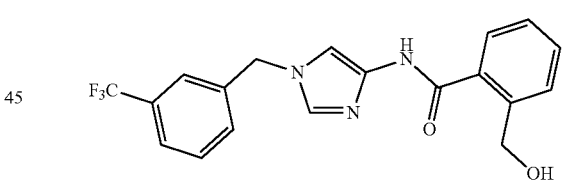 | D | 0.84 | 444.3 |

Example 250

2-(Hydroxymethyl)-N-{1-[3-(trifluoromethyl)benzyl]-1H-imidazol-4-yl}benzamide

To a solution of the compound of Reference example 37 (59 mg) in THF (5 mL) was added TBAF (1 mol/L THF solution, 180 μL), and the mixture was stirred at room temperature for 1 hour. The residue was purified by reverse phase HPLC (Mobile phase: water and acetonitrile). The residue was concentrated, neutralized with saturated sodium bicarbonate water, and then extracted with chloroform (50 mL). The resulting organic layer was dried over sodium sulfate and concentrated under reduced pressure to give the title compound (8 mg).

LC/MS, Condition D, Retention time 0.783 min, obs MS[M+1]376.2

Example 251

N-(3,4-Dimethoxyphenyl)-1-(3,4,5-trifluorobenzyl)-1H-imidazole-4-carboxamide

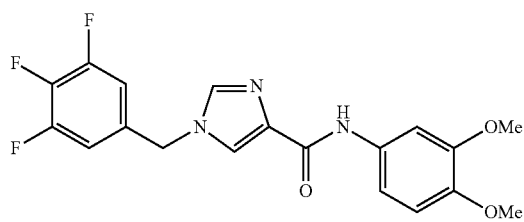 [SMILES: COc1ccc(NC(=O)c2cn(Cc3cc(F)c(F)c(F)c3)cn2)cc1OC]

To a solution of the compound of Reference example 35-2 (130 mg) and 3,4-dimethoxyaniline (78 mg) in DMF (5 mL) were added EDCl.HCl (117 mg), HOBt (82 mg), and N,N-diisopropylethylamine (0.177 mL), and the mixture was stirred at 80° C. for 4 hours. To the reaction mixture was added water and aqueous sodium hydroxide solution, and the mixture was extracted with chloroform. The organic layer was washed with brine, dried over magnesium sulfate, filtered, and then concentrated under reduced pressure. The resulting residue was purified by silica gel column chromatography (chloroform/methanol) to give the title compound (55.0 mg).

LC/MS, Condition D, Retention time 0.85 min, obs MS[M+1]392.2

Examples 252 to 254

The compounds of Examples 252 to 254 were obtained by reaction/treatment using corresponding starting compounds in a similar manner to the process of Example 251.

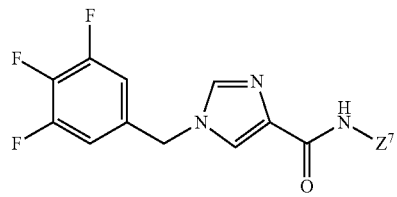

| Example | $Z^7$ | LC-MS Condition | LC-MS retention time (min) | LC-MS obs MS [M + 1] |
|---|---|---|---|---|
| 252 | 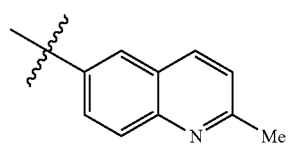 [SMILES: *c1ccc2nc(C)ccc2c1] | D | 0.691 | 397.25 |
| 253 | 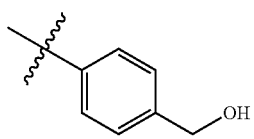 [SMILES: *c1ccc(CO)cc1] | D | 0.752 | 362.19 |
| 254 | 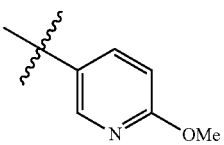 [SMILES: *c1ccc(OC)nc1] | D | 0.843 | 363.19 |

Example 255

1-(3-Chlorobenzyl)-N-(2-methylquinolin-6-yl)-1H-imidazole-4-carboxamide

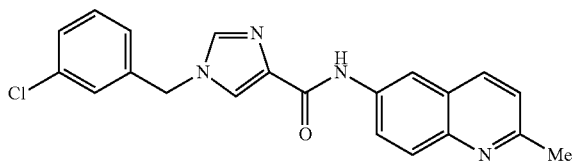 [SMILES: Cc1ccc2cc(NC(=O)c3cn(Cc4cccc(Cl)c4)cn3)ccc2n1]

1-(3-Chlorobenzyl)-1H-imidazole-4-carboxylic acid (47.3 mg) was dissolved in dry dichloromethane (1 mL) Thereto was added oxalyl chloride (27.9 mg), and the mixture was stirred at room temperature for 2 hours. The mixture was concentrated under reduced pressure, and then thereto were added pyridine (1 mL) and 2-methylquinolin-6-amine (31.6 mg). The mixture was stirred at room temperature overnight. Thereto was added methanol (1 mL), and the mixture was stirred for 1 hour, and then concentrated under reduced pressure to give the compound of Example 255 (crude). The crude compound was dissolved in methanol (1 mL), purified by reverse phase HPLC, and desalted with piperidine resin to give the title compound.

LC/MS, Condition C, Retention time 3.26 min, obs MS[M+1]377.5

Examples 256 to 264

The compounds of Examples 256 to 264 were obtained by reaction/treatment using corresponding starting compounds in a similar manner to the process of Example 255.

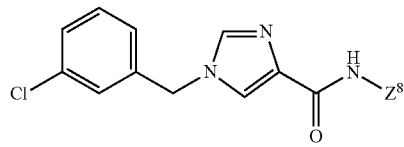

| Example | Z⁸ | LC-MS Condition | LC-MS retention time (min) | LC-MS obs MS [M + 1] |
|---|---|---|---|---|
| 256 | 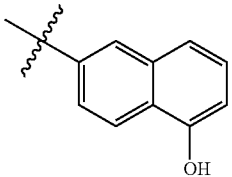 [SMILES: *c1ccc2c(O)cccc2c1] | C | 3.95 | 378.2 |
| 257 | 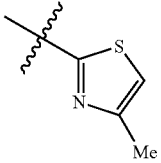 [SMILES: *c1nc(C)cs1] | C | 3.73 | 333.4 |
| 258 | 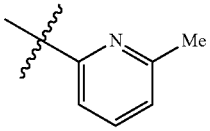 [SMILES: *c1cccc(C)n1] | C | 3.42 | 327.3 |
| 259 | 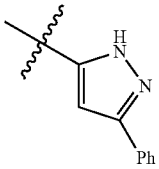 [SMILES: *c1cc(-c2ccccc2)n[nH]1] | C | 3.93 | 378.4 |
| 260 | 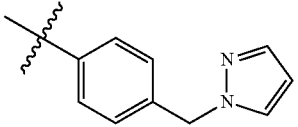 [SMILES: *c1ccc(Cn2cccn2)cc1] | E | 3.30 | 392.2 |

| Example | Z⁸ | LC-MS Condition | LC-MS retention time (min) | LC-MS obs MS [M + 1] |
|---|---|---|---|---|
| 261 | | C | 3.39 | 314.3 |
| 262 | | F | 3.04 | 372.3 |
| 263 | | D | 0.877 | 343.1 |
| 264 | | C | 3.02 | 313.3 |

Example 265

N-[1-(3-Chlorobenzyl)-1H-imidazol-4-yl]-4-(2-methoxyethoxy)benzamide

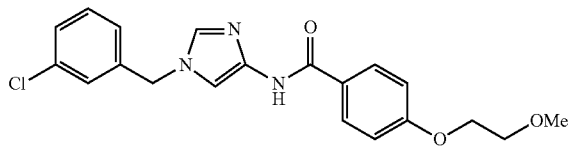 [SMILES: COCCOc1ccc(C(=O)Nc2cn(Cc3cccc(Cl)c3)cn2)cc1]

To a solution of the compound of Example 139 (57.0 mg) in tetrahydrofuran (1 mL) was added t-butoxypotassium (20 mg), followed by 2-bromoethyl methyl ether (16.5 μL) under nitrogen atmosphere, and the mixture was stirred at room temperature overnight. To the reaction solution was added water, and the mixture was extracted with ethyl acetate. The organic layer was washed with brine, dried over anhydrous sodium sulfate, and filtered, and then the solvent was removed under reduced pressure. The resulting residue was purified by silica gel column chromatography (chloroform/methanol) to give the compound of Example 265 (51.6 mg) as a white solid (yield 77%).

LC/MS, Condition C, Retention time 3.26 min, obs MS[M+1]377.5

¹H-NMR (300 MHz, DMSO-d₆) δ 10.63 (s, 1H), 7.97 (d, 2H, J=7.8 Hz), 7.67 (s, 1H), 7.41-7.28 (m, 5H), 7.00 (d, 1H, J=7.8 Hz), 5.20 (s, 2H), 4.15 (s, 2H), 3.67 (s, 2H), 3.31 (s, 3H).

Example 266

N-[1-(3-Chlorobenzyl)-1H-imidazol-4-yl]-3-(sulfamoylamino)benzamide

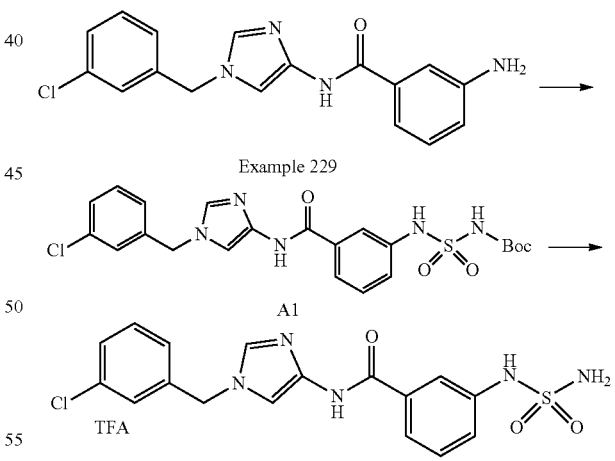

To a solution of the compound of Example 229 (36.3 mg) in dichloromethane (1 mL) were added N-(tert-butoxycarbonyl)-N-[4-(dimethylazaniumylidene)-1,4-dihydropyridine-1-ylsulfonyl]azanide (synthesized by the process of Org. lett., 2001, 3, 2241) (33.5 mg) and triethylamine (16 μL), and the mixture was stirred at room temperature for 2 days. To the reaction solution was added water, and the mixture was extracted with ethyl acetate. The organic layer was washed with brine, dried over anhydrous sodium sulfate, and filtered, and then the solvent was removed under reduced pressure. The resulting crude product A1 was dissolved in chloroform (1 mL), and thereto was added 4 mol/L hydrochloric acid/1,4-dioxane solution (0.5 mL). The mixture was stirred at room temperature overnight. The solvent was removed under reduced pressure and purified by reverse phase preparative chromatography (0.025% trifluoroacetic acid-acetonitrile/0.05% trifluoroacetic acid-water) to give the title compound (8.5 mg) as a trifluoroacetate salt.

LC/MS, Condition E, Retention time 2.55 min, obs MS[M+1]406.2

Examples 267 to 283

The compounds of Examples 267 to 283 were synthesized in a similar manner to Example 118.

| Example | Chemical structure | LC-MS Condition | LC-MS retention time (min) | LC-MS obs MS [M + 1] |
|---|---|---|---|---|
| 267 | 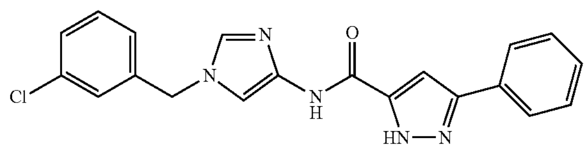 [SMILES: O=C(Nc1cn(Cc2cccc(Cl)c2)cn1)c1cc(-c2ccccc2)n[nH]1] | C | 3.55 | 378.4 |
| 268 | 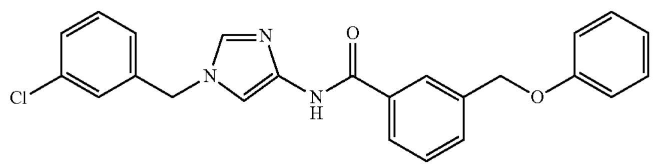 [SMILES: O=C(Nc1cn(Cc2cccc(Cl)c2)cn1)c1cccc(COc2ccccc2)c1] | E | 3.55 | 418.2 |
| 269 | 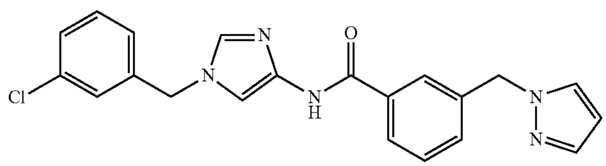 [SMILES: O=C(Nc1cn(Cc2cccc(Cl)c2)cn1)c1cccc(Cn2cccn2)c1] | E | 2.76 | 392.2 |
| 270 | 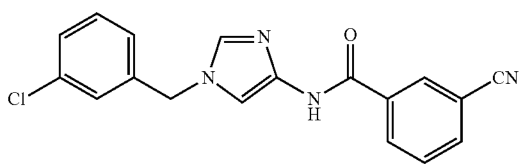 [SMILES: N#Cc1cccc(C(=O)Nc2cn(Cc3cccc(Cl)c3)cn2)c1] | E | 2.9 | 337.3 |
| 271 | 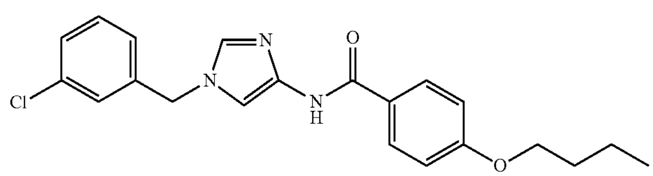 [SMILES: CCCCOc1ccc(C(=O)Nc2cn(Cc3cccc(Cl)c3)cn2)cc1] | E | 3.3 | 384.3 |
| 272 | 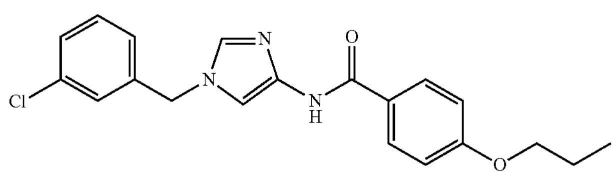 [SMILES: CCCOc1ccc(C(=O)Nc2cn(Cc3cccc(Cl)c3)cn2)cc1] | E | 3.17 | 370.3 |
| 273 | 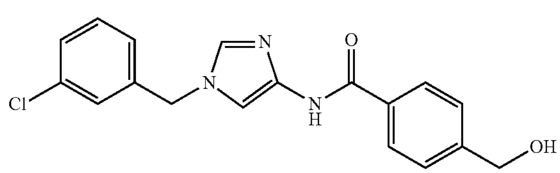 [SMILES: O=C(Nc1cn(Cc2cccc(Cl)c2)cn1)c1ccc(CO)cc1] | E | 2.57 | 342.3 |

| Example | Chemical structure | LC-MS Condition | LC-MS retention time (min) | LC-MS obs MS [M + 1] |
|---|---|---|---|---|
| 274 | 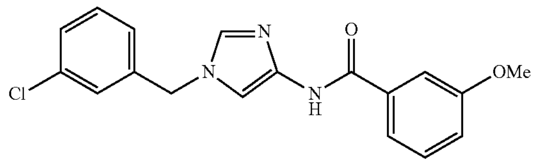 [SMILES: COc1cccc(C(=O)Nc2cn(Cc3cccc(Cl)c3)cn2)c1] | C | 3.76 | 342.3 |
| 275 | 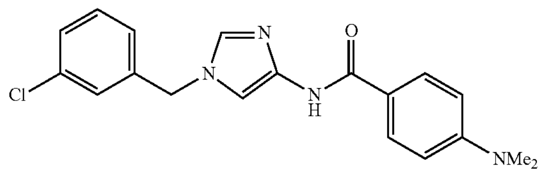 [SMILES: CN(C)c1ccc(C(=O)Nc2cn(Cc3cccc(Cl)c3)cn2)cc1] | C | 3.72 | 355.2 |
| 276 | 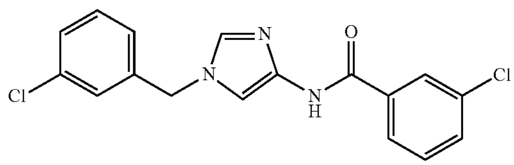 [SMILES: O=C(Nc1cn(Cc2cccc(Cl)c2)cn1)c1cccc(Cl)c1] | C | 3.95 | 346.2 |
| 277 | 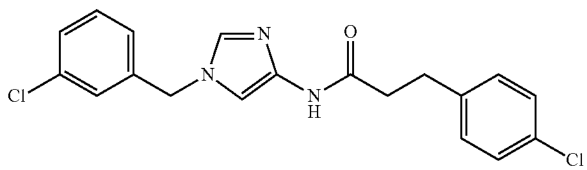 [SMILES: O=C(CCc1ccc(Cl)cc1)Nc1cn(Cc2cccc(Cl)c2)cn1] | C | 4.30 | 374.3 |
| 278 | 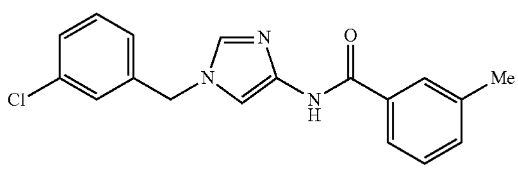 [SMILES: Cc1cccc(C(=O)Nc2cn(Cc3cccc(Cl)c3)cn2)c1] | C | 3.77 | 326.3 |
| 279 | 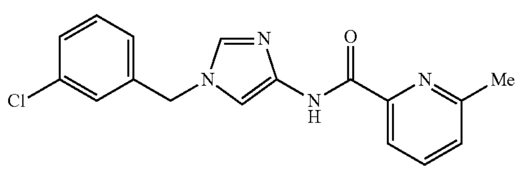 [SMILES: Cc1cccc(C(=O)Nc2cn(Cc3cccc(Cl)c3)cn2)n1] | C | 3.58 | 327.3 |
| 280 | 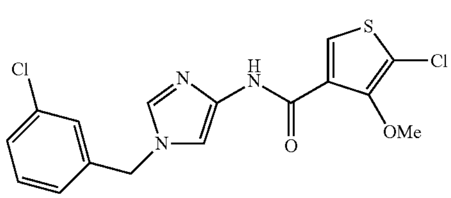 [SMILES: COc1c(C(=O)Nc2cn(Cc3cccc(Cl)c3)cn2)csc1Cl] | C | 3.95 | 382.2 |
| 281 | 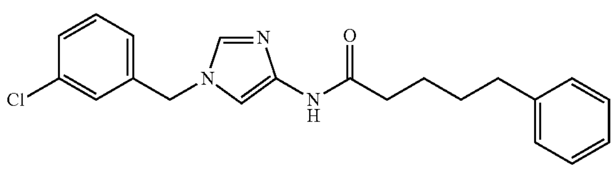 [SMILES: O=C(CCCCc1ccccc1)Nc1cn(Cc2cccc(Cl)c2)cn1] | C | 4.02 | 368.3 |

| Example | Chemical structure | LC-MS Condition | LC-MS retention time (min) | LC-MS obs MS [M + 1] |
|---|---|---|---|---|
| 282 | 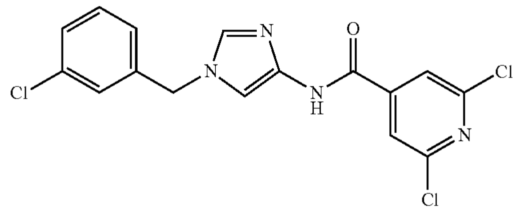 [SMILES: O=C(Nc1cn(Cc2cccc(Cl)c2)cn1)c1cc(Cl)nc(Cl)c1] | C | 4.15 | 383.1 |
| 283 | 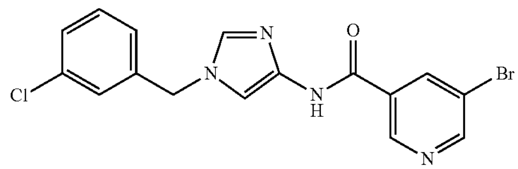 [SMILES: O=C(Nc1cn(Cc2cccc(Cl)c2)cn1)c1cncc(Br)c1] | C | 3.62 | 393.2 |

Examples 284 to 303

The compounds of Examples 284 to 303 were synthesized in a similar manner to Example 143.

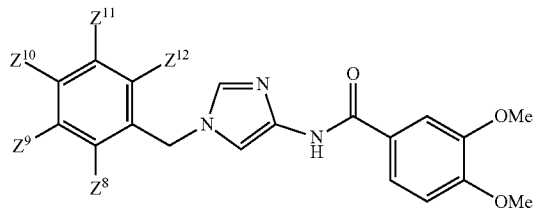

| Example | $Z^8$ | $Z^9$ | $Z^{10}$ | $Z^{11}$ | $Z^{12}$ | LC-MS Condition | LC-MS retention time (min) | LC-MS obs MS [M + 1] |
|---|---|---|---|---|---|---|---|---|
| 284 | H | NMe$_2$ | H | H | H | G | 3.02 | 381.4 |
| 285 | OMe | H | H | H | H | E | 2.63 | 368.1 |
| 286 | H | H | Me | H | H | C | 3.51 | 352.4 |
| 287 | H | H | CF$_3$ | H | H | C | 3.69 | 406.5 |
| 288 | Me | H | H | H | H | C | 3.42 | 352.4 |
| 289 | CF$_3$ | H | H | H | H | C | 3.63 | 406.5 |
| 290 | H | OMe | H | H | H | C | 3.40 | 368.4 |
| 291 | H | Me | H | H | H | C | 3.49 | 352.4 |
| 292 | H | H | H | H | H | C | 3.32 | 338.4 |
| 293 | H | CO$_2$Me | H | H | H | C | 3.34 | 396.4 |
| 294 | H | Ph | H | H | H | C | 3.85 | 414.6 |
| 295 | H | Cl | Me | H | H | C | 3.68 | 386.4 |
| 296 | F | Cl | H | H | H | C | 3.52 | 390.4 |
| 297 | H | OPh | H | H | H | C | 3.89 | 430.4 |
| 298 | H | OCHF$_2$ | H | H | H | C | 3.50 | 404.4 |
| 299 | Me | CF$_3$ | H | H | H | C | 3.75 | 420.4 |
| 300 | H | Br | H | Br | H | C | 3.88 | 496.2 |
| 301 | H | Cl | H | OCF$_3$ | H | C | 3.97 | 456.3 |
| 302 | H | CO$_2$Et | H | H | H | C | 3.32 | 410.6 |
| 303 | CF$_3$ | H | H | Cl | H | C | 3.64 | 440.5 |

Examples 304 to 314

The compounds of Examples 304 to 314 were synthesized in a similar manner to Example 143.

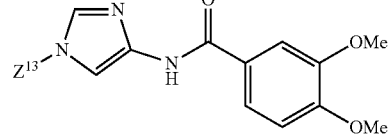

| Example | $Z^{13}$ | LC-MS Condition | LC-MS retention time (min) | LC-MS obs MS [M + 1] |
|---|---|---|---|---|
| 304 | | C | 3.80 | 358.6 |

-continued
| Example | Z¹³ | LC-MS Condition | LC-MS retention time (min) | LC-MS obs MS [M + 1] |
|---|---|---|---|---|
| 305 | 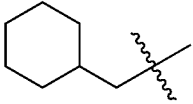 [SMILES: *CC1CCCCC1] | C | 3.57 | 344.3 |
| 306 | 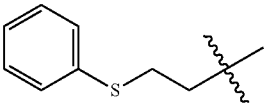 [SMILES: *CCSc1ccccc1] | C | 3.53 | 384.3 |
| 307 | 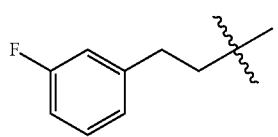 [SMILES: *CCc1cccc(F)c1] | C | 3.49 | 370.3 |
| 308 | 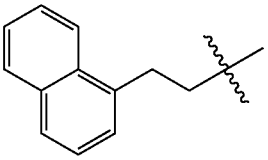 [SMILES: *CCc1cccc2ccccc12] | C | 3.76 | 402.5 |
| 309 | 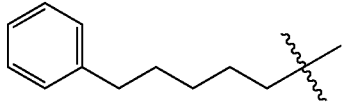 [SMILES: *CCCCCc1ccccc1] | C | 3.93 | 394.4 |
| 310 | 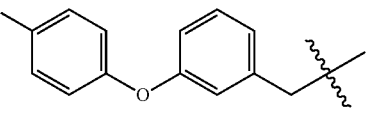 | C | 3.94 | 448.4 |
| 311 | 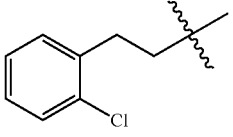 [SMILES: *CCc1ccccc1Cl] | C | 3.53 | 386.4 |
| 312 | 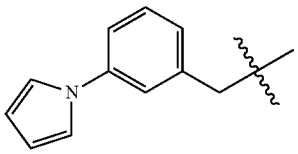 [SMILES: *Cc1cccc(-n2cccc2)c1] | C | 3.70 | 403.6 |
| 313 | 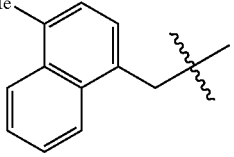 | C | 3.82 | 402.4 |
| 314 | 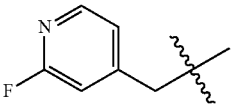 | G | 3.13 | 357.4 |

Examples 315 to 359

The compounds of Examples 315 to 359 were obtained by reaction/treatment using corresponding starting compounds in a similar manner to the process of Example 255.

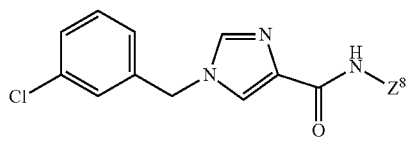

| Example | Z⁸ | LC-MS Condition | LC-MS retention time (min) | LC-MS obs MS [M + 1] |
|---------|----|----|----|----|
| 315 | 2-(methoxycarbonyl)thiophen-3-yl (MeO$_2$C-thiophene) | H | 3.44 | 376.4 |
| 316 | 6-ethoxybenzothiazol-2-yl | F | 4.14 | 413.2 |
| 317 | 4-ethoxyphenyl | F | 3.51 | 356.3 |
| 318 | 3-(ethoxycarbonyl)phenyl | E | 3.44 | 384.1 |
| 319 | 2-(ethoxycarbonyl)phenyl | E | 3.90 | 384.1 |
| 320 | 4-(methoxycarbonyl)phenyl | E | 3.34 | 370.3 |
| 321 | 5-methylthiazol-2-yl | E | 2.96 | 333.1 |

-continued
| Example | Z⁸ | LC-MS Condition | LC-MS retention time (min) | LC-MS obs MS [M + 1] |
|---|---|---|---|---|
| 322 | 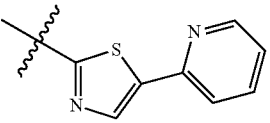 [SMILES: *c1ncc(-c2ccccn2)s1] | E | 2.67 | 396.1 |
| 323 | 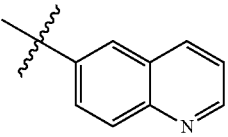 | C | 3.25 | 363.3 |
| 324 | 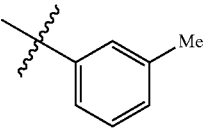 [SMILES: *c1cccc(C)c1] | C | 4.16 | 326.3 |
| 325 | 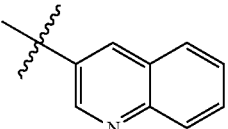 | C | 3.55 | 363.2 |
| 326 | 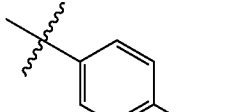 | H | 3.44 | 418.4 |
| 327 | 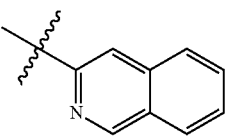 [SMILES: *c1cc2ccccc2cn1] | F | 3.64 | 363.1 |
| 328 | 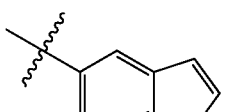 | C | 3.72 | 351.2 |
| 329 | 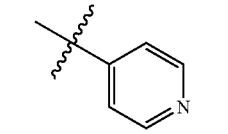 [SMILES: *c1ccncc1] | C | 3.16 | 313.2 |
| 330 | 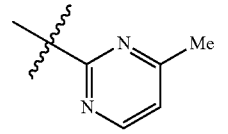 [SMILES: *c1nccc(C)n1] | C | 3.26 | 328.1 |
| 331 | 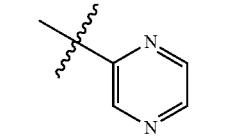 | C | 3.57 | 314.4 |

-continued

| Example | Z⁸ | LC-MS Condition | LC-MS retention time (min) | LC-MS obs MS [M + 1] |
|---------|-----|-----------------|----------------------------|----------------------|
| 332 | 2-methylquinolin-4-yl | C | 3.58 | 377.5 |
| 333 | 1-phenyl-1H-pyrazolo[3,4-d]pyrimidin-4-yl | H | 3.85 | 430.5 |
| 334 | 1H-pyrazolo[3,4-d]pyrimidin-4-yl | C | 3.23 | 354.0 |
| 335 | 6-chloropyrazin-2-yl | F | 3.66 | 348.4 |
| 336 | 4-methoxy-6-methylpyrimidin-2-yl | C | 3.35 | 358.5 |
| 337 | 6-ethylpyrazin-2-yl | C | 3.64 | 341.3 |
| 338 | 1H-indazol-6-yl | C | 3.56 | 352.2 |
| 339 | quinolin-5-yl | C | 3.12 | 363.3 |
| 340 | 7-hydroxyquinolin-5-yl | C | 3.02 | 379.3 |

-continued

| Example | Z⁸ | LC-MS Condition | LC-MS retention time (min) | LC-MS obs MS [M + 1] |
|---|---|---|---|---|
| 341 | benzothiazol-6-yl | C | 3.78 | 369.2 |
| 342 | 1H-indazol-5-yl | C | 3.39 | 352.3 |
| 343 | 1H-benzotriazol-5-yl | C | 3.39 | 353.1 |
| 344 | 4-(CH₂CO₂Et)-thiazol-2-yl | C | 4.06 | 405.4 |
| 345 | 4-(CH₂CO₂H)-thiazol-2-yl | C | 3.69 | 333.4 |
| 346 | 4-Me-5-acetyl-thiazol-2-yl | C | 3.94 | 375.4 |
| 347 | benzothiazol-2-yl | F | 3.84 | 369.1 |
| 348 | 1,3,4-thiadiazol-2-yl | C | 3.46 | 320.2 |
| 349 | 4-(C(O)CO₂Et)-thiazol-2-yl | F | 3.64 | 419.2 |

-continued

| Example | Z⁸ | LC-MS Condition | LC-MS retention time (min) | LC-MS obs MS [M + 1] |
| --- | --- | --- | --- | --- |
| 350 | 5-chlorobenzoxazol-2-yl | F | 3.56 | 387.4 |
| 351 | 5-hydroxy-1H-pyrazol-3-yl | C | 3.08 | 318.2 |
| 352 | 5-cyclopropyl-1,3,4-thiadiazol-2-yl | C | 3.87 | 360.2 |
| 353 | 5-(4-chlorophenyl)-1H-pyrazol-3-yl | F | 3.68 | 412.5 |
| 354 | 1-methyl-3-phenyl-1H-pyrazol-5-yl | C | 4.14 | 392.5 |
| 355 | 3-(4-chlorophenyl)-1-methyl-1H-pyrazol-5-yl | F | 3.99 | 426.2 |
| 356 | 5-(ethoxycarbonyl)-4-methylthiazol-2-yl | F | 3.91 | 405.5 |

| Example | $Z^8$ | LC-MS Condition | LC-MS retention time (min) | LC-MS obs MS [M + 1] |
|---|---|---|---|---|
| 357 | (structure: thiadiazole with SEt) | F | 3.66 | 380.4 |
| 358 | (structure: thiophene with C(O)NH2 and Me) | C | 4.00 | 375.2 |
| 359 | (structure: imidazole with NC) | C | 3.28 | 327.3 |

An elemental analysis result for a crystal of the hydrochloride monohydrate in Example 237 is shown as follows.

| $C_{19}H_{16}F_3N_3O_3 \cdot HCl\ H_2O$ | | C (%) | H (%) | Cl (%) | N (%) | F (%) |
|---|---|---|---|---|---|---|
| Example 237 | Calculated value | 51.19 | 4.30 | 7.95 | 9.43 | 12.78 |
| | Measured value | 51.21 | 4.30 | 7.95 | 9.42 | 12.92 |

An elemental analysis result for a crystal of the tosic acid in Example 238 is shown as follows.

| $C_{19}H_{16}F_3N_3O_3 \cdot C_7H_7SO_3H$ | | C (%) | H (%) | S (%) | N (%) | F (%) |
|---|---|---|---|---|---|---|
| Example 238 | Calculated value | 55.41 | 4.29 | 5.69 | 7.46 | 10.11 |
| | Measured value | 55.58 | 4.33 | 5.65 | 7.48 | 10.21 |

The solid state thermal stability was measured for the compounds of Examples 237 and 238 according to the following method. The compounds of Examples 237 and 238 were put into an isothermal vessel set at 70° C., and the samples were stored for 12 weeks under the condition that the vessel was left open. Each elemental analysis result for each compound after 12 weeks is shown as follows.

| $C_{19}H_{16}F_3N_3O_3 \cdot HCl\ H_2O$ | | C (%) | H (%) | Cl (%) | N (%) | F (%) |
|---|---|---|---|---|---|---|
| Example 237 | Calculated value | 51.19 | 4.30 | 7.95 | 9.43 | 12.78 |
| | Measured value | 54.71 | 4.31 | 4.00 | 10.28 | 13.74 |

| $C_{19}H_{16}F_3N_3O_3 \cdot C_7H_7SO_3H$ | | C (%) | H (%) | S (%) | N (%) | F (%) |
|---|---|---|---|---|---|---|
| Example 238 | Calculated value | 55.41 | 4.29 | 5.69 | 7.46 | 10.11 |
| | Measured value | 55.51 | 4.33 | 5.62 | 7.48 | 10.15 |

Under the above condition, it was observed that the compound of Example 237 was changed to 0.5 hydrochloride 0.5 hydrate after 12 weeks, while the compound of Example 238 was not changed.

Test Example 1: Inhibition Test for Sphere-Forming Ability of Cancer Cells

The reliable methods established for measuring the self-renewal ability of cells which is one of the CSC's properties include a method for measuring the sphere-forming ability of cancer cells in non-adherent condition in the absence of serum (Cancer Res 65, 5506-5511 (2005)). Human colorectal cancer-derived HCT-116 cells, human colon-adenocarcinoma-derived HT-29 cells, and human pharyngeal cancer-derived FaDu cells were available from American Type Culture Collection (ATCC). HCT-116 cells and HT-29 cells were cultured at 37° C. under 5% $CO_2$ using the McCoy's 5a medium containing 10% fetal bovine serum (FBS) and 1% penicillin/streptomycin, and FaDu cells were cultured at 37° C. under 5% $CO_2$ using the MEM medium containing 10% FBS, 1% non-essential amino acid, 1% sodium pyruvate, and 1% penicillin/streptomycin. HCT-116 cells, HT-29 cells, and FaDu cells were seeded in a 384 Well Black Clear Bottom Ultra-Low Attachment Microplate (Corning Cat. No. 3827) in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 µg/mL insulin (Sigma), and 1% penicillin/streptomycin. Each test compound was added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere $IC_{50}$ value; μmol/L).

The experiment of Test Example 1 was performed for each compound of each Example. The concentration of each test compound for 50% inhibition of cell proliferation (Sphere $IC_{50}$ value; μmol/L) is shown in the following Table. The value with % means (100%-inhibition rate of cell proliferation) at 1 μmol/L.

| Example | $IC_{50}$ (μmol/L) HCT-116 | FaDu | HT-29 |
| --- | --- | --- | --- |
| 1 | 0.32 | 0.05 | 0.02 |
| 3 | 6.76 | 3.13 | 3.58 |
| 4 | 5.79 | 0.67 | 0.69 |
| 6 | 0.55 | 0.17 | 0.18 |
| 7 | 0.66 | 0.35 | 0.13 |
| 8 | 0.31 | 0.06 | 0.05 |
| 9 | 0.22 | 0.03 | 0.03 |
| 10 | 0.63 | 0.07 | 0.07 |
| 11 | <0.01 | 0.08 | 0.08 |
| 12 | 7.54 | 1.44 | 0.92 |
| 13 | 8.72 | 2.84 | 0.74 |
| 14 | 0.06 | 0.04 | <0.01 |
| 15 | <0.01 | 0.07 | 0.06 |
| 16 | 0.31 | 0.08 | 0.06 |
| 17 | 0.08 | 0.08 | 0.04 |
| 18 | 0.07 | 0.06 | 0.02 |
| 19 | 0.89 | 0.66 | 0.60 |
| 20 | 0.45 | 0.06 | 0.01 |
| 21 | 7.05 | 0.66 | 6.65 |
| 22 | 0.08 | 0.06 | <0.01 |
| 23 | 0.61 | <0.01 | 0.47 |
| 24 | 7.42 | 5.97 | >10 |
| 25 | >10 | 0.89 | 2.61 |
| 26 | >10 | 5.49 | 5.83 |
| 27 | >10 | 5.84 | 3.38 |
| 28 | 7.89 | 0.80 | 0.91 |
| 29 | 5.87 | 0.76 | 0.89 |
| 30 | >10 | 0.71 | >10 |
| 31 | 0.84 | <0.01 | 0.65 |
| 32 | 0.06 | 0.06 | 0.07 |
| 33 | 0.06 | <0.01 | 0.01 |
| 34 | 0.09 | 0.09 | 0.06 |
| 35 | 0.08 | 0.08 | 0.07 |
| 36 | 0.08 | 0.08 | 0.06 |
| 37 | 0.25 | <0.01 | 0.93 |
| 38 | 0.15 | <0.01 | 0.89 |
| 39 | 0.42 | 0.07 | 0.45 |
| 40 | 0.48 | 0.05 | 0.18 |
| 41 | 0.89 | 0.73 | 0.54 |
| 42 | 0.96 | 5.77 | 0.70 |
| 43 | 0.85 | 0.69 | 0.49 |
| 44 | 0.10 | 0.07 | 0.05 |
| 45 | 6.38 | 0.81 | 0.88 |
| 46 | 2.62 | 0.79 | 0.62 |
| 47 | 0.89 | 0.76 | 0.70 |
| 48 | 0.76 | 0.09 | 0.08 |
| 49 | 0.10 | 0.08 | 0.06 |
| 50 | 2.48 | 6.70 | 0.89 |
| 51 | 7.20 | 6.13 | 3.75 |
| 52 | >10 | 0.01 | 7.54 |
| 53 | 0.87 | 0.87 | 0.84 |
| 54 | 8.38 | 0.82 | 8.11 |
| 55 | 0.96 | 3.77 | 1.20 |
| 56 | 5.74 | 4.50 | 6.62 |
| 57 | 0.94 | 4.36 | 3.30 |
| 58 | 6.99 | 6.52 | 4.89 |
| 59 | 7.78 | 0.86 | 0.79 |
| 60 | >10 | 8.20 | 9.79 |
| 61 | 0.09 | 0.07 | 0.02 |
| 62 | 0.74 | 0.56 | 0.09 |
| 63 | 0.53 | 0.08 | 0.07 |
| 64 | 9.79 | 0.59 | 0.69 |
| 65 | 0.95 | 0.06 | 2.66 |
| 66 | 0.09 | 0.06 | 0.07 |
| 67 | 7.34 | 0.79 | 8.37 |
| 68 | 0.07 | 0.01 | <0.01 |
| 69 | 0.82 | 0.54 | 0.38 |
| 70 | 8.98 | 0.09 | 0.08 |
| 71 | 0.23 | 0.06 | 0.03 |
| 72 | 4.42 | 0.29 | 0.09 |
| 73 | 4.53 | 0.85 | 1.49 |
| 74 | 0.05 | <0.01 | <0.01 |
| 75 | 7.56 | 7.19 | 6.45 |
| 76 | 6.18 | 4.11 | 2.71 |
| 77 | 0.84 | <0.01 | 0.38 |
| 78 | 7.31 | 8.90 | 6.34 |
| 79 | 0.79 | 0.86 | 0.70 |
| 80 | >10 | 0.87 | 7.04 |
| 81 | 3.82 | 0.76 | 6.12 |
| 82 | 6.51 | 1.76 | 0.99 |
| 83 | 0.80 | 0.91 | 0.60 |
| 84 | 0.59 | 0.68 | 0.52 |
| 85 | 17.96 | 13.73 | 25.90 |
| 87 | 2.37 | 5.14 | 5.53 |
| 88 | 0.88 | 0.91 | 0.83 |

| Example | $IC_{50}$ (μmol/L) HCT-116 | FaDu | HT-29 |
| --- | --- | --- | --- |
| 89 | 0.96 | 0.04 | 0.61 |
| 90 | 8.17 | 6.32 | 7.87 |
| 91 | 7.51 | 6.15 | 4.50 |
| 92 | 1.61 | 0.74 | 0.62 |
| 93 | 0.82 | 0.09 | 4.93 |
| 94 | 7.88 | 4.57 | 0.97 |
| 95 | >10 | 0.99 | 3.23 |
| 96 | 0.83 | 0.07 | 0.09 |
| 97 | 0.08 | 0.06 | 0.05 |
| 98 | >10 | 7.75 | 7.58 |
| 99 | 6.12 | — | 2.52 |
| 100 | 6.63 | — | 1.96 |
| 102 | 7.87 | — | 4.07 |
| 103 | 0.87 | 0.60 | 0.60 |
| 104 | 2.09 | 2.70 | 0.79 |
| 105 | 5.05 | 0.85 | 0.94 |
| 106 | 8.29 | 3.06 | 0.80 |
| 107 | >10 | 0.07 | 0.04 |
| 108 | 3.31 | 9.77 | 3.43 |
| 109 | 2.65 | 0.67 | 0.75 |
| 110 | 7.21 | 1.92 | 5.67 |
| 111 | 9.31 | 0.99 | 0.83 |
| 112 | >10 | 0.07 | 0.04 |
| 113 | 0.54 | >10 | 0.53 |
| 114 | 0.62 | 0.72 | 0.69 |
| 115 | 0.79 | 0.79 | 0.66 |
| 116 | >10 | 0.93 | 0.80 |
| 118 | 0.10 | 0.07 | <0.01 |
| 119 | 0.67 | 0.56 | 0.16 |
| 131 | >10 | — | 8.71 |
| 132 | 8.22 | — | 6.37 |
| 135 | 31.8% | 25.0% | 28.0% |
| 136 | 44.2% | 75.2% | 71.8% |
| 137 | 0.81 | — | 0.57 |
| 138 | 0.10 | — | 0.20 |
| 140 | 31.4% | 81.8% | 83.0% |
| 141 | 0.63 | 0.85 | 0.52 |
| 143 | 0.95 | 0.93 | 0.84 |
| 144 | 5.72 | 5.81 | 4.71 |
| 145 | 0.62 | 0.70 | 0.62 |
| 146 | 0.64 | 0.80 | 0.74 |

| Example | HCT-116 | FaDu | HT-29 |
|---|---|---|---|
| 147 | 0.78 | 3.12 | 0.83 |
| 148 | 5.20 | 8.00 | 4.74 |
| 149 | 4.77 | 0.89 | 0.75 |
| 150 | 0.69 | 6.21 | 3.56 |
| 151 | 0.35 | 0.31 | 0.09 |
| 152 | 0.09 | 0.42 | 0.09 |
| 153 | 0.66 | 0.82 | 0.73 |
| 154 | 0.71 | 0.88 | 0.80 |
| 155 | 3.05 | 8.72 | 6.62 |
| 156 | 0.54 | 0.55 | 0.39 |
| 157 | 7.33 | 8.46 | 6.89 |
| 158 | 0.57 | 0.50 | — |
| 159 | 0.06 | 0.07 | — |
| 160 | 0.07 | 0.07 | — |
| 161 | 0.04 | <0.01 | — |
| 162 | 0.06 | 0.06 | — |
| 163 | 3.56 | 1.73 | 1.51 |
| 164 | 37.4% | 92.3% | 89.0% |
| 165 | 31.9% | 24.1% | 28.0% |
| 166 | 36.8% | 23.8% | 33.0% |
| 167 | 30.5% | 59.3% | 15.6% |
| 168 | 32.1% | 32.3% | 8.6% |
| 169 | 50.9% | 68.6% | 35.4% |
| 170 | 33.8% | 27.1% | 24.9% |
| 171 | 36.4% | 29.6% | 33.8% |
| 172 | 34.3% | 42.3% | 16.6% |
| 173 | 29.5% | 21.4% | 21.6% |
| 174 | 0.65 | 0.58 | — |
| 175 | 0.29 | 0.22 | — |
| 176 | 7.16 | 5.16 | 3.43 |
| 177 | 9.96 | 3.62 | 6.75 |
| 178 | 9.60 | — | 8.13 |
| 179 | 2.91 | — | 4.65 |
| 180 | 8.73 | — | 0.76 |
| 181 | 0.77 | — | 0.19 |
| 182 | >10 | — | 5.60 |
| 183 | 0.94 | — | 0.29 |
| 184 | 8.16 | — | 9.07 |
| 185 | 8.25 | — | 5.73 |
| 186 | 0.08 | — | 0.05 |
| 187 | 7.31 | 8.64 | 3.74 |
| 188 | 0.72 | — | 0.63 |
| 189 | 4.94 | — | 4.64 |
| 190 | 0.06 | — | 0.06 |
| 191 | 0.31 | — | 0.09 |
| 192 | 0.05 | — | <0.01 |
| 193 | 0.07 | — | 0.06 |
| 194 | 6.05 | — | 2.84 |
| 195 | >10 | >10 | 5.55 |
| 196 | 0.76 | 0.89 | 3.78 |
| 197 | 44.3% | 28.9% | 39.0% |
| 198 | 55.3% | 64.5% | 99.8% |
| 199 | 39.8% | 25.9% | 31.2% |
| 202 | 0.96 | 6.87 | 5.68 |
| 203 | 0.90 | 0.90 | 0.71 |
| 204 | 4.56 | 0.86 | 0.72 |
| 205 | >10 | 6.39 | 2.39 |
| 206 | 0.69 | 0.09 | 0.09 |
| 207 | 0.83 | 0.89 | 0.67 |
| 208 | >10 | 5.33 | 0.81 |
| 209 | 4.24 | 6.45 | 4.95 |
| 210 | 0.81 | 0.79 | 0.82 |
| 211 | 0.80 | >10 | 0.87 |
| 212 | 0.78 | 0.84 | 0.99 |
| 213 | 0.81 | 0.79 | 0.65 |
| 214 | 5.31 | 3.52 | 0.90 |
| 215 | 0.88 | 0.85 | 0.66 |
| 216 | 0.08 | 0.09 | 0.07 |
| 217 | 0.22 | 0.75 | 0.48 |
| 218 | 0.58 | 0.08 | 0.06 |
| 219 | 0.92 | 9.4 | 8.34 |
| 220 | >10 | 0.77 | 4.25 |
| 221 | 0.51 | 0.89 | 0.59 |
| 222 | >10 | 9.74 | 4.81 |
| 223 | 0.76 | 0.81 | 0.65 |
| 224 | 6.71 | 5.44 | 5.51 |
| 225 | 6.76 | 6.00 | 0.99 |
| 226 | 45.7% | 87.9% | 91.7% |
| 227 | 9.06 | — | 8.00 |
| 228 | 6.39 | — | 4.17 |
| 230 | 6.02 | — | 0.94 |
| 231 | 0.56 | — | 0.07 |
| 233 | 4.35 | — | 5.46 |
| 234 | 45.7% | 87.9% | 91.7% |
| 235 | 3.84 | — | 8.77 |
| 236 | 0.06 | 0.05 | 0.05 |
| 242 | 0.38 | 0.11 | 0.29 |
| 243 | 23.8% | 29.0% | 19.5% |
| 244 | 46.7% | 36.7% | 27.0% |
| 246 | 6.72 | — | 6.36 |
| 247 | 9.22 | 7.25 | 0.42 |
| 248 | 1.00 | — | 0.83 |
| 249 | 0.49 | — | 0.29 |
| 250 | >10 | — | 8.19 |
| 251 | 0.21 | 0.43 | 0.54 |
| 252 | 0.03 | — | <0.01 |
| 253 | 0.07 | — | 0.08 |
| 254 | >10 | — | 6.45 |
| 255 | 0.06 | — | <0.01 |
| 256 | 4.97 | 0.65 | 7.24 |
| 257 | 0.80 | 0.71 | 0.80 |
| 258 | 0.77 | 0.71 | 0.70 |
| 259 | 0.92 | 0.74 | 0.74 |
| 260 | 0.76 | 0.67 | 0.71 |
| 261 | 0.61 | 0.59 | 0.46 |
| 262 | 0.83 | — | 0.60 |
| 263 | >10 | — | 8.49 |
| 264 | 8.49 | — | 6.04 |
| 265 | 41.7% | 41.2% | 33.1% |
| 279 | 87.4% | 47.2% | 42.3% |
| 283 | 75.6% | 50.0% | 44.7% |
| 287 | 95.8% | 53.0% | 124% |
| 291 | 70.8% | 37.8% | 37.1% |
| 295 | 83.0% | 31.8% | 37.8% |
| 297 | 56.6% | 31.4% | 33.7% |
| 310 | 59.1% | 30.0% | 40.2% |

The present compounds showed a potent inhibitory effect on the sphere-forming ability of cancer cells in the inhibition test for sphere-forming ability of cancer cells. The compounds of Examples 1, 8, 9, 11, 14, 15, 16, 17, 18, 22, 32, 33, 34, 35, 36, 37, 38, 44, 49, 61, 65, 66, 68, 71, 74, 77, 93, 96, 97, 112, 118, 138, 151, 152, 159, 160, 161, 162, 186, 190, 191, 192, 193, 206, 216, 218, 231, 236, 242, 252, 253, and 255 showed a particularly potent inhibitory effect on the sphere-forming ability of cancer cells.

Test Example 2: Inhibition Test for Sphere-Forming Ability of Cancer Cells (in the Presence of BSA)

Human colorectal cancer-derived HCT-116 cells, human colon-adenocarcinoma-derived HT-29 cells, and human pharyngeal cancer-derived FaDu cells were available from American Type Culture Collection (ATCC). HCT-116 cells and HT-29 cells were cultured at 37° C. under 5% $CO_2$ using the McCoy's 5a medium containing 10% fetal bovine serum (FBS) and 1% penicillin/streptomycin, and FaDu cells were cultured at 37° C. under 5% $CO_2$ using the MEM medium containing 10% FBS, 1% non-essential amino acid, 1% sodium pyruvate, 5% bovine serum albumin (BSA), and 1% penicillin/streptomycin. HCT-116 cells, HT-29 cells, and FaDu cells were seeded in a 384 Well Black Clear Bottom Ultra-Low Attachment Microplate (Corning Cat. No. 3827)

in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), 5% bovine serum albumin (BSA), and 1% penicillin/streptomycin. Each test compound was added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere IC$_{50}$ value; μmol/L).

The experiment of Test Example 2 was performed for each compound of each Example.

The concentration of each test compound for 50% inhibition of cell proliferation (Sphere IC$_{50}$ value; μmol/L) is shown in the following Table.

| Example | IC$_{50}$ (μmol/L) | | |
|---|---|---|---|
| | HCT-116 | FaDu | HT-29 |
| 4 | 6.40 | — | — |
| 6 | 0.83 | 0.60 | 0.62 |
| 7 | 0.79 | 0.46 | 0.55 |
| 8 | 0.63 | 0.07 | 0.37 |
| 9 | 0.91 | — | — |
| 10 | 0.83 | 0.28 | 0.55 |
| 11 | 0.26 | 0.06 | 0.07 |
| 14 | 0.36 | 0.06 | 0.06 |
| 15 | 0.08 | 0.06 | 0.06 |
| 16 | 0.64 | 0.07 | 0.50 |
| 17 | 0.64 | 0.05 | 0.35 |
| 18 | 0.58 | 0.03 | 0.05 |
| 22 | 0.64 | — | — |
| 23 | 0.37 | — | — |
| 31 | 0.09 | — | — |
| 32 | 0.06 | 0.03 | 0.06 |
| 33 | 0.59 | — | — |
| 34 | 0.63 | 0.07 | 0.58 |
| 35 | 0.72 | 0.06 | 0.54 |
| 36 | 0.69 | 0.06 | 0.52 |
| 37 | 0.55 | <0.01 | 0.10 |
| 38 | 0.72 | 0.03 | 0.58 |
| 39 | 6.86 | 0.58 | 2.71 |
| 40 | 7.45 | 0.58 | 3.33 |
| 41 | 5.79 | 0.59 | 4.29 |
| 46 | >10 | 4.67 | 7.60 |
| 100 | 8.38 | — | — |

| Example | IC$_{50}$ (μmol/L) | |
|---|---|---|
| | HCT-116 | FaDu |
| | | HT |
| 100 | >10 | — | 6.33 |
| 102 | >10 | — | 5.96 |
| 131 | 9.21 | — | 0.54 |
| 132 | >10 | — | 6.46 |
| 137 | >10 | — | 6.13 |
| 138 | >10 | — | 6.14 |
| 141 | 4.93 | 0.55 | 0.65 |
| 143 | 6.35 | 0.96 | 5.21 |
| 144 | >10 | 4.32 | 5.60 |
| 145 | 1.62 | 0.34 | 0.63 |
| 146 | 6.02 | 0.55 | 0.81 |
| 147 | 6.83 | 0.91 | 5.97 |
| 148 | >10 | 5.06 | 6.78 |
| 149 | 7.75 | 2.42 | 6.18 |
| 150 | >10 | 7.81 | >10 |
| 151 | 0.65 | 0.33 | 0.55 |
| 152 | 0.57 | 0.15 | 0.63 |
| 153 | 6.39 | 0.66 | 3.20 |
| 154 | >10 | 0.60 | 0.89 |
| 155 | >10 | 7.03 | >10 |
| 156 | 5.07 | 0.42 | 0.59 |
| 157 | >10 | 5.64 | 7.42 |
| 158 | 4.22 | — | — |
| 159 | 0.61 | — | — |
| 160 | 0.61 | — | — |
| 161 | 0.41 | — | — |
| 162 | 0.51 | — | — |
| 163 | >10 | 5.04 | 5.46 |
| 174 | 5.31 | — | — |
| 175 | 0.77 | — | — |
| 177 | >10 | 5.26 | 6.39 |
| 179 | 5.96 | — | 5.76 |
| | | | HT-29 |
| 180 | >10 | — | 4.93 |
| 181 | 8.00 | — | 3.31 |
| 183 | >10 | — | 6.40 |
| 185 | >10 | — | 6.16 |
| 186 | 0.56 | — | 0.10 |
| 188 | 5.54 | — | 0.85 |
| 190 | 0.27 | — | 0.06 |
| 191 | 0.69 | — | 0.53 |
| 192 | 0.07 | — | 0.07 |
| 193 | 0.60 | — | 0.61 |
| 225 | >10 | 5.90 | 6.52 |
| 228 | >10 | — | 4.88 |
| 230 | >10 | — | 5.84 |
| 231 | 0.70 | — | 0.52 |
| 236 | 0.36 | 0.04 | 0.06 |
| 242 | 2.14 | — | |
| 247 | 9.84 | 6.80 | 7.15 |
| 248 | 6.50 | — | 5.13 |
| 249 | 2.42 | — | 0.49 |
| 251 | 0.77 | 0.55 | 0.60 |
| 252 | 0.08 | — | 0.05 |
| 253 | 0.57 | — | 0.07 |
| 255 | 0.63 | — | 0.39 |
| 256 | 6.17 | 4.41 | 6.61 |
| 257 | 7.46 | 4.44 | 5.99 |
| 258 | 9.06 | 5.19 | 5.75 |
| 260 | 6.81 | 3.09 | 4.09 |
| 261 | 0.86 | 0.48 | 0.52 |
| 262 | 6.05 | — | 0.72 |
| 264 | >10 | — | 6.27 |

As shown in the above table, the present compounds showed a potent inhibitory effect on the sphere-forming ability of cancer cells in the inhibition test for the sphere-forming ability of cancer cells. The compounds of Examples 8, 11, 14, 15, 16, 17, 18, 22, 23, 31, 32, 33, 34, 36, 37, 186, 192, 236, 252, and 253 showed a particularly potent inhibitory effect on the sphere-forming ability of cancer cells.

Test Example 3: Pharmacokinetic Assay in Tumor-Bearing Mice where HCT-116 Cells were Transplanted A 7- to 12-week-old nude mouse (BALB/cAnNCrlj-nu/nu, female, CHARLES RIVER LABORATORIES JAPAN, INC.) received intradermal transplantation of human colorectal cancer-derived HCT-116 cells (ATCC) in an amount of 3×10$^6$ cells/mouse around the ventral part. A test compound suspended in 0.5% methylcellulose solution or 20% Labrasol solution was orally administered in a single dose of 100 mg/kg or 150 mg/kg one week or later after the transplantation. Blood was collected 1, 2, 6, and 24 hours after administration, and centrifuged to afford plasma samples. Methanol was added to the plasma samples so as to be adjusted to 80% of the final concentration. The samples were centrifuged and filtered to be deproteinized. Then, the test compound was detected and quantitated with LC-MS/MS (API4000, AB SCIEX). In quantitation, a calibration curve was prepared with mouse plasma comprising a known amount of the compound and Bezafibrate was used for the internal standard.

The test in Test Example 3 was performed for the compounds of Examples.

The following table and FIGS. 1 to 5 show temporal changes of the plasma concentrations of compounds after oral administration.

| Example | Dose (mg/kg) | Solution | Plasma concentrations after oral administration (ng/mL) | | | |
|---|---|---|---|---|---|---|
| | | | 1 hour | 2 hours | 6 hours | 24 hours |
| 120 | 150 | 0.5% methylcellulose | 9220 | 7037 | 1203 | 142 |
| 122 | 100 | 20% Labrasol | 160 | 642 | 467 | 221 |
| 123 | 100 | 20% Labrasol | 287 | 837 | 79 | 62 |
| 128 | 100 | 20% Labrasol | 4699 | 610 | 644 | 13 |
| 129 | 100 | 20% Labrasol | 465 | 309 | 271 | — |
| 237 | 60 | 0.5% methylcellulose | 13234 | 9761 | 3391 | 4 |

Test Example 4: Drug Efficacy Assay in Tumor-Bearing Mice where HCT-116 Cells were Transplanted The present compound can be used to evaluate the anti-tumor effect thereof according to the following assay. A 4- to 7-week-old nude mouse (BALB/cAnNCrj-nu/nu, female, CHARLES RIVER LABORATORIES JAPAN, INC.) received intradermal transplantation of human colorectal cancer-derived HCT-116 cells (ATCC) in an amount of $3 \times 10^6$ cells/mouse around the ventral portion. The engraftment of HCT-116 cells was observed 5 to 14 days after the transplantation, and then each compound suspended in a solvent such as 0.5% methylcellulose solution was orally administrated to the mouse in a dose of 1 to 200 mg/kg one to twice daily. The tumor volume was measured over time after the administration to evaluate the effect for reducing the tumor volume by the administration of each compound. The tumor volume can be calculated from the minor axis and major axis of the tumor measured with a digital caliper (Mitutoyo) according to the following equation:

Tumor volume $[mm^3] = 0.5 \times$ minor axis $[mm] \times$ (major axis $[mm])^2$ The tumor volume in the present-compound-administration group was compared with that of the control administration group treated with only a solvent such as 0.5% methylcellulose solution, and T/C value was calculated according to the following equation to evaluate the anti-tumor effect of the present compound.

T/C (%)=(Tumor volume at the end of administration in the present-compound-administration group−Tumor volume at the start of administration in the present-compound-administration group)/(Tumor volume at the end of administration in the control administration group−Tumor volume at the start of administration in the control administration group)×100

The T/C values (%) of the present compound on each dosage and administration period in the tumor-bearing mice where HCT-116 cells were transplanted are shown below.

| Example | Dosage (mg/kg) | Administration Period (day) | T/C (%) |
|---|---|---|---|
| 120 | 150 | 16 | 65 |
| 122 | 200 | 15 | 51 |
| 141-2 | 150 | 19 | 53 |
| 151-2 | 150 | 19 | 52 |
| 152-2 | 150 | 19 | 84 |
| 237 | 15 | 22 | 72 |
| 237 | 150 | 22 | 45 |

INDUSTRIAL APPLICABILITY

The present compound has a potent inhibitory effect on the sphere-forming ability of cancer cells and is useful for an orally-available anti-tumor agent.

What is claimed is:

1. A compound of Formula (1):

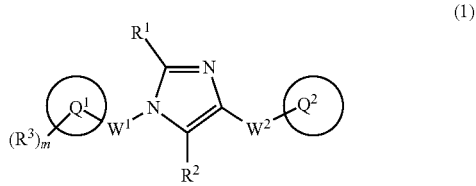

wherein $Q^1$ is $C_{6\text{-}10}$ aryl, $C_{6\text{-}10}$ aryloxy, $C_{6\text{-}10}$ arylthio, $C_{3\text{-}10}$ cycloalkyl, or 5- to 10-membered heteroaryl;
m is 0, 1, 2, 3, 4, or 5;
each $R^3$ is independently selected from:
(1) halogen,
(2) optionally-substituted $C_{1\text{-}6}$ alkyl,
(3) optionally-substituted $C_{1\text{-}6}$ alkoxy,
(4) optionally-substituted amino,
(5) optionally-substituted $C_{6\text{-}10}$ aryl,
(6) optionally-substituted $C_{6\text{-}10}$ aryloxy,
(7) optionally-substituted 5- to 10-membered heteroaryl,
(8) optionally-substituted $C_{1\text{-}6}$ alkoxy-carbonyl,
(9) optionally-substituted aminocarbonyl,
(10) optionally-substituted $C_{1\text{-}6}$ alkyl-carbonyl,
(11) optionally-substituted $C_{1\text{-}6}$ alkylsulfonyl,
(12) optionally-substituted $C_{1\text{-}6}$ alkyl-carbonylamino,
(13) optionally-substituted $C_{1\text{-}6}$ alkylsulfonylamino,
(14) optionally-substituted $C_{1\text{-}6}$ alkoxy-carbonylamino,
(15) optionally-substituted $C_{1\text{-}6}$ alkyl-carbonyloxy,
(16) hydroxy,
(17) cyano,
(18) optionally-substituted amino sulfonyl, and
(19) optionally-substituted $C_{3\text{-}10}$ cycloalkyl;
provided that when two $R^a$s bind to any of the adjacent carbon atoms on Ring $Q^1$, the $R^3$ groups may combine together with the carbon atoms to which they are attached to form a 5- to 8-membered saturated carbocyclic ring or non-aromatic heterocyclic ring, each of which is optionally substituted with 1 to 2 groups independently selected from the group consisting of halogen, $C_{1\text{-}6}$ alkyl, and $C_{1\text{-}6}$ alkoxy,
$R^1$ and $R^2$ are each independently hydrogen, halogen, or $C_{1\text{-}6}$ alkyl which is optionally substituted with 1 to 3 independently selected halogen atoms;

W¹ is $C_{1-4}$ alkylene which is optionally substituted with 1 to 3 fluorine atoms or $C_{3-7}$ cycloalkyl;

W²-Q² is —NHC(O)—CH=CH-Q²;

Ring Q² is:

(1) phenyl which is optionally substituted with 1 to 4 groups independently selected from the group consisting of:
(a) cyano;
(b) $C_{1-6}$ alkyl which is optionally substituted with 1 to 3 groups independently selected halogen and hydroxy;
(c) amino which is optionally substituted with 1 to 2 independently selected $C_{1-6}$ alkyl groups, wherein each alkyl group is optionally substituted with 1 to 3 independently selected halogen atoms;
(d) $C_{1-6}$ alkyl-carbonylamino wherein the alkyl moiety of the alkyl-carbonylamino is optionally substituted with 1 to 3 groups independently selected from halogen, hydroxy, and $C_{1-6}$ alkoxy;
(e) $C_{1-6}$ alkoxy which is optionally substituted with 1 to 3 groups independently selected from halogen, hydroxy, and $C_{1-6}$ alkoxy,
(f) phenoxy which is optionally substituted with 1 to 4 groups independently selected from the group consisting of halogen, $C_{1-6}$ alkyl, and $C_{1-6}$ alkoxy, and
(g) halogen atom;

or (2) pyridyl which is optionally substituted with 1 to 4 groups independently selected from the group consisting of:
(a) cyano,
(b) $C_{1-6}$ alkyl which is optionally substituted with 1 to 3 independently selected halogen atoms,
(c) amino which is optionally substituted with 1 to 2 independently selected $C_{1-6}$ alkyl groups, wherein each alkyl group is optionally substituted with 1 to 3 independently selected halogen atoms, and
(d) $C_{1-6}$ alkyl-carbonylamino wherein the alkyl moiety of the alkyl-carbonylamino is optionally substituted with 1 to 3 groups independently selected from halogen, hydroxy, and $C_{1-6}$ alkoxy;

or a pharmaceutically acceptable salt thereof.

2. The compound according to claim 1, or a pharmaceutically acceptable salt thereof, wherein Q¹ is phenyl.

3. The compound according to claim 1, or a pharmaceutically acceptable salt thereof, wherein m is 3 or 4.

4. The compound according to claim 1, or a pharmaceutically acceptable salt thereof, wherein each R³ is independently selected from
(1) halogen,
(2) $C_{1-6}$ alkyl which is optionally substituted with 1 to 3 groups independently selected from the group consisting of halogen, hydroxy, and $C_{1-6}$ alkoxy,
(3) $C_{1-6}$ alkoxy which is optionally substituted with 1 to 3 groups independently selected from the group consisting of halogen, hydroxy, $C_{1-6}$ alkoxy, and phenyl,
(4) amino which is optionally substituted with 1 to 2 independently selected $C_{1-6}$ alkyl groups,
(5) $C_{6-10}$ aryl which is optionally substituted with 1 to 4 groups independently selected from the group consisting of halogen, $C_{1-6}$ alkyl, and $C_{1-6}$ alkoxy,
(6) $C_{6-10}$ aryloxy which is optionally substituted with 1 to 4 groups independently selected from the group consisting of halogen, $C_{1-6}$ alkyl, and $C_{1-6}$ alkoxy,
(7) 5- to 10-membered heteroaryl which is optionally substituted with 1 to 4 groups independently selected from the group consisting of halogen, $C_{1-6}$ alkyl, and $C_{1-6}$ alkoxy, and
(8) $C_{1-6}$ alkoxy-carbonyl.

5. The compound according to claim 4, or a pharmaceutically acceptable salt thereof, wherein each R³ is independently a halogen atom or $C_{1-6}$ alkyl which is optionally substituted with 1 to 3 independently selected halogen atoms.

6. The compound according to claim 4, or a pharmaceutically acceptable salt thereof, wherein any or all of R³ is fluorine.

7. The compound according to claim 1, or a pharmaceutically acceptable salt thereof, wherein W¹ is methylene.

8. The compound according to claim 7, wherein Ring Q² is phenyl substituted with 1 to 3 groups independently selected from the group consisting of $C_{1-6}$ alkoxy which is optionally substituted with 1 to 3 groups independently selected from halogen, hydroxy, and $C_{1-6}$ alkoxy, and $C_{1-6}$ alkyl-carbonylamino, wherein the alkyl moiety of the alkyl-carbonylamino is optionally substituted with 1 to 3 groups independently selected from halogen, hydroxy, and $C_{1-6}$ alkoxy.

9. The compound according to claim 1, or a pharmaceutically acceptable salt thereof, wherein Ring Q² is phenyl substituted with 1 to 3 $C_{1-6}$ alkoxy groups, each of which is optionally substituted with 1 to 3 groups independently selected from halogen, hydroxy, and $C_{1-6}$ alkoxy.

10. The compound according to claim 1, or a pharmaceutically acceptable salt thereof, wherein both R¹ and R² are hydrogen.

11. The compound according to claim 1, or a pharmaceutically acceptable salt thereof, which has the structure of Formula (1a):

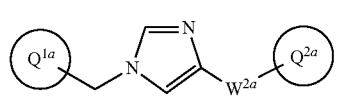

(1a)

wherein Ring $Q^{1a}$ is trifluorophenyl or trifluoromethylphenyl;

Ring $Q^{2a}$ is phenyl substituted with 1 to 3 groups independently selected from the group consisting of hydroxy, $C_{1-6}$ alkoxy which is optionally substituted with 1 to 3 groups independently selected from halogen, hydroxy, and $C_{1-6}$ alkoxy, and $C_{1-6}$ alkyl-carbonylamino, wherein the alkyl moiety of the alkyl-carbonylamino is optionally substituted with 1 to 3 groups independently selected from halogen, hydroxy, and $C_{1-6}$ alkoxy, and $W^{2a}$-$Q^{2a}$ is —NHC(O)—CH=CH-$Q^{2a}$;

or a pharmaceutically acceptable salt thereof.

12. The compound according to claim 11, or a pharmaceutically acceptable salt thereof, wherein Ring $Q^{1a}$ is trifluorophenyl.

13. The compound according to claim 1, which is selected from the following compounds:
(2E)-3-[4-(acetylamino)phenyl]-N-[1-(3-chlorobenzyl)-1H-imidazol-4-yl]prop-2-enamide,
(2E)-N-[1-(3-chlorobenzyl)-1H-imidazol-4-yl]-3-(pyridin-3-yl)prop-2-enamide,
(2E)-N-[1-(3-chlorobenzyl)-1H-imidazol-4-yl]-3-[4-cyano-3-(2-hydroxyethoxy)phenyl]prop-2-enamide, (2E)-3-[4-(acetylamino)phenyl]-N-{1-[3-(trifluoromethyl)benzyl]-1H-imidazol-4-yl}prop-2-enamide, (2E)-3-[3-(2-hydroxyethoxy)-4-methoxyphenyl]-N-{1[3-(trifluoromethyl)benzyl]-1H-imidazol-4-yl}prop-2-enamide, (2E)-N-[1-(3-chlorobenzyl)-1H-imidazol-4-yl]-3-[3-(2-hydroxyethoxy)-4-methoxyphenyl]prop-2-enamide, (2E)-3-[4-(acetylamino)phenyl]-N-[1-(3,4,5-trifluorobenzyl)-1H-imidazol-4-yl]prop-2-enamide, and (2E)-3-[4-(acetylamino)phenyl]-N-{1-[3-(trifluoromethoxy)benzyl]-1H-imidazol-4-yl}prop-2-enamide, or a pharmaceutically acceptable salt thereof.

14. The compound according to claim 1, which is (2E)-3-[4-(acetylamino)phenyl]-N-{1-[3-(trifluoromethyl)benzyl]-1H-imidazol-4-yl}prop-2-enamide, or a pharmaceutically acceptable salt thereof.

15. A method for inhibiting the sphere-forming ability of cancer cells, comprising administering an effective amount of a compound according to claim 1, or a pharmaceutically acceptable salt thereof, to a patient in need thereof.

16. A pharmaceutical composition, comprising a compound according to claim 1, or a pharmaceutically acceptable salt thereof, and one or more pharmaceutically acceptable additives.

17. A pharmaceutical composition, comprising a compound according to claim 11, or a pharmaceutically acceptable salt thereof, and one or more pharmaceutically acceptable additives.

18. A pharmaceutical composition, comprising a compound according to claim 13, or a pharmaceutically acceptable salt thereof, and one or more pharmaceutically acceptable additives.

* * * * *

UNITED STATES PATENT AND TRADEMARK OFFICE
CERTIFICATE OF CORRECTION

PATENT NO. : 10,898,469 B2
APPLICATION NO. : 16/079952
DATED : January 26, 2021
INVENTOR(S) : Hitoshi Ban et al.

Page 1 of 1

It is certified that error appears in the above-identified patent and that said Letters Patent is hereby corrected as shown below:

On the Title Page

Column 2 (item (57) Abstract), Line 14, delete "arylgroup" and insert -- aryl group --;

Column 2 (item (57) Abstract), Line 14, delete "like]" and insert -- like.] --.

In the Claims

Column 166, Lines 26-33 (approx.), Claim 1, should read:

-- 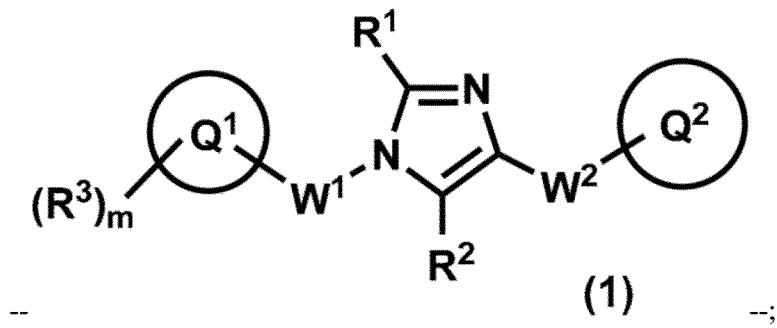 --;

Column 166, Line 55, Claim 1, delete "amino sulfonyl," and insert -- aminosylfonyl, --;

Column 166, Line 57, Claim 1, delete "R$^a$s" and insert -- R$^3$s --;

Column 168, Line 17, Claim 8, delete "claim 7" and insert -- claim 1 --;

Column 169, Lines 3-4 (approx.), Claim 13, delete "-N-{1[3-" and insert -- -N-{1-[3- --.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*